(12) United States Patent
Pastor Fernández et al.

(10) Patent No.: US 8,778,935 B2
(45) Date of Patent: Jul. 15, 2014

(54) IMIDAZOPYRAZINES FOR USE AS KINASE INHIBITORS

(75) Inventors: Joaquin Pastor Fernández, Madrid (ES); Sonia Martínez Gonzalez, Madrid (ES); Julen Oyarzabal Santamarina, Madrid (ES)

(73) Assignee: Centro Nacional de Investigaciones Oncologicas (CNIO), Madrid (ES)

( * ) Notice: Subject to any disclaimer, the term of this patent is extended or adjusted under 35 U.S.C. 154(b) by 0 days.

(21) Appl. No.: 13/264,544

(22) PCT Filed: Apr. 16, 2010

(86) PCT No.: PCT/GB2010/000773
§ 371 (c)(1),
(2), (4) Date: Dec. 20, 2011

(87) PCT Pub. No.: WO2010/119264
PCT Pub. Date: Oct. 21, 2010

(65) Prior Publication Data
US 2012/0083492 A1    Apr. 5, 2012

(30) Foreign Application Priority Data

Apr. 16, 2009   (EP) .................................. 09380079

(51) Int. Cl.
C07D 487/04 (2006.01)
A61K 31/4985 (2006.01)
A61P 35/00 (2006.01)
A61P 37/00 (2006.01)

(52) U.S. Cl.
USPC ......... 514/233.2; 514/249; 544/117; 544/350

(58) Field of Classification Search
USPC ....................... 514/233.2, 249; 544/117, 350
See application file for complete search history.

(56) References Cited

U.S. PATENT DOCUMENTS

2003/0139427 A1    7/2003    Castelhano et al.

FOREIGN PATENT DOCUMENTS

| WO | 88/04298 A1 | 6/1988 |
| WO | 99/64401 A2 | 12/1999 |
| WO | 02/10140 A2 | 2/2002 |
| WO | 02/060492 A1 | 8/2002 |
| WO | 02/062800 A1 | 8/2002 |
| WO | 2004/022562 A1 | 3/2004 |
| WO | 2004/072080 A1 | 8/2004 |
| WO | 2004/072081 A1 | 8/2004 |
| WO | 2006/046040 A1 | 5/2006 |
| WO | 2007/028051 A1 | 3/2007 |
| WO | 2007/096764 A1 | 8/2007 |
| WO | 2007/127175 A2 | 11/2007 |
| WO | 2008/059373 A1 | 5/2008 |
| WO | 2008/156614 A2 | 12/2008 |
| WO | 2009/007029 A1 | 1/2009 |

OTHER PUBLICATIONS

Abdel-Magid A. F., et al., J. Org. Chem., (1996), vol. 61, p. 3849.
Abdel-Magid A. F., et al., Synthesis, (1990), p. 537.
Abignente E. et al., II Farmaco, (1990), vol. 45, p. 1075.
Andanappa K. Gadad et al., Bioorg. Med. Chem. (2004), vol. 12, pp. 5651-5659.
Asunción Marin et al., Farmaco (1992), vol. 47 (1), pp. 63-75.
Bellamy F.D., et al., Tetrahedron Letters, (1985), vol. 25, p. 839.
Bretonnet et al., J. Med. Chem. (2007), vol. 50, p. 1872.
Cohen, Current Opinion in Chemical Biology (1999), vol. 3, pp. 459-465.
Defacqz N., et al., Tetrahedron Letters, (2003), vol. 44, p. 9111.
Dermer O. C., Chem. Rev., (1934), vol. 14, p. 385.
Easton et al., Oncogene (2006), vol. 25 (48), pp. 6436-6446.
El-Sherbeny M.A. et al., Boll. Chim. Farm. (1997), vol. 136, pp. 253-256.
Fabio, P. F. et al., Journal of Labelled Compounds and Pharmaceuticals, (1978), vol. 15, p. 407.
Gregson S.J. et al., J. Med. Chem., (2004), vol. 47, p. 1161.
Han S. Y., et al., Tetrahedron, (2004), vol. 60, p. 2447.
Hennessey et al., Nature Rev. Drug Discovery 4: (2005) pp. 988-1004.
Ikemoto T., et al., Heterocycles, (2001), vol. 55, p. 99.
Ikemoto T., et al., Tetrahedron, (2000), vol. 56, p. 7915.
Katritzky, J., Org.Chem, (2003), vol. 68, pp. 4935-4937.
Katritzky, J., Org.Chem. (1990), vol. 55, pp. 3209-3213.
Katso et al., Annu. Rev. Cell. Dev. Boil. (2001), vol. 17, pp. 615-675.
Kobe J. et al., Tetrahedron, (1968), vol. 24, pp. 239.
Kuwahara M. et al., Chem. Pharm Bull., (1996), vol. 44, p. 122.
Lainton J. A. H. et al., J. Comb. Chem., (2003), vol. 5, p. 400.
Leslie et al., Chem. Rev., (2001), vol. 101 (8), pp. 2365-2380.

(Continued)

Primary Examiner — Sreeni Padmanabhan
Assistant Examiner — Irina Neagu
(74) Attorney, Agent, or Firm — McCarter & English, LLP; Steven G. Davis

(57) ABSTRACT

There is provided compounds of formula (I), wherein $R^1$, $R^2$, $R^3$, $R^4$ and $R^5$ have meanings given in the description, and pharmaceutically-acceptable esters, amides, solvates or salts thereof, which compounds are useful in the treatment of diseases in which inhibition of a protein or lipid kinase (e.g. a PI3-K and/or mTOR) is desired and/or required, and particularly in the treatment of cancer or a proliferative disease.

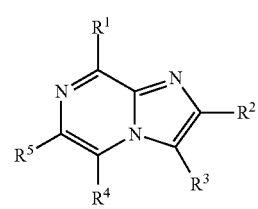

(I)

9 Claims, No Drawings

(56) References Cited

OTHER PUBLICATIONS

Lumma W. C., et al., J. Med. Chem., (1983), vol. 26 (3), pp. 357-363.
Parsons et al., Nature, (2005) vol. 436, p. 792.
Paul Heinz et al., Monatshefte für Chemie, (1977), vol. 108, p. 665-680.
Plotkin M. et al., Tetrahedron Letters, (2000), vol. 41, p. 2269.
Schlosser M. et al., "Organometallics in Synthesis. A Manual", (M. Schlosser, Ed.), Wiley & Sons Ltd: Chichester, UK, (2002) ISBN 0471984167.
Severinsen, R. et al., Tetrahedron (2005), vol. 61, pp. 5565-5575.
Seyden-Penne, J., "Reductions by the Alumino- and Borohydrides in Organic Synthesis", VCH, NY, (1991).
Shintani, R., et al., Org. Letters (2005), vol. 7 (21), pp. 4757-4759.
Toker et al., Cell. Mol. Life Science, (2002), vol. 59 (5), 761-79.
Vanhaesebroeck et al., Exp. Cell. Res. (1999), vol. 25 (1), pp. 239-254.
Vanhaesebroeck et al., Trends Biochem. Science, 22 (7), pp. 267-272 (1997).
Vitse O., et al., Bioorganic & Medicinal Chemistry 7, (1999), pp. 1059-1065.
Wenwei L. et al., Tetrahedron Letters, (2006), vol. 47, p. 1941.
Werber, G. et al., J. Heterocycl. Chem. (1977), vol. 14, pp. 823-827.
Wiggins, J. M., Synthetic Communication, (1988), vol. 18(7), p. 741-749.
Wipf, P. et al., J. Org. Chem. (2000), vol. 65(20), pp. 6319-6337.
Vasudevan, Krishna M. et al., "AKT-Independent Signaling Downstream of Oncogenic PIK3CA Mutations in Human Cancer" Cancer Cell (2009), vol. 16, pp. 21-32.
Engelman, Jeffrey A., "Targeting PI3K signaling in cancer: opportunities, challenges and limitations" Nature Rev. (2009), vol. 9, pp. 550-552.
Dorland's Medical Dictionary, p. 478-483. (copyright 1994).
Wikipedia entry for "Cardiovascular Disease", accessed May 16, 2013.
Black's Medical Dictionary, p. 62-63 (copyright 1995).

US 8,778,935 B2

IMIDAZOPYRAZINES FOR USE AS KINASE INHIBITORS

The instant application is a National Stage entry of PCT/GB2010/000773, filed on 16 Apr. 2010, claiming priority from European Patent Application Number 09380079.5, filed on 16 Apr. 2009.

FIELD OF THE INVENTION

This invention relates to novel pharmaceutically-useful compounds, which compounds are useful as inhibitors of protein or lipid kinases (such as inhibitors of the phosphoinositide 3'OH kinase (PI3 kinase) family, particularly the PI3K class I sub-type, or, inhibitors of the mammalian target of rapamycin (mTOR)). The compounds are of potential utility in the treatment of diseases such as cancer. The invention also relates to the use of such compounds as medicaments, to the use of such compounds for in vitro, in situ and in vivo diagnosis or treatment of mammalian cells (or associated pathological conditions), to pharmaceutical compositions containing them, and to synthetic routes for their production.

BACKGROUND OF THE INVENTION

The malfunctioning of protein kinases (PKs) is the hallmark of numerous diseases. A large share of the oncogenes and proto-oncogenes involved in human cancers code for PKs. The enhanced activities of PKs are also implicated in many non-malignant diseases, such as benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis. PKs are also implicated in inflammatory conditions and in the multiplication of viruses and parasites. PKs may also play a major role in the pathogenesis and development of neurodegenerative disorders.

For a general reference to PKs malfunctioning or disregulation see, for instance, *Current Opinion in Chemical Biology* 1999, 3, 459-465.

Phosphatidylinositol 3-kinases (PI3Ks) are a family of lipid and serine/threonine kinases that catalyze the phosphorylation of the membrane lipid phosphatidylinositol (PI) on the 3'-OH of the inositol ring to produce phosphoinositol-3-phosphate (PIP), phosphoinositol-3,4-diphosphate ($PIP_2$) and phosphoinositol-3,4,5-triphosphate ($PIP_3$), which act as recruitment sites for various intracellular signalling proteins, which in turn form signalling complexes to relay extracellular signals to the cytoplasmic face of the plasma membrane. These 3'-phosphoinositide subtypes function as second messengers in intra-cellular signal transduction pathways (see e.g. Trends Biochem. Sci 22 87, 267-72 (1997) by Vanhaesebroeck et al.; Chem. Rev. 101 (8), 2365-80 (2001) by Leslie et al (2001); Annu. Rev. Cell. Dev. Boil. 17, 615-75 (2001) by Katso et al; and Cell. Mol. Life. Sci. 59 (5), 761-79 (2002) by Toker et al).

Multiple PI3K isoforms categorized by their catalytic sub-units, their regulation by corresponding regulatory subunits, expression patterns and signalling specific functions (p110α, β, δ, γ) perform this enzymatic reaction (Exp. Cell. Res. 25 (1), 239-54 (1999) by Vanhaesebroeck and Katso et al., 2001, above).

The closely related isoforms p110α and β are ubiquitously expressed, while δ and γ are more specifically expressed in the haematopoietic cell system, smooth muscle cells, myocytes and endothelial cells (see e.g. Trends Biochem. Sci 22 (7), 267-72 (1997) by Vanhaesebroeck et al). Their expression might also be regulated in an inducible manner depending on the cellular, tissue type and stimuli as well as disease context. Inductibility of protein expression includes synthesis of protein as well as protein stabilization that is in part regulated by association with regulatory subunits.

Eight mammalian PI3Ks have been identified so far, including four class I PI3Ks. Class Ia includes PI3Kα, PI3Kβ and PI3Kδ. All of the class Ia enzymes are heterodimeric complexes comprising a catalytic subunit (p110α, p110β or p110δ) associated with an SH2 domain containing p85 adapter subunit. Class Ia PI3Ks are activated through tyrosine kinase signalling and are involved in cell proliferation and survival. PI3Kα and PI3Kβ have also been implicated in tumorigenesis in a variety of human cancers. Thus, pharmacological inhibitors of PI3Kα and PI3Kβ are useful for treating various types of cancer.

PI3Kγ, the only member of the Class Ib PI3Ks, consists of a catalytic subunit p110γ, which is associated with a p110 regulatory subunit. PI3Kγ is regulated by G protein coupled receptors (GPCRs) via association with βγ subunits of heterotrimeric G proteins. PI3Kγ is expressed primarily in hematopoietic cells and cardiomyocytes and is involved in inflammation and mast cell function. Thus, pharmacological inhibitors of PI3Kγ are useful for treating a variety of inflammatory diseases, allergies and cardiovascular diseases.

These observations show that deregulation of phosphoinositol-3-kinase and the upstream and downstream components of this signalling pathway is one of the most common deregulations associated with human cancers and proliferative diseases (see e.g. Parsons et al., Nature 436:792 (2005); Hennessey et al., Nature Rev. Drug Discovery 4: 988-1004 (2005).

The mammalian target of rapamycin (mTOR) also known as FK506 binding protein 12-rapamycin associated protein 1 (FRAP1) is a protein which in humans is encoded by the FRAP1 gene. mTOR is a serine/threonine protein kinase that regulates cell growth, cell proliferation, cell motility, cell survival, protein synthesis, and transcription. The inhibition of mTORs are believed to be useful for treating various diseases/conditions, such as cancer (for example, as described in Easton et al. (2006). "mTOR and cancer therapy". Oncogene 25 (48): 6436-46).

The listing or discussion of an apparently prior-published document in this specification should not necessarily be taken as an acknowledgement that the document is part of the state of the art or is common general knowledge.

International patent applications WO 99/64401 and WO 02/10140 both disclose compounds that may be useful as agonists or antagonists of somatostatin receptors. These documents do not predominantly relate to imidazopyrazines.

International patent applications WO 2007/028051 and WO 2008/156614 disclose inter alia imidazopyrazines that may be useful as kinase inhibitors. International patent application WO 2009/007029 discloses various compounds that may be useful in the treatment of haematological diseases. However, none of these documents predominantly relate to imidazopyrazines that are substituted at the 8-position with a cyclic group.

International patent applications WO 2004/072080 and WO 2004/072081 both disclose various imidazopyrazines, which may be useful as modulators of HSP90 complex or as modulators of a certain protein kinase. International patent application WO 02/060492 also discloses various imidazopyrazines, which may be useful as inhibitors of a certain protein kinase (JAK kinases). However, all of these documents predominantly relate to imidazopyrazines that are unsubstituted at the 2-, 3- and 5-position.

International patent application WO 2004/022562 discloses various imidazopyrazines that may be useful as modulators of kinase activity. However, this document predominantly relates to imidazopyrazines that are substituted at the 8-position with an amino group containing an aromatic ring and/or imidazopyrazines that are unsubstituted at the 2-, 3-, and 4-position.

International patent application WO 02/062800 discloses various compounds for use as antagonists on a corticotropin-releasing-factor receptor. International patent application WO 88/04298 also discloses certain compounds for use as medicaments. However, these documents do not predominantly relate to imidazopyrazines substituted at the 6-position with an aromatic group and/or relate to those imidazopyrazines unsubstituted at the 2-, 3-, and 4-position.

DISCLOSURE OF THE INVENTION

According to the invention, there is provided a compound of formula I,

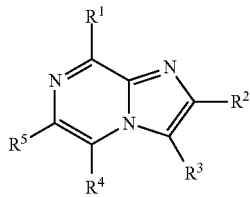

(I)

wherein:
$R^1$ represents:
(a) $-N(R^{1a})R^{1b}$,
in which $R^{1a}$ and $R^{1b}$ are linked together to form, together with the nitrogen atom to which they are necessarily attached, a 5- to 7-membered ring optionally containing a further one or two heteroatoms (e.g. selected from nitrogen, oxygen and sulfur), optionally containing one or two double bonds, and which ring is optionally substituted by one or more substituents selected from =O and $B^1$;
(b) a heterocycloalkyl (e.g. a 3- to 7-membered) group (attached to the requisite imidazopyrazine via a carbon atom), optionally substituted by one or more substituents selected from =O and $B^2$;
(c) a monocyclic heteroaryl group optionally substituted by one or more substituents selected from $B^3$;
$R^2$ and $R^3$ independently represent:
(i) hydrogen;
(ii) $Q^1$;
(iii) $C_{1-12}$ alkyl optionally substituted by one or more substituents selected from =O, =S, =N($R^{10a}$) and $Q^2$; or
$R^2$ or $R^3$ may represent a fragment of formula IA,

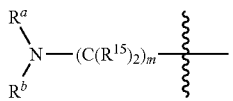

IA m represents 0, 1, 2, 3, 4, 5 or 6;

each $R^{15}$ represents hydrogen, halo (e.g. fluoro) or $C_{1-6}$ alkyl optionally substituted by one or more substituents selected from $E^1$; or
the two $R^{15}$ groups may linked together to form (along with the requisite carbon atom to which those $R^{15}$ groups are necessarily attached) a 3- to 6-membered (spiro-cyclic) ring, which ring optionally contains one or more double bonds, and optionally contains a further heteroatom selected from nitrogen, sulfur and oxygen, and which ring is optionally substituted by one or more substituents selected from $E^2$;
$R^a$ and $R^b$ are linked together, along with the requisite nitrogen atom to which they are necessarily attached, to form a first 3- to 7-membered cyclic group, optionally containing one further heteroatom selected from nitrogen, sulfur and oxygen, and which ring:
(a) is fused to a second ring that is either a 3- to 7-membered saturated heterocycloalkyl group containing one to four heteroatoms selected from oxygen, sulfur and nitrogen (preferably oxygen and nitrogen), a 3- to 12-membered saturated carbocyclic ring, or an unsaturated 5- to 12-membered carbocyclic or heterocyclic ring (in which the heteroatoms are preferably selected from sulfur and, especially, nitrogen and oxygen);
(b) comprises a linker group $-(C(R^x)_2)_p-$ and/or $-(C(R^x)_2)_r-O-(C(R^x)_2)_s-$ (wherein p is 1 or 2; r is 0 or 1; s is 0 or 1; and each $R^x$ independently represents hydrogen or $C_{1-6}$ alkyl), linking together any two non-adjacent atoms of the first 3- to 7-membered ring (i.e. forming a bridged structure); or
(c) comprises a second ring that is either a 3- to 12-membered saturated carbocyclic ring or a 3- to 7-membered saturated heterocycloalkyl group containing one to four heteroatoms selected from oxygen and nitrogen, and which second ring is linked together with the first ring via a single carbon atom common to both rings (i.e. forming a spiro-cycle),
all of which cyclic groups, defined by the linkage of $R^a$ and $R^b$, are optionally substituted by one or more substituents selected from =O and $E^3$;
$R^4$ represents hydrogen or a substituent selected from halo, $-CN$, $-OR^{10b}$, $-N(R^{10b})R^{11b}$, $-C(O)N(R^{10b})R^{11b}$, $-C(O)R^{10b}$, $C_{1-6}$ alkyl and heterocycloalkyl (e.g. a 3- to 7-membered heterocycloalkyl), which latter two groups are optionally substituted by one or more substituents selected from $E^4$ and =O;
but wherein at least one of $R^2$, $R^3$ and $R^4$ represents a substituent other than hydrogen;
$R^5$ represents aryl or heteroaryl (both of which are optionally substituted by one or more substituents selected from $E^5$);
each $Q^1$ and $Q^2$ independently represents, on each occasion when used herein: halo, $-CN$, $-NO_2$, $-N(R^{10a})R^{11a}$, $-OR^{10a}$, $-C(=Y)-R^{10a}$, $-C(=Y)-OR^{10a}$, $-C(=Y)N(R^{10a})R^{11a}$, $-OC(=Y)-R^{10a}$, $-OC(=Y)-OR^{10a}$, $-OC(=Y)N(R^{10a})R^{11a}$, $-OS(O)_2OR^{10a}$, $-OP(=Y)(OR^{10a})(OR^{11a})$, $-OP(OR^{10a})(OR^{11a})$, $-N(R^{12a})C(=Y)R^{11a}$, $-N(R^{12a})C(=Y)OR^{11a}$, $-N(R^{12a})C(=Y)N(R^{10a})R^{11a}$, $-NR^{12a}S(O)_2R^{10a}$, $-NR^{12a}S(O)_2N(R^{10a})R^{11a}$, $-S(O)_2N(R^{10a})R^{11a}$, $-SC(=Y)R^{10a}$, $-S(O)_2R^{10a}$, $-SR^{10a}$, $-S(O)R^{10a}$, $C_{1-12}$ alkyl, heterocycloalkyl (which latter two groups are optionally substituted by one or more substituents selected from =O, =S, =N($R^{10a}$) and $E^6$), aryl or heteroaryl (which latter two groups are optionally substituted by one or more substituents selected from $E^7$);
each $B^1$, $B^2$ and $B^3$ independently represent halo, $-NO_2$, $-CN$, $-N(R^{10a})R^{11a}$, $-OR^{10a}$, $-C(=Y)-R^{10a}$, $-C(=Y)-OR^{10a}$, $-C(=Y)N(R^{10a})R^{11a}$, $-N(R^{12a})C$ (=Y)R$^{11a}$, —N(R$^{12a}$)C(=Y)OR$^{11a}$, —N(R$^{12a}$)C(=Y)N(R$^{10a}$)R$^{11a}$, —NR$^{12a}$S(O)$_2$R$^{10a}$, —NR$^{12a}$S(O)$_2$N(R$^{10a}$)R$^{11a}$, —S(O)$_2$N(R$^{10a}$)R$^{11a}$, —SC(=Y)R$^{10a}$, —SC(=Y)OR$^{10a}$, —S(O)$_2$R$^{10a}$, C$_{1-12}$ alkyl, heterocycloalkyl (which latter two groups are optionally substituted by one or more substituents selected from =O and E$^8$), aryl or heteroaryl (which latter two groups are optionally substituted by one or more substituents selected from E$^9$);

or, any two B$^1$ substituents, when attached to the same carbon atom (thereby forming a spiro-cycle), may be linked together to form, a 3- to 12-membered (e.g. 3- to 6-membered) ring, optionally containing one or more (e.g. one to three) heteroatoms (preferably selected from sulfur, oxygen and nitrogen), which ring optionally contains one or more (e.g. one to three) double bonds, and which ring is itself optionally substituted by one or more substituents selected from halo, =O and C$_{1-3}$ alkyl optionally substituted by one or more fluoro atoms;

each R$^{10a}$, R$^{11a}$, R$^{12a}$, R$^{10b}$, R$^{11b}$ and R$^{12b}$ independently represent, on each occasion when used herein, hydrogen, C$_{1-12}$ alkyl, heterocycloalkyl (which latter two groups are optionally substituted by one or more substituents selected from =O, =S, =N(R$^{20}$) and E$^{10}$), aryl or heteroaryl (which latter two groups are optionally substituted by one or more substituents selected from E$^{11}$); or any relevant pair of R$^{10a}$, R$^{11a}$ and R$^{12a}$ (for example, when attached to the same atom, adjacent atom (i.e. 1,2-relationship) or to atoms that are two atom atoms apart, i.e. in a 1,3-relationship) and/or any pair of R$^{10b}$ and R$^{11b}$ may be linked together to form (e.g. along with the requisite nitrogen atom to which they may be attached) a 4- to 20- (e.g. 4- to 12-) membered ring, optionally containing one or more heteroatoms (for example, in addition to those that may already be present, e.g. (a) heteroatom(s) selected from oxygen, nitrogen and sulfur), optionally containing one or more unsaturations (preferably, double bonds), and which ring is optionally substituted by one or more substituents selected from =O, =S, =N(R$^{20}$) and E$^{12}$;

each E$^1$, E$^2$, E$^3$, E$^4$, E$^5$, E$^6$, E$^7$, E$^8$, E$^9$, E$^{10}$, E$^{11}$ and E$^{12}$ independently represents, on each occasion when used herein:
(i) Q$^4$;
(ii) C$_{1-12}$ alkyl optionally substituted by one or more substituents selected from =O and Q$^5$; or any two E$^1$, E$^2$, E$^3$, E$^4$, E$^5$, E$^6$, E$^7$, E$^8$, E$^9$, E$^{10}$, E$^{11}$ or E$^{12}$ groups, for example on C$_{1-12}$ alkyl groups, e.g. when they are attached to the same or adjacent carbon atoms or on aryl groups, e.g. when attached to adjacent carbon atoms, may be linked together to form a 3- to 12-membered ring, optionally containing one or more (e.g. one to three) unsaturations (preferably, double bonds), and which ring is optionally substituted by one or more substituents selected from =O and J$^1$;

each Q$^4$ and Q$^5$ independently represent, on each occasion when used herein: halo, —CN, —NO$_2$, —N(R$^{20}$)R$^{21}$, —OR$^{20}$, —C(=Y)—R$^{20}$, —C(=Y)—OR$^{20}$, —C(=Y)N(R$^{20}$)R$^{21}$, —OC(=Y)—R$^{20}$, —OC(=Y)—OR$^{20}$, —OC(=Y)N(R$^{20}$)R$^{21}$, —OS(O)$_2$OR$^{20}$, —OP(=Y)(OR$^{20}$)(OR$^{21}$), —OP(OR$^{20}$)(OR$^{21}$), —N(R$^{22}$)C(=Y)R$^{21}$, —N(R$^{22}$)C(=Y)OR$^{21}$, —N(R$^{22}$)C(=Y)N(R$^{20}$)R$^{21}$, —NR$^{22}$S(O)$_2$R$^{20}$), —NR$^{22}$S(O)$_2$N(R$^{20}$)R$^{21}$, —S(O)$_2$N(R$^{20}$)R$^{21}$, —SC(=Y)R$^{20}$, —S(O)$_2$R$^{20}$, —SR$^{20}$, —S(O)R$^{20}$, C$_{1-6}$ alkyl, heterocycloalkyl (which latter two groups are optionally substituted by one or more substituents selected from =O and J$^2$), aryl or heteroaryl (which latter two groups are optionally substituted by one or more substituents selected from J$^3$);

each Y independently represents, on each occasion when used herein, =O, =S, =NR$^{23}$ or =N—CN;

each R$^{20}$, R$^{21}$, R$^{22}$ and R$^{23}$ independently represent, on each occasion when used herein, hydrogen, C$_{1-6}$ alkyl, heterocycloalkyl (which latter two groups are optionally substituted by one or more substituents selected from J$^4$ and =O), aryl or heteroaryl (which latter two groups are optionally substituted by one or more substituents selected from J$^5$); or any relevant pair of R$^{20}$, R$^{21}$ and R$^{22}$, may (for example, when attached to the same atom, adjacent atom (i.e. 1,2-relationship) or to atoms that are two atom atoms apart, i.e. in a 1,3-relationship) be linked together to form (e.g. along with the requisite nitrogen atom to which they may be attached) a 4- to 20- (e.g. 4- to 12-) membered ring, optionally containing one or more heteroatoms (for example, in addition to those that may already be present, e.g. (a) heteroatom(s) selected from oxygen, nitrogen and sulfur), optionally containing one or more unsaturations (preferably, double bonds), and which ring is optionally substituted by one or more substituents selected from J$^6$ and =O;

each J$^1$, J$^2$, J$^3$, J$^4$, J$^5$ and J$^6$ independently represents, on each occasion when used herein:
(i) Q$^7$;
(ii) C$_{1-6}$ alkyl or heterocycloalkyl, both of which are optionally substituted by one or more substituents selected from =O and Q$^8$;

each Q$^7$ and Q$^8$ independently represents, on each occasion when used herein: —CN or, preferably, halo, —N(R$^{50}$)R$^{51}$, —OR$^{50}$, —C(=Y$^a$)—R$^{50}$, —C(=Y$^a$)—OR$^{50}$, —C(=Y$^a$)N(R$^{50}$)R$^{51}$, —N(R$^{52}$)C(=Y$^a$)R$^{51}$, —NR$^{52}$S(O)$_2$R$^{50}$, —S(O)$_2$R$^{50}$, —SR$^{50}$, —S(O)R$^{50}$ or C$_{1-6}$ alkyl optionally substituted by one or more fluoro atoms;

each Y$^a$ independently represents, on each occasion when used herein, =O, =S, =NR$^{53}$ or =N—CN;

each R$^{50}$, R$^{51}$, R$^{52}$ and R$^{53}$ independently represents, on each occasion when used herein, hydrogen or C$_{1-6}$ alkyl optionally substituted by one or more substituents selected from fluoro, —OR$^{60}$ and —N(R$^{61}$)R$^{62}$; or any relevant pair of R$^{50}$, R$^{51}$ and R$^{52}$ may (for example when attached to the same or adjacent atoms) be linked together to form, a 3- to 8-membered ring, optionally containing one or more heteroatoms (for example, in addition to those that may already be present, heteroatoms selected from oxygen, nitrogen and sulfur), optionally containing one or more unsaturations (preferably, double bonds), and which ring is optionally substituted by one or more substituents selected from =O and C$_{1-3}$ alkyl;

R$^{60}$, R$^{61}$ and R$^{62}$ independently represent hydrogen or C$_{1-6}$ alkyl optionally substituted by one or more fluoro atoms;

or a pharmaceutically acceptable ester, amide, solvate or salt thereof, which compounds, esters, amides, solvates and salts are referred to hereinafter as "the compounds of the invention".

Pharmaceutically-acceptable salts include acid addition salts and base addition salts. Such salts may be formed by conventional means, for example by reaction of a free acid or a free base form of a compound of formula I with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin.

By "pharmaceutically acceptable ester, amide, solvate or salt thereof", we include salts of pharmaceutically acceptable esters or amides, and solvates of pharmaceutically acceptable esters, amides or salts. For instance, pharmaceutically acceptable esters and amides such as those defined herein may be mentioned, as well as pharmaceutically acceptable solvates or salts.

Pharmaceutically acceptable esters and amides of the compounds of the invention are also included within the scope of the invention. Pharmaceutically acceptable esters and amides of compounds of the invention may be formed from corresponding compounds that have an appropriate group, for example an acid group, converted to the appropriate ester or amide. For example, pharmaceutically acceptable esters (of carboxylic acids of compounds of the invention) that may be mentioned include optionally substituted $C_{1-6}$ alkyl, $C_{5-10}$ aryl and/or $C_{5-10}$ aryl-$C_{1-6}$ alkyl-esters. Pharmaceutically acceptable amides (of carboxylic acids of compounds of the invention) that may be mentioned include those of the formula —$C(O)N(R^{z1})R^{z2}$, in which $R^{z1}$ and $R^{z2}$ independently represent optionally substituted $C_{1-6}$ alkyl, $C_{5-10}$ aryl, or $C_{5-10}$ aryl-$C_{1-6}$ alkylene-. Preferably, $C_{1-6}$ alkyl groups that may be mentioned in the context of such pharmaceutically acceptable esters and amides are not cyclic, e.g. linear and/or branched.

Further compounds of the invention that may be mentioned include carbamate, carboxamido or ureido derivatives, e.g. such derivatives of existing amino functional groups.

For the purposes of this invention, therefore, prodrugs of compounds of the invention are also included within the scope of the invention.

The term "prodrug" of a relevant compound of the invention includes any compound that, following oral or parenteral administration, is metabolised in vivo to form that compound in an experimentally-detectable amount, and within a predetermined time (e.g. within a dosing interval of between 6 and 24 hours (i.e. once to four times daily)). For the avoidance of doubt, the term "parenteral" administration includes all forms of administration other than oral administration.

Prodrugs of compounds of the invention may be prepared by modifying functional groups present on the compound in such a way that the modifications are cleaved, in vivo when such prodrug is administered to a mammalian subject. The modifications typically are achieved by synthesising the parent compound with a prodrug substituent. Prodrugs include compounds of the invention wherein a hydroxyl, amino, sulfhydryl, carboxy or carbonyl group in a compound of the invention is bonded to any group that may be cleaved in vivo to regenerate the free hydroxyl, amino, sulfhydryl, carboxy or carbonyl group, respectively.

Examples of prodrugs include, but are not limited to, esters and carbamates of hydroxy functional groups, esters groups of carboxyl functional groups, N-acyl derivatives and N-Mannich bases. General information on prodrugs may be found e.g. in Bundegaard, H. "Design of Prodrugs" p. 1-92, Elesevier, New York-Oxford (1985).

Compounds of the invention may contain double bonds and may thus exist as E (entgegen) and Z (zusammen) geometric isomers about each individual double bond. Positional isomers may also be embraced by the compounds of the invention. All such isomers (e.g. if a compound of the invention incorporates a double bond or a fused ring, the cis- and trans-forms, are embraced) and mixtures thereof are included within the scope of the invention (e.g. single positional isomers and mixtures of positional isomers may be included within the scope of the invention).

Compounds of the invention may also exhibit tautomerism. All tautomeric forms (or tautomers) and mixtures thereof are included within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerisations. Valence tautomers include interconversions by reorganisation of some of the bonding electrons.

Compounds of the invention may also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution), for example with a homochiral acid followed by separation of the diastereomeric derivatives by conventional means such as chromatography, or by reaction with an appropriate chiral reagent or chiral catalyst all under conditions known to the skilled person.

All stereoisomers (including but not limited to diastereoisomers, enantiomers and atropisomers) and mixtures thereof (e.g. racemic mixtures) are included within the scope of the invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the present invention may exist in unsolvated as well as solvated forms with pharmaceutically acceptable solvents such as water, ethanol, and the like, and it is intended that the invention embrace both solvated and unsolvated forms.

The present invention also embraces isotopically-labeled compounds of the present invention which are identical to those recited herein, but for the fact that one or more atoms are replaced by an atom having an atomic mass or mass number different from the atomic mass or mass number usually found in nature (or the most abundant one found in nature). All isotopes of any particular atom or element as specified herein are contemplated within the scope of the compounds of the invention. Exemplary isotopes that can be incorporated into compounds of the invention include isotopes of hydrogen, carbon, nitrogen, oxygen, phosphorus, sulfur, fluorine, chlorine and iodine, such as $^2H$, $^3H$, $^{11}C$, $^{13}C$, $^{14}C$, $^{13}N$, $^{15}O$, $^{17}O$, $^{18}O$, $^{32}P$, $^{33}P$, $^{35}S$, $^{18}F$, $^{36}Cl$, $^{123}I$ and $^{125}I$. Certain isotopically-labeled compounds of the present invention (e.g., those labeled with $^3H$ and $^{14}C$) are useful in compound and for substrate tissue distribution assays. Tritiated ($^3H$) and carbon-14 ($^{14}C$) isotopes are useful for their ease of preparation and detectability. Further, substitution with heavier isotopes such as deuterium (i.e., $^2H$ may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$ and $^{18}F$ are useful for positron emission tomography (PET) studies to examine substrate receptor occupancy. Isotopically labeled compounds of the present invention can generally be prepared by following procedures analogous to those disclosed in the Scheme 1 and/or in the Examples herein below, by substituting an isotopically labeled reagent for a non-isotopically labeled reagent.

Unless otherwise specified, $C_{1-q}$ alkyl groups (where q is the upper limit of the range) defined herein may be straight-chain or, when there is a sufficient number (i.e. a minimum of two or three, as appropriate) of carbon atoms, be branched-chain, and/or cyclic (so forming a $C_{3-q}$-cycloalkyl group). Such cycloalkyl groups may be monocyclic or bicyclic and may further be bridged. Further, when there is a sufficient number (i.e. a minimum of four) of carbon atoms, such groups may also be part cyclic. Such alkyl groups may also be saturated or, when there is a sufficient number (i.e. a minimum of two) of carbon atoms, be unsaturated (forming, for example, a $C_{2-q}$ alkenyl or a $C_{2-q}$ alkynyl group).

Unless otherwise stated, the term $C_{1-q}$ alkylene (where q is the upper limit of the range) defined herein may be straight-chain or, when there is a sufficient number of carbon atoms, be saturated or unsaturated (so forming, for example, an alkenylene or alkynylene linker group). However, such $C_{1-q}$ alkylene groups may not be branched.

$C_{3-q}$ cycloalkyl groups (where q is the upper limit of the range) that may be specifically mentioned may be monocyclic or bicyclic alkyl groups, which cycloalkyl groups may further be bridged (so forming, for example, fused ring systems such as three fused cycloalkyl groups). Such cycloalkyl groups may be saturated or unsaturated containing one or more double bonds (forming for example a cycloalkenyl group). Substituents may be attached at any point on the cycloalkyl group. Further, where there is a sufficient number (i.e. a minimum of four) such cycloalkyl groups may also be part cyclic.

The term "halo", when used herein, preferably includes fluoro, chloro, bromo and iodo.

Heterocycloalkyl groups that may be mentioned include non-aromatic monocyclic and bicyclic heterocycloalkyl groups in which at least one (e.g. one to four) of the atoms in the ring system is other than carbon (i.e. a heteroatom), and in which the total number of atoms in the ring system is between 3 and 20 (e.g. between three and ten, e.g between 3 and 8, such as 5- to 8-). Such heterocycloalkyl groups may also be bridged. Further, such heterocycloalkyl groups may be saturated or unsaturated containing one or more double and/or triple bonds, forming for example a $C_{2-q}$ heterocycloalkenyl (where q is the upper limit of the range) group. $C_{2-q}$ heterocycloalkyl groups that may be mentioned include 7-azabicyclo[2.2.1]heptanyl, 6-azabicyclo[3.1.1]heptanyl, 6-azabicyclo[3.2.1]-octanyl, 8-azabicyclo-[3.2.1]octanyl, aziridinyl, azetidinyl, dihydropyranyl, dihydropyridyl, dihydropyrrolyl (including 2,5-dihydropyrrolyl), dioxolanyl (including 1,3-dioxolanyl), dioxanyl (including 1,3-dioxanyl and 1,4-dioxanyl), dithianyl (including 1,4-dithianyl), dithiolanyl (including 1,3-dithiolanyl), imidazolidinyl, imidazolinyl, morpholinyl, 7-oxabicyclo[2.2.1]heptanyl, 6-oxabicyclo-[3.2.1]octanyl, oxetanyl, oxiranyl, piperazinyl, piperidinyl, pyranyl, pyrazolidinyl, pyrrolidinonyl, pyrrolidinyl, pyrrolinyl, quinuclidinyl, sulfolanyl, 3-sulfolenyl, tetrahydropyranyl, tetrahydrofuranyl, tetrahydropyridyl (such as 1,2,3,4-tetrahydropyridyl and 1,2,3,6-tetrahydropyridyl), thietanyl, thiiranyl, thiolanyl, thiomorpholinyl, trithianyl (including 1,3,5-trithianyl), tropanyl and the like. Substituents on heterocycloalkyl groups may, where appropriate, be located on any atom in the ring system including a heteroatom. The point of attachment of heterocycloalkyl groups may be via any atom in the ring system including (where appropriate) a heteroatom (such as a nitrogen atom), or an atom on any fused carbocyclic ring that may be present as part of the ring system. Heterocycloalkyl groups may also be in the N- or S-oxidised form. Heterocycloalkyl mentioned herein may be stated to be specifically monocyclic or bicyclic.

For the avoidance of doubt, the term "bicyclic" (e.g. when employed in the context of heterocycloalkyl groups) refers to groups in which the second ring of a two-ring system is formed between two adjacent atoms of the first ring. The term "bridged" (e.g. when employed in the context of cycloalkyl or heterocycloalkyl groups) refers to monocyclic or bicyclic groups in which two non-adjacent atoms are linked by either an alkylene or heteroalkylene chain (as appropriate).

Aryl groups that may be mentioned include $C_{6-20}$, such as $C_{6-12}$ (e.g. $C_{6-10}$) aryl groups. Such groups may be monocyclic, bicyclic or tricyclic and have between 6 and 12 (e.g. 6 and 10) ring carbon atoms, in which at least one ring is aromatic. $C_{6-10}$ aryl groups include phenyl, naphthyl and the like, such as 1,2,3,4-tetrahydronaphthyl. The point of attachment of aryl groups may be via any atom of the ring system. For example, when the aryl group is polycyclic the point of attachment may be via atom including an atom of a non-aromatic ring. However, when aryl groups are polycyclic (e.g. bicyclic or tricyclic), they are preferably linked to the rest of the molecule via an aromatic ring.

Unless otherwise specified, the term "heteroaryl" when used herein refers to an aromatic group containing one or more heteroatom(s) (e.g. one to four heteroatoms) preferably selected from N, O and S. Heteroaryl groups include those which have between 5 and 20 members (e.g. between 5 and 10) and may be monocyclic, bicyclic or tricyclic, provided that at least one of the rings is aromatic (so forming, for example, a mono-, bi-, or tricyclic heteroaromatic group). When the heteroaryl group is polycyclic the point of attachment may be via atom including an atom of a non-aromatic ring. However, when heteroaryl groups are polycyclic (e.g. bicyclic or tricyclic), they are preferably linked to the rest of the molecule via an aromatic ring. Heteroaryl groups that may be mentioned include 3,4-dihydro-1H-isoquinolinyl, 1,3-dihydroisoindolyl, 1,3-dihydroisoindolyl (e.g. 3,4-dihydro-1H-isoquinolin-2-yl, 1,3-dihydroisoindol-2-yl, 1,3-dihydroisoindol-2-yl; i.e. heteroaryl groups that are linked via a non-aromatic ring), or, preferably, acridinyl, benzimidazolyl, benzodioxanyl, benzodioxepinyl, benzodioxolyl (including 1,3-benzodioxolyl), benzofuranyl, benzofurazanyl, benzothiadiazolyl (including 2,1,3-benzothiadiazolyl), benzothiazolyl, benzoxadiazolyl (including 2,1,3-benzoxadiazolyl), benzoxazinyl (including 3,4-dihydro-2H-1,4-benzoxazinyl), benzoxazolyl, benzomorpholinyl, benzoselenadiazolyl (including 2,1,3-benzoselenadiazolyl), benzothienyl, carbazolyl, chromanyl, cinnolinyl, furanyl, imidazolyl, imidazo[1,2-a]pyridyl, indazolyl, indolinyl, indolyl, isobenzofuranyl, isochromanyl, isoindolinyl, isoindolyl, isoquinolinyl, isothiazolyl, isothiochromanyl, isoxazolyl, naphthyridinyl (including 1,6-naphthyridinyl or, preferably, 1,5-naphthyridinyl and 1,8-naphthyridinyl), oxadiazolyl (including 1,2,3-oxadiazolyl, 1,2,4-oxadiazolyl and 1,3,4-oxadiazolyl), oxazolyl, phenazinyl, phenothiazinyl, phthalazinyl, pteridinyl, purinyl, pyranyl, pyrazinyl, pyrazolyl, pyridazinyl, pyridyl, pyrimidinyl, pyrrolyl, quinazolinyl, quinolinyl, quinolizinyl, quinoxalinyl, tetrahydroisoquinolinyl (including 1,2,3,4-tetrahydroisoquinolinyl and 5,6,7,8-tetrahydroisoquinolinyl), tetrahydroquinolinyl (including 1,2,3,4-tetrahydroquinolinyl and 5,6,7,8-tetrahydroquinolinyl), tetrazolyl, thiadiazolyl (including 1,2,3-thiadiazolyl, 1,2,4-thiadiazolyl and 1,3,4-thiadiazolyl), thiazolyl, thiochromanyl, thiophenetyl, thienyl, triazolyl (including 1,2,3-triazolyl, 1,2,4-triazolyl and 1,3,4-triazolyl) and the like. Substituents on heteroaryl groups may, where appropriate, be located on any atom in the ring system including a heteroatom. The point of attachment of heteroaryl groups may be via any atom in the ring system including (where appropriate) a heteroatom (such as a nitrogen atom), or an atom on any fused carbocyclic ring that may be present as part of the ring system. Heteroaryl groups may also be in the N- or S-oxidised form. Heteroaryl groups mentioned herein may be stated to be specifically monocyclic or bicyclic. When heteroaryl groups are polycyclic in which there is a non-aromatic ring present, then that non-aromatic ring may be substituted by one or more =O group.

It may be specifically stated that the heteroaryl group is monocyclic or bicyclic. In the case where it is specified that the heteroaryl is bicyclic, then it may be consist of a five-, six- or seven-membered monocyclic ring (e.g. a monocyclic heteroaryl ring) fused with another a five-, six- or seven-membered ring (e.g. a monocyclic aryl or heteroaryl ring).

Heteroatoms that may be mentioned include phosphorus, silicon, boron and, preferably, oxygen, nitrogen and sulfur.

For the avoidance of doubt, where it is stated herein that a group (e.g. a $C_{1-12}$ alkyl group) may be substituted by one or more substituents (e.g. selected from $E^6$), then those substituents (e.g. defined by $E^6$) are independent of one another. That is, such groups may be substituted with the same substituent (e.g. defined by $E^6$) or different substituents (defined by $E^6$).

For the avoidance of doubt, in cases in which the identity of two or more substituents in a compound of the invention may be the same, the actual identities of the respective substituents are not in any way interdependent. For example, in the situation in which there is more than one $Q^1$ (or e.g. $E^6$) substituent present, then those $Q^1$ (or e.g. $E^6$) substituents may be the same or different. Further, in the case where there are two $Q^1$ (or two $E^6$) substituents present, in which one represents —$OR^{10a}$ (or e.g. —$OR^{20}$, as appropriate) and the other represents —$C(O)_2R^{10a}$ (or e.g. —$C(O)_2R^{20}$, as appropriate), then those $R^{10a}$ or $R^{20}$ groups are not to be regarded as being interdependent. Also, when e.g. there are two —$OR^{10a}$ substituents present, then those —$OR^{10a}$ groups may be the same or different (i.e. each $R^{10a}$ group may be the same or different).

For the avoidance of doubt, when a term such as "$E^1$ to $E^{12}$" is employed herein, this will be understood by the skilled person to mean $E^1$, $E^2$, $E^3$, $E^4$, $E^5$, $E^6$, $E^7$, $E^8$, $E^9$, $E^{10}$, $E^{11}$ and $E^{12}$, inclusively.

All individual features (e.g. preferred features) mentioned herein may be taken in isolation or in combination with any other feature (including preferred feature) mentioned herein (hence, preferred features may be taken in conjunction with other preferred features, or independently of them).

The skilled person will appreciate that compounds of the invention that are the subject of this invention include those that are stable. That is, compounds of the invention include those that are sufficiently robust to survive isolation from e.g. a reaction mixture to a useful degree of purity.

Compounds of the invention that may be mentioned include those in which:

$R^4$ represents hydrogen or a substituent selected from halo, —CN, —$OR^{10b}$, —$N(R^{10b})R^{11b}$, —$C(O)N(R^{10b})R^{11b}$, $C_{1-6}$ alkyl and heterocycloalkyl (e.g. a 3- to 7-membered heterocycloalkyl), which latter two groups are optionally substituted by one or more substituents selected from $E^4$ and =O.

Preferred compounds of the invention that may be mentioned include those in which:

$R^1$ does not represent an optionally substituted heteroaryl group (especially a monocyclic heteroaryl group, e.g. a 5- or 6-membered heteroaryl group), such as a 5-membered heteroaryl group containing two heteroatoms (e.g. a pyrazolyl, such as 1-pyrazolyl, or, especially, imidazolyl, such as 1-imidazolyl);

$R^1$ represents: (a) as defined herein, (b) as defined herein or (c) in which the heteroaryl group is a 5-membered heteroaryl group, in which the heteroatom(s) is/are selected from oxygen and sulphur, or a 6-membered heteroaryl group;

$R^1$ preferably represents (a) or (b);

$R^5$ does not represent phenyl or 3-pyridyl (especially phenyl) (e.g. in which the latter two groups are substituted (for example, meta to the point of attachment to the imidazopyrazine), with e.g. a urea (e.g. —$N(R^{22})C(=Y)N(R^{20})R^{21}$, in which Y is preferably =O).

Further preferred compounds of the invention that may be mentioned include those in which, for example especially when $R^1$ represents a group defined by (c) above, i.e. an optionally substituted monocyclic heteroaryl group (e.g. a 5-membered heteroaryl group such as pyrazolyl (e.g. 1-pyrazolyl) or, especially, imidazolyl (e.g. 1-imidazolyl)) and/or $R^5$ represents phenyl or 3-pyridyl (e.g. in which the latter two groups are substituted, for example (e.g. meta to the point of attachment to the imidazopyrazine), with e.g. a urea (e.g. —$N(R^{22})C(=Y)N(R^{20})R^{21}$, in which Y is preferably =O), then preferably:

$R^3$ represents a substituent other than hydrogen;

when $R^3$ represents a substituent other than hydrogen, then it is preferably $Q^1$, in which $Q^1$ represents heterocycloalkyl (e.g. piperidinyl, which heterocycloalkyl group is attached to the imidazopyrazine via a carbon or, preferably, nitrogen atom) or $Q^1$ more preferably represents halo, —CN, —$NO_2$, —$N(R^{10a})R^{11a}$, —$OR^{10a}$, —$C(=Y)$—$R^{10a}$, —$C(=Y)$—$OR^{10a}$, —$C(=Y)N(R^{10a})R^{11a}$, —$OC(=Y)$—$R^{10a}$, —$OC(=Y)$—$OR^{10a}$, —$OC(=Y)N(R^{10a})R^{11a}$, —$OS(O)_2OR^{10a}$, —$OP(=Y)(OR^{10a})(OR^{11a})$, —$OP(OR^{10a})OR^{11a}$, —$N(R^{12a})C(=Y)R^{11a}$, —$N(R^{12a})C(=Y)OR^{11a}$, —$N(R^{12a})C(=Y)N(R^{10a})R^{11a}$, —$NR^{12a}S(O)_2R^{10a}$, —$NR^{12a}S(O)_2N(R^{10a})R^{11a}$, —$S(O)_2N(R^{10a})R^{11a}$, —$SC(=Y)R^{10a}$, —$S(O)_2R^{10a}$, —$SR^{10a}$ or —$S(O)R^{10a}$ (and $Q^1$ preferably represents halo, —CN, —$NO_2$, —$OR^{10a}$, —$C(=Y)N(R^{10a})R^{11a}$, —$N(R^{12a})C(=Y)R^{11a}$, —$NR^{12a}S(O)_2R^{10a}$, and, especially, —$N(R^{10a})R^{11a}$);

when $R^3$ represents a substituent other than hydrogen, then it is preferably does not represent optionally substituted $C_{1-12}$ (e.g. $C_{1-6}$) alkyl, heterocycloalkyl (preferably linked to the imidazopyrazine via a carbon atom), aryl (e.g. phenyl) or heteroaryl; and/or at least one of $R^2$ and $R^4$ do not represent hydrogen, i.e. either one of $R^2$ and $R^4$ may represent hydrogen, and the other (or both) represent(s) a substituent as defined herein.

Further preferred compounds of the invention that may be mentioned include those in which, for example especially in the case when $R^1$ represents a group defined by (c) above, i.e. an optionally substituted monocyclic heteroaryl group (e.g. a 5-membered heteroaryl group such as (e.g. 1-pyrazolyl) or, especially, imidazolyl (e.g. 1-imidazolyl)) and/or $R^5$ represents phenyl or 3-pyridyl (e.g. in which the latter two groups are substituted, for example, meta to the point of attachment to the imidazopyrazine, with e.g. a urea such as —$N(R^{22})C(=Y)N(R^{20})R^{21}$, in which Y is preferably =O), then preferably:

$B^1$, $B^2$ and/or $B^3$ (e.g. $B^3$) do not represent or do not contain aromatic groups (such as pyridyl, e.g. 4-pyridyl);

B$^1$, B$^2$ and/or B$^3$ (e.g. B$^3$) independently represent halo, —NO$_2$, —CN, —N(R$^{10a}$)R$^{11a}$, —OR$^{10a}$, —C(=Y)—R$^{10a}$, —C(=Y)—OR$^{10a}$, —C(=Y)N(R$^{10a}$)R$^{11a}$, —N(R$^{12a}$)C(=Y)R$^{11a}$, —N(R$^{12a}$)C(=Y)OR$^{11a}$, —N(R$^{12a}$)C(=Y)N(R$^{10a}$)R$^{11a}$, —NR$^{12a}$S(O)$_2$R$^{10a}$, —NR$^{12a}$S(O)$_2$N(R$^{10a}$)R$^{11a}$, —S(O)$_2$N(R$^{10a}$)R$^{11a}$, —SC(=Y)R$^{10a}$, —SC(=Y)OR$^{10a}$, —S(O)$_2$R$^{10a}$, C$_{1-12}$ alkyl or heterocycloalkyl (which latter two groups are optionally substituted by one or more substituents selected from =O and E$^8$), or, two B$^1$ substituents may be linked together as herein defined (i.e./e.g. to form a spiro-cycle);

each R$^{10a}$, R$^{11a}$, R$^{12a}$, R$^{10b}$, R$^{11b}$ and R$^{12b}$ (for example when there is a B$^3$ group present) independently represent, on each occasion when used herein, hydrogen, C$_{1-12}$ alkyl or heterocycloalkyl (which latter two groups are optionally substituted by one or more substituents selected from =O, =S, =N(R$^{20}$) and)E$^{10}$); or any relevant pair of R$^{10a}$, R$^{11a}$ and R$^{12a}$ and/or any pair of R$^{10b}$ and R$^{11b}$ may be linked together as defined herein, but wherein when e.g. there are one or more E$^8$, E$^{10}$ and/or E$^{12}$ groups present (which independently represent Q$^4$ or C$_{1-12}$ alkyl optionally substituted by one or more substituents selected from =O and Q$^5$), then those Q$^4$ and Q$^5$ groups do not represent, or contain, aromatic rings, i.e. then:

each Q$^4$ and Q$^5$ independently represent, on each occasion when used herein: halo, —CN, —NO$_2$, —N(R$^{20}$)R$^{21}$, —OR$^{20}$, —C(=Y)—R$^{20}$, —C(=Y)—OR$^{20}$, —C(=Y)N(R$^{20}$)R$^{21}$, —OC(=Y)—R$^{20}$, —OC(=Y)—OR$^{20}$, —OC(=Y)N(R$^{20}$)R$^{21}$, —OS(O)$_2$OR$^{20}$, —OP(=Y)(OR$^2$)(OR$^{21}$), —OP(OR$^2$)(OR$^{21}$), —N(R$^{22}$)C(=Y)R$^{21}$, —N(R$^{22}$)C(=Y)OR$^{21}$, —N(R$^{22}$)C(=Y)N(R$^{20}$)R$^{21}$, —NR$^{22}$S(O)$_2$R$^{20}$, —NR$^{22}$S(O)$_2$N(R$^{20}$)R$^{21}$, —S(O)$_2$N(R$^{20}$)R$^{21}$, —SC(=Y)R$^{20}$, —S(O)$_2$R$^{20}$, —SR$^{20}$, —S(O)R$^{20}$, C$_{1-5}$ alkyl or heterocycloalkyl (which latter two groups are optionally substituted by one or more substituents selected from =O and J$^2$);

each R$^{20}$, R$^{21}$, R$^{22}$ and R$^{23}$ independently represent hydrogen, C$_{1-6}$ alkyl or heterocycloalkyl (which latter two groups are optionally substituted by one or more substituents selected from J$^4$ and =O).

Further preferred compounds of the invention that may be mentioned include those in which (for example, when R$^5$ represents a monocyclic aromatic group, such as phenyl or pyridyl, e.g. 3-pyridyl, e.g. in which the latter two groups are substituted, for example meta to the point of attachment to the imidazopyrazine, with e.g. a urea such as —N(R$^{22}$)C(=Y)N(R$^{20}$)R$^{21}$, in which Y is preferably =O):

R$^3$ preferably does not represent —C(=Y)—OR$^{10a}$ (particularly when, for example, R$^1$ represents a heteroaryl group, e.g. pyridyl);

R$^3$ preferably represents (particularly when, for example, R$^1$ represents a heteroaryl group, e.g. pyridyl)hydrogen or, more preferably, a substituent selected from heterocycloalkyl (e.g. one that is attached to the imidazopyrazine via a nitrogen atom) or, especially, halo, —CN, —NO$_2$, —N(R$^{10a}$)R$^{11a}$, —C(=Y)—R$^{10a}$, —C(=Y)N(R$^{10a}$)R$^{11a}$, —OC(=Y)—R$^{10a}$, —OC(=Y)—OR$^{10a}$, —OC(=Y)N(R$^{10a}$)R$^{11a}$, —OS(O)$_2$OR$^{10a}$, —OP(=Y)(OR$^{10a}$)(OR$^{11a}$), —OP(OR$^{10a}$)(OR$^{11a}$), —N(R$^{12a}$)C(=Y)R$^{11a}$, —N(R$^{12a}$)C(=Y)OR$^{11a}$, —N(R$^{12a}$)C(=Y)N(R$^{10a}$)R$^{11a}$, —NR$^{12a}$S(O)$_2$R$^{10a}$, —NR$^{12a}$S(O)$_2$N(R$^{10a}$)R$^{11a}$, —S(O)$_2$N(R$^{10a}$)R$^{11a}$, —SC(=Y)R$^{10a}$, —S(O)$_2$R$^{10a}$, —SR$^{10a}$ and —S(O)R$^{10a}$, or a fragment of formula IA as defined hereinbefore; and/or when, for example, R$^1$ represents a heteroaryl group (e.g. pyridyl), then R$^3$ preferably does not represent, or contain, an aromatic group (especially when R$^3$ represents —N(R$^{10a}$)R$^{11a}$, e.g. in which R$^{10a}$ and R$^{11a}$ are linked together to form, e.g. a piperazinyl group), i.e.:

each R$^{10a}$, R$^{11a}$, R$^{12a}$, R$^{10b}$, R$^{11b}$ and R$^{12b}$ (for example when R$^1$ represents a (c) group, such as pyridyl) independently represent, on each occasion when used herein, hydrogen, C$_{1-12}$ alkyl or heterocycloalkyl (which latter two groups are optionally substituted by one or more substituents selected from =O, =S, =N(R$^{20}$) and E$^{10}$); or any relevant pair of R$^{10a}$, R$^{11a}$ and R$^{12a}$ and/or any pair of R$^{10b}$ and R$^{11b}$ may be linked together as defined herein (and therefore be substituted by one or more E$^{12}$ groups), but wherein when there are one or more E$^{10}$ and/or E$^{12}$ groups present, which independently represent Q$^4$ or C$_{1-12}$ alkyl optionally substituted by one or more substituents selected from =O and Q$^5$, then those Q$^4$ and Q$^5$ groups do not represent, or contain, aromatic rings, i.e. then:

each Q$^4$ and Q$^5$ independently represent, on each occasion when used herein: halo, —CN, —NO$_2$, —N(R$^{20}$)R$^{21}$, OR$^{20}$, —C(=Y)—R$^{20}$, —C(=Y)—OR$^{20}$, —C(=Y)N(R$^{20}$)R$^{21}$, —OC(=Y)—R$^{20}$, —OC(=Y)—OR$^{20}$, —OC(=Y)N(R$^{20}$)R$^{21}$, —OS(O)$_2$OR$^{20}$, —OP(=Y)(OR$^{20}$)(OR$^{21}$), —OP(OR$^{20}$)(OR$^{21}$), —N(R$^{22}$)C(=Y)R$^{21}$, —N(R$^{22}$)C(=Y)OR$^{21}$, —N(R$^{22}$)C(=Y)N(R$^{20}$)R$^{21}$, —NR$^{22}$S(O)$_2$R$^{20}$, —NR$^{22}$S(O)$_2$N(R$^{20}$)R$^{21}$, —S(O)$_2$N(R$^{20}$)R$^{21}$, —SC(=Y)R$^{20}$, —S(O)$_2$R$^{20}$, —SR$^{20}$, —S(O)R$^{20}$, C$_{1-6}$ alkyl or heterocycloalkyl (which latter two groups are optionally substituted by one or more substituents selected from =O and J$^2$);

each R$^{20}$, R$^{21}$, R$^{22}$ and R$^{23}$ independently represent hydrogen, C$_{1-6}$ alkyl or heterocycloalkyl (which latter two groups are optionally substituted by one or more substituents selected from J$^4$ and =O).

Further preferred compounds of the invention that may be mentioned include those in which:

an R$^1$ group may not be substituted by an aromatic ring (e.g. a heteroaryl group);

B$^1$, B$^2$ and/or B$^3$ (e.g. B$^1$) do not represent or do not contain aromatic (e.g. heteroaromatic) groups (especially when R$^1$ represents an (a) group, i.e. —N(R$^{1a}$)R$^{1b}$);

B$^1$, B$^2$ and B$^3$ (e.g. B$^1$) independently represent aryl (optionally substituted by one or more substituents selected from E$^9$) or, preferably, halo, —NO$_2$, —CN, —N(R$^{10a}$)R$^{11a}$, —OR$^{10a}$, —C(=Y)—R$^{10a}$, —C(=Y)—OR$^{10a}$, —C(=Y)N(R$^{10a}$)R$^{11a}$, —N(R$^{12a}$)C(=Y)R$^{11a}$, —N(R$^{12a}$)C(=Y)OR$^{11a}$, —N(R$^{12a}$)C(=Y)N(R$^{10a}$)R$^{11a}$, —NR$^{12a}$S(O)$_2$R$^{10a}$, —NR$^{12a}$S(O)$_2$N(R$^{10a}$)R$^{11a}$, —S(O)$_2$N(R$^{10a}$)R$^{11a}$, —SC(=Y)R$^{10a}$, —SC(=Y)OR$^{10a}$, —S(O)$_2$, C$_{1-12}$ alkyl or heterocycloalkyl (which latter two groups are optionally substituted by one or more substituents selected from =O and E$^8$), or, two B$^1$ substituents may be linked together (to form a spiro-cycle) as herein defined (this is especially the case when R$^1$ represents an (a) group, i.e. —N(R$^{1a}$)R$^{1b}$);

each R$^{10a}$, R$^{11a}$, R$^{12a}$, R$^{10b}$, R$^{11b}$ and R$^{12b}$ (for example when a B$^1$ substituent is present containing such a moiety) independently represent, on each occasion when used herein, aryl (optionally substituted by one or more substituents selected from E$^{11}$) or, preferably, hydrogen, C$_{1-12}$ alkyl or heterocycloalkyl (which latter two groups are optionally substituted by one or more substituents selected from =O, =S, =N(R$^{20}$) and E$^{10}$); or any relevant pair of R$^{10a}$, R$^{11a}$ and R$^{12a}$ and/or any pair of R$^{10b}$ and R$^{11b}$ may be linked together as defined herein (and therefore be substituted by one or more E$^{12}$ groups), but wherein when there are one or more E$^{10}$, E$^{11}$ and/or E$^{12}$ groups present, which independently represent Q$^4$ or C$_{1-12}$ alkyl optionally substituted by one or more substituents selected from =O and Q$^5$, then those $Q^4$ and $Q^5$ groups do not represent, or contain, aromatic (e.g. heteroaryl) rings, i.e. then:

each $Q^4$ and $Q^5$ independently represent, on each occasion when used herein:

aryl (optionally substituted by one or more substituents selected from $J^3$) or, preferably, halo, —CN, —NO$_2$, —N(R$^{20}$)R$^{21}$, —OR$^{20}$, —C(=Y)—R$^{20}$, —C(=Y)—OR$^{20}$, —C(=Y)N(R$^{20}$)R$^{21}$, —OC(=Y)—R$^{20}$, —OC(=Y)—OR$^{20}$, —OC(=Y)N(R$^{20}$)R$^{21}$, —OS(O)$_2$OR$^{20}$, —OP(=Y)(OR$^{20}$)(OR$^{21}$), —OP(OR$^{20}$)(OR$^{21}$), —N(R$^{22}$)C(=Y)R$^{21}$, —N(R$^{22}$)C(=Y)OR$^{21}$, —N(R$^{22}$)C(=Y)N(R$^{20}$)R$^{21}$, —NR$^{22}$S(O)$_2$R$^{20}$, —NR$^{22}$S(O)$_2$N(R$^{20}$)R$^{21}$, —S(O)$_2$N(R$^{20}$)R$^{21}$, —SC(=Y)R$^{20}$, —S(O)$_2$R$^{20}$, —SR$^{20}$, —S(O)R$^{20}$, C$_{1-6}$ alkyl or heterocycloalkyl (which latter two groups are optionally substituted by one or more substituents selected from =O and J$^2$);

each R$^{20}$, R$^{21}$, R$^{22}$ and R$^{23}$ independently represent hydrogen, C$_{1-6}$ alkyl or heterocycloalkyl (which latter two groups are optionally substituted by one or more substituents selected from J$^4$ and =O);

R$^{1a}$ and R$^{1b}$ are preferably linked together to form a 5- or 6-membered ring as defined herein;

when R$^1$ represents an (a) group, then, preferably, the ring formed by the linkage of the R$^{1a}$ and R$^{1b}$ groups contains at least one (further) heteroatom (in addition to the requisite nitrogen atom to which R$^{1a}$ and R$^{1b}$ are necessarily attached) as defined herein;

when R$^1$ represents an (a) group, then the ring so formed (by the linkage of the R$^{1a}$ and R$^{1b}$ groups), preferably does not represent a 1-pyrrolidinyl or 1-piperidinyl ring (e.g. one in which that ring is substituted at the 2-position, by for example an a methyl group substituted by an amino moiety (a methylamino group, i.e. substituted by B$^1$, in which B$^1$ represents methyl substituted by E$^8$, in which E$^8$ represents Q$^4$ and Q$^4$ represents —N(R$^{20}$)R$^{21}$) or, in which that ring is substituted at the 3-position by an amino moiety (i.e. by B$^1$, in which B$^1$ represents —N(R$^{10a}$)R$^{11a}$).

Further compounds of the invention that may be mentioned include those in which for example when R$^1$ represents an (a) group (e.g. in which R$^{1a}$ and R$^{1b}$ are linked together to form a 5- or 6-membered ring, e.g. a 1-pyrrolidinyl or 1-piperidinyl group), then preferably:

such groups are unsubstituted (i.e. do not contain any B$^1$ groups);

when substituted (e.g. at the 3-position or, especially, at the 2-position with a B$^1$ group), then:

B$^1$ preferably represents —N(R$^{10a}$)R$^{11a}$, or, preferably, halo, —NO$_2$, —CN, —OR$^{10a}$, —C(=Y)—R$^{10a}$, —C(=Y)—OR$^{10a}$, —C(=Y)N(R$^{10a}$)R$^{11a}$, —N(R$^{12a}$)C(=Y)R$^{11a}$, —N(R$^{12a}$)C(=Y)OR$^{11a}$, —N(R$^{12a}$)C(=Y)N(R$^{10a}$)R$^{11a}$, —NR$^{12a}$S(O)$_2$R$^{10a}$, —NR$^{12a}$S(O)$_2$N(R$^{10a}$)R$^{11a}$, —S(O)$_2$N(R$^{10a}$)R$^{11a}$, —SC(=Y)R$^{10a}$, —SC(=Y)OR$^{10a}$, —S(O)$_2$R$^{10a}$, heterocycloalkyl (optionally substituted by one or more substituents selected from =O and E$^8$), aryl or heteroaryl (which latter two groups are optionally substituted by one or more substituents selected from E$^9$);

when B$^1$ represents optionally substituted C$_{1-12}$ alkyl (e.g. methyl), then either that alkyl group is unsubstituted or, when substituted by one or more =O and/or E$^8$ groups, then when E$^8$ represents Q$^4$, Q$^4$ represents halo, —CN, —NO$_2$, —OR$^{20}$, —C(=Y)—R$^{20}$, —C(=Y)—OR$^{20}$, —C(=Y)N(R$^{20}$)R$^{21}$, —OC(=Y)—R$^{20}$, —OC(=Y)—OR$^{20}$, —OC(=Y)N(R$^{20}$)R$^{21}$, —OS(O)$_2$OR$^{20}$, —OP(=Y)(OR$^{20}$)(OR$^{21}$), —OP(OR$^{20}$)(OR$^{21}$), —N(R$^{22}$)C(=Y)R$^{21}$, —N(R$^{22}$)C(=Y)OR$^{21}$, —N(R$^{22}$)C(=Y)N(R$^{20}$)R$^{21}$, —NR$^{22}$S(O)$_2$R$^{20}$, —NR$^{22}$S(O)$_2$N(R$^{20}$)R$^{21}$, —S(O)$_2$N(R$^{20}$)R$^{21}$, —SC(=Y)R$^{20}$, —S(O)$_2$R$^{20}$, —SR$^{20}$, —S(O)R$^{20}$, C$_{1-6}$ alkyl, heterocycloalkyl (which latter two groups are optionally substituted by one or more substituents selected from =O and J$^2$), aryl or heteroaryl (which latter two groups are optionally substituted by one or more substituents selected from J$^3$);

when substituted (e.g. at the 3-position with a B$^1$ group), then:

B$^1$ preferably represents halo, —NO$_2$, —CN, —OR$^{10a}$, —C(=Y)—R$^{10a}$, —C(=Y)—OR$^{10a}$, —C(=Y)N(R$^{10a}$)R$^{11a}$, —N(R$^{12a}$)C(=Y)R$^{11a}$, —N(R$^{12a}$)C(=Y)OR$^{11a}$, —N(R$^{12a}$)C(=Y)N(R$^{10a}$)R$^{11a}$, —NR$^{12a}$S(O)$_2$R$^{10a}$, —NR$^{12a}$S(O)$_2$N(R$^{10a}$)R$^{11a}$, —S(O)$_2$N(R$^{10a}$)R$^{11a}$, —SC(=Y)R$^{10a}$, —SC(=Y)OR$^{10a}$, —S(O)$_2$R$^{10a}$, C$_{1-12}$ alkyl, heterocycloalkyl (which latter two groups are optionally substituted by one or more substituents selected from =O and E$^8$), aryl or heteroaryl (which latter two groups are optionally substituted by one or more substituents selected from E$^9$).

Further preferred compounds of the invention that may be mentioned include those in which:

at least one of R$^2$ and R$^3$ does not represent an aromatic group (i.e. an optionally substituted aryl or heteroaryl group);

at least one of R$^2$ and R$^3$ represents hydrogen or a substituent as defined herein, but wherein each Q$^1$ and, optionally, Q$^2$ are independently selected from halo, —CN, —NO$_2$, —N(R$^{10a}$)R$^{11a}$, —OR$^{10a}$, —C(=Y)—R$^{10a}$, —C(=Y)—OR$^{10a}$, —OC(=Y)—R$^{10a}$, —OC(=Y)—OR$^{10a}$, —OC(=Y)N(R$^{10a}$)R$^{11a}$, —OS(O)$_2$OR$^{10a}$, —OP(=Y)(OR$^{10a}$)(OR$^{11a}$), —OP(OR$^{10a}$)(OR$^{11a}$), —N(R$^{12a}$)C(=Y)R$^{11a}$, —N(R$^{12a}$)C(=Y)OR$^{11a}$, —N(R$^{12a}$)C(=Y)N(R$^{10a}$)R$^{11a}$, —NR$^{12a}$S(O)$_2$R$^{10a}$, —NR$^{12a}$S(O)$_2$N(R$^{10a}$)R$^{11a}$, —S(O)$_2$N(R$^{10a}$)R$^{11a}$, —SC(=Y)R$^{10a}$, —S(O)$_2$R$^{10a}$, —SR$^{10a}$, —S(O)R$^{10a}$, C$_{1-12}$ alkyl or heterocycloalkyl (which latter two groups are optionally substituted by one or more substituents selected from =O, =S, =N(R$^{10a}$) and E$^6$), or a fragment of formula IA as defined hereinbefore;

more preferably neither R$^2$ or R$^3$ represent an aromatic group, i.e. these groups preferably represent hydrogen or a substituent as defined above.

Further preferred compounds of the invention that may be mentioned include those in which, for example, when R$^1$ represents amino (i.e. a group defined by (a) above) or, in particular, when R$^1$ represents a group defined by (c) above (in particular pyridyl or imidazolyl), then:

R$^5$ does not represent optionally substituted phenyl, naphthyl, indolyl, thiophenyl, benzo[b]furanyl, benzo[b]thiophenyl, isoxazolyl, or:

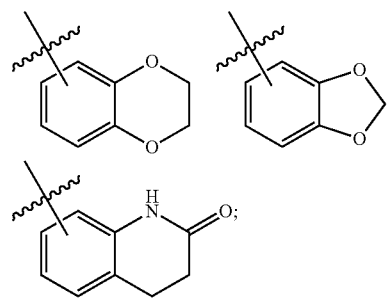

and/or

R$^2$ does not represent C$_1$-C$_{12}$ alkyl, —C(O)—O—R$^{10a}$, —C(O)—N(R$^{10a}$)R$^{11a}$ and/or R$^3$ does not represent H or C$_1$-C$_6$ alkyl; and/or R² represents hydrogen or Q¹ (most preferably R² represents hydrogen), in which Q¹ is preferably selected from halo, —CN, —NO₂, —N(R¹⁰ᵃ)R¹¹ᵃ, —OR¹⁰ᵃ, —C(=Y)—R¹⁰ᵃ, —OC(=Y)—R¹⁰ᵃ, —OC(=Y)—OR¹⁰ᵃ, —OC(=Y)N(R¹⁰ᵃ)R¹¹ᵃ, —OS(O)₂OR¹⁰ᵃ, —OP(=Y)(OR¹⁰ᵃ)(OR¹¹ᵃ), —OP(OR¹⁰ᵃ)(OR¹¹ᵃ), —N(R¹²ᵃ)C(=Y)R¹¹ᵃ, —N(R¹²ᵃ)C(=Y)OR¹¹ᵃ, —N(R¹²ᵃ)C(=Y)N(R¹⁰ᵃ)R¹¹ᵃ, —NR¹²ᵃS(O)₂R¹⁰ᵃ, —NR¹²ᵃS(O)₂N(R¹⁰ᵃ)R¹¹ᵃ, —S(O)₂N(R¹⁰ᵃ)R¹¹ᵃ, —SC(=Y)R¹⁰ᵃ, —S(O)₂R¹⁰ᵃ, —SR¹⁰ᵃ, —S(O)R¹⁰ᵃ, heterocycloalkyl (optionally substituted by one or more substituents selected from =O, =S, =N(R¹⁰ᵃ) and E⁶), aryl or heteroaryl (which latter two groups are optionally substituted by one or more substituents selected from E⁷);

R³ represents C₇₋₁₂ alkyl (optionally substituted by one or more substituents selected from =O, =S, =N(R¹⁰ᵃ) and Q²), or R³ more preferably represents hydrogen or Q¹, in which Q¹ preferably represents C₇₋₁₂ alkyl (optionally substituted by one or more substituents selected from =O, =S, =N(R¹⁰ᵃ) and E⁶) and in which Q¹ more preferably represents halo, —CN, —NO₂, —N(R¹⁰ᵃ)R¹¹ᵃ, —OR¹⁰ᵃ, —C(=Y)—R¹⁰ᵃ, —C(=Y)—OR¹⁰ᵃ, —C(=Y)N(R¹⁰ᵃ)R¹¹ᵃ, —OC(=Y)—R¹⁰ᵃ, —OC(=Y)—OR¹⁰ᵃ, —OC(=Y)N(R¹⁰ᵃ)R¹¹ᵃ, —OS(O)₂OR¹⁰ᵃ, —OP(=Y)(OR¹⁰ᵃ)(OR¹¹ᵃ), —OP(OR¹⁰ᵃ)(OR¹¹ᵃ), —N(R¹²ᵃ)C(=Y)R¹¹ᵃ, —N(R¹²ᵃ)C(=Y)OR¹¹ᵃ, —N(R¹²ᵃ)C(=Y)N(R¹⁰ᵃ)R¹¹ᵃ, —NR¹²ᵃS(O)₂R¹⁰ᵃ, —NR¹²ᵃS(O)₂N(R¹⁰ᵃ)R¹¹ᵃ, —S(O)₂N(R¹⁰ᵃ)R¹¹ᵃ, —SC(=Y)R¹⁰ᵃ, —S(O)₂R¹⁰ᵃ, —SR¹⁰ᵃ, —S(O)R¹⁰ᵃ, heterocycloalkyl (optionally substituted by one or more substituents selected from =O, =S, =N(R¹⁰ᵃ) and E⁶), aryl or heteroaryl (which latter two groups are optionally substituted by one or more substituents selected from E⁷); or R² or R³ may represent a fragment of formula IA.

Preferred compounds of the invention that may be mentioned include those in which, when R¹ represents —N(R¹ᵃ)R¹ᵇ, then:

R¹ᵃ and R¹ᵇ are preferably linked together to form a saturated 5-, 6- or 7-membered ring, optionally containing one further heteroatom (selected from nitrogen or, preferably oxygen and sulfur), optionally substituted by one or more =O substituents (especially so in the case where there is a sulfur atom present, which may be substituted with one or two =O groups) and/or B¹ substituents; the ring formed when R¹ᵃ and R¹ᵇ are linked together may, when there is a sulfur atom present, be substituted by one or two =O groups (e.g. such that the ring contains a —S(O)— or —S(O)₂— moiety), and, further, such a ring is preferably not substituted with any B¹ substituents;

when two B¹ groups are linked together to form a spiro-cyclic group, then such a cyclic moiety is preferably a saturated 3- to 7- (e.g. 3- to 6-) membered ring, optionally containing a heteroatom (but which ring is preferably carbocyclic; and may be substituted by one or more fluoro, =O and methyl groups) and which group is preferably attached to the 2- or 3-position of the ring formed by the linkage of the integers R¹ᵃ and R¹ᵇ (for example, when R¹ᵃ and R¹ᵇ are linked together to form a morpholinyl group);

the linkage of the R¹ᵃ and R¹ᵇ group preferably forms a N-morpholinyl, N-thiomorpholinyl (in which the sulfur atom may be substituted with one or two =O groups), oxazepanyl (e.g. 1,4-oxazepanyl) or thiazepanyl (e.g. 1,4-thiazepanyl) group, all of which are optionally substituted as hereinbefore defined (e.g. by one or more =O and/or B¹ substituents).

In certain embodiments, the present invention provides compounds of the invention in which R¹ is typically:

N-morpholinyl which is unsubstituted or substituted, for instance by one or more B¹ and/or =O substituents;

tetrahydropyranyl, tetrahydrofuranyl or C-morpholinyl, which is unsubstituted or substituted, for instance by one or more B² and/or =O substituents;

2-, 3- or 4-pyridyl, which is unsubstituted or substituted, for instance by one or more B³ substituents;

when R¹ represents substituted morpholinyl, it is preferably selected from the following structures:

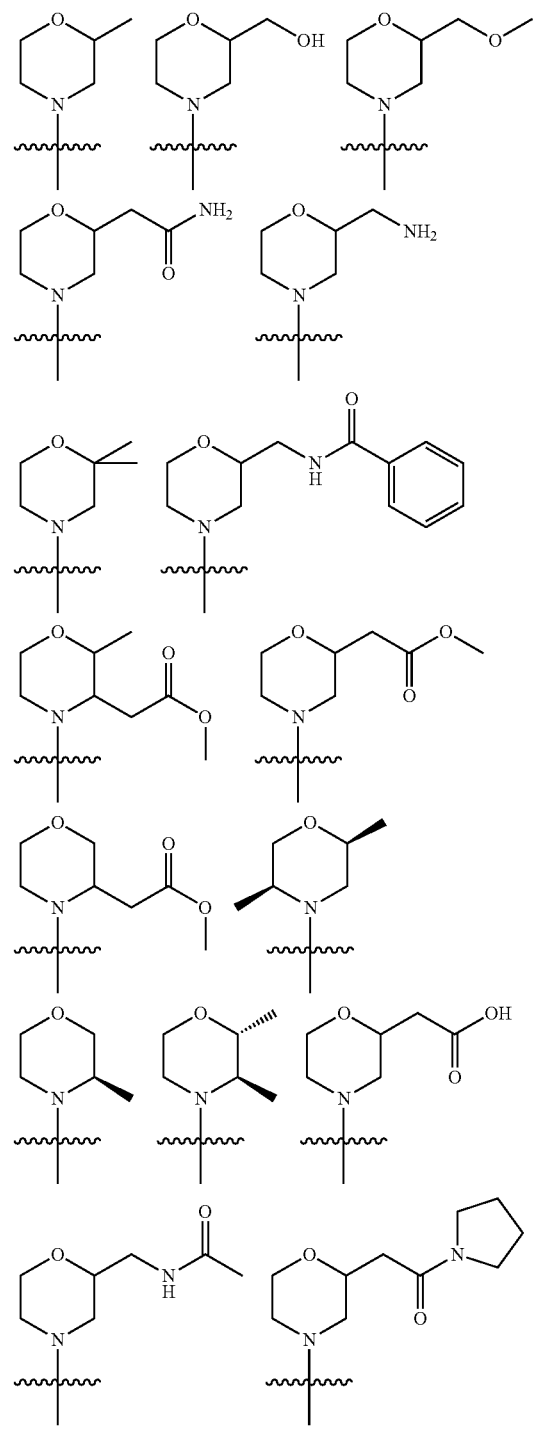

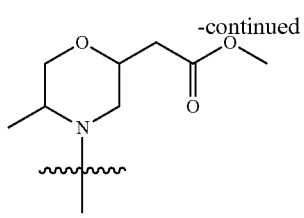

In certain embodiments, the present invention provides compounds of the invention in which:

- $R^2$ is —$(CR^6R^7)_m NR^{10}R^{11}$ where m is 1, 2 or 3, and $R^{10}$ and $R^{11}$ together with the nitrogen to which they are attached form the $C_3$-$C_{20}$ heterocyclic ring; and $R^3$ is H, halo, CN, $C_{1-6}$ alkyl, $C_3$-$C_6$ cycloalkyl, $C_2$-$C_6$ heterocycloalkyl, C(O)N($R^{16}R^{17}$), $OR^{16}$ or $NR^{16}R^{17}$;
- $R^2$ is —$(CR^6R^7)_n NR^{12}S(O)_2 R^{10}$ where n is 1 or 2; $R^{12}$, $R^6$, and $R^7$ are independently selected from H and $C_{1-12}$ alkyl; and $R^{10}$ is $C_1$-$C_{12}$ alkyl or $C_6$-$C_{20}$ aryl; and $R^3$ is H, halo, CN, $C_{1-6}$ alkyl, $C_3$-$C_6$ cycloalkyl, $C_2$-$C_6$ heterocycloalkyl, C(O)N($R^{16}R^{17}$), $OR^{16}$ or $NR^{16}R^{17}$;
- $R^2$ is —$(CR^6R^7)_n OR^{10}$ where n is 1 or 2, and $R^{10}$, $R^6$ are independently selected from H and $C_{1-12}$ alkyl; and $R^3$ is H, halo, CN, $C_{1-6}$ alkyl, $C_3$-$C_6$ cycloalkyl, $C_2$-$C_6$ heterocycloalkyl, C(O)N($R^{16}R^{17}$), $OR^{16}$ or $NR^{16}R^{17}$;
- $R^2$ is —$(CR^6R^7)_n S(O)_2 R^{10}$ where n is 1 or 2; and $R^6$, and $R^7$ are H, $R^{10}$ may be $C_{1-12}$ alkyl or $C_6$-$C_{20}$ aryl; and $R^3$ is H, halo, CN, $C_{1-6}$ alkyl, $C_3$-$C_6$ cycloalkyl, $C_2$-$C_6$ heterocycloalkyl, C(O)N($R^{16}R^{17}$), $OR^{16}$ or $NR^{16}R^{17}$;
- $R^2$ is —$(CR^6R^7)_n S(O)_2 NR^{10}R^{11}$ where n is 1 or 2; and $R^6$, and $R^7$ are H; and $R^3$ is H, halo, CN, $C_{1-6}$ alkyl, $C_3$-$C_6$ cycloalkyl, $C_2$-$C_6$ heterocycloalkyl, C(O)N($R^{16}R^{17}$), $OR^{16}$ or $NR^{16}R^{17}$;
- $R^2$ is —C(=Y)$NR^{10}R^{11}$ where Y is O, and $R^{10}$ and $R^{11}$ together with the nitrogen to which they are attached form the $C_2$-$C_{20}$ heterocyclic ring. $R^{10}$ and $R^{11}$ together with the nitrogen to which they are attached may form a $C_2$-$C_{20}$ heterocyclic ring selected from morpholinyl, piperidinyl, piperazinyl, and pyrrolidinyl; and $R^3$ is H, halo, CN, $C_{1-6}$ alkyl, $C_3$-$C_6$ cycloalkyl, $C_2$-$C_6$ heterocycloalkyl, C(O)N($R^{16}R^{17}$), $OR^{16}$ or $NR^{16}R^{17}$;
- $R^2$ is —C(=Y)$NR^{10}R^{11}$ where Y is O, and $R^{10}$ and $R^{11}$ are independently selected from H and $C_1$-$C_{12}$ alkyl; and $R^3$ is H, halo, CN, $C_{1-6}$ alkyl, $C_3$-$C_6$ cycloalkyl, $C_2$-$C_6$ heterocycloalkyl, C(O)N($R^{16}R^{17}$), $OR^{16}$ or $NR^{16}R^{17}$;
- $R^2$ is —C(=Y)$NR^{10}R^{11}$ where Y is O, and $R^{10}$ and $R^{11}$ are independently selected from H and $C_3$-$C_{12}$ carbocyclyl, $C_2$-$C_{20}$ heterocyclyl, $C_6$-$C_{20}$ aryl, and $C_1$-$C_{20}$ heteroaryl; and $R^3$ is H, halo, CN, $C_{1-6}$ alkyl, $C_3$-$C_6$ cycloalkyl, $C_2$-$C_6$ heterocycloalkyl, C(O)N($R^{16}R^{17}$), $OR^{16}$ or $NR^{16}R^{17}$;
- $R^2$ is —$NHR^{12}$ where $R^{12}$ is $C_3$-$C_{12}$ carbocyclyl, $C_2$-$C_{20}$ heterocyclyl, $C_6$-$C_{20}$ aryl or $C_1$-$C_{20}$ heteroaryl, or, $R^{12}$ may be phenyl or 4-pyridyl; and $R^3$ is H, halo, CN, $C_{1-6}$ alkyl, $C_3$-$C_6$ cycloalkyl, $C_2$-$C_6$ heterocycloalkyl, C(O)N($R^{16}R^{17}$), $OR^{16}$ or $NR^{16}R^{17}$;
- $R^2$ is —$NR^{12}C(=Y)R^{11}$ where Y is O, $R^{12}$ is H or $C_1$-$C_{12}$ alkyl, and $R^{11}$ is $C_1$-$C_{12}$ alkyl, $C_3$-$C_{12}$ carbocyclyl, $C_2$-$C_{20}$ heterocyclyl, $C_6$-$C_{20}$ aryl, or $C_1$-$C_{20}$ heteroaryl; and $R^3$ is H, halo, CN, $C_{1-6}$ alkyl, $C_3$-$C_6$ cycloalkyl, $C_2$-$C_6$ heterocycloalkyl, C(O)N($R^{16}R^{17}$), $OR^{16}$ or $NR^{16}R^{17}$;
- $R^2$ is —$NR^{12}S(O)_2 R^{10}$ where $R^{12}$ is H or $C_1$-$C_{12}$ alkyl, and $R^{10}$ is $C_1$-$C_{12}$ alkyl, $C_3$-$C_{12}$ carbocyclyl, $C_2$-$C_{20}$ heterocyclyl, $C_6$-$C_{20}$ aryl, or $C_1$-$C_{20}$ heteroaryl; and $R^3$ is H, halo, CN, $C_{1-6}$ alkyl, $C_3$-$C_6$ cycloalkyl, $C_2$-$C_6$ heterocycloalkyl, C(O)N($R^{16}R^{17}$), $OR^{16}$ or $NR^{16}R^{17}$;
- $R^2$ is —$S(O)_2 NR^{10}R^{11}$ where $R^{10}$ and $R^{11}$ together with the nitrogen to which they are attached form a $C_2$-$C_{20}$ heterocyclyl ring selected from morpholinyl, piperidinyl, piperazinyl, and pyrrolidinyl; and $R^3$ is H, halo, CN, $C_{1-6}$ alkyl, $C_3$-$C_6$ cycloalkyl, $C_2$-$C_6$ heterocycloalkyl, C(O)N($R^{16}R^{17}$), $OR^{16}$ or $NR^{16}R^{17}$;
- $R^2$ is —$S(O)_2 NR^{10}R^{11}$ where $R^{10}$ and $R^{11}$ are independently selected from H and $C_1$-$C_{12}$ alkyl; $R^{10}$ and $R^{11}$ may be independently selected from H, substituted ethyl, and substituted propyl; and $R^3$ is H, halo, CN, $C_{1-6}$ alkyl, $C_3$-$C_6$ cycloalkyl, $C_2$-$C_6$ heterocycloalkyl, C(O)N($R^{16}R^{17}$), $OR^{16}$ or $NR^{16}R^{17}$;
- $R^2$ is $C_1$-$C_{12}$ alkyl, and $R^3$ is H, halo, CN, $C_{1-6}$ alkyl, $C_3$-$C_6$ cycloalkyl, $C_2$-$C_6$ heterocycloalkyl, C(O)N($R^{16}R^{17}$), $OR^{16}$ or $NR^{16}R^{17}$;
- $R^2$ is $C_2$-$C_8$ alkenyl, and $R^3$ is H, halo, CN, $C_{1-6}$ alkyl, $C_3$-$C_6$ cycloalkyl, $C_2$-$C_6$ heterocycloalkyl, C(O)N($R^{16}R^{17}$), $OR^{16}$ or $NR^{16}R^{17}$;
- $R^2$ is $C_2$-$C_8$ alkynyl may be substituted with $C_2$-$C_{20}$ heterocyclyl, which includes, but is not limited to, morpholinyl, piperidinyl, piperazinyl, and pyrrolidinyl); and $R^3$ is H, halo, CN, $C_{1-6}$ alkyl, $C_3$-$C_6$ cycloalkyl, $C_2$-$C_6$ heterocycloalkyl, C(O)N($R^{16}R^{17}$), $OR^{16}$ or $NR^{16}R^{17}$;
- $R^2$ is $C_6$-$C_{20}$ aryl, such as phenyl; and $R^3$ is H, halo, CN, $C_{1-6}$ alkyl, $C_3$-$C_6$ cycloalkyl, $C_2$-$C_6$ heterocycloalkyl, C(O)N($R^{16}R^{17}$), $OR^{16}$, $NR^{16}R^{17}$;
- $R^2$ is $C_3$-$C_{12}$ carbocyclyl; and $R^3$ is H, halo, CN, $C_{1-6}$ alkyl, $C_3$-$C_6$ cycloalkyl, $C_2$-$C_6$ heterocycloalkyl, C(O)N($R^{16}R^{17}$), $OR^{16}$ or $NR^{16}R^{17}$;
- $R^2$ is $C_2$-$C_{20}$ heterocyclyl; and $R^3$ is H, halo, CN, $C_{1-6}$ alkyl, $C_3$-$C_6$ cycloalkyl, $C_2$-$C_6$ heterocycloalkyl, C(O)N($R^{16}R^{17}$), $OR^{16}$ or $NR^{16}R^{17}$;
- $R^2$ is $C_1$-$C_{20}$ heteroaryl; and $R^3$ is H, halo, CN, $C_{1-6}$ alkyl, $C_3$-$C_6$ cycloalkyl, $C_2$-$C_6$ heterocycloalkyl, C(O)N($R^{16}R^{17}$), $OR^{16}$ or $NR^{16}R^{17}$;
- $R^2$ is H;
- $R^2$ is methyl ($CH_3$), cyclopropyl, $CF_3$, CN or $CONH_2$.

In certain embodiments of the invention:

- $R^3$ is —$(CR^6R^7)_m NR^{10}R^{11}$ where m is 1, 2 or 3, and $R^{10}$ and $R^{11}$ together with the nitrogen to which they are attached form the $C_3$-$C_{20}$ heterocyclic ring; and $R^2$ is H, halo, CN, $C_{1-6}$ alkyl, $C_3$-$C_6$ cycloalkyl, $C_2$-$C_6$ heterocycloalkyl, C(O)N($R^{16}R^{17}$), $OR^{16}$ or $NR^{16}R^{17}$;
- $R^3$ is —$(CR^6R^7)_n NR^{12}S(O)_2 R^{10}$ where n is 1 or 2; $R^{12}$, $R^6$, and $R^7$ are independently selected from H and $C_{1-12}$ alkyl; and $R^{10}$ is $C_1$-$C_{12}$ alkyl or $C_6$-$C_{20}$ aryl; and $R^2$ is H, halo, CN, $C_{1-6}$ alkyl, $C_3$-$C_6$ cycloalkyl, $C_2$-$C_6$ heterocycloalkyl, C(O)N($R^{16}R^{17}$), $OR^{16}$ or $NR^{16}R^{17}$;
- $R^3$ is —$(CR^6R^7)_n OR^{10}$ where n is 1 or 2, and $R^{10}$, $R^6$ are independently selected from H and $C_{1-12}$ alkyl; and $R^2$ is H, halo, CN, $C_{1-6}$ alkyl, $C_3$-$C_6$ cycloalkyl, $C_2$-$C_6$ heterocycloalkyl, C(O)N($R^{16}R^{17}$), $OR^{16}$ or $NR^{16}R^{17}$;
- $R^3$ is —$(CR^6R^7)_n S(O)_2 R^{10}$ where n is 1 or 2; and $R^6$, and $R^7$ are H, $R^{10}$ may be $C_{1-12}$ alkyl or $C_6$-$C_{20}$ aryl; and $R^2$ is H, halo, CN, $C_{1-6}$ alkyl, $C_3$-$C_6$ cycloalkyl, $C_2$-$C_6$ heterocycloalkyl, C(O)N($R^{16}R^{17}$), $OR^{16}$ or $NR^{16}R^{17}$;
- $R^3$ is —$(CR^6R^7)_n S(O)_2 NR^{10}R^{11}$ where n is 1 or 2; and $R^6$, and $R^7$ are H; and $R^2$ is H, halo, CN, $C_{1-6}$ alkyl, $C_3$-$C_6$ cycloalkyl, $C_2$-$C_6$ heterocycloalkyl, C(O)N($R^{16}R^{17}$), $OR^{16}$ or $NR^{16}R^{17}$;
- $R^3$ is —C(=Y)$NR^{10}R^{11}$ where Y is O, and $R^{10}$ and $R^{11}$ together with the nitrogen to which they are attached form the $C_2$-$C_{20}$ heterocyclic ring; $R^{10}$ and $R^{11}$ together with the nitrogen to which they are attached may form a $C_2$-$C_{20}$ heterocyclic ring selected from morpholinyl, piperidinyl, piperazinyl, and pyrrolidinyl; and $R^2$ is H, halo, CN, $C_{1-6}$ alkyl, $C_3$-$C_6$ cycloalkyl, $C_2$-$C_6$ heterocycloalkyl, $C(O)N(R^{16}R^{17})$, $OR^{16}$ or $NR^{16}R^{17}$;

$R^3$ is —$C(=Y)NR^{10}R^{11}$ where Y is O, and $R^{10}$ and $R^{11}$ are independently selected from H and $C_1$-$C_{12}$ alkyl; and $R^2$ is H, halo, CN, $C_{1-6}$ alkyl, $C_3$-$C_6$ cycloalkyl, $C_2$-$C_6$ heterocycloalkyl, $C(O)N(R^{16}R^{17})$, $OR^{16}$ or $NR^{16}R^{17}$;

$R^3$ is —$C(=Y)NR^{10}R^{11}$ where Y is O, and $R^{10}$ and $R^{11}$ are independently selected from H and $C_3$-$C_{12}$ carbocyclyl, $C_2$-$C_{20}$ heterocyclyl, $C_6$-$C_{20}$ aryl, and $C_1$-$C_{20}$ heteroaryl; and $R^2$ is H, halo, CN, $C_{1-6}$ alkyl, $C_3$-$C_6$ cycloalkyl, $C_2$-$C_6$ heterocycloalkyl, $C(O)N(R^{16}R^{17})$, $OR^{16}$ or $NR^{16}R^{17}$;

$R^3$ is —$NHR^{12}$ where $R^{12}$ is $C_3$-$C_{12}$ carbocyclyl, $C_2$-$C_{20}$ heterocyclyl, $C_6$-$C_{20}$ aryl or $C_1$-$C_{20}$ heteroaryl, or, $R^{12}$ may be phenyl or 4-pyridyl; and $R^2$ is H, halo, CN, $C_{1-6}$ alkyl, $C_3$-$C_6$ cycloalkyl, $C_2$-$C_6$ heterocycloalkyl, $C(O)N(R^{16}R^{17})$, $OR^{16}$ or $NR^{16}R^{17}$;

$R^3$ is —$NR^{12}C(=Y)R^{11}$ where Y is O, $R^{12}$ is H or $C_1$-$C_{12}$ alkyl, and $R^{11}$ is $C_1$-$C_{12}$ alkyl, $C_3$-$C_{12}$ carbocyclyl, $C_2$-$C_{20}$ heterocyclyl, $C_6$-$C_{20}$ aryl, or $C_1$-$C_{20}$ heteroaryl; and $R^2$ is H, halo, CN, $C_{1-6}$ alkyl, $C_3$-$C_6$ cycloalkyl, $C_2$-$C_6$ heterocycloalkyl, $C(O)N(R^{16}R^{17})$, $OR^{16}$ or $NR^{16}R^{17}$;

$R^3$ is —$NR^{12}S(O)_2R^{10}$ where $R^{12}$ is H or $C_1$-$C_{12}$ alkyl, and $R^{10}$ is $C_1$-$C_{12}$ alkyl, $C_3$-$C_{12}$ carbocyclyl, $C_2$-$C_{20}$ heterocyclyl, $C_6$-$C_{20}$ aryl, or $C_1$-$C_{20}$ heteroaryl; and $R^2$ is H, halo, CN, $C_{1-6}$ alkyl, $C_3$-$C_6$ cycloalkyl, $C_2$-$C_6$ heterocycloalkyl, $C(O)N(R^{16}R^{17})$, $OR^{16}$ or $NR^{16}R^{17}$;

$R^3$ is —$S(O)_2NR^{10}R^{11}$ where $R^{10}$ and $R^{11}$ together with the nitrogen to which they are attached form a $C_2$-$C_{20}$ heterocyclyl ring selected from morpholinyl, piperidinyl, piperazinyl, and pyrrolidinyl; and $R^2$ is H, halo, CN, $C_{1-6}$ alkyl, $C_3$-$C_6$ cycloalkyl, $C_2$-$C_6$ heterocycloalkyl, $C(O)N(R^{16}R^{17})$, $OR^{16}$ or $NR^{16}R^{17}$;

$R^3$ is —$S(O)_2NR^{10}R^{11}$ where $R^{10}$ and $R^{11}$ are independently selected from H and $C_1$-$C_{12}$ alkyl. $R^{10}$ and $R^{11}$ may be independently selected from H, substituted ethyl, and substituted propyl; and $R^2$ is H, halo, CN, $C_{1-6}$ alkyl, $C_3$-$C_6$ cycloalkyl, $C_2$-$C_6$ heterocycloalkyl, $C(O)N(R^{16}R^{17})$, $OR^{16}$ or $NR^{16}R^{17}$;

$R^3$ is $C_1$-$C_{12}$ alkyl, and $R^2$ is H, halo, CN, $C_{1-6}$ alkyl, $C_3$-$C_6$ cycloalkyl, $C_2$-$C_6$ heterocycloalkyl, $C(O)N(R^{16}R^{17})$, $OR^{16}$ or $NR^{16}R^{17}$;

$R^3$ is $C_2$-$C_8$ alkenyl, and $R^2$ is H, halo, CN, $C_{1-6}$ alkyl, $C_3$-$C_8$ cycloalkyl, $C_2$-$C_6$ heterocycloalkyl, $C(O)N(R^{16}R^{17})$, $OR^{16}$ or $NR^{16}R^{17}$;

$R^3$ is $C_2$-$C_8$ alkynyl (the $C_2$-$C_8$ alkynyl may be substituted with $C_2$-$C_{20}$ heterocyclyl, which includes, but is not limited to, morpholinyl, piperidinyl, piperazinyl, and pyrrolidinyl); and $R^2$ is H, halo, CN, $C_{1-6}$ alkyl, $C_3$-$C_6$ cycloalkyl, $C_2$-$C_6$ heterocycloalkyl, $C(O)N(R^{16}R^{17})$, $OR^{16}$ or $NR^{16}R^{17}$;

$R^3$ is $C_6$-$C_{20}$ aryl, such as phenyl; and $R^2$ is H, halo, CN, $C_{1-6}$ alkyl, $C_3$-$C_6$ cycloalkyl, $C_2$-$C_6$ heterocycloalkyl, $C(O)N(R^{16}R^{17})$, $OR^{16}$ or $NR^{16}R^{17}$;

$R^3$ is $C_3$-$C_{12}$ carbocyclyl; and $R^2$ is H, halo, CN, $C_{1-6}$ alkyl, $C_3$-$C_6$ cycloalkyl, $C_2$-$C_6$ heterocycloalkyl, $C(O)N(R^{16}R^{17})$, $OR^{16}$ or $NR^{16}R^{17}$;

$R^3$ is $C_2$-$C_{20}$ heterocyclyl; and $R^2$ is H, halo, CN, $C_{1-6}$ alkyl, $C_3$-$C_6$ cycloalkyl, $C_2$-$C_6$ heterocycloalkyl, $C(O)N(R^{16}R^{17})$, $OR^{16}$ or $NR^{16}R^{17}$;

$R^3$ is $C_1$-$C_{20}$ heteroaryl; and $R^2$ is H, halo, CN, $C_{1-6}$ alkyl, $C_3$-$C_6$ cycloalkyl, $C_2$-$C_6$ heterocycloalkyl, $C(O)N(R^{16}R^{17})$, $OR^{16}$ or $NR^{16}R^{17}$.

In the above two paragraphs (and in certain other paragraphs herein), any relevant alkyl, cycloalkyl, heterocycloalkyl, aryl or heteroaryl groups may be optionally substituted by relevant substituents defined herein (for example, by a substituent defined by $Q^1$, $Q^2$, $E^6$, $E^7$, $Q^4$, $Q^5$, $J^2$ or $J^3$ (e.g. by $Q^1$, $E^6$ and/or $E^7$)).

Further, unless otherwise specified in the above two paragraphs:

(i) each $R^{16}$ and $R^{17}$ respectively represents substituents $R^{20}$ and $R^{21}$ as defined herein (and more preferably, they respectively represent substituents $R^{50}$ and $R^{51}$ as defined herein);

(ii) each $R^6$ and $R^7$ may independently represent a substituent as defined by $R^{15}$ herein (i.e. each may independently represent hydrogen, a substituent as defined herein, or, $R^6$ and $R^7$ may be linked together in the same manner as two $R^{15}$ groups attached to the same carbon atom may be);

(iii) each $R^{10}$, $R^{11}$ and $R^{12}$ respectively represents a substituent as defined by the substituents $R^{10a}$, $R^{11a}$ and $R^{12a}$.

In certain embodiments, $R^2$ or $R^3$ represent a fragment of formula IA, as hereinbefore depicted, wherein:

$R^a$ and $R^b$ form, together with the N atom to which they are attached, a group of the following formula:

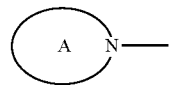

in which:

(a) ring A is a first 3- to 7-membered saturated N-containing heterocyclic ring which is fused to a second ring as hereinbefore defined to form a heteropolycyclic ring system in which the first ring is selected from, but not limited to, azetidine, pyrrolidine, piperidine, piperazine, morpholine, thiomorpholine and homopiperazine, said group being fused to a second ring as hereinbefore defined. The second ring is typically a 3- to 7-membered saturated N-containing heterocyclic ring as defined above in respect of the first ring, the second ring is a 5- to 12-membered unsaturated heterocyclic group. More typically the second ring is a 5-, 6- or 7-membered saturated N-containing heterocyclic ring or a 5- to 7-membered unsaturated heterocyclic ring. Typical examples of the second ring include azetidine, pyrrolidine, piperidine, piperazine, morpholine, thiomorpholine, homopiperazine, pyrrole, imidazole, pyridine, pyridazine, pyrimidine, pyrazine, tetrahydrofuran and tetrahydropyran. Examples of the resulting heteropolycyclic system include octahydropyrrolo[1,2-a]pyrazine and octahydropyrrolo[3,4-c]pyrrole. Specific examples of the heteropolycyclic system include the following structures:

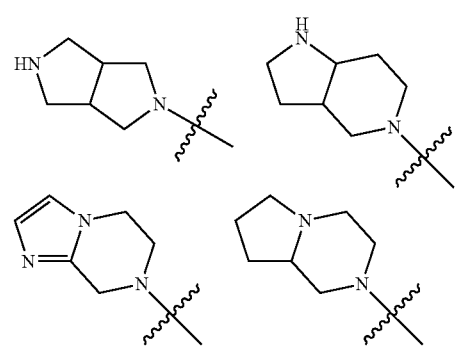

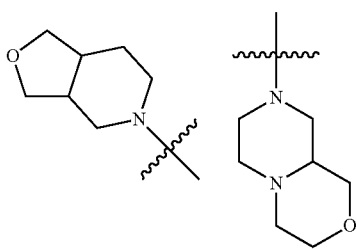

(b) ring A is a first 3- to 7-membered saturated N-containing heterocyclic group as hereinbefore defined (which contains a linker group), which includes, but is not limited to, a bridgehead group (i.e. a linker group linking any two non-adjacent atoms of the first ring), thereby forming, for example 3,8-diaza-bicyclo[3.2.1]octane, 2,5-diaza-bicyclo[2.2.1]heptane, 8-aza-bicyclo[3.2.1]octane, 2-aza-bicyclo[2.2.1]heptane, 3,6-diaza-bicyclo[3.1.1]heptane, 6-aza-bicyclo[3.1.1]heptane, 3,9-diaza-bicyclo[4.2.1]nonane and/or 2-oxa-7,9-diazabicyclo[3.3.1]nonane. Specific examples of this group include the following structures:

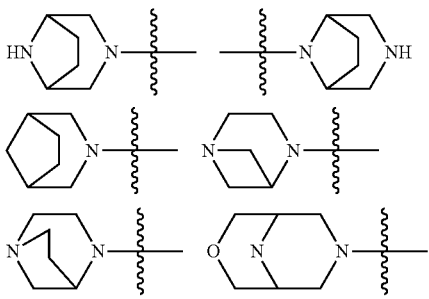

(c) ring A is a first 3- to 7-membered saturated N-containing heterocyclic group as hereinbefore defined, which is spiro-fused at any available ring carbon atom to a second 3- to 12-membered saturated carbocyclic ring, typically to a 3- to 6-membered saturated carbocyclic ring, or to a 4- to 7-membered saturated N-containing heterocyclic group. Examples include a group in which the first ring is selected from azetidine, pyrrolidine, piperidine and piperazine which is spiro-fused at a ring carbon atom to a second ring selected from cyclopropane, cyclobutane, cyclopentane, cyclohexane, azetidine, pyrrolidine, piperidine, piperazine and tetrahydropyran. The ring so formed may, for instance, be a group derived from 3,9-diazaspiro[5.5]undecane, 2,7-diazaspiro[3.5]nonane, 2,8-diazaspiro[4.5]decane or 2,7-diazaspiro[4.4]nonane. Specific examples of this group include the following structures:

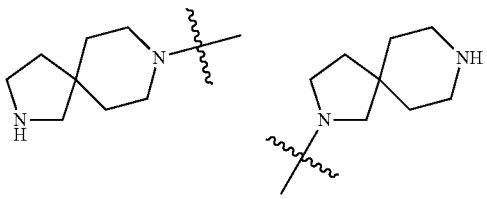

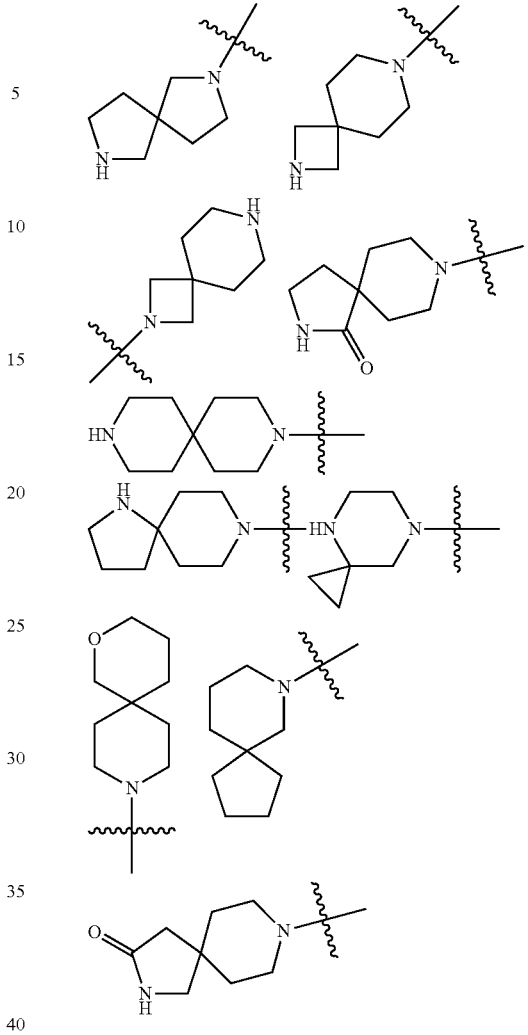

In certain embodiments, $R^2$ represent a fragments of formula IA as depicted hereinbefore, in which $R^a$ and $R^b$ are as described above; and $R^3$ is H, halo, CN, $C_{1-6}$ alkyl, $C_3$-$C_6$ cycloalkyl, $C_2$-$C_6$ heterocycloalkyl, $C(O)N(R^{16}R^{17})$, $OR^{16}$, $NR^{16}R^{17}$. The integers $R^{16}$ and $R^{17}$ are as defined herein.

In certain embodiments, $R^3$ represent a fragment of formula IA as depicted hereinbefore; and $R^2$ is H, halo, CN, $C_{1-6}$ alkyl, $C_3$-$C_6$ cycloalkyl, $C_2$-$C_6$ heterocycloalkyl, $C(O)N(R^{16}R^{17})$, $OR^{16}$, $NR^{16}R^{17}$. The integers $R^{16}$ and $R^{17}$ are as defined herein.

Exemplary embodiments of $R^5$ include, but are not limited to: pyrrole, pyrazole, triazole, tetrazole, thiazole, isothiazole, oxazole, isoxazole, isoindole, 1,3-dihydro-indol-2-one, pyridine-2-one, pyridine, pyridine-3-ol, imidazole, 1H-indazole, 1H-indole, indolin-2-one, 1-(indolin-1-yl)ethanone, pyrimidine, pyridazine, pyrazine and isatin groups. 1H-benzo[d][1,2,3]triazole, 1H-pyrazolo[3,4-b]pyridine, 1H-pyrazolo[3,4-d]pyrimidine, 1H-benzo[d]imidazole, 1H-benzo[d]imidazol-2(3H)-one, 1H-pyrazolo[3,4-c]pyridine, 1H-pyrazolo[4,3-d]pyrimidine, 5H-pyrrolo[3,2-d]pyrimidine, 2-amino-1H-purin-6(9H)-one, quinoline, quinazoline, quinoxaline, isoquinoline, isoquinolin-1(2H)-one, 3,4-dihydroisoquinolin-1(2H)-one, 3,4-dihydroquinolin-2(1H)-one, quinazolin-2(1H)-one, quinoxalin-2(1H)-one, 1,8-napthyridine, pyrido[3,4-d]pyrimidine, and pyrido[3,2-b]pyrazine, 1,3-dihydro benzimidazolone, benzimidazole, benzothiazole and benzothiadiazole, groups. These groups may be unsubstituted or substituted.

The attachment site of the $R^5$ group to the C-6 position of the requisite imidazopyrazine ring of formula I may be at any carbon (carbon-linked) of the $R^5$ group (e.g. fused bicyclic $C_4$-$C_{20}$ heterocyclyl or fused bicyclic $C_1$-$C_{20}$ heteroaryl group $R_5$ group).

More exemplary embodiments of $R^5$ include, but are not limited to, the following groups, where the wavy line indicates the site of attachment to the pyrazine ring:

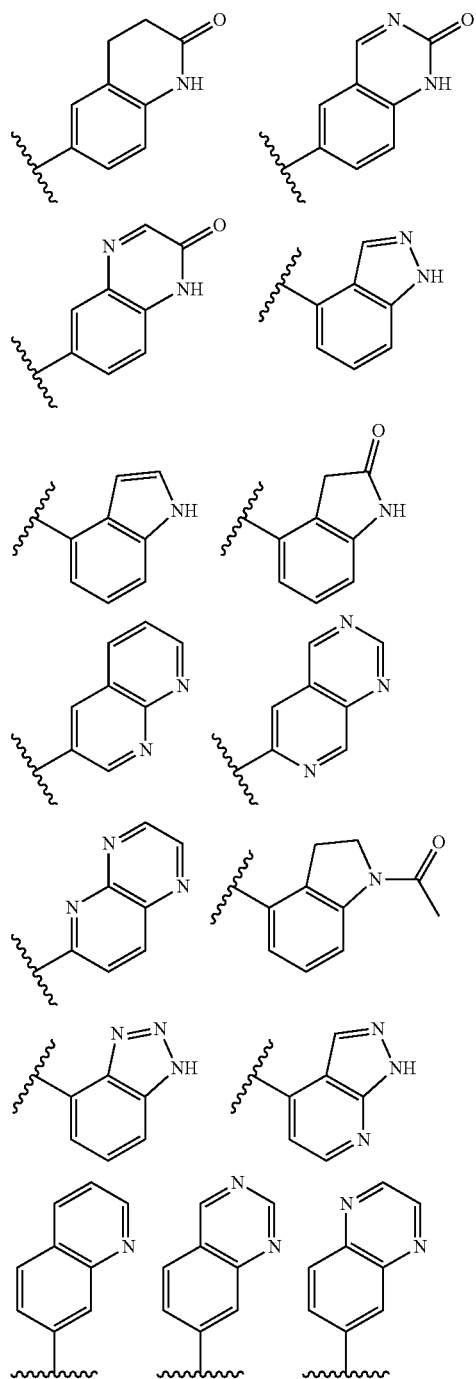
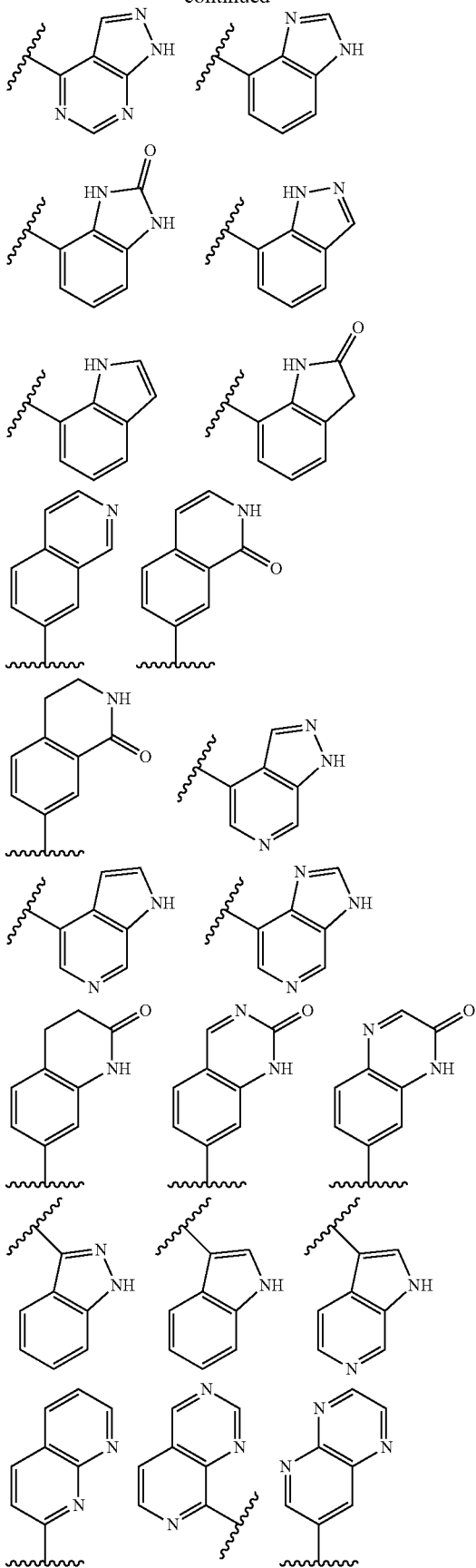

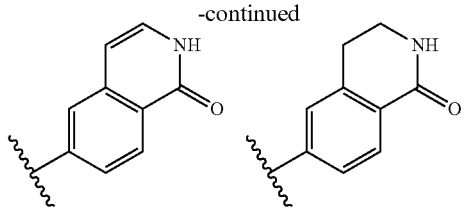

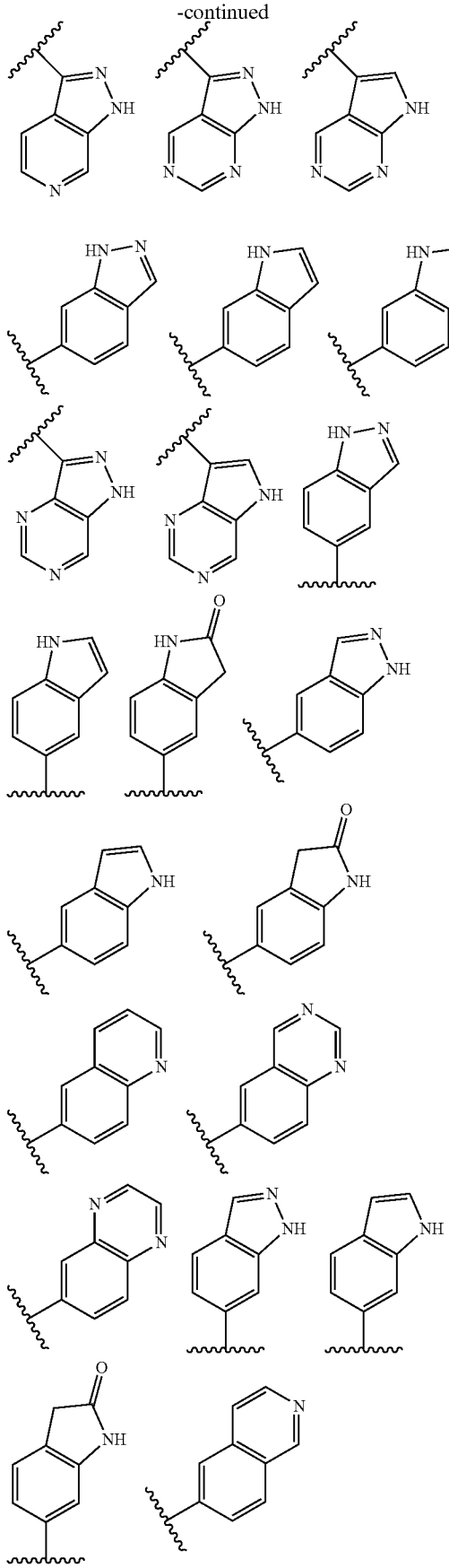

Preferred compounds of the invention include those in which:

R$^1$ represents:
(a) —N(R$^{1a}$)R$^{1b}$, in which R$^{1a}$ and R$^{1b}$ are linked together to form, together with the nitrogen atom to which they are necessarily attached, a 5- to 7-membered ring, optionally containing a further one or two heteroatoms (e.g. selected from nitrogen, oxygen and sulfur), optionally containing one or two double bonds, and which ring is optionally substituted by one or more (e.g. by one to three) substituents selected from =O and B$^1$;
(b) a heterocycloalkyl (e.g. a 3- to 7-membered) heterocycloalkyl group (attached to the requisite imidazopyrazine via a carbon atom), optionally substituted by one or more (e.g. by one to three) substituents selected from =O and B$^2$;
(c) a monocyclic heteroaryl group optionally substituted by one or more (e.g. by one to three) substituents selected from B$^3$;

when R$^1$ represents optionally substituted heterocycloalkyl, then that heterocycloalkyl group preferably contains 1, 2 or 3 heteroatoms preferably selected from nitrogen, oxygen and sulfur;

when R$^1$ represents optionally substituted monocyclic heteroaryl, then that heteroaryl group preferably contains 1, 2, 3 or 4 nitrogen heteroatoms and, optionally, 1 or 2 additional heteroatoms preferably selected from nitrogen, oxygen and sulfur;

R$^2$ and R$^3$ may represent a fragment of formula IA, although R$^2$ and R$^3$ more preferably, and independently, represent C$_{1-12}$ (e.g. C$_{1-6}$) alkyl optionally substituted by one or more substituents selected from =O and Q$^2$, or, R$^2$ and R$^3$ more preferably represent a substituent selected from Q$^1$;

m represents 0, 1 or 2;

each R$^{15}$ represents hydrogen or C$_{1-6}$ (e.g. C$_{1-3}$) alkyl, which latter group is preferably unsubstituted;

when R$^a$ and R$^b$ are linked together, they form a first 5- or 6-membered cyclic group, optionally containing one further heteroatom selected from nitrogen, sulfur and oxygen, which cyclic group is optionally substituted by one or more substituents selected from =O and, preferably, E$^3$;

R$^4$ represents hydrogen or a substituent selected from halo, —CN, —OR$^{10b}$, —N(R$^{10b}$)R$^{11b}$, C$_{1-6}$ alkyl and/or heterocycloalkyl (e.g. a 5- or 6-membered heterocycloalkyl), which latter two groups are optionally substituted by one or more substituents selected from E$^4$ and =O;

when R$^4$ represents heterocycloalkyl, then it is preferably a 5- or 6-membered heterocycloalkyl group containing one or two heteroatoms preferably selected from nitrogen, oxygen and sulfur, which group is optionally substituted by one or more substituents selected from E$^4$ and =O;

when R$^4$ represents C$_{1-6}$ alkyl, then that group is preferably an acyclic C$_{1-4}$ alkyl group, optionally substituted by one or more substituents selected from E$^4$ and =O;

when R$^5$ represents aryl (e.g. phenyl), then that group may be unsubstituted but is preferably substituted by at least one (e.g. two or, preferably, one) substituent(s) selected from E$^5$;

when $R^5$ represents monocyclic heteroaryl (e.g. a 5- or 6-membered heteroaryl group), then that group preferably contains 1, 2, 3 or 4 nitrogen atoms and, optionally 1 or 2 additional heteroatoms selected from oxygen and sulfur, and which heteroaryl group is optionally substituted by one or more substituents selected from $E^5$;

when $R^5$ represents bicyclic heteroaryl (e.g. a 8-, 9- or 10-membered heteroaryl group), then that group preferably consists of a 5- or 6-membered ring fused to another 5- or 6-membered ring (in which either one of those rings may contain one or more (e.g. four, or, preferably one to three) heteroatoms), in which the total number of heteroatoms is preferably one to four, and which ring is optionally substituted by one or more (e.g. two or, preferably, one) substituent(s) selected from $E^5$ (and, if there is a non-aromatic ring present in the bicyclic heteroaryl group, then such a group may also be substituted by one or more (e.g. one) =O groups);

optional substituents (e.g. the first optional substituent) on the $R^5$ group (e.g. when it represents aryl, such as phenyl) are preferably selected from —OR, —SR, —CH$_2$OR, CO$_2$R, CF$_2$OH, CH(CF$_3$)OH, C(CF$_3$)$_2$OH, —(CH$_2$)$_w$OR, —(CH$_2$)$_w$NR$_2$, —C(O)N(R)$_2$, —NR$_2$, —NRC(O)R, —NRC(O)NHR, —NRC(O)N(R)$_2$, —S(O)$_y$N(R)$_2$, —OC(O)R, OC(O)N(R)$_2$, —NRS(O)$_y$R, —NRC(O)N(R)$_2$, CN, halogen and —NO$_2$ (in which each R is independently selected from H, C$_1$-C$_6$ alkyl, C$_3$-C$_{10}$ cycloalkyl and a 5- to 12-membered aryl or heteroaryl group, the groups being unsubstituted or substituted (for example by one or more substituents as defined herein, e.g. substituents on $E^5$ moieties, e.g. =O, J$^2$, J$^3$, J$^4$ and/or J$^5$), w is 0, 1 or 2 and y is 1 or 2);

when $R^5$ represents aryl (e.g. phenyl), then that group is substituted by one or two substituents (e.g. by a first substituent as defined above, and, optionally a further substituent (or a further two substituents) preferably selected from halo, C$_{1-12}$ alkyl, CN, NO$_2$, OR$^d$, SR$^d$, NR$^d_2$, C(O)R$^d$, SOR$^d$, SO$_2$R$^d$, SO$_2$N(R)$^d_2$, NC(O)R$^d$ and CO$_2$R$^d$ (wherein each R$^d$ is independently H or C$_1$-C$_6$ alkyl);

when $R^5$ represents substituted aryl (e.g. phenyl), the substituent may be situated at the 2-, 3-, 4-, 5- or 6-position of the phenyl ring (typically it is situated at position 3 or 4; particularly preferred are phenyl groups substituted by —OR$^d$ (in which R$^d$ is independently H or C$_1$-C$_6$ alkyl, e.g. methyl), e.g. —OH; in this embodiment the —OR$^d$ group, or —OH group, is typically situated at the 3- or 4-position of the phenyl ring, so forming a 3-hydroxyphenyl or 4-hydroxyphenyl group or an isostere thereof, which is unsubstituted or substituted; an isostere as used herein is a functional group which possesses binding properties which are the same as, or similar to, the 3-hydroxyphenyl or 4-hydroxyphenyl group in the context of the compounds of the invention; isosteres of 3-hydroxyphenyl and 4-hydroxyphenyl groups are encompassed within definitions above for $R^5$);

when $R^5$ represents heteroaryl, it is unsubstituted or substituted (when substituted, it may be substituted by one or more substitutents selected from those listed in respect of substituents on $R^5$, when $R^5$ is a phenyl group; typically, the substituents are selected from OH and NH$_2$);

each $Q^1$ and $Q^2$ independently represent —S(O)$_2$R$^{10a}$, —SR$^{10a}$, —S(O)R$^{10a}$, —S(O)$_2$N(R$^{10a}$)R$^{11a}$, or, preferably, halo, —CN, —NO$_2$, —N(R$^{10a}$)R$^{11a}$, —OR$^{10a}$, —C(=Y)—R$^{10a}$, —C(=Y)—OR$^{10a}$, —C(=Y)N(R$^{10a}$)R$^{11a}$, —N(R$^{12a}$)C(=Y)R$^{11a}$, —NR$^{12a}$S(O)$_2$R$^{10a}$, C$_{1-12}$ (e.g. C$_{1-6}$) alkyl, heterocycloalkyl (which latter two groups are optionally substituted by one or more substituents selected from =O and E$^6$), aryl or heteroaryl (which latter two groups are optionally substituted by one or more substituents selected from E$^7$);

any two $B^1$ substituents may be linked together as hereinbefore defined, for example to form a C$_{3-6}$ cycloalkyl group, or, more preferably, B$^1$, B$^2$ and B$^3$ independently represent halo, —NO$_2$, —CN, —N(R$^{10a}$)R$^{11a}$, —OR$^{10a}$, —C(=Y)—R$^{10a}$, —C(=Y)—OR$^{10a}$, —C(=Y)N(R$^{10a}$)R$^{11a}$ or C$_{1-12}$ (e.g. C$_{1-6}$) alkyl optionally substituted by one or more substituents selected from =O and E$^8$);

each R$^{10a}$, R$^{11a}$, R$^{12a}$, R$^{10b}$, R$^{11b}$ and R$^{12b}$ independently represent, on each occasion when used herein, hydrogen or C$_{1-12}$ (e.g. C$_{1-6}$) alkyl (which latter group is optionally substituted by one or more substituents selected from =O and E$^{10}$); or any relevant pair of R$^{10a}$, R$^{11a}$ and R$^{12a}$ (e.g. R$^{10a}$ and R$^{11a}$), and/or R$^{10b}$ and R$^{11b}$ may, when attached to the same nitrogen atom, be linked together to form (along with the requisite nitrogen atom to which they are attached) a 3- to 12- (e.g. 4- to 12-) membered ring, optionally containing one or more (e.g. one to three) double bonds, and which ring is optionally substituted by one or more substituents selected from E$^{10}$ and =O;

each of E$^1$, E$^2$, E$^3$, E$^4$, E$^5$, E$^6$, E$^7$, E$^8$, E$^9$, E$^{10}$, E$^{11}$ and E$^{12}$ independently represents, on each occasion when used herein, Q$^4$ or C$_{1-16}$ alkyl (e.g. C$_{1-6}$, preferably, C$_{1-3}$) alkyl optionally substituted by one or more substituents selected from =O and Q$^5$;

each Q$^4$ and Q$^5$ independently represent halo, —CN, —NO$_2$, —N(R$^{20}$)R$^{21}$, —OR$^{20}$, —C(=Y)—R$^{20}$, —C(=Y)—OR$^{20}$, —C(=Y)N(R$^{20}$)R$^{21}$, —N(R$^{22}$)C(=Y)R$^{21}$, —N(R$^{22}$)C(=Y)OR$^{21}$, —N(R$^{22}$)C(=Y)N(R$^{20}$)R$^{21}$, —NR$^{22}$S(O)$_2$R$^{20}$, —NR$^{22}$S(O)$_2$N(R$^{20}$)R$^{21}$, —S(O)$_2$N(R$^{20}$)R$^{21}$, —S(O)$_2$R$^{20}$, —SR$^{20}$, —S(O)R$^{20}$ or C$_{1-6}$ alkyl optionally substituted by one or more fluoro atoms (and each Q$^5$ more preferably represents halo, such as fluoro);

any two E$^1$, E$^2$, E$^3$, E$^4$, E$^5$, E$^6$, E$^7$, E$^8$, E$^9$, E$^{10}$, E$^{11}$ or E$^{12}$ groups may not be linked together;

each R$^{20}$, R$^{21}$, R$^{22}$ and R$^{23}$ independently represent, on each occasion when used herein, aryl (e.g. phenyl; preferably unsubstituted, but which may be substituted by one to three J$^5$ groups) or, more preferably, hydrogen or C$_{1-6}$ (e.g. C$_{1-3}$) alkyl optionally substituted by one or more substituents selected from =O and J$^4$; or any pair of R$^{20}$ and R$^{21}$, may, when attached to the same nitrogen atom, be linked together to form a 4- to 8-membered (e.g. 5- or 6-membered) ring, optionally containing one further heteroatom selected from nitrogen and oxygen, optionally containing one double bond, and which ring is optionally substituted by one or more substituents selected from J$^6$ and =O;

each J$^1$, J$^2$, J$^3$, J$^4$, J$^5$ and J$^6$ independently represent C$_{1-6}$ (e.g. C$_{1-3}$) alkyl optionally substituted by one or more substituents selected from =O and Q$^8$, or, more preferably, such groups independently represent a substituent selected from Q$^7$;

each Q$^7$ and Q$^8$ independently represents a substituent selected from fluoro, —N(R$^{50}$)R$^{51}$, —OR$^{50}$, —C(=Y$^a$)—R$^{50}$, —C(=Y$^a$)—OR$^{50}$, —C(=Y$^a$)N(R$^{50}$)R$^{51}$, —NR$^{52}$S(O)$_2$R$^{50}$, —S(O)$_2$R$^{50}$ and/or C$_{1-6}$ alkyl optionally substituted by one or more fluoro atoms;

each Y and Y$^a$ independently represent =S or, preferably, =O;

each R$^{50}$, R$^{51}$, R$^{52}$ and R$^{53}$ substituent independently represents, on each occasion when used herein, hydrogen or C$_{1-6}$ (e.g. C$_{1-3}$) alkyl optionally substituted by one or more substituents selected from fluoro;

when any relevant pair of $R^{50}$, $R^{51}$ and $R^{52}$ are linked together, then those pairs that are attached to the same nitrogen atom may be linked together (i.e. any pair of $R^{50}$ and $R^{51}$), and the ring so formed is preferably a 5- or 6-membered ring, optionally containing one further nitrogen or oxygen heteroatom, and which ring is optionally substituted by one or more substituents selected from =O and $C_{1-3}$ alkyl (e.g. methyl);

$R^{60}$, $R^{61}$ and $R^{62}$ independently represent hydrogen or $C_{1-3}$ (e.g. $C_{1-2}$) alkyl optionally substituted by one or more fluoro atoms.

Preferred optional substituents on $R^1$ and $R^5$ (and, when they represent a substituent other than hydrogen on $R^2$, $R^3$ and $R^4$ groups) include:

=O (e.g. in the case of alkyl, cycloalkyl or heterocycloalkyl groups);
—CN;
halo (e.g. fluoro, chloro or bromo);
$C_{1-4}$ alkyl, which alkyl group may be cyclic, part-cyclic, unsaturated or, preferably, linear or branched (e.g. $C_{1-4}$ alkyl (such as ethyl, n-propyl, isopropyl, t-butyl or, preferably, n-butyl or methyl), all of which are optionally substituted with one or more halo (e.g. fluoro) groups (so forming, for example, fluoromethyl, difluoromethyl or, preferably, trifluoromethyl);
aryl (e.g. phenyl), if appropriate (e.g. when the substituent is on an alkyl group, thereby forming e.g. a benzyl group);
—$OR^{z1}$;
—$C(O)R^{z2}$;
—$C(O)OR^{z3}$;
—$N(R^{z4})R^{z5}$;
—$S(O)_2R^{z6}$;
—$S(O)_2N(R^{z7})R^{z8}$;
—$N(R^{z9})$—$C(O)$—$R^{z10}$;
—$C(O)$—$N(R^{z11})R^{z12}$;
—$N(R^{z9})$—$C(O)$—$N(R^{z10})$;
wherein each $R^{z1}$ to $R^{z12}$ independently represents, on each occasion when used herein, H or $C_{1-4}$ alkyl (e.g. ethyl, n-propyl, t-butyl or, preferably, n-butyl, methyl or isopropyl) optionally substituted by one or more halo (e.g. fluoro) groups (so forming e.g. a trifluoromethyl group). Further, any two $R^z$ groups (e.g. $R^{z4}$ and $R^{z5}$), when attached to the same nitrogen heteroatom may also be linked together to form a ring such as one hereinbefore defined in respect of corresponding linkage of $R^{10}$ and $R^{11}$ or $R^{10a}$ and $R^{11a}$ groups.

Preferred compounds of the invention include those in which:
$R^1$ represents: (i) —$N(R^{1a})R^{1b}$; (ii) an optionally substituted 5- or 6-membered heterocycloalkyl group (attached via a carbon atom); or (iii) an optionally substituted 5- or 6-membered heteroaryl group;
when $R^1$ represents —$N(R^{1a})R^{1b}$, then $R^{1a}$ and $R^{1b}$ are preferably linked together to form a 6-membered ring containing a further oxygen heteroatom (so forming a morpholinyl group), which ring may be unsubstituted, or may be substituted by one or more $B^1$ groups (such groups are preferably unsubstituted, i.e. most preferably an unsubstituted morpholinyl group);
when $R^1$ represents an optionally substituted 5- or 6-membered heterocycloalkyl group, then such a group may contain two or preferably one heteroatom(s) (in which the heteroatom is selected from sulfur, preferably nitrogen, and, especially, oxygen). Such a ring may be substituted with one or more substituents selected from =O and $B^2$, but it is preferably unsubstituted. Further, it is preferably 6-membered (e.g. a tetrahydropyranyl group);
when $R^1$ represents optionally substituted 5- or 6-membered heteroaryl, then such a group may contain two or, preferably, one heteroatom(s) (in which the heteroatom is selected from sulfur, preferably oxygen and, especially, nitrogen). Such a ring may be substituted with one or more substituents selected from $B^3$, but it is preferably unsubstituted. Further, it is preferably 6-membered (e.g. a pyridyl group);
$R^2$ and $R^3$ independently represent hydrogen or a substituent selected from $Q^1$;
each $Q^1$ and $Q^2$ (e.g. each $Q^1$) independently represent(s) halo, —CN, —$NO_2$, —$N(R^{10a})R^{11a}$, —$C(=Y)$—$R^{10a}$, —$C(=Y)$—$OR^{10a}$, —$C(=Y)N(R^{10a})R^{11a}$, $C_{1-12}$ alkyl or heterocycloalkyl (which latter two groups are optionally substituted by one or more substituents selected from =O, =S, =$N(R^{10a})$ and $E^6$);
$R^4$ represents hydrogen or a substituent selected from —$N(R^{10b})R^{11b}$ and, preferably, halo (e.g. chloro, bromo or iodo) and —CN;
at least one (e.g. one) of $R^2$, $R^3$ and $R^4$ represents hydrogen;
$R^5$ represents aryl (e.g. phenyl) or heteroaryl (e.g. a 5- or preferably a 6-membered monocyclic heteroaryl group, or a 8-, 9- or 10-membered bicyclic heteroaryl group), both of which are optionally substituted by one or more substituents selected from $E^5$;
$B^1$, $B^2$ and $B^3$ (e.g. $B^1$) independently represent $C_{1-6}$ (e.g. $C_{1-3}$) alkyl optionally substituted by one or more substituents selected from =O and $E^8$;
each $R^{10a}$, $R^{11a}$, $R^{12a}$, $R^{10b}$, $R^{11b}$ and $R^{12b}$ (e.g. each $R^{10a}$ and $R^{11a}$) independently represents hydrogen or $C_{1-6}$ (e.g. $C_{1-4}$) alkyl optionally substituted by one or more substituents selected from =O and $E^{10}$; or
any relevant pair of $R^{10a}$, $R^{11a}$ and $R^{12a}$ (e.g. $R^{10a}$ and $R^{11a}$) may (e.g. when both are attached to the same nitrogen atom) be linked together to form a 3- to 8- (e.g. 4- to 8-) membered ring, optionally containing a further heteroatom, and optionally substituted by one or more substituents selected from =O and $E^{12}$;
each $E^1$, $E^2$, $E^3$, $E^4$, $E^5$, $E^6$, $E^7$, $E^8$, $E^9$, $E^{10}$, $E^{11}$ and $E^{12}$ independently represents $C_{1-12}$ alkyl optionally substituted by one or more substituents selected from =O and $Q^5$, or, preferably (each $E^1$ to $E^{12}$ independently represent) $Q^4$;
each $Q^4$ and $Q^5$ (e.g. each $Q^4$) independently represent halo, —$N(R^{20})R^{21}$, —$OR^{20}$, —$C(=Y)$—$OR^{20}$, —$C(=Y)N(R^{20})R^{21}$, —$N(R^{22})C(=Y)R^{21}$, —$N(R^{22})C(=Y)N(R^{20})R^{21}$, —$NR^{22}S(O)_2R^{20}$, —$S(O)_2R^{20}$ and/or $C_{1-6}$ alkyl (optionally substituted by one or more substituents selected from =O and $J^2$);
when $E^8$ represents $Q^4$, then $Q^4$ preferably represents —$N(R^{20})R^{21}$, —$OR^{20}$, —$C(=Y)$—$OR^{20}$, —$C(=Y)N(R^{20})R^{21}$ or —$N(R^{22})C(=Y)R^{21}$;
each $R^{20}$, $R^{21}$, $R^{22}$ and $R^{23}$ (e.g. each $R^{20}$ and $R^{21}$) independently represents heteroaryl, preferably, aryl (e.g. phenyl) (which latter two groups are optionally substituted by one or more substituents selected from $J^5$), or, more preferably, hydrogen or $C_{1-6}$ (e.g. $C_{1-4}$) alkyl optionally substituted by one or more substituents selected from =O and $J^4$; or
any relevant pair of $R^{20}$, $R^{21}$ and $R^{22}$ (e.g. $R^{20}$ and $R^{21}$) may (e.g. when both are attached to the same nitrogen atom) may be linked together to form a 3- to 8- (e.g. 4- to 8-) membered ring, optionally containing a further heteroatom, and optionally substituted by one or more substituents selected from =O and $J^6$;
each $J^1$, $J^2$, $J^3$, $J^4$, $J^5$ and $J^6$ independently represent $C_{1-6}$ (e.g. $C_{1-3}$) alkyl optionally substituted by one or more substituents selected from $Q^8$, or, $J^1$ to $J^6$ more preferably represent a substituent selected from $Q^7$;

each $Q^7$ and $Q^8$ independently represent halo, —N($R^{50}$)$R^{51}$, —$OR^{50}$, —C(=$Y^a$)—$OR^{50}$, —C(=$Y^a$)—$R^{50}$, —S(O)$_2$$R^{50}$ or $C_{1-3}$ alkyl optionally substituted by one or more fluoro atoms;

Y and $Y^a$ independently represent =O;

each $R^{50}$, $R^{51}$, $R^{52}$ and $R^{53}$ independently represents hydrogen or $C_{1-6}$ (e.g. $C_{1-4}$) alkyl optionally substituted by one or more fluoro atoms;

each $R^{60}$, $R^{61}$ and $R^{62}$ independently represents hydrogen or $C_{1-2}$ alkyl (e.g. methyl).

More preferred compounds of the invention include those in which:

$R^1$ represents —N($R^{1a}$)$R^{1b}$, in which $R^{1a}$ and $R^{1b}$ are linked together to form a 6-membered ring containing a further oxygen heteroatom (so forming a morpholinyl group), which ring may be unsubstituted, or may be substituted by one or more $B^1$ groups (such groups are preferably unsubstituted);

$R^2$ and $R^3$ independently represent(s) hydrogen or a substituent selected from halo (e.g. bromo, chloro, iodo) —CN, —N($R^{10a}$)$R^{11a}$, —C(=Y)$OR^{10a}$, —C(=Y)—$R^{10a}$, —C(=Y)—N($R^{10a}$)$R^{11a}$, $C_{1-6}$ alkyl (optionally substituted by one or more (e.g. one) substituent(s) selected from $E^6$) and heterocycloalkyl (e.g. a 5- or, preferably, a 6-membered heterocycloalkyl group, which preferably contains one heteroatom (e.g. nitrogen), and which may contain one unsaturation, e.g a double bond, so forming e.g. a piperidinyl ring, e.g. 4-piperidinyl, for example in which the 1,2-position optionally contains a double bond), which heterocycloalkyl group is optionally substituted by one or more substituents selected from =O and, preferably, $E^6$ (e.g. in which the $E^6$ substituent is located on a nitrogen heteroatom);

when $R^2$ or $R^3$ represents $C_{1-12}$ (e.g. $C_{1-6}$) alkyl, then it may be straight-chained, e.g. acyclic $C_{1-3}$ alkyl (e.g. methyl) or $C_{3-6}$ cycloalkyl (e.g. cyclopropyl), all of which are optionally substituted by one or more fluoro atoms (so forming for example a trifluoromethyl group);

$R^4$ represents hydrogen, chloro, bromo, iodo or —CN;

one of $R^2$ and $R^3$ represents a substituent as defined herein, and the other represents hydrogen or a substituent as defined herein;

$R^5$ represents aryl (e.g. phenyl) or heteroaryl (e.g. a 5- or preferably a 6-membered monocyclic heteroaryl group, or a 10- or, preferably, 9-membered bicyclic heteroaryl group, in which, in both cases, there is one or two heteroatom(s) present, preferably selected from nitrogen, so forming e.g. pyridyl, indazolyl, indolyl, pyrimidinyl, indolonyl or pyrrolopyridine, such as pyrrolo[2,3]pyridine), both of which $R^5$ groups are optionally substituted by one or more (e.g. one or two) substituents selected from $E^5$;

each $R^{10a}$, $R^{11a}$, $R^{12a}$, $R^{10b}$, $R^{11b}$ and $R^{12b}$ (e.g. each $R^{10a}$ and $R^{11a}$) independently represents hydrogen or $C_{1-4}$ (e.g. $C_{1-3}$) alkyl (e.g. ethyl); or any relevant pair of $R^{10a}$, $R^{11a}$ and $R^{12a}$ (e.g. $R^{10a}$ and $R^{11a}$) may (e.g. when both are attached to the same nitrogen atom) be linked together to form a 5- or, preferably, a 6-membered ring, optionally containing a further heteroatom (preferably selected from nitrogen and oxygen), which ring is preferably saturated (so forming, for example, a piperazinyl or morpholinyl group), and optionally substituted by one or more substituents selected from =O and $E^{12}$ (which $E^{12}$ substituent may be situated on a nitrogen heteroatom; and/or $E^{12}$ is preferably halo (e.g. fluoro) or $C_{1-3}$ alkyl optionally substituted by one or more fluoro atoms);

each $E^1$, $E^2$, $E^3$, $E^4$, $E^5$, $E^6$, $E^7$, $E^8$, $E^9$, $E^{10}$, $E^{11}$ and $E^{12}$ (e.g. each $E^5$ and $E^6$) independently represents a substituent selected from $Q^4$;

each $E^5$ independently represents halo (e.g. fluoro), —$OR^{20}$, —N($R^{20}$)$R^{21}$, —C(=Y)$OR^{20}$, —C(=Y)N($R^{20}$)$R^{21}$, —N$R^{22}$S(O)$_2$$R^{20}$ and/or —N($R^{22}$)C(=Y)N($R^{20}$)$R^{21}$;

each $E^6$ independently represents —$OR^{20}$ (in which $R^{20}$ preferably represents hydrogen), —N($R^{20}$)$R^{21}$, —C(=Y)$OR^{20}$, —C(=Y)N($R^{20}$)$R^{21}$, —S(O)$_2$$R^{20}$ and/or $C_{1-6}$ alkyl (e.g. $C_{1-3}$ alkyl) optionally substituted by one or more fluoro atoms;

each Y represents, on each occasion when used herein, =S, or preferably =O;

each $R^{20}$, $R^{21}$, $R^{22}$ and $R^{23}$ (e.g. each $R^{20}$ and $R^{21}$) independently represents hydrogen or $C_{1-4}$ (e.g. $C_{1-3}$) alkyl (e.g. tert-butyl, ethyl or methyl); or any relevant pair of $R^{20}$, $R^{21}$ and $R^{22}$ (e.g. $R^{20}$ and $R^{21}$) may (e.g. when both are attached to the same nitrogen atom) may be linked together to form a 5- or, preferably, a 6-membered ring, optionally containing a further heteroatom (preferably selected from nitrogen and oxygen), which ring is preferably saturated (so forming, for example, a piperazinyl or morpholinyl group), and optionally substituted by one or more substituents selected from =O and $J^6$ (which $J^6$ substituent may be situated on a nitrogen heteroatom);

$R^{22}$ represents $C_{1-3}$ alkyl or, preferably, hydrogen;

each $J^1$, $J^2$, $J^3$, $J^4$, $J^5$ and $J^6$ independently represent a substituent selected from $Q^7$;

each $Q^7$ and $Q^8$ independently represent —C(=$Y^a$)—$OR^{50}$, —C(=$Y^a$)—$R^{50}$, —S(O)$_2$$R^{50}$ or $C_{1-3}$ alkyl optionally substituted by one or more fluoro atoms;

each $Y^a$ independently represents =S or, preferably, =O;

each $R^{50}$ independently represents $C_{1-4}$ alkyl (e.g. tert-butyl or methyl).

Particularly preferred compounds of the invention include those in which:

$R^1$ represents: (a) —N($R^{1a}$)$R^{1b}$, in which $R^{1a}$ and $R^{1b}$ are linked together to form a 6-membered ring optionally containing a further heteroatom (e.g. an oxygen heteroatom) (so forming e.g. a morpholinyl or piperidinyl group), which ring may be unsubstituted, or may be substituted by one or more $B^1$ groups; (b) a monocyclic heteroaryl group (preferably containing one or two heteroatoms (preferably selected from nitrogen; so forming e.g. a pyrimidinyl or pyridyl group) optionally (and preferably) substituted by one or more (e.g. one) substituent selected from $B^3$; or (c) a 6-membered heterocycloalkyl group (containing two or, preferably, one heteroatom preferably selected from nitrogen and, especially, oxygen, so forming for example a tetrahydropyranyl group);

$B^1$, $B^2$ and $B^3$ (e.g. $B^3$) preferably represents halo (e.g. fluoro), —N($R^{10a}$)$R^{11a}$ (e.g —NH$_2$) or $C_{1-2}$ alkyl optionally substituted by one or more $E^3$ group;

$R^2$ and $R^3$ independently represent(s) hydrogen, a fragment of formula IA, $C_{1-6}$ alkyl (optionally substituted by one or more (e.g. one) substituent(s) selected from $Q^2$) or a substituent selected from $Q^1$;

$Q^1$ represents halo (e.g. bromo, chloro, iodo) —CN, —N($R^{10a}$)$R^{11a}$, —C(=Y)$OR^{10a}$, —C(=Y)—$R^{10a}$, —C(=Y)—N($R^{10a}$)$R^{11a}$, $C_{1-6}$ alkyl (optionally substituted by one or more (e.g. one) substituent(s) selected from $E^6$) and heterocycloalkyl (e.g. a 5-, 7- or, preferably, a 6-membered heterocycloalkyl group, which preferably contains one or two heteroatoms (e.g. selected from nitrogen, oxygen and sulfur), and which may contain one unsaturation, e.g a double bond, so forming e.g. azepanyl or, preferably, piperazinyl (e.g. 1-piperazinyl), morpholinyl, thiomorpholinyl, piperidinyl (e.g. 4-piperidinyl, for example in which the 1,2-position optionally contains a double bond) or tetrahydropyranyl (e.g. 4-tetrahydropyranyl), which heterocycloalkyl group is optionally substituted by one or more substituents selected from =O (which may be present on a sulfur atom to form e.g. a —S(O)$_2$-moiety) and, preferably, $E^6$ (e.g. in which the $E^6$ substituent is located on a nitrogen heteroatom);

when $R^2$ or $R^3$ represents a fragment of formula IA, then it is preferably $R^2$ that represents such a fragment;

when $R^2$ or $R^3$ represents a fragment of formula IA (in an embodiment of the invention one of $R^2$ and $R^3$, e.g. $R^2$, represents a fragment of formula IA), then preferably m represents 1 and each $R^{15}$ independently represent hydrogen (so forming a fragment —CH$_2$—N(R$^a$)(R$^b$));

$R^a$ and $R^b$ are linked together to form a 4-, 5- or 6-membered cyclic group (preferably containing no further heteroatoms, and so forming a azetidinyl, pyrrolidinyl, piperidinyl or piperazinyl group), which further comprises: (a) a fused 6- or preferably 5-membered heterocycloalkyl (e.g. pyrrolidinyl) group (preferably containing one heteroatom, e.g. nitrogen, so forming e.g. a 5,5-fused bicycle); (b) a —CH$_2$—CH$_2$— linker group (thereby forming a bridged cyclic structure) or (c) a 4-, 5- or 6-membered heterocycloalkyl group (in which there is preferably one nitrogen heteroatom, so forming e.g. pyrrolidinyl or piperidinyl) linked together via a single common carbon atom to form a spiro-cycle (e.g. 2,8-diaza-spiro[4,5]-decane-8-yl, 2,8-diaza-spiro[4,5]-decane-2-yl, 3,9-diaza-spiro[5,5]undecane-3-yl, 2,7-diaza-spiro[3.5]nonane-7-yl or 2,7-diaza-spiro[3.5]nonane-2-yl), which rings are optionally substituted by one or more substituents selected from =O and $E^3$ (for instance the second ring may be substituted with such substituents);

when $R^2$ or $R^3$ represents $C_{1-12}$ (e.g. $C_{1-6}$) alkyl, then it may be straight-chained, e.g. acyclic $C_{1-3}$ alkyl (e.g. methyl) or $C_{3-6}$ cycloalkyl (e.g. cyclopropyl), all of which are optionally substituted by one or more fluoro atoms (so forming for example a trifluoromethyl group);

$R^4$ represents hydrogen, chloro, bromo, iodo, —CN, —C(O)R$^{10b}$ (e.g. —C(O)H) or methyl optionally substituted by one or more (e.g. one) substituent(s) selected from $E^4$ (in which $E^4$ preferably represents heteroaryl (e.g. imidazolyl) or, especially, —OR$^{20}$, so forming e.g. a —CH$_2$OH group or a —CH$_2$-heteroaryl moiety);

one of $R^2$ and $R^3$ represents a substituent as defined herein, and the other represents hydrogen or a substituent as defined herein;

$R^5$ represents aryl (e.g. phenyl) or heteroaryl (e.g. a 5- or 6-membered monocyclic heteroaryl group, or a 10- or, preferably, 9-membered bicyclic heteroaryl group, in which, in both cases, there is one or two heteroatom(s) present, preferably selected from nitrogen, so forming e.g. pyrazolyl, pyridyl, indazolyl, indolyl, pyrimidinyl, indolonyl or pyrrolopyridine, such as pyrrolo[2,3]pyridine), both of which $R^5$ groups are optionally substituted by one or more (e.g. one or two) substituents selected from $E^5$;

each $Q^2$ independently represents halo (e.g. fluoro; and hence when substituted on alkyl, may form e.g. a —CF$_3$ group), —OR$^{10a}$ (in which R$^{10a}$ preferably represents hydrogen or $C_{1-2}$ alkyl), —N(R$^{10a}$)R$^{10b}$, —C(=Y)OR$^{10a}$, —C(=Y)R$^{10a}$, —C(=Y)N(R$^{10a}$)R$^{10b}$, —S(O)$_2$R$^{10a}$, $C_{1-6}$ alkyl (e.g. $C_{1-3}$ alkyl; optionally substituted by one or more fluoro atoms), heterocycloalkyl (optionally substituted by one or more substituents selected from =O and $E^6$), aryl and/or heteroaryl (e.g. pyrimidinyl; which latter two aryl and heteroaryl groups are optionally substituted by one or more substituents selected from $E^7$);

each R$^{10a}$, R$^{11a}$, R$^{12a}$, R$^{10b}$, R$^{11b}$ and R$^{12b}$ (e.g. each R$^{10a}$ and R$^{11a}$) independently represents hydrogen or $C_{1-6}$ alkyl (e.g. ethyl or propyl or $C_{3-6}$ cycloalkyl, such as cyclohexyl) optionally substituted by one or more (e.g. one) substituent(s) selected from $E^{10}$; or one of R$^{10a}$ and R$^{11a}$ may represent heterocyloalkyl (e.g. a 5- or preferably 6-membered heterocycloalkyl group e.g. containing one heteroatom, so forming e.g. a piperidinyl or a tetrahydropyranyl group; which heterocycloalkyl group is optionally substituted by one or more (e.g. one) substituent selected from $E^{10}$); or any relevant pair of R$^{10a}$, R$^{11a}$ and R$^{12a}$ (e.g. R$^{10a}$ and R$^{11a}$) may (e.g. when both are attached to the same nitrogen atom) be linked together to form a 5-, 6- or 7-membered ring, optionally containing a further heteroatom (preferably selected from nitrogen, oxygen and sulfur), which ring is preferably saturated (so forming, for example, a pyrrolidinyl, piperidinyl, azepanyl, piperazinyl, morpholinyl or thiomorpholinyl group), and optionally substituted by one or more substituents selected from =O and $E^{12}$ (which $E^{12}$ substituent may be situated on a nitrogen heteroatom; and/or $E^{12}$ is preferably halo (e.g. fluoro), —N(R$^{20}$)R$^{21}$, —OR$^{20}$, —C(O)OR$^{20}$, —OC(O)R$^{20}$, —C(O)R$^{20}$, —S(O)$_2$R$^{20}$ or $C_{1-3}$ alkyl optionally substituted by one or more fluoro atoms or substituents selected from $Q^5$);

each $E^1$, $E^2$, $E^3$, $E^4$, $E^5$, $E^6$, $E^7$, $E^8$, $E^9$, $E^{10}$, $E^{11}$ and $E^{12}$ (e.g. each $E^5$ and $E^6$) independently represents a substituent selected from $Q^4$ or $C_{1-2}$ alkyl optionally substituted by one or more substituents selected from $Q^5$ and =O;

$Q^4$ represents halo (e.g. fluoro or chloro), —CN, —OR$^{20}$, —N(R$^{20}$)R$^{21}$, —C(=Y)OR$^{20}$, —C(=Y)R$^{20}$, —C(=Y)N(R$^{20}$)R$^{21}$, —N(R$^{22}$)—C(=Y)—R$^{21}$, —NR$^{22}$S(O)$_2$R$^{20}$, —S(O)$_2$R$^{20}$, —N(R$^{22}$)C(=Y)N(R$^{20}$)R$^{21}$, —OC(O)R$^{20}$, $C_{1-6}$ alkyl (e.g. $C_{1-3}$ alkyl; optionally substituted by one or more fluoro atoms), aryl (which latter group, when attached to an alkyl group may form e.g. a benzyl moiety) or heteroaryl (e.g. imidazolyl), which latter two aryl and heteroaryl groups are optionally substituted by one or more $J^3$ substituents;

$Q^5$ represents halo (e.g. fluoro), —N(R$^{20}$)R$^{21}$, —OR$^{20}$ and —O—C(O)R$^{20}$;

each $E^3$ independently represents —C(=Y)OR$^{20}$ or —S(O)$_2$R$^{20}$;

each $E^4$ independently represents halo (e.g. fluoro), —OR$^{20}$ (e.g. —OH) or heteroaryl (e.g. imidazolyl);

each $E^5$ independently represents halo (e.g. fluoro or chloro), —CN, —OR$^{20}$, —N(R$^{20}$)R$^{21}$, —C(=Y)OR$^{20}$, —C(=Y)N(R$^{20}$)R$^{21}$, —N(R$^{22}$)—C(=Y)—R$^{21}$, —NR$^{22}$S(O)$_2$R$^{20}$, —N(R$^{22}$)C(=Y)N(R$^{20}$)R$^{21}$ and/or $C_{1-6}$ alkyl (e.g. $C_{1-3}$ alkyl) optionally substituted by one or more fluoro atoms;

each $E^6$ independently represents halo (e.g. fluoro), —OR$^{20}$ (in which R$^{20}$ preferably represents hydrogen or $C_{1-2}$ alkyl), —N(R$^{20}$)R$^{21}$, —C(=Y)OR$^{20}$, —C(=Y)R$^{20}$, —C(=Y)N(R$^{20}$)R$^{21}$, —S(O)$_2$R$^{20}$ and/or $C_{1-6}$ alkyl (e.g. $C_{1-3}$ alkyl) optionally substituted by one or more fluoro atoms;

each $E^7$ independently represents) —N(R$^{20}$)R$^{21}$;

each $E^8$ independently represents —OR$^{20}$ or —C(=Y)OR$^{20}$;

each $E^{10}$ (which is preferably located on a nitrogen heteroatom, when a substituent on a heterocycloalkyl group) represents —S(O)$_2$R$^{20}$, —OR$^{20}$, —N(R$^{20}$)R$^{21}$, —N(R$^{22}$)—C(O)—R$^{21}$, —C(O)—OR$^{20}$ or aryl (which latter group, when attached to an alkyl group may form e.g. a benzyl moiety; and which may be substituted by one or more $J^3$ substituents);

each Y represents, on each occasion when used herein, =S, or preferably =O;

each $R^{20}$, $R^{21}$, $R^{22}$ and $R^{23}$ (e.g. each $R^{20}$ and $R^{21}$) independently represents hydrogen, $C_{1-4}$ (e.g. $C_{1-3}$) alkyl (e.g. tert-butyl, ethyl or methyl; which alkyl group is optionally substituted by one or more substituents selected from $J^4$) or aryl (e.g. phenyl; especially in the case of —S(O)$_2R^{20}$, and which aryl group is optionally substituted by one or more $J^5$ substituents); or any relevant pair of $R^{20}$, $R^{21}$ and $R^{22}$ (e.g. $R^{20}$ and $R^{21}$) may (e.g. when both are attached to the same nitrogen atom) may be linked together to form a 5- or 6-membered ring, optionally containing a further heteroatom (preferably selected from nitrogen and oxygen), which ring is preferably saturated (so forming, for example, a pyrrolidinyl, piperazinyl or morpholinyl group), and optionally substituted by one or more substituents selected from =O and $J^6$ (which $J^6$ substituent may be situated on a nitrogen heteroatom);

$R^{22}$ represents $C_{1-3}$ alkyl or, preferably, hydrogen;

each $J^1$, $J^2$, $J^3$, $J^4$, $J^5$ and $J^6$ independently represent a substituent selected from $Q^7$;

each $Q^7$ and $Q^8$ independently represent halo, —N($R^{50})R^{51}$, —C(=$Y^a$)—O$R^{50}$, —C(=$Y^a$)—N($R^{50})R^{51}$, —C(=$Y^a$)—$R^{50}$, —S(O)$_2R^{50}$ or $C_{1-3}$ alkyl optionally substituted by one or more fluoro atoms;

each $Y^a$ independently represents =S or, preferably, =O;

each $R^{50}$ and $R^{51}$ independently represents hydrogen, $C_{1-4}$ alkyl (e.g. tert-butyl or methyl) or $R^{50}$ and $R^{51}$, when attached to the same carbon atom, may be linked together to form a 5- or preferably, 6-membered ring (e.g. containing a further heteroatom, so forming e.g. piperazinyl) optionally substituted by methyl (e.g. which substituent is located in the additional nitrogen heteroatom).

Other preferred compounds of the invention that may be mentioned include:

$R^1$ represents —N($R^{1a})R^{1b}$ as hereinbefore defined (especially in which $R^{1a}$ and $R^{1b}$ are linked together to form a 6-membered ring optionally (and preferably) containing a further heteroatom (e.g. oxygen), so forming e.g. a piperidinyl or, preferably, a morpholinyl group;

$R^2$ represents a substituent other than hydrogen, and $R^3$ and $R^4$ independently represent hydrogen or a substituent other than hydrogen;

$R^2$ represents a substituent other than hydrogen;

$R^2$ represents $Q^1$ or $C_{1-2}$ alkyl (e.g. methyl) optionally substituted by $Q^2$ (e.g. at the terminal position of the methyl group);

$R^3$ and $R^4$ independently represent $C_{1-2}$ alkyl or, preferably, hydrogen or $Q^1$ (e.g. in which $Q^1$ preferably represents halo (e.g. chloro) or heterocycloalkyl optionally substituted by one or more $E^6$ groups);

at least one of $R^3$ and $R^4$ represent hydrogen;

$R^5$ represents: (a) phenyl (which is preferably substituted e.g. by one $E^5$ substituent located preferably at the meta position); (b) a 5- or 6-membered (e.g. 6-membered) monocyclic heteroaryl group (e.g. containing one or two heteroatoms preferably selected from nitrogen, so forming e.g. pyrimidinyl, such as 5-pyrimidinyl, or pyridyl, such as 3-pyridyl), which monocyclic heteroaryl group is optionally substituted e.g. by one or two $E^5$ substituent(s) (e.g. located at the 2-position (and optionally 6-position), when $R^5$ represents pyrimidinyl, or, at the 6-position when $R^5$ represents 3-pyridyl; in each case a substituent is preferably at the position para relative to the point of attachment to the requisite imidazopyrazine of formula I); or (c) a 9- or 10-membered (e.g. 9-membered) bicyclic heteroaryl group (e.g. indazolyl, such as 4-indazolyl, or azaindolyl, such as 7-azaindolyl i.e. pyrrolo[2,3-b]pyridyl, such as 7-azaindol-5-yl), which bicyclic heteroaryl group is preferably unsubstituted;

$Q^1$ represents —C(O)N($R^{10a})R^{11a}$ or —C(O)O$R^{10a}$ (e.g. in which $R^{10a}$ is $C_{1-2}$ alkyl);

$Q^2$ represents fluoro, —N($R^{10a}) R^{11a}$ or heterocycloalkyl (e.g. piperazinyl or morpholinyl) optionally (and preferably) substituted by one or more (e.g. one) substituent(s) (preferably located on a nitrogen heteroatom) selected from =O and, preferably, $E^6$;

$R^{10a}$ and $R^{11a}$ (for instance when $Q^1$ represents —C(O)N ($R^{10a})R^{11a}$) independently represent hydrogen, acyclic $C_{1-3}$ (e.g. $C_{1-2}$) alkyl (e.g. methyl or ethyl) (optionally substituted by one or more (e.g. one) $E^{10}$ substituent), $C_{5-6}$ cycloalkyl (e.g. cyclohexyl) (optionally substituted by one or more (e.g. one) $E^{10}$ substituent) or heterocycloalkyl (e.g. a 5- or 6-membered heterocycloalkyl group (e.g. containing one heteroatom, so forming e.g. piperidinyl, such as 4-piperidinyl, or tetrahydropyranyl, such as 4-tetrahydropyranyl) (optionally substituted by one or more (e.g. one) $E^{10}$ substituent, which may be located on a nitrogen heteroatom);

when $Q^2$ represents —N($R^{10a})R^{11a}$, then $R^{10a}$ and $R^{11a}$ are preferably linked together to form a 5- or preferably 6-membered ring preferably containing a further (e.g. nitrogen, oxygen or sulfur) heteroatom (so forming, e.g., piperazinyl, morpholinyl or thiomorpholinyl) optionally (and preferably) substituted by one or more (e.g. one) substituent(s) (optionally located on a nitrogen heteroatom) selected from =O, $E^{12}$ and $C_{1-2}$ alkyl (e.g. methyl) optionally substituted by one or more fluoro atoms (and, e.g. in the case of rings containing S, with one or more (e.g. one or two)=O, which carbonyl group(s) are located on the S to form e.g. a —S(O)$_2$— moiety);

when $E^5$ represents a substituent on phenyl, then it is preferably $Q^4$ (e.g. —O$R^{20}$);

when $E^5$ represents a substituent on monocyclic heteroaryl, then it is preferably $Q^4$ (e.g. —N($R^{20})R^{21}$) or $C_{1-2}$ alkyl (e.g. methyl) optionally substituted by one or more fluoro atoms (so forming e.g. a —CF$_3$ group);

$E^6$ and $E^{12}$ preferably represent $Q^4$;

$E^{10}$ represents $Q^4$;

for instance when $E^5$ represents $Q^4$, then $Q^4$ represents —O$R^{20}$ or) —N($R^{20})R^{21}$;

for instance when $E^6$ and $E^{12}$ represent $Q^4$, then $Q^4$ represents —S(O)$_2R^{20}$ (e.g. —S(O)$_2C_{1-4}$ alkyl), —C(O)$R^{20}$ or —OC(O)$R^{20}$;

$E^{10}$ represents —N($R^{20})R^{21}$, —O$R^{20}$ or —C(O)O$R^{20}$;

for instance when $E^{10}$ represents $Q^4$ (and $E^{10}$ is a substituent on an alkyl or cycloalkyl group), then $Q^4$ represents —N($R^{20})R^{21}$ or —O$R^{20}$ (e.g. —OCH$_3$ or —OH);

for instance when $E^{10}$ represents $Q^4$ (and $E^{10}$ is a substituent on a heterocycloalkyl group), then $Q^4$ represents —C(O) O$R^{26}$;

$R^{20}$ and $R^{21}$ independently represent hydrogen or $C_{1-4}$ alkyl (e.g. methyl, ethyl or butyl (e.g isobutyl)), which alkyl group may (e.g. in the case when $E^{12}$ represents —C(O) $R^{20}$) be substituted with a $J^4$ substituent; or for instance, when $E^{10}$ represents —N($R^{20})R^{21}$, then $R^{20}$ and $R^{21}$ may be linked together to form a 5- or preferably 6-membered ring, optionally containing a further heteroatom (e.g. oxygen, so forming e.g. morpholinyl);

$J^4$ represents $Q^7$;

$Q^7$ represents —N($R^{50}$)$R^{51}$;

$R^{50}$ and $R^{51}$ independently represent hydrogen, or, preferably, $C_{1-2}$ alkyl (e.g. methyl).

Most preferred compounds of the invention include those in which:

$R^1$ represents 1-piperidinyl or, preferably, 4-morpholinyl;

$R^2$ represents hydrogen or, preferably, methyl, —$CF_3$, —$CH_2$-[4-S(O)$_2$$CH_3$-piperazinyl], —C(O)N(H)ethyl, —C(O)$NH_2$, —C(O)Oethyl, —C(O)N(H)—$CH_2$$CH_2$—N($CH_3$)$_2$, —C(O)N(H)methyl, —$CH_2$-[4-morpholinyl], —C(O)N(H)—$CH_2$$CH_2$—$OCH_3$, —C(O)N(H)-[(1-C(O)$OCH_2$$CH_3$)-piperidin-4-yl], —C(O)N(H)-[4-tetrahydropyranyl], —C(O)N(H)-[4—OH-cyclohexyl], —$CH_2$-[4-C(O)t-butyl-2,6-dimethyl-piperazinyl], —$CH_2$-[4-S(O)$_2$$CH_3$-2,6-dimethyl-piperazinyl], —$CH_2$-[4-(S(O)$_2$$CH_2$$CH_3$)-piperazinyl], —$CH_2$-[4-(S(O)$_2$$CH_2$—C(H)($CH_3$)$_2$)-piperazinyl], —$CH_2$-[1,1-dioxo-thiomorpholinyl], —$CH_2$-[piperazinyl], —$CH_2$-[4-(C(O)$CH_2$N($CH_3$)$_2$)-piperazinyl] or —$CH_2$-[4-(C(O)C(H)($CH_3$)—O—C(O)$CH_3$)-piperazinyl];

$R^3$ represents 4-piperidinyl (e.g. containing a double bond at the 3,4-position and a —C(O)—C(H)($CH_3$)$_2$ substituent at the 1-position) or, preferably, hydrogen;

$R^4$ represents hydrogen or halo (e.g. chloro);

at least one of $R^3$ and $R^4$ (preferably both) represent hydrogen;

$R^5$ represents 3-hydroxyphenyl, 2-amino-5-pyrimidinyl, 4-indazolyl, 3-pyridyl, 6-amino-pyridyl, 7-azaindol-5-yl (i.e. pyrrolo[2,3-b]pyrid-5-yl), 2-methyl-5-pyrimidinyl, 2-amino-6-methyl-5-pyrimidinyl or 2-N(H)$CH_3$-5-pyrimidinyl.

Particularly preferred compounds of the invention include those of the examples described hereinafter. For example:

ethyl 6-(3-hydroxyphenyl)-8-morpholinoimidazo[1,2-a]pyrazine-2-carboxylate (2-01);
6-(3-hydroxyphenyl)-8-morpholinoimidazo[1,2-a]pyrazine-2-carboxylic acid (2-02);
6-(3-hydroxyphenyl)-8-morpholinoimidazo[1,2-a]pyrazine-2-carbaldehyde (2-03);
3-(2-(hydroxymethyl)-8-morpholinoimidazo[1,2-a]pyrazin-6-yl)phenol (2-04);
tert-butyl 4-((6-(3-hydroxyphenyl)-8-morpholinoimidazo[1,2-a]pyrazin-2-yl)methyl)-piperazine-1-carboxylate (2-05);
1-(4-((6-(3-hydroxyphenyl)-8-morpholinoimidazo[1,2-a]pyrazin-2-yl)methyl)-piperazin-1-yl)ethanone (2-06);
3-(2a-((4-methylpiperazin-1-yl)methyl)-8-morpholinoimidazo[1,2-a]pyrazin-6-yl)phenol (2-07);
4-((6-(3-hydroxyphenyl)-8-morpholinoimidazo[1,2-a]pyrazin-2-yl)methyl)piperazin-2-one (2-08);
3-(8-morpholino-2-(morpholinomethyl)imidazo[1,2-a]pyrazin-6-yl)phenol (2-09);
1-(4-((6-(3-hydroxyphenyl)-8-morpholinoimidazo[1,2-a]pyrazin-2-yl)methyl)-piperazin-1-yl)sulfonylmethane (2-10);
(6-(3-hydroxyphenyl)-8-morpholinoimidazo[1,2-a]pyrazin-2-yl)(4-sulfonylmethyl-piperazin-1-yl)methanone (2-11);
3-(8-morpholinoimidazo[1,2-a]pyrazin-6-yl)phenol (2-12);
3-(2-(trifluoromethyl)-8-morpholinoimidazo[1,2-a]pyrazin-6-yl)phenol (2-13);
3-(2-cyclopropyl-8-morpholinoimidazo[1,2-a]pyrazin-6-yl)phenol (2-14);
(6-(1H-indazol-4-yl)-8-morpholinoimidazo[1,2-a]pyrazin-2-yl)(4-methylpiperazin-1-yl)methanone (2-15);
(6-(1H-indazol-4-yl)-8-morpholinoimidazo[1,2-a]pyrazin-2-yl)(4-sulfonylmethyl-piperazin-1-yl)methanone (2-16);
6-(1H-indazol-4-yl)-2-((4-sulfonylmethylpiperazin-1-yl)methyl)-8-morpholino-imidazo[1,2-a]pyrazine (2-17);
(6-(1H-indazol-4-yl)-8-morpholinoimidazo[1,2-a]pyrazin-2-yl)(piperazin-1-yl)-methanone (2-18);
2-cyclopropyl-6-(1H-indazol-4-yl)-8-morpholinoimidazo[1,2-a]pyrazine (2-19);
2-(trifluoromethyl)-6-(1H-indazol-4-yl)-8-morpholinoimidazo[1,2-a]pyrazine (2-20);
6-(1H-indazol-4-yl)-8-morpholinoimidazo[1,2-a]pyrazine-2-carboxamide (2-21);
6-(1H-indazol-4-yl)-8-morpholinoimidazo[1,2-a]pyrazine-2-carbonitrile (2-22);
3-(2-methyl-8-morpholinoimidazo[1,2-a]pyrazin-6-yl)phenol (2-23);
6-(1H-indazol-4-yl)-2-methyl-8-morpholinoimidazo[1,2-a]pyrazine (2-24);
6-(1H-indol-5-yl)-2-methyl-8-morpholinoimidazo[1,2-a]pyrazine (2-25);
2-methyl-8-morpholino-6-(pyridin-3-yl)imidazo[1,2-a]pyrazine (2-26);
6-(5-methoxypyridin-3-yl)-2-methyl-8-morpholinoimidazo[1,2-a]pyrazine (2-27);
N-sulfonylmethyl-3-(2-methyl-8-morpholinoimidazo[1,2-a]pyrazin-6-yl)benzen-amine (2-28);
1-methyl-3-(4-(2-methyl-8-morpholinoimidazo[1,2-a]pyrazin-6-yl)phenyl)urea (2-29);
5-(2-methyl-8-morpholinoimidazo[1,2-a]pyrazin-6-yl)pyridin-3-ol (2-30);
2-methyl-8-morpholino-6-(pyridin-4-yl)imidazo[1,2-a]pyrazine (2-31);
6-(3-methoxyphenyl)-2-methyl-8-morpholinoimidazo[1,2-a]pyrazine (2-32);
5-chloro-2-methyl-8-morpholino-6-(pyridin-4-yl)imidazo[1,2-a]pyrazine (2-33);
5-chloro-2-methyl-8-morpholino-6-(pyridin-3-yl)imidazo[1,2-a]pyrazine (2-34);
8-morpholino-6-phenylimidazo[1,2-a]pyrazine-2-carboxamide (2-35);
6-(1H-indazol-4-yl)-2-methyl-8-morpholinoimidazo[1,2-a]pyrazine-5-carbonitrile (2-36);
3-(3-(4-methylpiperazin-1-yl)-8-morpholinoimidazo[1,2-a]pyrazin-6-yl)phenol (2-37);
6-(1H-indazol-4-yl)-3-(4-methylpiperazin-1-yl)-8-morpholinoimidazo[1,2-a]-pyrazine (2-38);
3-(3-(4-sulfonylmethylpiperazin-1-yl)-8-morpholinoimidazo[1,2-a]pyrazin-6-yl)phenol (2-39);
3-(8-morpholino-3-(piperazin-1-yl)imidazo[1,2-a]pyrazin-6-yl)phenol (2-40);
6-(1H-indazol-4-yl)-3-(4-sulfonylmethylpiperazin-1-yl)-8-morpholinoimidazo[1,2-a]pyrazine (2-41);
3-bromo-6-(1H-indazol-4-yl)-2-methyl-8-morpholinoimidazo[1,2-a]pyrazine (2-42);
tert-butyl 2-(4-(6-(1H-indazol-4-yl)-2-methyl-8-morpholinoimidazo[1,2-a]pyrazin-3-yl)-5,6-dihydropyridin-1(2H)-yl)acetate (2-43);
3-(1,2,3,6-tetrahydropyridin-4-yl)-6-(1H-indazol-4-yl)-2-methyl-8-morpholino-imidazo[1,2-a]pyrazine (2-44);
3-(1,2,3,6-tetrahydro-1-methylpyridin-4-yl)-6-(1H-indazol-4-yl)-2-methyl-8-morpholinoimidazo[1,2-a]pyrazine (2-45);
3-(1,2,3,6-tetrahydro-1-sulfonylmethylpyridin-4-yl)-6-(1H-indazol-4-yl)-2-methyl-8-morpholinoimidazo[1,2-a]pyrazine (2-46);
tert-butyl 2-(4-(6-(1H-indazol-4-yl)-2-methyl-8-morpholinoimidazo[1,2-a]pyrazin-3-yl)piperidin-1-yl)acetate (2-47);

5-chloro-6-(3-methoxyphenyl)-2-methyl-8-morpholinoimidazo[1,2-a]pyrazine (2-48);
3-(5-chloro-2-methyl-8-morpholinoimidazo[1,2-a]pyrazin-6-yl)phenol (2-49);
5-(2-((4-sulfonylmethylpiperazin-1-yl)methyl)-8-morpholinoimidazo[1,2-a]pyrazin-6-yl)pyrimidin-2-amine (2-50);
6-(1H-indazol-4-yl)-8-morpholino-3-(piperazin-1-yl)imidazo[1,2-a]pyrazine (2-51);
ethyl 6-(1H-indazol-4-yl)-8-morpholinoimidazo[1,2-a]pyrazine-2-carboxylate (2-52);
5-iodo-6-(3-methoxyphenyl)-2-methyl-8-morpholinoimidazo[1,2-a]pyrazine (2-53);
5-chloro-6-(1H-indazol-4-yl)-2-methyl-8-morpholinoimidazo[1,2-a]pyrazine (2-54);
5-bromo-6-(1H-indazol-4-yl)-2-methyl-8-morpholinoimidazo[1,2-a]pyrazine (2-55);
5-iodo-2-methyl-8-morpholino-6-(pyridin-3-yl)imidazo[1,2-a]pyrazine (2-56);
6-(1H-indazol-4-yl)-2-methyl-8-morpholino-3-(piperidin-4-yl)imidazo[1,2-a]-pyrazine (2-57);
6-(1H-indazol-4-yl)-2-methyl-3-(1-methylpiperidin-4-yl)-8-morpholinoimidazo[1,2-a]pyrazine (2-58);
6-(1H-indazol-4-yl)-2-methyl-3-(1-sulfonylmethylpiperidin-4-yl)-8-morpholino imidazo[1,2-a]pyrazine (2-59);
5-chloro-6-(1H-indazol-4-yl)-8-morpholino-2-((4-sulfonylmethylpiperazin-1-yl)-methyl)imidazo[1,2-a]pyrazine (2-60);
6-(6-methoxypyridin-3-yl)-2-((4-sulfonylmethylpiperazin-1-yl)methyl)-8-morpholinoimidazo[1,2-a]pyrazine (2-61);
6-(3-methoxyphenyl)-2-methyl-8-morpholinoimidazo[1,2-a]pyrazine-3-carbonitrile (2-62);
tert-butyl 4-(6-(1H-indazol-4-yl)-2-methyl-8-morpholinoimidazo[1,2-a]pyrazine-3-carboxamido)piperidine-1-carboxylate (2-63);
6-(1H-indazol-4-yl)-2-methyl-8-morpholino-N-(piperidin-4-yl)imidazo[1,2-a]-pyrazine-3-carboxamide (2-64);
6-(5-methoxypyridin-3-yl)-2-((4-sulfonylmethylpiperazin-1-yl)methyl)-8-morpholinoimidazo[1,2-a]pyrazine (2-65);
5-(2-((4-sulfonyl methylpiperazin-1-yl)methyl)-8-morpholinoimidazo[1,2-a]pyrazin-6-yl)pyridin-2-amine (2-66);
6-(2-methoxypyrimidin-5-yl)-2-((4-sulfonylmethylpiperazin-1-yl)methyl)-8-morpholinoimidazo[1,2-a]pyrazine (2-67);
4-(2-((4-sulfonylmethylpiperazin-1-yl)methyl)-8-morpholinoimidazo[1,2-a]pyrazin-6-yl)benzamide (2-68);
5-(2-((4-sulfonylmethylpiperazin-1-yl)methyl)-8-morpholinoimidazo[1,2-a]pyrazin-6-yl)indolin-2-one (2-69);
6-(5-fluoro-1H-indol-4-yl)-2-((4-sulfonylmethylpiperazin-1-yl)methyl)-8-morpholino-imidazo[1,2-a]pyrazine (2-70);
6-(1H-indol-4-yl)-2-((4-sulfonylmethylpiperazin-1-yl)methyl)-8-morpholino-imidazo[1,2-a]pyrazine (2-71);
3-(2-((4-sulfonylmethylpiperazin-1-yl)methyl)-8-morpholinoimidazo[1,2-a]pyrazin-6-yl)benzamide (2-72);
6-(1H-indazol-4-yl)-3-iodo-2-methyl-8-morpholinoimidazo[1,2-a]pyrazine (2-73);
N-ethyl-6-(1H-indazol-4-yl)-8-morpholinoimidazo[1,2-a]pyrazine-2-carboxamide (2-74);
2-((4-sulfonylmethylpiperazin-1-yl)methyl)-8-morpholino-6-(1H-pyrrolo[2,3-b]pyridin-5-yl)imidazo[1,2-a]pyrazine (2-75).

Compounds of the invention may be made in accordance with techniques that are well known to those skilled in the art, for example as described hereinafter.

According to a further aspect of the invention there is provided a process for the preparation of a compound of formula I which process comprises:
(i) reaction of a compound of formula IB,

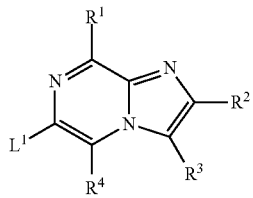

wherein $L^1$ represents a suitable leaving group, such as iodo, bromo, chloro or a sulfonate group (e.g. —OS(O)$_2$CF$_3$, —OS(O)$_2$CH$_3$ or —OS(O)$_2$PhMe), and $R^1$, $R^2$, $R^3$, and $R^4$ are as hereinbefore defined, with a compound of formula IC, $$R^5\text{-}L^2 \quad \text{IC}$$

wherein $L^2$ represents a suitable group such as —B(OH)$_2$, —B(OR$^{wx}$)$_2$ or —Sn(R$^{wx}$)$_3$, in which each R$^{wx}$ independently represents a C$_{1-6}$ alkyl group, or, in the case of —B(OR$^{wx}$)$_2$, the respective R$^{wx}$ groups may be linked together to form a 4- to 6-membered cyclic group (such as a 4,4,5,5-tetramethyl-1,3,2-dioxaborolan-2-yl group), thereby forming e.g. a pinacolato boronate ester group, (or $L^2$ may represent iodo, bromo or chloro, provided that $L^1$ and $L^2$ are mutually compatible) and $R^5$ is as hereinbefore defined. The reaction may be performed, for example in the presence of a suitable catalyst system, e.g. a metal (or a salt or complex thereof) such as Pd, CuI, Pd/C, PdCl$_2$, Pd(OAc)$_2$, Pd(Ph$_3$P)$_2$Cl$_2$, Pd(Ph$_3$P)$_4$ (i.e. palladium tetrakistriphenylphosphine), Pd$_2$(dba)$_3$ and/or NiCl$_2$ (preferred catalysts include palladium) and a ligand such as PdCl$_2$(dppf).DCM, t-Bu$_3$P, (C$_6$H$_{11}$)$_3$P, Ph$_3$P, AsPh$_3$, P(o-Tol)$_3$, 1,2-bis(diphenylphosphino)ethane, 2,2'-bis(di-tert-butylphosphino)-1,1'-biphenyl, 2,2'-bis(diphenylphosphino)-1,1'-bi-naphthyl, 1,1'-bis(diphenyl-phosphino-ferrocene), 1,3-bis(diphenylphosphino)propane, xantphos, or a mixture thereof (preferred ligands include PdCl$_2$(dppf).DCM), together with a suitable base such as, Na$_2$CO$_3$, K$_3$PO$_4$, Cs$_2$CO$_3$, NaOH, KOH, K$_2$CO$_3$, CsF, Et$_3$N, (i-Pr)$_2$NEt, t-BuONa or t-BuOK (or mixtures thereof; preferred bases include Na$_2$CO$_3$ and K$_2$CO$_3$) in a suitable solvent such as dioxane, toluene, ethanol, dimethylformamide, dimethoxyethane, ethylene glycol dimethyl ether, water, dimethylsulfoxide, acetonitrile, dimethylacetamide, N-methylpyrrolidinone, tetrahydrofuran or mixtures thereof (preferred solvents include dimethylformamide and dimethoxyethane). The reaction may be carried out for example at room temperature or above (e.g. at a high temperature such as at about the reflux temperature of the solvent system). Alternative reaction conditions include microwave irradiation conditions, for example at elevated temperature of about 130° C.;
(ii) reaction of a compound of formula ID,

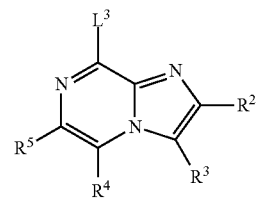

wherein $L^3$ represents a suitable leaving group, such as one hereinbefore defined in respect of $L^1$, and $R^2$, $R^3$, $R^4$ and $R^5$ are as hereinbefore defined, with a compound of formula IE, $$R^1\text{-}L^4 \qquad \text{IE}$$

wherein $L^4$ represents a suitable leaving group, such as one hereinbefore described in respect of $L^2$, under reaction conditions such as those described in respect of process step (i) above, or, in the case where $R^1$ represents —N($R^{1a}$)$R^{1b}$, $L^4$ may represents hydrogen (so forming an amine group), and the reaction may be performed in the presence of an appropriate metal catalyst (or a salt or complex thereof) such as Cu, Cu(OAc)$_2$, CuI (or CuI/diamine complex), copper tris(triphenylphosphine)bromide, Pd(OAc)$_2$, tris(dibenzylideneacetone)-dipalladium(0) (Pd$_2$(dba)$_3$) or NiCl$_2$ and an optional additive such as Ph$_3$P, 2,2'-bis(diphenylphosphino)-1,1'-binaphthyl, xantphos, NaI or an appropriate crown ether such as 18-crown-6-benzene, in the presence of an appropriate base such as NaH, Et$_3$N, pyridine, N,N'-dimethylethylenediamine, Na$_2$CO$_3$, K$_2$CO$_3$, K$_3$PO$_4$, Cs$_2$CO$_3$, t-BuONa or t-BuOK (or a mixture thereof, optionally in the presence of 4 Å molecular sieves), in a suitable solvent (e.g. dichloromethane, dioxane, toluene, ethanol, isopropanol, dimethylformamide, ethylene glycol, ethylene glycol dimethyl ether, water, dimethylsulfoxide, acetonitrile, dimethylacetamide, N-methylpyrrolidinone, tetrahydrofuran or a mixture thereof). This reaction may be performed at elevated temperature or under microwave irradiation reaction conditions, for example as described in process step (i). The compound of formula ID (e.g. in which $L^4$ is chloro) may be prepared in situ, for example from a compound corresponding to a compound of formula ID, but in which $L^4$ represents —OC$_{1-3}$ alkyl (e.g. methoxy) by reaction in the presence of e.g. a chlorinating agent (such as POCl$_3$);

(iii) reaction of a compound of formula IF,

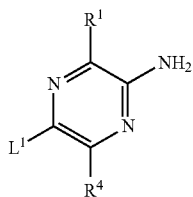

wherein $R^1$, $R^4$ and $L^1$ are as hereinbefore defined, with a compound of formula IG, $$R^2\text{—C(O)—C}(R^3)(H)\text{-}L^5 \qquad \text{IG}$$

wherein $L^5$ represents a suitable leaving group, such as one hereinbefore defined in respect of $L^1$ (and, especially, $L^5$ represents halo, such as chloro or bromo), and $R^2$ and $R^3$ are as hereinbefore defined, under standard reaction conditions, for example in the presence of a suitable reaction solvent such as DME or 2-propanol, at a convenient temperature, typically heating at 90° C., followed by reaction with a compound of formula IC as hereinbefore defined. The compounds of formula IG may be a protected derivative thereof (e.g. it may be a carbonyl derivative, for instance $R^2$—C(—OCH$_3$)$_2$—C($R^3$)(H)-$L^5$, in which $R^2$ preferably represents H). Such an intermediate compound of formula IG in which $R^3$ represents —N($R^{10a}$)$R^{11a}$ (in which $R^{10a}$ and $R^{11a}$ may be linked together to form an optionally piperazinyl group) and $L^5$ may represent a suitable leaving group, may also be prepared by reaction of glyoxal with benzotraizole and an amine (e.g. a cyclic amine such as piperazine or a substituted derivative thereof), which may be an intermediate compound that is not isolated (e.g. which may be used in situ);

(iv) reaction of a compound of formula IFA,

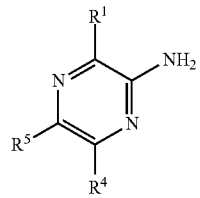

wherein $R^1$, $R^4$ and $R^5$ are as hereinbefore defined, with a compound of formula IH, $$R^3\text{—C(H)}(L^{6a})\text{-C(H)}(L^{6b})\text{-}R^3 \qquad \text{IH}$$

wherein $L^{6a}$ and $L^{6b}$ independently represent a suitable leaving group, for example benzotriazole groups (or the like), and each $R^3$ is as hereinbefore defined (e.g. each of the $R^3$ groups are the same), which reaction may be performed following similar conditions reported in literature (*J. Org. Chem.* 1990, 55, 3209-3213, *J. Org. Chem.*, 2003, 68, 4935-4937), in a suitable solvent, such as DCE, heating at a convenient temperature, for a period of time to ensure completion of the reaction, typically at reflux for 5 h. Additionally an inorganic base can be added to ensure completion of the reaction;

(v) for compounds of formula I in which $R^3$ or $R^4$ represents bromo, iodo or chloro, reaction of a corresponding compound of formula I, in which $R^3$ or $R^4$ (as appropriate) represents hydrogen, with a reagent that is a source of halide ions (a halogenating reagent). For instance, an electrophile that provides a source of iodide ions includes iodine, diiodoethane, diiodotetrachloroethane or, preferably, N-iodosuccinimide, a source of bromide ions includes N-bromosuccinimide and bromine, and a source of chloride ions includes N-chlorosuccinimide, chlorine and iodine monochloride, for instance in the presence of a suitable solvent, such as CHCl$_3$ or an alcohol (e.g. methanol), optionally in the presence of a suitable base, such as a weak inorganic base, e.g. sodium bicarbonate. Typically, the reaction maybe performed by heating at a convenient temperature, either by conventional heating under reflux or under microwave irradiation;

(vi) for compounds of formula I in which $R^3$ or $R^4$ represents a substituent other that hydrogen, or halo (e.g. bromo, iodo or chloro), reaction of a corresponding compound of formula I, in which $R^3$ or $R^4$ (as appropriate) represents bromo, chloro or iodo, with a compound of formula IJ, $$R^{3/4}\text{-}L^7 \qquad \text{IJ}$$

wherein $R^{3/4}$ represents $R^3$ or $R^4$ (as appropriate), and $L^7$ represents a suitable leaving group such as one hereinbefore described in respect of process step (i) or (ii) above. Alternatively, the skilled person will appreciate that different reagents and reaction steps may be employed, depending on the particular $R^3$ or $R^4$ substituent required (for instance in order to introduce a —CN substituent, zinc cyanide (or the like) may be employed).

Other specific transformation steps that may be mentioned include:

(i) reductions of a carboxylic acid (or ester) to either an aldehyde or an alcohol, using appropriate reducing conditions (e.g. when $R^2$ represents —C(O)OH (or an ester thereof), it may be converted to a —C(O)H or —CH$_2$—OH group, using DIBAL and LiAlH$_4$, respectively (or similar chemoselective reducing agents);

(ii) reductions of an aldehyde (—C(O)H) group to an alcohol group (—CH$_2$OH), using appropriate reduction conditions such as those mentioned at point (i) above;

(iii) oxidations, for example of a moiety containing an alcohol group (e.g. —CH$_2$OH) to an aldehyde (e.g. —C(O)H) or of a —S— moiety to a —S(O)— or —S(O)$_2$— moiety (or the reverse reduction reaction), for example in the presence of a suitable oxidising agent, e.g. MnO$_2$ or mcpba or the like;

(iv) reductive amination of an aldehyde and an amine, under appropriate reaction conditions, for example in "one-pot" procedure in the presence of an appropriate reducing agent, such as sodium cyanoborohydride or, preferably, sodium triacetoxyborohydride, or the like (and hence when e.g. $R^2$ represents —C(O)H, such a group may be converted to a —CH$_2$—N($R^{10a}$) $R^{11a}$ group (or —CH$_2$—N($R^a$)($R^b$), i.e. a specific fragment of formula Ia), in which $R^{10a}$ and $R^{11a}$ are as hereinbefore defined, and may be linked together as hereinbefore defined to form e.g. a 5- or 6-membered ring optionally containing a further heteroatom such as oxygen or nitrogen);

(v) formation of an amide or sulfonamide, for example by reaction of a sulfonyl chloride with an amine or by an amide coupling reaction, i.e. the formation of an amide from a carboxylic acid (or ester thereof), for example —C(O)OH (or an ester thereof), may be converted to —C(O)N($R^{10a}$)$R^{11a}$ group (in which $R^{10a}$ and $R^{11a}$ are as hereinbefore defined, and may be linked together, e.g. as defined above), and which reaction may (e.g. for —COOH) be performed in the presence of a suitable coupling reagent (e.g. 1,1'-carbonyldiimidazole, N,N'-dicyclohexylcarbodiimide, or the like) or, in the case of an ester (e.g. —C(O)OCH$_3$ or —C(O)OCH$_2$CH$_3$), be performed in the presence of e.g. trimethylaluminium, or, alternatively the —C(O)OH group may first be activated to the corresponding acyl halide (e.g —C(O)Cl, by treatment with oxalyl chloride, thionyl chloride, phosphorous pentachloride, phosphorous oxychloride, or the like), and, in all cases, the relevant compound is reacted with a compound of formula HN($R^{10a}$)$R^{11a}$ (in which $R^{10a}$ and $R^{11a}$ are as hereinbefore defined), under standard conditions known to those skilled in the art (e.g. optionally in the presence of a suitable solvent, suitable base and/or in an inert atmosphere);

(vi) conversion of a primary amide to a nitrile functional group, for example under dehydration reaction conditions, e.g. in the presence of POCl$_3$, or the like;

(vii) nucleophilic substitution (e.g. aromatic nucleophilic substitution) reactions, where any nucleophile replaces a leaving group, e.g. an amine may replace a —S(O)CH$_3$ leaving group, such reactions include "Mitsunobu"-type reactions (or variants thereof), i.e. in which a —OH is the leaving group, which is activated by treatment with e.g. iodine and triphenylphosphine);

(viii) transformation of a methoxy group to a hydroxy group, by reaction in the presence of an appropriate reagent, such as boron fluoride-dimethyl sulfide complex or BBr$_3$ (e.g. in the presence of a suitable solvent such as dichloromethane);

(ix) alkylation, acylation or sulfonylation reactions, which may be performed in the presence of base and solvent (such as those described hereinbefore);

(x) specific deprotection steps, such as deprotection of an N-Boc protecting group by reaction in the presence of an acid, or, a hydroxy group protected as a silyl ether (e.g. a tert-butyl-dimethylsilyl protecting group) may be deprotected by reaction with a source of fluoride ions, e.g. by employing the reagent tetrabutylammonium fluoride (TBAF). Further, a —O—C(O)—CH$_3$ may be converted to a —OH group by reaction with sodium methoxide in methanol, or similar hydrolysis reactions may be performed;

(xi) hydrogenations, e.g. of a double bond to a single bond for instance under standard hydrogenation reaction conditions, e.g. under a hydrogen atmosphere in the presence of a catalyst such as Pd/C;

(xii) Grignard reactions, e.g. the addition of a nucleophilic organometalic reagent, for instance the addition of MeMgCl to a carbonyl group;

(xiii) formation of a urea functional group by reaction of a isocyanate with an amine, e.g. when $R^5$ represent phenyl substituted by —NH$_2$, this may be converted to a —N(H)—C(O)—N($R^{20}$)$R^{21}$ moiety.

Intermediate compounds described herein are either commercially available, are known in the literature, or may be obtained either by analogy with the processes described herein, or by conventional synthetic procedures, in accordance with standard techniques, from available starting materials using appropriate reagents and reaction conditions. Further, processes to prepare compounds of formula I may be described in the literature, for example in:

Werber, G. et al.; *J. Heterocycl. Chem.; EN;* 14; 1977; 823-827;

Andanappa K. Gadad et al. *Bioorg. Med. Chem.* 2004, 12, 5651-5659;

Paul Heinz et al. *Monatshefte für Chemie,* 1977, 108, 665-680;

M. A. El-Sherbeny et al. *Boll. Chim. Farm.* 1997, 136, 253-256;

Nicolaou, K. C.; Bulger, P. G.; Sarlah, D. *Angew. Chem. Int. Ed.* 2005, 44, 2-49;

Bretonnet et al. *J. Med. Chem.* 2007, 50, 1872;

Asuncion Marin et al. *Farmaco* 1992, 47 (1), 63-75;

Severinsen, R. et al. *Tetrahedron* 2005, 61, 5565-5575;

Nicolaou, K. C.; Bulger, P. G.; Sarlah, D. *Angew. Chem. Int. Ed.* 2005, 44, 2-49;

M. Kuwahara et al., *Chem. Pharm Bull.,* 1996, 44, 122;

Wipf, P.; Jung, J.-K. *J. Org. Chem.* 2000, 65(20), 6319-6337;

Shintani, R.; Okamoto, K. *Org. Lett.* 2005, 7 (21), 4757-4759;

Nicolaou, K. C.; Bulger, P. G.; Sarlah, D. *Angew. Chem. Int. Ed.* 2005, 44, 2-49;

J. Kobe et al., *Tetrahedron,* 1968, 24, 239;

P. F. Fabio, A. F. Lanzilotti and S. A. Lang, *Journal of Labelled Compounds and Pharmaceuticals,* 1978, 15, 407;

F. D. Bellamy and K. Ou, *Tetrahedron Lett.,* 1985, 25, 839;

M. Kuwahara et al., *Chem. Pharm Bull.,* 1996, 44, 122;

A. F. Abdel-Magid and C. A Maryanoff. *Synthesis,* 1990, 537;

M. Schlosser et al. *Organometallics in Synthesis. A Manual,* (M. Schlosser, Ed.), Wiley &Sons Ltd: Chichester, UK, 2002, and references cited therein;

L. Wengwei et al., *Tetrahedron Lett.,* 2006, 47, 1941;

M. Plotkin et al. *Tetrahedron Lett.,* 2000, 41, 2269;

Seyden-Penne, J. *Reductions by the Alumino and Borohydrides,* VCH, NY, 1991;

O. C. Dermer, *Chem. Rev.,* 1934, 14, 385;

N. Defacqz, et al., *Tetrahedron Lett.,* 2003, 44, 9111;

S. J. Gregson et al., *J. Med. Chem.,* 2004, 47, 1161;

A. M. Abdel Magib, et al., *J. Org. Chem.,* 1996, 61, 3849;

A. F. Abdel-Magid and C. A Maryanoff. *Synthesis,* 1990, 537;

T. Ikemoto and M. Wakimasu, *Heterocycles,* 2001, 55, 99;

E. Abignente et al., *Il Farmaco,* 1990, 45, 1075;

T. Ikemoto et al., *Tetrahedron,* 2000, 56, 7915;

T. W. Greene and P. G. M. Wuts, *Protective Groups in Organic Synthesis*, Wiley, NY, 1999;
S. Y. Han and Y.-A. Kim. *Tetrahedron,* 2004, 60, 2447;
J. A. H. Lainton et al., *J. Comb. Chem.,* 2003, 5, 400; or Wiggins, J. M. *Synth. Commun.,* 1988, 18, 741.

For example, intermediate compounds, and compounds of the invention may be prepared in accordance with the following scheme (Scheme I).

Compound I-01 was reacted with an intermediate (III-a) of formula $R^2$—C(=O)—$CH_2$—X or an intermediate (III-b) of formula $R^2$—C(=O)—CH—$R^3$—X, where $R^2$ and $R^3$ are as hereinbefore defined and X represents a suitable leaving group (e.g. a halide), without solvent or in the presence of a suitable reaction solvent such as DME or 2-propanol, at a convenient temperature, typically heating at 90° C., to obtain compounds of formula (II-a) or formula (II-b).

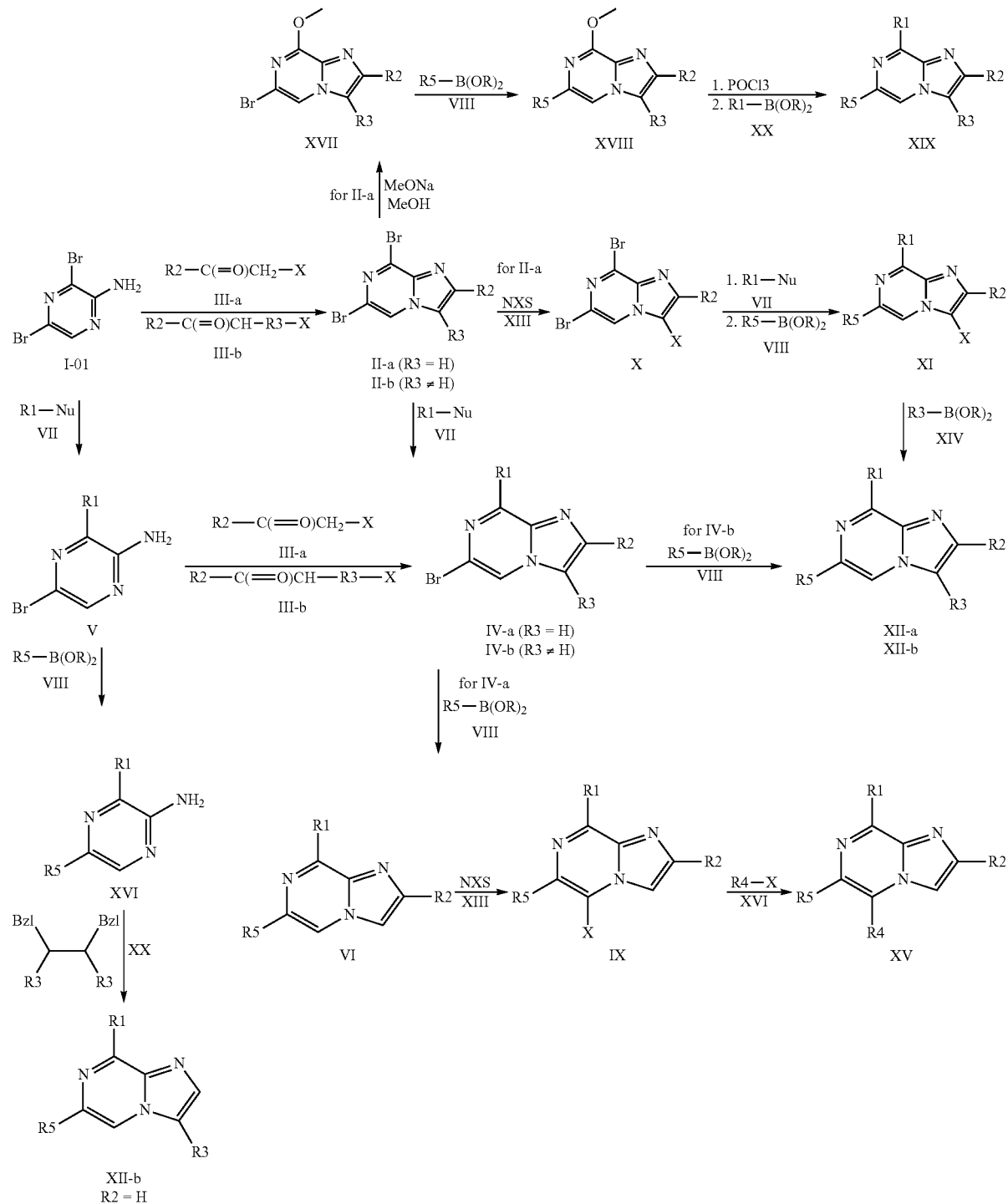

Compounds of formula (II-a) can be reacted with a halogenating agent, such as N-bromoSuccinimide, N-iodosucciinide, N-chlorosuccinimide or others, and X represents an halogen group such as Cl, Br or Iodine atom, in the presence of a suitable reaction solvent such as $CHCl_3$, typically heating at a convenient temperature, either by conventional heating under reflux or under microwave irradiation, for a period of time to ensure the completion of the reaction, to obtain compounds of formula (X).

Compounds of formula (X) can react with an intermediate (VII) of formula $R^1$-Nu, where $R^1$ is as hereinbefore defined and Nu represents a nucleophilic group, such as an amine (and $R^1$-Nu together form the group that is to be linked to the imidazopyrazine) in a suitable solvent such as DCM, dioxane at room temperature or by heating at a convenient temperature, for a period of time to ensure the completion of the reaction. Further, reaction may be with an intermediate (VIII) of formula $R^5$—$B(OR)_2$, which R is H or $C_1$-$C_6$ alkyl or the two groups OR form, together with the boron atom to which they are attached a pinacolato boronate ester group, and where $R^5$ is as defined before, in a suitable solvent such as DME or DMF, in the presence of a suitable base, such as an inorganic aqueous base $Na_2CO_3$ or $K_2CO_3$, in the presence of a metal catalyst, such as palladium, and a suitable ligand, such as $PdCl_2(dppf).DCM$, $Pd(PPh_3)_4$ by heating at a convenient temperature, such as 130° C. under microwave irradiation or reflux temperature under traditional heating, for a period of time that allows the completion of reaction, to obtain compounds of formula (XI).

Compounds of formula (XI) can react with an intermediate (XIV) of formula $R^3$—$B(OR)_2$, in which the —$B(OR)_2$ moeity is as defined above, and $R^3$ is as hereinbefore defined, under conditions such as those described hereinbefore (e.g. reaction of (X) with (VIII); e.g. microwave irradiation conditions at about 140° C. may be deployed), to obtain compounds of formula (XII-a).

Compounds of formula (II-b) can react with an intermediate (VII) of formula $R^1$-Nu (as hereinbefore defined), in a suitable solvent such as DCM, dioxane at room temperature or by heating, for a period of time to ensure the completion of the reaction to afford compounds of formula (IV-b).

Compounds of formula (IV-b) can react with an intermediate (VIII) of formula $R^5$—$B(OR)_2$ as hereinbefore defined, under reaction conditions hereinbefore described (e.g. the reaction of (X) with (VIII)), to obtain compounds of formula (XII-b).

Compound 1-01 can react with an intermediate (VII) of formula $R^1$-Nu (as hereinbefore defined), at a convenient temperature, such as 120° C., for a period of time that allows the completion of reaction, to afford compound (V).

Compound (V) was reacted with an intermediate (III-a) of formula $R^2$—C(=O)—$CH_2$—X or an intermediate (III-b) of formula $R^2$—C(=O)—CH—$R^3$—X, both of which are as hereinbefore defined, under reaction conditions hereinbefore described (e.g. the reaction of (I-01) with (III-a) or (III-b)), to obtain compounds of formula (IV-a).

Compounds of formula (IV-a) can react with an intermediate (VIII) of formula $R^5$—$B(OR)_2$, as hereinbefore defined, e.g. under reaction conditions hereinbefore described (e.g. the reaction of (X) with (VIII)), to obtain compounds of formula (VI).

Compounds of formula (VI) can be reacted with a halogenating agent, for example as described hereinbefore (e.g. reaction of (II-a) to (X)), to obtain compounds of formula (IX).

The halogen atom X of compounds of formula (IX) can be substituted via a coupling reaction with an intermediate (XVI) of formula $R^4$—$B(OR)_2$, in which the —$B(OR)_2$ moiety is as hereinbefore defined, and $R^4$ is as hereinbefore defined, e.g. under reaction conditions hereinbefore described (e.g. the reaction of (X) with (VIII)), for a period of time that allows the completion of reaction, to obtain compounds of formula XV.

The halogen atom X of compounds of formula (IX) can be substituted via coupling reaction of a CN group, by treatment with $Zn(CN)_2$, in a suitable solvent such as DMF, AcCN and in the presence of a Pd catalyst, such as $Pd(PPh_3)_4$ or $PdCl_2(dppf)_2$. Additionally an inorganic aqueous base can be added such as $Na_2CO_3$ aq. Heating at a convenient temperature, such as 130° C. under microwave irradiation or reflux temperature under traditional heating, for a period of time that allows the completion of reaction, to obtain compounds of formula XV.

Compounds of formula (V) can react with an intermediate (VIII) of formula $R^5$—$B(OR)_2$ as hereinbefore defined, e.g. under reaction conditions hereinbefore described (e.g. the reaction of (X) with (VIII)), to obtain compounds of formula (XVI).

Compounds of formula (XVI) can react with an intermediate of formula XX, in which Bzt is Benzotriazol, following similar conditions reported in literature (*J. Org. Chem.* 1990, 55, 3209-3213, *J. Org. Chem.*, 2003, 68, 4935-4937), in a suitable solvent, such as DCE, heating at a convenient temperature, in a period of time to ensure completion of the reaction, typically at reflux for 5 h. Additionally an inorganic base can be added to ensure completion of the reaction.

Compounds of formula (II-a) can react with sodium methoxide in the presence of methanol, at room temperature or by heating at a convenient temperature, such as 60° C., to obtain compounds of formula (XVII).

Compounds of formula (XVII) can react with an intermediate (VIII) of formula $R^5$—$B(OR)_2$ as hereinbefore defined, e.g. under reaction conditions hereinbefore described (e.g. the reaction of (X) with (VIII)), to obtain compounds of formula (XVIII).

Compound of formula (XVIII) can react with $POCl_3$ by heating, typically to reflux, for a period of time to ensure the completion of the reaction, to afford the replacement of the methoxy group by chlorine atom. Coupling of the chlorine atom with an intermediate (XX) of formula $R^1$—$B(OR)_2$ in which the —$B(OR)_2$ moiety and $R^1$ are as hereinbefore defined, e.g. under reaction conditions hereinbefore described (e.g. the reaction of (X) with (VIII)), to obtain compounds of formula (XIX).

Those skilled in the art will appreciate that other synthetic routes may be used to synthesize the compounds of the invention. Although specific starting materials and reagents are depicted in the Scheme 1 and discussed below, other starting materials and reagents can be easily substituted to provide a variety of derivatives and/or reaction conditions.

The substituents $R^1$, $R^2$, $R^3$, $R^4$ and $R^5$ in final compounds of the invention or relevant intermediates may be modified one or more times, after or during the processes described above by way of methods that are well known to those skilled in the art. Examples of such methods include substitutions, reductions, oxidations, alkylations, acylations, hydrolyses, esterifications, etherifications, halogenations or nitrations. Such reactions may result in the formation of a symmetric or asymmetric final compound of the invention or intermediate. The precursor groups can be changed to a different such group, or to the groups defined in formula I, at any time during the reaction sequence.

For example, when $R^2$, $R^3$ and $R^4$ groups such as $CO_2Et$, CHO, CN and/or $CH_2Cl$, are present, these groups can be further derivatized to other fragments described in $R^2$, $R^3$ and $R^4$ in compounds of the invention, following synthetic protocols very well know to the person skilled in the art and/or according to the experimental part described in the patent. Other specific transformation steps that may be mentioned include: the reduction of a nitro or azido group to an amino group; the hydrolysis of a nitrile group to a carboxylic acid group; and standard nucleophilic aromatic substitution reactions, for example in which an iodo-, preferably, fluoro- or bromo-phenyl group is converted into a cyanophenyl group by employing a source of cyanide ions (e.g. by reaction with a compound which is a source of cyano anions, e.g. sodium, copper (I), zinc or potassium cyanide, optionally in the presence of a palladium catalyst) as a reagent (alternatively, in this case, palladium catalysed cyanation reaction conditions may also be employed).

Other transformations that may be mentioned include: the conversion of a halo group (preferably iodo or bromo) to a 1-alkynyl group (e.g. by reaction with a 1-alkyne), which latter reaction may be performed in the presence of a suitable coupling catalyst (e.g. a palladium and/or a copper based catalyst) and a suitable base (e.g. a tri-($C_{1-6}$ alkyl)amine such as triethylamine, tributylamine or ethyldiisopropylamine); the introduction of amino groups and hydroxy groups in accordance with standard conditions using reagents known to those skilled in the art; the conversion of an amino group to a halo, azido or a cyano group, for example via diazotisation (e.g. generated in situ by reaction with $NaNO_2$ and a strong acid, such as HCl or $H_2SO_4$, at low temperature such as at 0° C. or below, e.g. at about −5° C.) followed by reaction with the appropriate nucleophile e.g. a source of the relevant anions, for example by reaction in the presence of a halogen gas (e.g. bromine, iodine or chlorine), or a reagent that is a source of azido or cyanide anions, such as $NaN_3$ or NaCN; the conversion of —C(O)OH to a —$NH_2$ group, under Schmidt reaction conditions, or variants thereof, for example in the presence of $HN_3$ (which may be formed in by contacting $NaN_3$ with a strong acid such as $H_2SO_4$), or, for variants, by reaction with diphenyl phosphoryl azide (($PhO)_2P(O)N_3$) in the presence of an alcohol, such as tert-butanol, which may result in the formation of a carbamate intermediate; the conversion of —C(O)$NH_2$ to —$NH_2$, for example under Hofmann rearrangement reaction conditions, for example in the presence of NaOBr (which may be formed by contacting NaOH and $Br_2$) which may result in the formation of a carbamate intermediate; the conversion of —C(O)$N_3$ (which compound itself may be prepared from the corresponding acyl hydrazide under standard diazotisation reaction conditions, e.g. in the presence of $NaNO_2$ and a strong acid such as $H_2SO_4$ or HCl) to —$NH_2$, for example under Curtius rearrangement reaction conditions, which may result in the formation of an intermediate isocyanate (or a carbamate if treated with an alcohol); the conversion of an alkyl carbamate to —$NH_2$, by hydrolysis, for example in the presence of water and base or under acidic conditions, or, when a benzyl carbamate intermediate is formed, under hydrogenation reaction conditions (e.g. catalytic hydrogenation reaction conditions in the presence of a precious metal catalyst such as Pd); halogenation of an aromatic ring, for example by an electrophilic aromatic substitution reaction in the presence of halogen atoms (e.g. chlorine, bromine, etc, or an equivalent source thereof) and, if necessary an appropriate catalyst/Lewis acid (e.g. $AlCl_3$ or $FeCl_3$).

Compounds of the invention bearing a carboxyester functional group may be converted into a variety of derivatives according to methods well known in the art to convert carboxyester groups into carboxamides, N-substituted carboxamides, N,N-disubstituted carboxamides, carboxylic acids, and the like. The operative conditions are those widely known in the art and may comprise, for instance in the conversion of a carboxyester group into a carboxamide group, the reaction with ammonia or ammonium hydroxide in the presence of a suitable solvent such as a lower alcohol, dimethylformamide or a mixture thereof; preferably the reaction is carried out with ammonium hydroxide in a methanol/dimethyl-formamide mixture, at a temperature ranging from about 50° C. to about 100° C. Analogous operative conditions apply in the preparation of N-substituted or N,N-disubstituted carboxamides wherein a suitable primary or secondary amine is used in place of ammonia or ammonium hydroxide. Likewise, carboxyester groups may be converted into carboxylic acid derivatives through basic or acidic hydrolysis conditions, widely known in the art. Further, amino derivatives of compounds of the invention may easily be converted into the corresponding carbamate, carboxamido or ureido derivatives.

Compounds of the invention may be isolated from their reaction mixtures using conventional techniques (e.g. recrystallisations).

It will be appreciated by those skilled in the art that, in the processes described above and hereinafter, the functional groups of intermediate compounds may need to be protected by protecting groups.

The need for such protection will vary depending on the nature of the remote functionality and the conditions of the preparation methods (and the need can be readily determined by one skilled in the art). Suitable amino-protecting groups include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art.

The protection and deprotection of functional groups may take place before or after a reaction in the above-mentioned schemes.

Protecting groups may be removed in accordance with techniques that are well known to those skilled in the art and as described hereinafter. For example, protected compounds/intermediates described herein may be converted chemically to unprotected compounds using standard deprotection techniques.

The type of chemistry involved will dictate the need, and type, of protecting groups as well as the sequence for accomplishing the synthesis.

The use of protecting groups is fully described in "Protective Groups in Organic Synthesis", $3^{rd}$ edition, T. W. Greene & P. G. M. Wutz, Wiley-Interscience (1999).

Medical and Pharmaceutical Uses

Compounds of the invention are indicated as pharmaceuticals. According to a further aspect of the invention there is provided a compound of the invention, as hereinbefore defined, for use as a pharmaceutical.

For the avoidance of doubt, although compounds of the invention may possess pharmacological activity as such, certain pharmaceutically-acceptable (e.g. "protected") derivatives of compounds of the invention may exist or be prepared which may not possess such activity, but may be administered parenterally or orally and thereafter be metabolised in the body to form compounds of the invention. Such compounds (which may possess some pharmacological activity, provided that such activity is appreciably lower than that of the "active" compounds to which they are metabolised) may therefore be described as "prodrugs" of compounds of the invention.

A "prodrug of a compound of the invention" is as hereinbefore defined, including compounds that form a compound of the invention, in an experimentally-detectable amount, within a predetermined time (e.g. about 1 hour), following oral or parenteral administration. All prodrugs of the compounds of the invention are included within the scope of the invention.

Furthermore, certain compounds of the invention may possess no or minimal pharmacological activity as such, but may be administered parenterally or orally, and thereafter be metabolised in the body to form compounds of the invention that possess pharmacological activity as such. Such compounds (which also includes compounds that may possess some pharmacological activity, but that activity is appreciably lower than that of the "active" compounds of the invention to which they are metabolised), may also be described as "prodrugs".

Thus, the compounds of the invention are useful because they possess pharmacological activity, and/or are metabolised in the body following oral or parenteral administration to form compounds which possess pharmacological activity.

Compounds of the invention may inhibit protein or lipid kinases, such as a PI3 kinase (especially a class I PI3K) or mTOR, for example as may be shown in the tests described below (for example, the test for PI3Kα inhibition described below) and/or in tests known to the skilled person. Thus, the compounds of the invention may be useful in the treatment of those disorders in an individual in which the inhibition of such protein or lipid kinases (e.g. PI3K, particularly class I PI3K, and/or mTOR) is desired and/or required.

The term "inhibit" may refer to any measurable reduction and/or prevention of catalytic kinase (e.g. PI3K, particularly class I PI3K, and/or mTOR) activity. The reduction and/or prevention of kinase activity may be measured by comparing the kinase activity in a sample containing a compound of the invention and an equivalent sample of kinase (e.g. PI3K, particularly class I PI3K, and/or mTOR) in the absence of a compound of the invention, as would be apparent to those skilled in the art. The measurable change may be objective (e.g. measurable by some test or marker, for example in an in vitro or in vivo assay or test, such as one described hereinafter, or otherwise another suitable assay or test known to those skilled in the art) or subjective (e.g. the subject gives an indication of or feels an effect).

Compounds of the invention may be found to exhibit 50% inhibition of a protein or lipid kinase (e.g. PI3K, such as class I PI3K, and/or mTOR) at a concentration of 100 μM or below (for example at a concentration of below 50 μM, or even below 10 μM, such as below 1 μM), when tested in an assay (or other test), for example as described hereinafter, or otherwise another suitable assay or test known to the skilled person.

Compounds of the invention are thus expected to be useful in the treatment of a disorder in which a protein or lipid kinase (e.g. PI3K, such as class I PI3K, and/or mTOR) is known to play a role and which are characterised by or associated with an overall elevated activity of that kinase (due to, for example, increased amount of the kinase or increased catalytic activity of the kinase). Hence, compounds of the invention are expected to be useful in the treatment of a disease/disorder arising from abnormal cell growth, function or behaviour associated with the protein or lipid kinase (e.g. PI3K, such as class I PI3K, and/or mTOR). Such conditions/disorders include cancer, immune disorders, cardiovascular diseases, viral infections, inflammation, metabolism/endocrine function disorders and neurological disorders.

The disorders/conditions that the compounds of the invention may be useful in treating hence includes cancer (such as lymphomas, solid tumours or a cancer as described hereinafter), obstructive airways diseases, allergic diseases, inflammatory diseases (such as asthma, allergy and Chrohn's disease), immunosuppression (such as transplantation rejection and autoimmune diseases), disorders commonly connected with organ transplantation, AIDS-related diseases and other associated diseases. Other associated diseases that may be mentioned (particularly due to the key role of kinases in the regulation of cellular proliferation) include other cell proliferative disorders and/or non-malignant diseases, such as benign prostate hyperplasia, familial adenomatosis, polyposis, neuro-fibromatosis, psoriasis, bone disorders, atherosclerosis, vascular smooth cell proliferation associated with atherosclerosis, pulmonary fibrosis, arthritis glomerulonephritis and post-surgical stenosis and restenosis. Other disease states that may be mentioned include cardiovascular disease, stroke, diabetes, hepatomegaly, Alzheimer's disease, cystic fibrosis, hormone-related diseases, immunodeficiency disorders, destructive bone disorders, infectious diseases, conditions associated with cell death, thrombin-induced platelet aggregation, chronic myelogenous leukaemia, liver disease, pathologic immune conditions involving T cell activation and CNS disorders.

As stated above, the compounds of the invention may be useful in the treatment of cancer. More, specifically, the compounds of the invention may therefore be useful in the treatment of a variety of cancer including, but not limited to: carcinoma such as cancer of the bladder, breast, colon, kidney, liver, lung (including non-small cell cancer and small cell lung cancer), esophagus, gall-bladder, ovary, pancreas, stomach, cervix, thyroid, prostate, skin, squamous cell carcinoma, testis, genitourinary tract, larynx, glioblastoma, neuroblastoma, keratoacanthoma, epidermoid carcinoma, large cell carcinoma, non-small cell lung carcinoma, small cell lung carcinoma, lung adenocarcinoma, bone, adenoma, adenocarcinoma, follicular carcinoma, undifferentiated carcinoma, papilliary carcinoma, seminona, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's and leukaemia; hematopoietic tumors of lymphoid lineage, including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; and other tumors, including melanoma, seminoma, teratocarcinoma, osteosarcoma, xeroderma pigmentosum, keratoxanthoma, thyroid follicular cancer and Kaposi's sarcoma.

Further, the protein or lipid kinases (e.g. PI3K, such as class I PI3K, and/or mTOR) may also be implicated in the multiplication of viruses and parasites. They may also play a major role in the pathogenesis and development of neurodegenerative disorders. Hence, compounds of the invention may also be useful in the treatment of viral conditions, parasitic conditions, as well as neurodegenerative disorders.

Compounds of the invention are indicated both in the therapeutic and/or prophylactic treatment of the above-mentioned conditions.

According to a further aspect of the present invention, there is provided a method of treatment of a disease (e.g. cancer or another disease as mentioned herein) which is associated with the inhibition of protein or lipid kinase (e.g. PI3K, such as class I PI3K, and/or mTOR) is desired and/or required (for example, a method of treatment of a disease/disorder arising from abnormal cell growth, function or behaviour associated with protein or lipid kinases, e.g. PI3K, such as class I PI3K, and/or mTOR), which method comprises administration of a therapeutically effective amount of a compound of the invention, as hereinbefore defined, to a patient suffering from, or susceptible to, such a condition.

"Patients" include mammalian (including human) patients. Hence, the method of treatment discussed above may include the treatment of a human or animal body.

The term "effective amount" refers to an amount of a compound, which confers a therapeutic effect on the treated patient. The effect may be objective (e.g. measurable by some test or marker) or subjective (e.g. the subject gives an indication of or feels an effect).

Compounds of the invention may be administered orally, intravenously, subcutaneously, buccally, rectally, dermally, nasally, tracheally, bronchially, sublingually, by any other parenteral route or via inhalation, in a pharmaceutically acceptable dosage form.

Compounds of the invention may be administered alone, but are preferably administered by way of known pharmaceutical formulations, including tablets, capsules or elixirs for oral administration, suppositories for rectal administration, sterile solutions or suspensions for parenteral or intramuscular administration, and the like. The type of pharmaceutical formulation may be selected with due regard to the intended route of administration and standard pharmaceutical practice. Such pharmaceutically acceptable carriers may be chemically inert to the active compounds and may have no detrimental side effects or toxicity under the conditions of use.

Such formulations may be prepared in accordance with standard and/or accepted pharmaceutical practice. Otherwise, the preparation of suitable formulations may be achieved non-inventively by the skilled person using routine techniques and/or in accordance with standard and/or accepted pharmaceutical practice.

According to a further aspect of the invention there is thus provided a pharmaceutical formulation including a compound of the invention, as hereinbefore defined, in admixture with a pharmaceutically acceptable adjuvant, diluent and/or carrier.

Depending on e.g. potency and physical characteristics of the compound of the invention (i.e. active ingredient), pharmaceutical formulations that may be mentioned include those in which the active ingredient is present in at least 1% (or at least 10%, at least 30% or at least 50%) by weight. That is, the ratio of active ingredient to the other components (i.e. the addition of adjuvant, diluent and carrier) of the pharmaceutical composition is at least 1:99 (or at least 10:90, at least 30:70 or at least 50:50) by weight.

The amount of compound of the invention in the formulation will depend on the severity of the condition, and on the patient, to be treated, as well as the compound(s) which is/are employed, but may be determined non-inventively by the skilled person.

The invention further provides a process for the preparation of a pharmaceutical formulation, as hereinbefore defined, which process comprises bringing into association a compound of the invention, as hereinbefore defined, or a pharmaceutically acceptable ester, amide, solvate or salt thereof with a pharmaceutically-acceptable adjuvant, diluent or carrier.

Compounds of the invention may also be combined with other therapeutic agents that are inhibitors of protein or lipid kinases (e.g. PI3K, such as class I PI3K, and/or mTOR) and/or useful in the treatment of a cancer and/or a proliferative disease. Compounds of the invention may also be combined with other therapies.

According to a further aspect of the invention, there is provided a combination product comprising:
(A) a compound of the invention, as hereinbefore defined; and
(B) another therapeutic agent that is useful in the treatment of cancer and/or a proliferative disease,
wherein each of components (A) and (B) is formulated in admixture with a pharmaceutically-acceptable adjuvant, diluent or carrier.

Such combination products provide for the administration of a compound of the invention in conjunction with the other therapeutic agent, and may thus be presented either as separate formulations, wherein at least one of those formulations comprises a compound of the invention, and at least one comprises the other therapeutic agent, or may be presented (i.e. formulated) as a combined preparation (i.e. presented as a single formulation including a compound of the invention and the other therapeutic agent).

Thus, there is further provided:
(1) a pharmaceutical formulation including a compound of the invention, as hereinbefore defined, another therapeutic agent that is useful in the treatment of cancer and/or a proliferative disease, and a pharmaceutically-acceptable adjuvant, diluent or carrier; and
(2) a kit of parts comprising components:
(a) a pharmaceutical formulation including a compound of the invention, as hereinbefore defined, in admixture with a pharmaceutically-acceptable adjuvant, diluent or carrier; and
(b) a pharmaceutical formulation including another therapeutic agent that is useful in the treatment of cancer and/or a proliferative disease in admixture with a pharmaceutically-acceptable adjuvant, diluent or carrier, which components (a) and (b) are each provided in a form that is suitable for administration in conjunction with the other.

The invention further provides a process for the preparation of a combination product as hereinbefore defined, which process comprises bringing into association a compound of the invention, as hereinbefore defined, or a pharmaceutically acceptable ester, amide, solvate or salt thereof with the other therapeutic agent that is useful in the treatment of cancer and/or a proliferative disease, and at least one pharmaceutically-acceptable adjuvant, diluent or carrier.

By "bringing into association", we mean that the two components are rendered suitable for administration in conjunction with each other.

Thus, in relation to the process for the preparation of a kit of parts as hereinbefore defined, by bringing the two components "into association with" each other, we include that the two components of the kit of parts may be:
(i) provided as separate formulations (i.e. independently of one another), which are subsequently brought together for use in conjunction with each other in combination therapy; or
(ii) packaged and presented together as separate components of a "combination pack" for use in conjunction with each other in combination therapy.

Depending on the disorder, and the patient, to be treated, as well as the route of administration, compounds of the invention may be administered at varying therapeutically effective doses to a patient in need thereof. However, the dose administered to a mammal, particularly a human, in the context of the present invention should be sufficient to effect a therapeutic response in the mammal over a reasonable timeframe. One skilled in the art will recognize that the selection of the exact dose and composition and the most appropriate delivery regimen will also be influenced by inter alia the pharmacological properties of the formulation, the nature and severity of the condition being treated, and the physical condition and mental acuity of the recipient, as well as the potency of the specific compound, the age, condition, body weight, sex and response of the patient to be treated, and the stage/severity of the disease.

Administration may be continuous or intermittent (e.g. by bolus injection). The dosage may also be determined by the timing and frequency of administration. In the case of oral or parenteral administration the dosage can vary from about 0.01 mg to about 1000 mg per day of a compound of the invention.

In any event, the medical practitioner, or other skilled person, will be able to determine routinely the actual dosage, which will be most suitable for an individual patient. The above-mentioned dosages are exemplary of the average case; there can, of course, be individual instances where higher or lower dosage ranges are merited, and such are within the scope of this invention.

Compounds of the invention may have the advantage that they are effective inhibitors of protein or lipid kinases (e.g. PI3K, such as class I PI3K, and/or mTOR).

Compounds of the invention may also have the advantage that they may be more efficacious than, be less toxic than, be longer acting than, be more potent than, produce fewer side effects than, be more easily absorbed than, and/or have a better pharmacokinetic profile (e.g. higher oral bioavailability and/or lower clearance) than, and/or have other useful pharmacological, physical, or chemical properties over, compounds known in the prior art, whether for use in the above-stated indications or otherwise.

EXAMPLES

Biological Tests

Determination of the activity of PI3 kinase activity of compounds of the invention is possible by a number of direct and indirect detection methods. Certain exemplary compounds described herein were prepared, characterized, and tested for their PI3K binding activity and in vitro activity against tumor cells. The range of PI3K binding activities was less than 1 nM to about 10 µM (i.e. certain compounds of the examples/invention had PI3K binding activity $IC_{50}$ values of less than 10 nM). Compounds of the examples/invention had tumor cell-based activity $IC_{50}$ values less than 100 nM (see Table 4 below).

PI3K Activity Assay

The kinase activity was measured by using the commercial ADP Hunter™ Plus assay available from DiscoveR$_x$ (#33-016), which is a homogeneous assay to measure the accumulation of ADP, a universal product of kinase activity. The enzyme, PI3k (p110α/p85α was purchased from Carna Biosciences (#07CBS-0402A). The assay was done following the manufacturer recommendations with slight modifications: Mainly the kinase buffer was replace by 50 mM HEPES, pH 7.5, 3 mM $MgCl_2$, 100 mM NaCl, 1 mM EGTA, 0.04% CHAPS, 2 mM TCEP and 0.01 mg/ml BGG. The PI3K was assayed in a titration experiment to determine the optimal protein concentration for the inhibition assay. To calculate the $IC_{50}$ of the ETP-compounds, serial 1:5 dilutions of the compounds were added to the enzyme at a fixed concentration (2.5 µg/ml. The enzyme was preincubated with the inhibitor and 30 µM $PIP_2$ substrate (P9763, Sigma) for 5 min and then ATP was added to a final 50 µM concentration. Reaction was carried out for 1 hour at 25° C. Reagent A and B were sequentially added to the wells and plates were incubated for 30 min at 37° C. Fluorescence counts were read in a Victor instrument (Perkin Elmer) with the recommended settings (544 and 580 nm as excitation and emission wavelengths, respectively). Values were normalized against the control activity included for each enzyme (i.e., 100% PI3 kinase activity, without compound). These values were plot against the inhibitor concentration and were fit to a sigmoid dose-response curve by using the Graphad software.

Cellular Mode of Action

Cell culture: The cell lines were obtained from the American Type Culture Collection (ATCC). U2OS (human osteosarcoma) was cultured in Dulbecco's modified Eagle's medium (DMEM). PC3 (human prostate carcinoma), MCF7 (human breast cardinoma), HCT116 (human colon carcinoma), 768-0 (human neuroblastoma), U251 (human glyoblastoma) were grown in RPMI. All media were supplemented with 10% fetal bovine serum (FBS) (Sigma) and antibiotics-antimycotics. Cell were maintained in a humidified incubator at 37° C. with 5% $CO_2$ and passaged when confluent using trypsin/EDTA.

U2foxRELOC and U2nesRELOC assay: The U2foxRELOC assay and the U2nesRELOC assay have been described previously (1, 2). Briefly, cells were seeded at a density of $1.0 \times 10^5$ cells/ml into black-wall clear-bottom 96-well microplates (BD Biosciences) After incubation at 37° C. with 5% $CO_2$ for 12 hours, 2 µl of each test compound were transferred from the mother plates to the assay plates. Cells were incubated in the presence of the compounds for one hour. Then cells were fixed and the nucleus stained with DAPI (Invitrogen). Finally the plates were washed with 1×PBS twice and stored at 4° C. before analysis. Compounds of the invention have a range of in vitro cell potency activities from about 1 nM to about 10 µM.

Image acquirement and processing: Assay plates were read on the BD Pathway™ 855 Bioimager equipped with a 488/10 nm EGFP excitation filter, a 380/10 nm DAPI excitation filter, a 515LP nm EGFP emission filter and a 435LP nm DAPI emission filter. Images were acquired in the DAPI and GFP channels of each well using 10× dry objective. The plates were exposed 0.066 ms (Gain 31) to acquire DAPI images and 0.55 ms (Gain 30) for GFP images.

Data analysis: The BD Pathway Bioimager outputs its data in standard text files. Data were imported into the data analysis software BD Image Data Explorer. The nuclear/cytoplasmic (Nuc/Cyt) ratios of fluorescence intensity were determined by dividing the fluorescence intensity of the nucleus by the cytoplasmic. A threshold ratio of greater than 1.8 was employed to define nuclear accumulation of fluorescent signal for each cell. Based on this procedure we calculated the percentage of cells per well displaying nuclear translocation or inhibition of nuclear export. Compounds that induced a nuclear accumulation of the fluorescent signal greater than 60% of that obtained from wells treated with 4 nM LMB were considered as hits. In order to estimate the quality of the HCS assay, the Z' factor was calculated by the equation: Z'=1−[(3× std. dev. of positive controls)+(3×std. dev. of negative controls)/(mean of positive controls)−(mean of negative controls)].

PI3K Signalling

AKT phosphorylation Inhibition. Western Blot Analysis: Subconfluent cells were incubated under different conditions and washed twice with TBS prior to lysis. Lysis buffer was added containing 50 mM Tris HCl, 150 mM NaCl, 1% NP-40, 2 mM $Na_3VO_4$, 100 mM NaF, 20 mM $Na_4P_2O_7$ and protease inhibitor cocktail (Roche Molecular Biochemicals). The proteins were resolved on 10% SDS-PAGE and transferred to nitrocellulose membrane (Schleicher & Schuell, Dassel, Germany). The membranes were incubated overnight at 4° C. with antibodies specific for Akt, phospho-Ser-473-Akt (Cell Signaling Technology) and α-tubulin (Sigma), they were washed and then incubated with IRDye800 conjugated anti-mouse and Alexa Fluor 680 goat anti-rabbit IgG secondary antibodies. The bands were visualized using an Odyssey infrared imaging system (Li-Cor Biosciences). Compounds of the invention have a range of in vitro cell potency activities from about 1 nM to about 10 µM.

Cytotoxicity Assessment

The compounds were tested on 96-well trays. Cells growing in a flask were harvested just before they became confluent, counted using a haemocytometer and diluted down with media adjusting the concentration to the required number of cells per 0.2 ml (volume for each well). Cells were then seeded in 96-well trays at a density between 1000 and 4000 cells/well, depending of the cell size. Cells were left to plate down and grow for 24 hours before adding the drugs. Drugs were weighed out and diluted with DMSO to get them into solution to a concentration of 10 mM. From here a "mother plate" with serial dilutions was prepared at 200× the final concentration in the culture. The final concentration of DMSO in the tissue culture media should not exceed 0.5%. The appropriate volume of the compound solution (usually 2 microliters) was added automatically (Beckman FX 96 tip) to media to make it up to the final concentration for each drug. The medium was removed from the cells and replaced with 0.2 ml of medium dosed with drug. Each concentration was assayed in triplicate. Two sets of control wells were left on each plate, containing either medium without drug or medium with the same concentration of DMSO. A third control set was obtained with the cells untreated just before adding the drugs (seeding control, number of cells starting the culture). Cells were exposed to the drugs for 72 hours and then processed for MTT colorimetric read-out. Compounds of the invention have a range of in vitro cell potency activities from about 1 nM to about 10 µM.

mTOR Assay

Mammalian target of rapamycin (mTOR) was assayed by monitoring phosphorylation of GFP-4EBP using a homogeneous time-resolved fluorescence resonant energy transfer format and assay reagents from Invitrogen. In the presence of 10 µM ATP, 50 mM Hepes (pH 7.5), 0.01% (v/v) Polysorbate 20, 10 mM $MnCl_2$, 1 mM EGTA, and 2.5 mM DTT, the mTOR-mediated phosphorylation of 200 nM GFP-4E-BP1 was measured under initial rate conditions. After incubation at room temperature for 60 min, the reaction was terminated by addition of 10 mM EDTA, and phosphorylated GFP-4E-BP1 was detected with 2 nM Tb-anti-p4E-BP1 antibody before reading on a Perkin-Elmer Wallac 1420 Fluorescence Reader (exc 340; em 490/520).

Where compound names are given herein, they are typically generated with ChemDraw.

The invention is illustrated by way of the following examples, in which the following abbreviations (or chemical symbols) may be employed:

"dba" dibenzylidene acetone; "DCM" dichloromethane; "MeOH" methanol; "EtOH" ethanol; "THF" tetrahydrofuran; "DMF" dimethylformamide; "$CHCl_3$" chloroform; "DME" dimethoxyethane; "$Et_2O$" diethyl ether; "Hex" hexane; "EtOAc" ethyl acetate; "$Pd(PPh_3)_4$" tetrakis(triphenylphosphine)palladium; "KOAc" potassium acetate; "DIPEA" diisopropylethylamine; "$Pd(PPh_3)_4$" tetrakis(triphenylphosphine)-palladium; "$Pd(dppf)Cl_2.DCM$" 1,1'-bis(diphenylphosphino)ferrocenepalladium(II) dichloride, dichloromethane; "min." minutes; and "h." hours.

Examples and Experimental

The intermediate compounds of Table 1 were prepared according to the procedures A-1, A-2 and A-3 described hereinafter. The intermediate compounds of Table 2 were prepared according to the procedures A-4 to A-28 described hereinafter. The final examples of compounds of the invention were prepared according to the procedures B-1 to B-26 (and A-13) described hereinafter. Procedures of methods A and B are described in more detail in the experimental hereinafter. If an experimental procedure is not specifically described, the synthesis is performed in accordance with the methods described herein, optionally with reference to procedures known to the skilled person. A procedure to prepare a final compound may or may not be accompanied by characterising data for that final compound.

TABLE 1

Pyrazine Intermediates

| Exp. No. | Meth. | —R1 | —R2 |
|---|---|---|---|
| I-01 | A-1 | —Br | —Br |
| I-02 | A-2 | morpholine | —Br |
| I-03 | A-3 | morpholine | 1H-indazol-4-yl |
| I-04 | A-3 | morpholine | 3-hydroxyphenyl |
| I-53 | A1 | —Cl | —I |
| I-54 | A3 | morpholine | 2-aminopyrimidin-5-yl |

TABLE 2

Intermediates

[Core structure: imidazo[1,2-a]pyrazine with R1 at position 8, R2 at position 2, R3 at position 3, R4 at position 5, R5 at position 6]

| No. | Exp. Meth. | —R1 | —R2 | —R3 | —R4 | —R5 |
|---|---|---|---|---|---|---|
| I-05 | A4 | —Br | —Me | —H | —H | —Br |
| I-06 | A5 | —Br | —Me | —Br | —H | —Br |
| I-07 | A4 | —Br | —CO₂Et | —H | —H | —Br |
| I-08 | A4 | —Br | —CF₃ | —H | —H | —Br |
| I-09 | A6 | —Br | —CO₂Et | —Br | —H | —Br |
| I-10 | A7 | morpholinyl (N-linked) | —Me | —H | —H | —Br |
| I-11 | A7 | morpholinyl (N-linked) | —Me | —Br | —H | —Br |
| I-12 | A7 | morpholinyl (N-linked) | —CO₂Et | —H | —H | —Br |
| I-13 | A8 | morpholinyl (N-linked) | —CHO | —H | —H | —Br |
| I-14 | A9 | morpholinyl (N-linked) | —CH₂OH | —H | —H | —Br |
| I-15 | A7 | morpholinyl (N-linked) | cyclopropyl | —H | —H | —Br |
| I-16 | A10 | morpholinyl (N-linked) | 4-Boc-piperazin-1-yl | —H | —H | —Br |
| I-17 | A11 | morpholinyl (N-linked) | piperazin-1-yl | —H | —H | —Br |
| I-18 | A10 | morpholinyl (N-linked) | 4-(methylsulfonyl)piperazin-1-yl | —H | —H | —Br |
| I-19 | A10 | morpholinyl (N-linked) | 4-acetylpiperazin-1-yl | —H | —H | —Br |

TABLE 2-continued

Intermediates

[Structure: imidazo[1,2-a]pyrazine core with substituents R1 (position 8), R2 (position 2), R3 (position 3), R4 (position 5), R5 (position 6)]

| No. | Exp. Meth. | —R1 | —R2 | —R3 | —R4 | —R5 |
|---|---|---|---|---|---|---|
| I-20 | A10 | morpholin-4-yl | 4-methylpiperazin-1-yl | —H | —H | —Br |
| I-21 | A10 | morpholin-4-yl | 3-oxopiperazin-1-yl | —H | —H | —Br |
| I-22 | A10 | morpholin-4-yl | (morpholin-4-yl)methyl | —H | —H | —Br |
| I-23 | A12 | morpholin-4-yl | (4-methylpiperazin-1-yl)carbonyl | —H | —H | —Br |
| I-24 | A12 | morpholin-4-yl | [4-(methylsulfonyl)piperazin-1-yl]carbonyl | —H | —H | —Br |
| I-25 | A12 | morpholin-4-yl | [4-(tert-butoxycarbonyl)piperazin-1-yl]carbonyl | —H | —H | —Br |
| I-26 | A7 | morpholin-4-yl | —CF$_3$ | —H | —H | —Br |
| I-27 | A14 | morpholin-4-yl | —Me | [1-(tert-butoxycarbonyl)piperidin-4-yl]aminocarbonyl | —H | —Cl |

TABLE 2-continued

Intermediates

| No. | Exp. Meth. | —R1 | —R2 | —R3 | —R4 | —R5 |
|---|---|---|---|---|---|---|
| I-28 | A4 | morpholin-4-yl | —Me | —CO$_2$Et | —H | —Cl |
| I-29 | A13 | morpholin-4-yl | —Me | —CO$_2$H | —H | —Cl |
| I-30 | A15 | morpholin-4-yl | —CONH$_2$ | —H | —H | —Br |
| I-35 | A4 | morpholin-4-yl | —CH(CH$_3$)CH$_2$CO$_2$Me | | —H | —Cl |
| I-36 | A7 | piperidin-1-yl | —CO$_2$Et | —H | —H | —Br |
| I-37 | A16 | piperidin-1-yl | —CO$_2$Et | —H | —H | pyridin-3-yl |
| I-38 | A16 | piperidin-1-yl | —CO$_2$Et | —H | —H | 2-aminopyrimidin-5-yl |
| I-39 | A18 | morpholin-4-ylmethyl | —CH(CH$_3$)CH$_2$CO$_2$Me | —H | —CHO | —Cl |
| I-40 | A9 | morpholin-4-ylmethyl | —CH(CH$_3$)CH$_2$CO$_2$Me | —H | —CH$_2$OH | —Cl |
| I-43 | A4 | —Cl | —Me | —H | —H | —I |

TABLE 2-continued

Intermediates

[Core structure: imidazo[1,2-a]pyrazine with substituents R1 (8-position), R2 (2-position), R3 (3-position), R4 (5-position), R5 (6-position)]

| No. | Exp. Meth. | —R1 | —R2 | —R3 | —R4 | —R5 |
|---|---|---|---|---|---|---|
| I-44 | A16 | —Cl | —Me | —H | —H | 5-(2-aminopyrimidinyl) |
| I-45 | A4 | morpholin-4-yl | —H | —H | —H | —Br |
| I-46 | A4 | —Cl | —CO₂Et | —H | —H | —I |
| I-47 | A6 | —Cl | —CO₂Et | —Br | —H | —I |
| I-48 | A7 | morpholin-4-yl | —CO₂Et | —Br | —H | —I |
| I-49 | A9 | morpholin-4-yl | —CH₂OH | —Br | —H | —I |
| I-50 | A20 | morpholin-4-yl | —CHO | —Br | —H | —I |
| I-51 | A10 | morpholin-4-yl | —CH₂-(4-methylsulfonylpiperazin-1-yl) | —Br | —H | —I |
| I-55 | A4 | 1-(morpholin-4-yl)-1-methyl | 1-(tetrahydropyran-4-yl)-1-methyl | —H | —H | —Br |
| I-56 | A4 | 1-(morpholin-4-yl)-1-methyl | —CO₂Et | —Me | —H | —Br |
| I-57 | A4 | 1-(morpholin-4-yl)-1-methyl | —CH₂Cl | —H | —H | —Br |

TABLE 2-continued

Intermediates

| No. | Exp. Meth. | —R1 | —R2 | —R3 | —R4 | —R5 |
|---|---|---|---|---|---|---|
| I-58 | A21 | morpholinyl-C(CH₃) | 3-(methylsulfonyl)-3,8-diazabicyclo[3.2.1]octan-8-yl-CH₂-C(CH₃) | —H | —H | —Br |
| I-59 | A21 | morpholinyl-C(CH₃) | 4-hydroxypiperidin-1-yl-CH₂-C(CH₃) | —H | —H | —Br |
| I-59A | A21 | morpholinyl-C(CH₃) | 4-(2-(dimethylamino)acetyl)piperazin-1-yl-CH₂-C(CH₃) | —H | —H | —Br |
| I-60 | A22 | morpholinyl-C(CH₃) | 4-((S)-2-acetoxypropanoyl)piperazin-1-yl-CH₂-C(CH₃) | —H | —H | —Br |
| I-61 | A23 | morpholinyl-C(CH₃) | N-methoxy-N-methylcarboxamide | —H | —H | —Br |

TABLE 2-continued
Intermediates
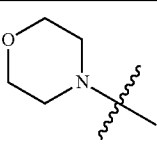
| No. | Exp. Meth. | —R1 | —R2 | —R3 | —R4 | —R5 |
|---|---|---|---|---|---|---|
| I-62 | A24 | 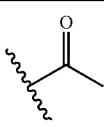 | 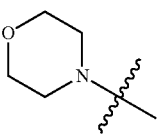 [SMILES: *N1CCOCC1] | —H | —H | —Br |
| I-63 | A25 | 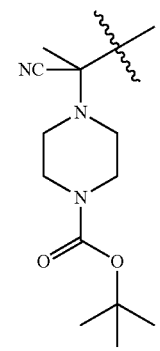 [SMILES: *C(C)(C#N)N1CCN(C(=O)OC(C)(C)C)CC1] | 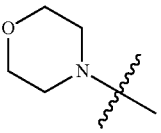 [SMILES: *N1CCOCC1] | —H | —H | —Br |
| I-64 | A26 | 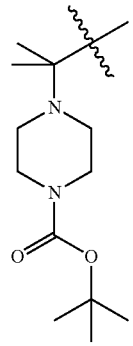 [SMILES: *C(C)(C)N1CCN(C(=O)OC(C)(C)C)CC1] | 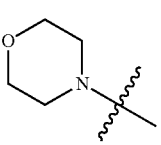 [SMILES: *N1CCOCC1] | —H | —H | —Br |
| I-65 | A10 | 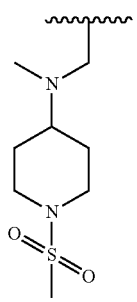 [SMILES: *CN(C)C1CCN(S(C)(=O)=O)CC1] |  | —H | —H | —Br |

TABLE 2-continued

Intermediates

[Structure: imidazo[1,2-a]pyrazine core with R1 at 8-position, R2 at 2-position, R3 at 3-position, R4 at 5-position, R5 at 6-position]

| No. | Exp. Meth. | —R1 | —R2 | —R3 | —R4 | —R5 |
|---|---|---|---|---|---|---|
| I-66 | A10 | morpholin-4-yl | 1-(methylsulfonyl)-1,4-diazepan-4-yl | —H | —H | —Br |
| I-67 | A11 | morpholin-4-yl | piperazin-1-yl (via C(CH$_3$)$_2$ linker) | —H | —H | —Br |
| I-68 | A27 | morpholin-4-yl | 4-(methylsulfonyl)piperazin-1-yl (via C(CH$_3$)$_2$ linker) | —H | —H | —Br |
| I-69 | A3 | morpholin-4-yl | —H | —Me | —H | 4-aminophenyl |
| I-70 | A28 | morpholin-4-yl | —H | —Me | —H | —Br |

TABLE 3
Final Products prepared in accordance with the procedures described herein
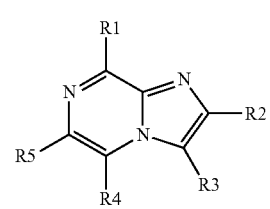
| No. | Exp. | —R1 | —R2 | —R3 | —R4 | —R5 |
|---|---|---|---|---|---|---|
| 2-01 | B1 | 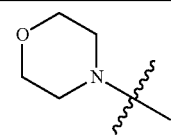 | —CO$_2$Et | —H | —H | 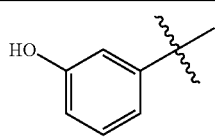 |
| 2-02 | B1 | 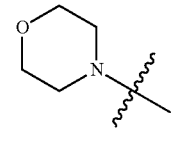 [SMILES: *N1CCOCC1] | —CO$_2$H | —H | —H | 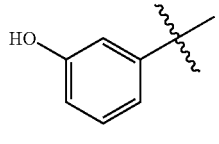 |
| 2-03 | B1 | 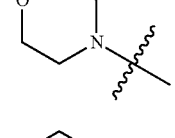 | —CHO | —H | —H | 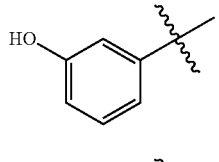 |
| 2-04 | B1 | 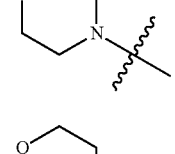 | —CH$_2$OH | —H | —H | 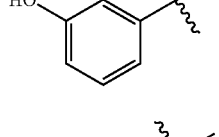 |
| 2-05 | B1 | 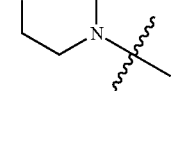 | 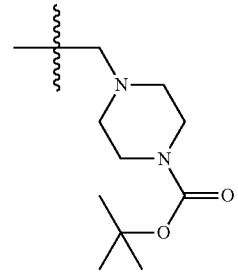 [SMILES: *CN1CCN(C(=O)OC(C)(C)C)CC1] | —H | —H | 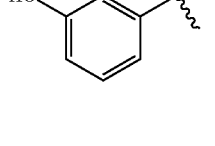 |
| 2-06 | B1 | 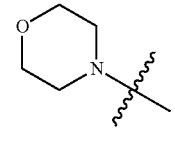 [SMILES: *N1CCOCC1] | 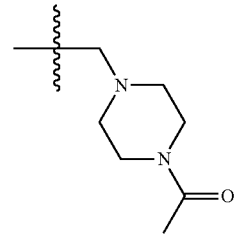 [SMILES: *CN1CCN(C(C)=O)CC1] | —H | —H | 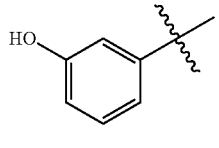 |
| 2-07 | B1 | 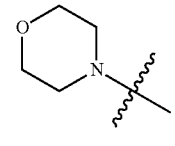 [SMILES: *N1CCOCC1] | 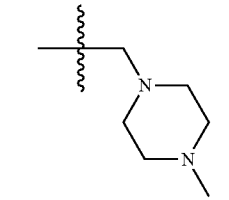 [SMILES: *CN1CCN(C)CC1] | —H | —H | 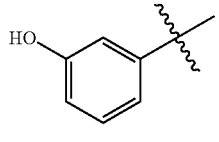 |

TABLE 3-continued

Final Products prepared in accordance with the procedures described herein

| No. | Exp. | —R1 | —R2 | —R3 | —R4 | —R5 |
|---|---|---|---|---|---|---|
| 2-08 | B1 | morpholine | piperazinone-CH2- | —H | —H | 3-hydroxyphenyl |
| 2-09 | B1 | morpholine | morpholine-CH2- | —H | —H | 3-hydroxyphenyl |
| 2-10 | B1 | morpholine | 4-(methylsulfonyl)piperazine-CH2- | —H | —H | 3-hydroxyphenyl |
| 2-11 | B1 | morpholine | 4-(methylsulfonyl)piperazine-C(O)- | —H | —H | 3-hydroxyphenyl |
| 2-12 | B4 | morpholine | —Me | —I | —H | 3-methoxyphenyl |
| 2-13 | B1 | morpholine | —CF3 | —H | —H | 3-hydroxyphenyl |
| 2-14 | B1 | morpholine | cyclopropyl | —H | —H | 3-hydroxyphenyl |

TABLE 3-continued

Final Products prepared in accordance with the procedures described herein

| No. | Exp. | —R1 | —R2 | —R3 | —R4 | —R5 |
|---|---|---|---|---|---|---|
| 2-15 | B1 | morpholinyl | 4-methylpiperazin-1-yl carbonyl | —H | —H | 1H-indazol-4-yl |
| 2-16 | B1 | morpholinyl | 4-(methylsulfonyl)piperazin-1-yl carbonyl | —H | —H | 1H-indazol-4-yl |
| 2-17 | B1 | morpholinyl | [4-(methylsulfonyl)piperazin-1-yl]methyl | —H | —H | 1H-indazol-4-yl |
| 2-18 | B1 | morpholinyl | piperazin-1-yl carbonyl | —H | —H | 1H-indazol-4-yl |
| 2-19 | B1 | morpholinyl | cyclopropyl | —H | —H | 1H-indazol-4-yl |
| 2-20 | B1 | morpholinyl | —CF$_3$ | —H | —H | 1H-indazol-4-yl |

TABLE 3-continued

Final Products prepared in accordance with the procedures described herein

| No. | Exp. | —R1 | —R2 | —R3 | —R4 | —R5 |
|---|---|---|---|---|---|---|
| 2-21 | B2 | morpholin-4-yl | —CONH₂ | —H | —H | 1H-indazol-4-yl |
| 2-22 | B3 | morpholin-4-yl | —CN | —H | —H | 1H-indazol-4-yl |
| 2-23 | B1 | morpholin-4-yl | —Me | —H | —H | 3-hydroxyphenyl |
| 2-24 | B1 | morpholin-4-yl | —Me | —H | —H | 2H-indazol-4-yl |
| 2-25 | B1 | morpholin-4-yl | —Me | —H | —H | 1H-indol-6-yl |
| 2-26 | B1 | morpholin-4-yl | —Me | —H | —H | pyridin-3-yl |
| 2-27 | B1 | morpholin-4-yl | —Me | —H | —H | 5-methoxypyridin-3-yl |

TABLE 3-continued
Final Products prepared in accordance with the procedures described herein
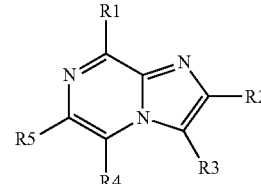
| No. | Exp. | —R1 | —R2 | —R3 | —R4 | —R5 |
|---|---|---|---|---|---|---|
| 2-28 | B1 | 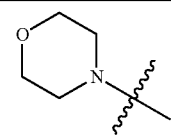 | —Me | —H | —H | 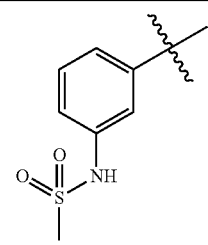 |
| 2-29 | B1 | 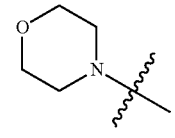 [SMILES: *N1CCOCC1] | —Me | —H | —H | 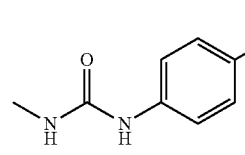 |
| 2-30 | B11 | 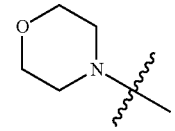 [SMILES: *N1CCOCC1] | —Me | —H | —H | 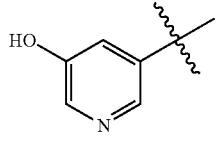 |
| 2-31 | B1 | 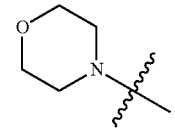 [SMILES: *N1CCOCC1] | —Me | —H | —H | 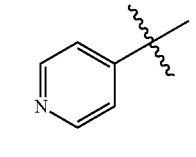 |
| 2-32 | B1 | 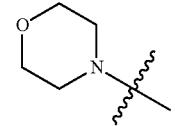 [SMILES: *N1CCOCC1] | —Me | —H | —H | 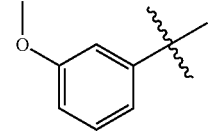 [SMILES: *c1cccc(OC)c1] |
| 2-33 | B4 | 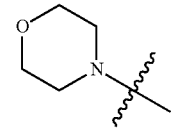 [SMILES: *N1CCOCC1] | —Me | —H | —Cl | 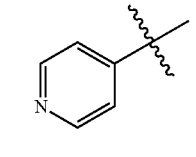 |
| 2-34 | B4 | 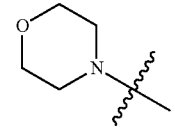 [SMILES: *N1CCOCC1] | —Me | —H | —Cl | 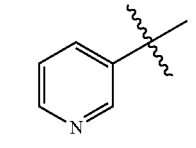 [SMILES: *c1cccnc1] |
| 2-35 | B2 | 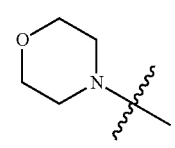 [SMILES: *N1CCOCC1] | —CONH$_2$ | —H | —H | 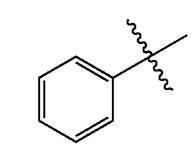 [SMILES: *c1ccccc1] |

TABLE 3-continued
Final Products prepared in accordance with the procedures described herein
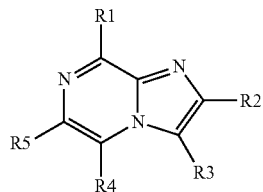
| No. | Exp. | —R1 | —R2 | —R3 | —R4 | —R5 |
|---|---|---|---|---|---|---|
| 2-36 | B14 | morpholinyl | —Me | —H | —CN | 1H-indazol-4-yl |
| 2-37 | B5 | morpholinyl | —H | 4-methylpiperazin-1-yl | —H | 3-hydroxyphenyl |
| 2-38 | B5 | morpholinyl | —H | 4-methylpiperazin-1-yl | —H | 1H-indazol-4-yl |
| 2-39 | B5 | morpholinyl | —H | 4-(methylsulfonyl)piperazin-1-yl | —H | 3-hydroxyphenyl |
| 2-40 | B5 | morpholinyl | —H | piperazin-1-yl | —H | 3-hydroxyphenyl |

TABLE 3-continued
Final Products prepared in accordance with the procedures described herein
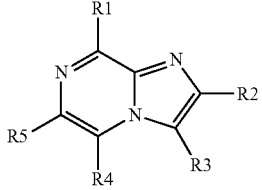
| No. | Exp. | —R1 | —R2 | —R3 | —R4 | —R5 |
|---|---|---|---|---|---|---|
| 2-41 | B5 | 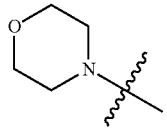 [SMILES: *N1CCOCC1] | —H | 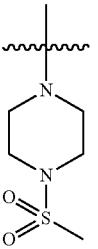 | —H | 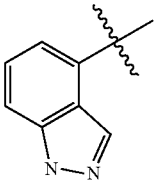 [SMILES: *c1cccc2[nH]ncc12] |
| 2-42 | B1 | 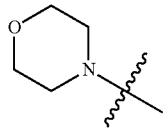 | —Me | —Br | —H | 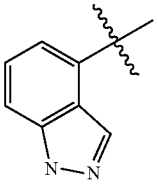 [SMILES: *c1cccc2[nH]ncc12] |
| 2-43 | B6 | 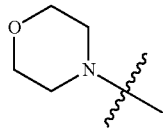 | —Me | 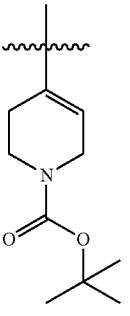 [SMILES: *C1=CCN(C(=O)OC(C)(C)C)CC1] | —H | 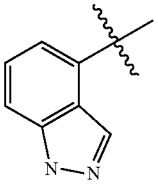 [SMILES: *c1cccc2[nH]ncc12] |
| 2-44 | B7 | 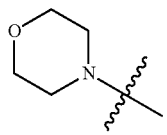 | —Me | 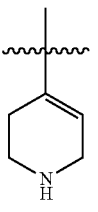 | —H | 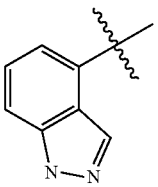 [SMILES: *c1cccc2[nH]ncc12] |
| 2-45 | B8 | 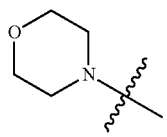 | —Me | 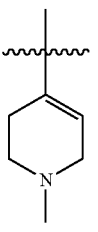 | —H | 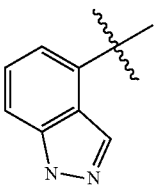 [SMILES: *c1cccc2[nH]ncc12] |

TABLE 3-continued
Final Products prepared in accordance with the procedures described herein
| No. | Exp. | —R1 | —R2 | —R3 | —R4 | —R5 |
|---|---|---|---|---|---|---|
| 2-46 | B9 | 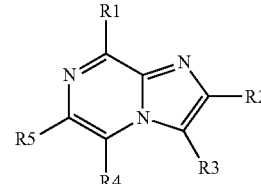 | —Me | 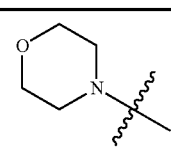 | —H | 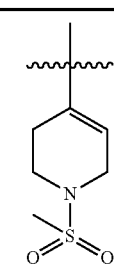 |
| 2-47 | B10 | 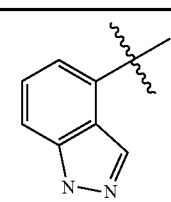 | —Me | 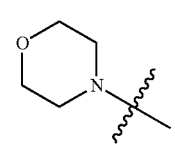 | —H | 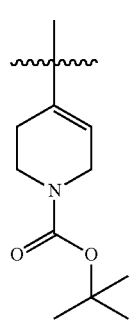 [SMILES: *C1=CCN(C(=O)OC(C)(C)C)CC1] |
| 2-48 | B4 | 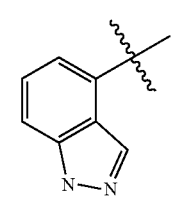 [SMILES: *c1cccc2[nH]ncc12] | —Me | —H | —Cl | 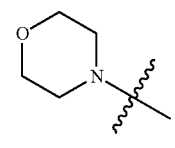 [SMILES: *N1CCOCC1] |
| 2-49 | B11 | 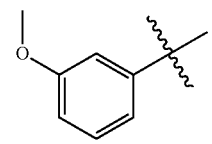 [SMILES: *c1cccc(OC)c1] | —Me | —H | —Cl | 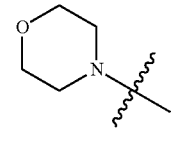 |
| 2-50 | B1 | 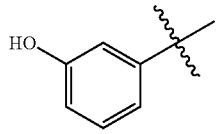 [SMILES: *c1cccc(O)c1] | 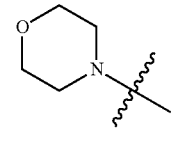 | —H | —H | 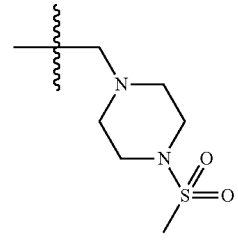 [SMILES: *CN1CCN(S(C)(=O)=O)CC1] |
| 2-51 | B5 | 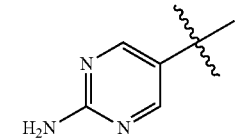 [SMILES: *c1cnc(N)nc1] | —H | 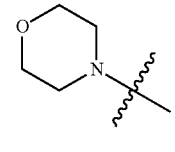 [SMILES: *N1CCOCC1] | —H | 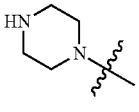 |

TABLE 3-continued

Final Products prepared in accordance with the procedures described herein

| No. | Exp. | —R1 | —R2 | —R3 | —R4 | —R5 |
|---|---|---|---|---|---|---|
| 2-52 | B13 | morpholine (N-linked) | —CO$_2$Et | —H | —H | 1H-indazol-4-yl |
| 2-53 | B4 | morpholine (N-linked) | —Me | —H | —I | 3-methoxyphenyl |
| 2-54 | B4 | morpholine (N-linked) | —Me | —H | —Cl | indazol-4-yl |
| 2-55 | B4 | morpholine (N-linked) | —Me | —H | —Br | indazol-4-yl |
| 2-56 | B4 | morpholine (N-linked) | —Me | —H | —I | pyridin-3-yl |
| 2-57 | B12 | morpholine (N-linked) | —Me | piperidin-4-yl | —H | indazol-4-yl |
| 2-58 | B8 | morpholine (N-linked) | —Me | 1-methylpiperidin-4-yl | —H | indazol-4-yl |

TABLE 3-continued

Final Products prepared in accordance with the procedures described herein

| No. | Exp. | —R1 | —R2 | —R3 | —R4 | —R5 |
|---|---|---|---|---|---|---|
| 2-59 | B9 | morpholine-N- | —Me | 1-(methylsulfonyl)piperidin-4-yl | —H | 1H-indazol-4-yl |
| 2-60 | B4 | morpholine-N- | (4-(methylsulfonyl)piperazin-1-yl)methyl | —H | —Cl | 1H-indazol-4-yl |
| 2-61 | B1 | morpholine-N- | (4-(methylsulfonyl)piperazin-1-yl)methyl | —H | —H | 6-methoxypyridin-3-yl |
| 2-62 | B14 | morpholine-N- | —Me | —CN | —H | 3-methoxyphenyl |
| 2-63 | B1 | morpholine-N- | —Me | N-(1-(tert-butoxycarbonyl)piperidin-4-yl)-2-methylpropanamide-2-yl | —H | 1H-indazol-4-yl |

TABLE 3-continued

Final Products prepared in accordance with the procedures described herein

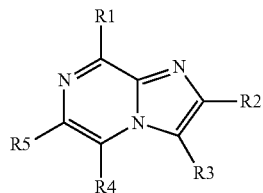

| No. | Exp. | —R1 | —R2 | —R3 | —R4 | —R5 |
|-----|------|-----|-----|-----|-----|-----|
| 2-64 | B12 | morpholinyl | —Me | 2-(piperidin-4-ylamino)-2-oxo-propyl | —H | 1H-indazol-4-yl |
| 2-65 | B1 | morpholinyl | (4-(methylsulfonyl)piperazin-1-yl)methyl | —H | —H | 5-methoxypyridin-3-yl |
| 2-66 | B1 | morpholinyl | (4-(methylsulfonyl)piperazin-1-yl)methyl | —H | —H | 6-aminopyridin-3-yl |
| 2-67 | B1 | morpholinyl | (4-(methylsulfonyl)piperazin-1-yl)methyl | —H | —H | 2-methoxypyrimidin-5-yl |
| 2-68 | B1 | morpholinyl | (4-(methylsulfonyl)piperazin-1-yl)methyl | —H | —H | 4-carbamoylphenyl |

TABLE 3-continued
Final Products prepared in accordance with the procedures described herein
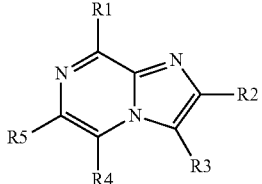
| No. | Exp. | —R1 | —R2 | —R3 | —R4 | —R5 |
|---|---|---|---|---|---|---|
| 2-69 | B1 | 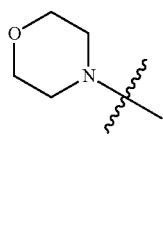 [SMILES: *N1CCOCC1] | 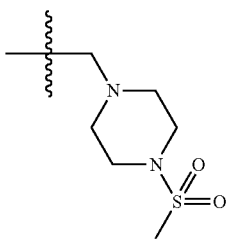 [SMILES: *CN1CCN(S(C)(=O)=O)CC1] | —H | —H | 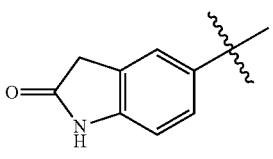 [SMILES: *c1ccc2c(c1)CC(=O)N2] |
| 2-70 | B1 | 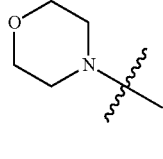 [SMILES: *N1CCOCC1] | 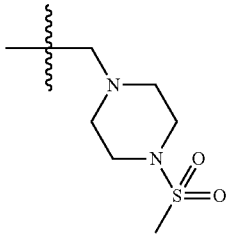 [SMILES: *CN1CCN(S(C)(=O)=O)CC1] | —H | —H | 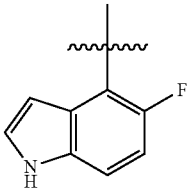 [SMILES: *c1c(F)ccc2[nH]ccc12] |
| 2-71 | B1 | 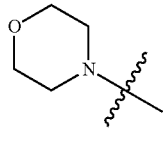 [SMILES: *N1CCOCC1] | 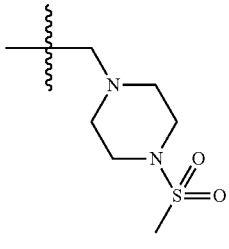 [SMILES: *CN1CCN(S(C)(=O)=O)CC1] | —H | —H | 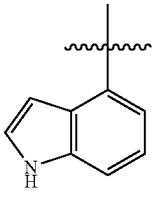 [SMILES: *c1cccc2[nH]ccc12] |
| 2-72 | B1 | 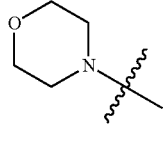 [SMILES: *N1CCOCC1] | 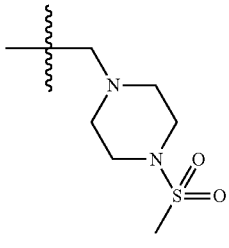 [SMILES: *CN1CCN(S(C)(=O)=O)CC1] | —H | —H | 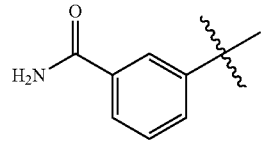 |
| 2-73 | B4 | 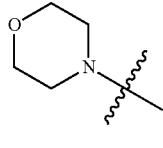 [SMILES: *N1CCOCC1] | —Me | —H | —I | 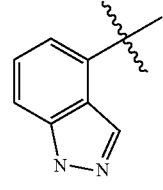 [SMILES: *c1cccc2[nH]ncc12] |

TABLE 3-continued
Final Products prepared in accordance with the procedures described herein
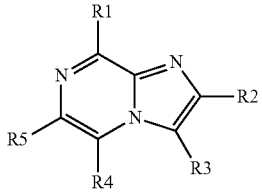
| No. | Exp. | —R1 | —R2 | —R3 | —R4 | —R5 |
|---|---|---|---|---|---|---|
| 2-74 | B2 | 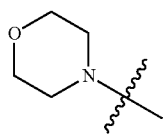 | —CONHEt | —H | —H | 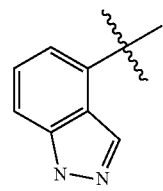 [SMILES: *c1cccc2[nH]ncc12] |
| 2-75 | B1 | 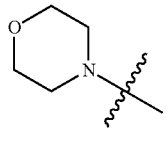 [SMILES: *N1CCOCC1] | 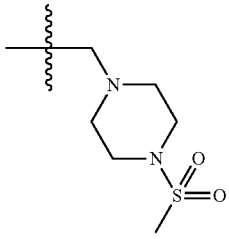 [SMILES: *CN1CCN(S(C)(=O)=O)CC1] | | —H | 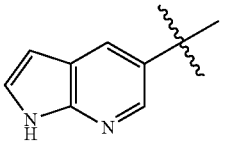 [SMILES: *c1cnc2[nH]ccc2c1] |
| 2-76 | B9 | 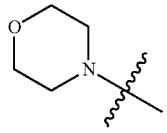 [SMILES: *N1CCOCC1] | —Me | 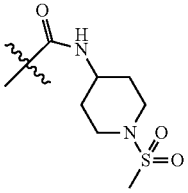 [SMILES: *C(=O)NC1CCN(S(C)(=O)=O)CC1] | —H | 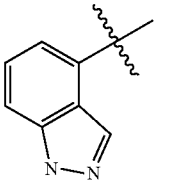 [SMILES: *c1cccc2[nH]ncc12] |
| 2-77 | B12 | 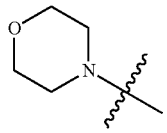 | —Me | —CONH$_2$ | —H | 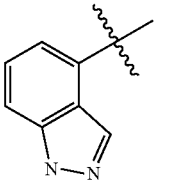 [SMILES: *c1cccc2[nH]ncc12] |
| 2-78 | B5 | 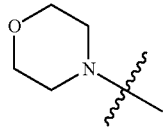 [SMILES: *N1CCOCC1] | —H | 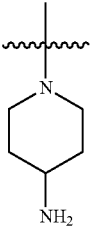 | —H | 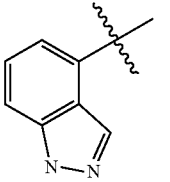 [SMILES: *c1cccc2[nH]ncc12] |
| 2-79 | B15 | 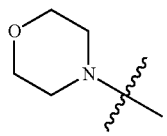 | —CONHMe | —H | —H | 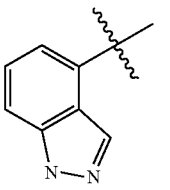 [SMILES: *c1cccc2[nH]ncc12] |

TABLE 3-continued
Final Products prepared in accordance with the procedures described herein
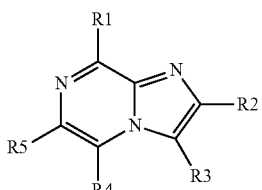
| No. | Exp. | —R1 | —R2 | —R3 | —R4 | —R5 |
|---|---|---|---|---|---|---|
| 2-81 | B1 | 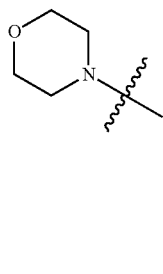 [SMILES: *N1CCOCC1] | 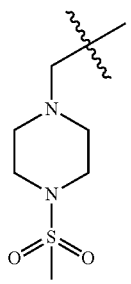 [SMILES: *CN1CCN(S(C)(=O)=O)CC1] | —H | —H | 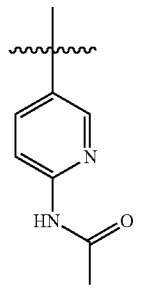 [SMILES: *c1ccc(NC(C)=O)nc1] |
| 2-82 | B1 | 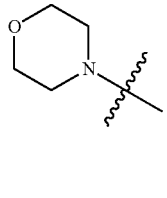 | 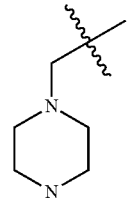 | —H | —H | 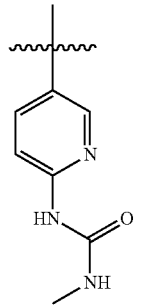 [SMILES: *c1ccc(NC(=O)NC)nc1] |
| 2-83 | B1 | 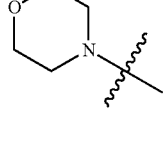 | 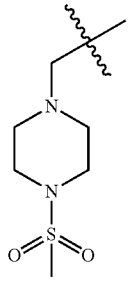 [SMILES: *CN1CCN(S(C)(=O)=O)CC1] | —H | —H | 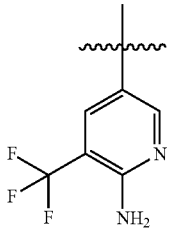 |
| 2-84 | B14 | 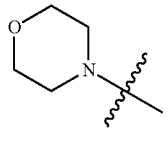 [SMILES: *N1CCOCC1] | 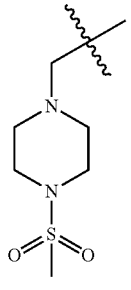 [SMILES: *CN1CCN(S(C)(=O)=O)CC1] | —H | —CN | 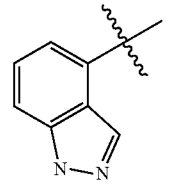 [SMILES: *c1cccc2[nH]ncc12] |

TABLE 3-continued
Final Products prepared in accordance with the procedures described herein
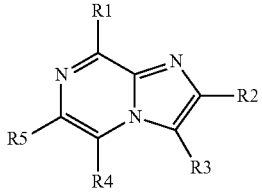
| No. | Exp. | —R1 | —R2 | —R3 | —R4 | —R5 |
|---|---|---|---|---|---|---|
| 2-86 | B15 | 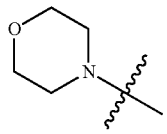 [SMILES: *N1CCOCC1] | —CONMe2 | —H | —H | 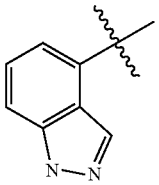 [SMILES: *c1cccc2[nH]ncc12] |
| 2-87 | B16 | 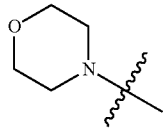 [SMILES: *N1CCOCC1] | 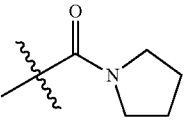 | —H | —H | 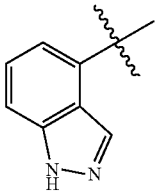 [SMILES: *c1cccc2[nH]ncc12] |
| 2-88 | B11 | 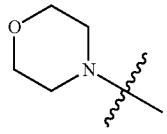 [SMILES: *N1CCOCC1] | —Me | —CN | —H | 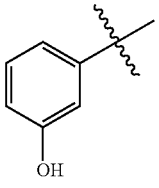 [SMILES: *c1cccc(O)c1] |
| 2-89 | B1 | 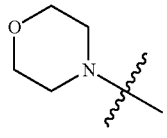 [SMILES: *N1CCOCC1] | 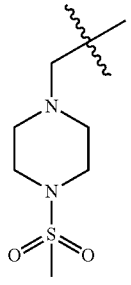 [SMILES: *CN1CCN(S(C)(=O)=O)CC1] | —H | —H | 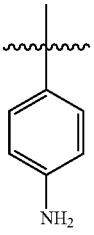 |
| 2-90 | B1 | 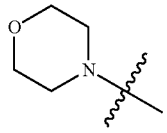 [SMILES: *N1CCOCC1] | 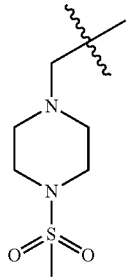 [SMILES: *CN1CCN(S(C)(=O)=O)CC1] | —H | —H | 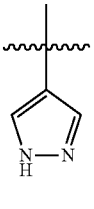 [SMILES: *c1cn[nH]c1] |

TABLE 3-continued

Final Products prepared in accordance with the procedures described herein

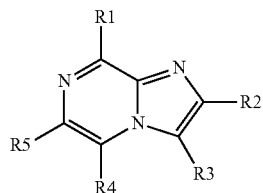

| No. | Exp. | —R1 | —R2 | —R3 | —R4 | —R5 |
|---|---|---|---|---|---|---|
| 2-91 | B13 | morpholinyl-CH< | —CONH2 | —H | —H | pyridin-4-yl (with CH) |
| 2-92 | B13 | morpholinyl-CH< | —CONH2 | —H | —H | pyridin-3-yl (with CH) |
| 2-93 | B13 | morpholinyl-CH< | —CONH2 | —H | —H | 2-aminopyrimidin-5-yl (with CH) |
| 2-94 | B13 | morpholinyl-CH< | —CONH2 | —H | —H | 1H-indol-4-yl (with CH) |
| 2-95 | B13 | morpholinyl-CH< | —CONH2 | —H | —H | 5-fluoro-1H-indol-4-yl (with CH) |
| 2-96 | B4 | morpholinyl-CH< | —CONH2 | —H | —Cl | 2-aminopyrimidin-5-yl (with CH) |

TABLE 3-continued
Final Products prepared in accordance with the procedures described herein
| No. | Exp. | —R1 | —R2 | —R3 | —R4 | —R5 |
|---|---|---|---|---|---|---|
| 2-97 | B17 | 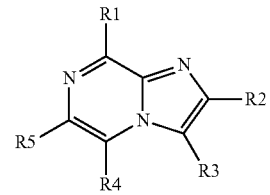 | 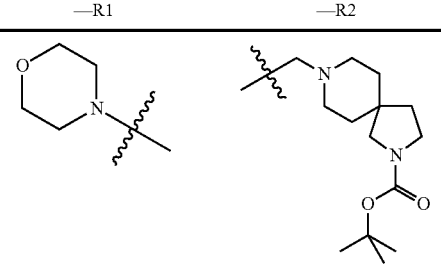 | —H | —H | 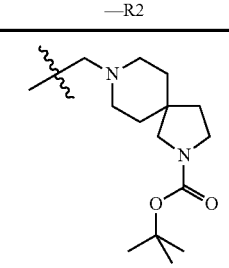 |
| 2-98 | B17 | 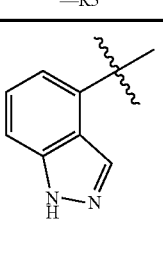 | 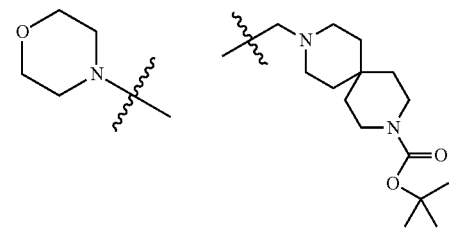 | —H | —H | 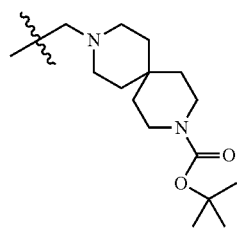 [SMILES: *CN1CCC2(CC1)CCN(C(=O)OC(C)(C)C)CC2] |
| 2-99 | B17 | 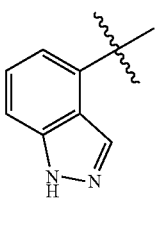 [SMILES: *c1cccc2[nH]ncc12] | 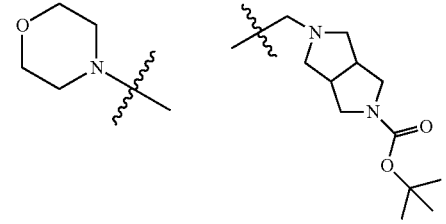 | —H | —H | 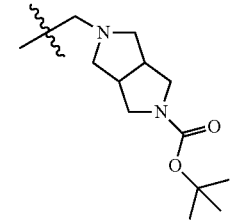 [SMILES: *CN1CC2CN(C(=O)OC(C)(C)C)CC2C1] |
| 2-100 | B17 | 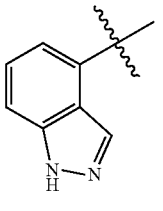 [SMILES: *c1cccc2[nH]ncc12] | 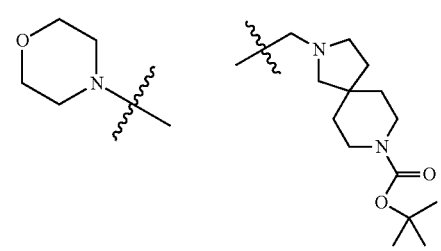 | —H | —H | 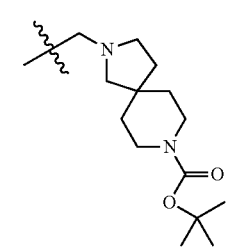 [SMILES: *CN1CCC2(CCN(C(=O)OC(C)(C)C)CC2)C1] |
| 2-101 | B4 | 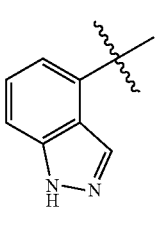 [SMILES: *c1cccc2[nH]ncc12] | —CONH2 | —H | —Cl | 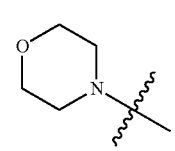 |
| 2-102 | B4 | 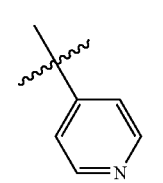 [SMILES: *c1ccncc1] | —CONH2 | —H | —Cl | 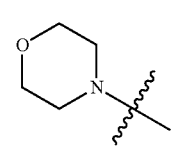 |

TABLE 3-continued

Final Products prepared in accordance with the procedures described herein

| No. | Exp. | —R1 | —R2 | —R3 | —R4 | —R5 |
|---|---|---|---|---|---|---|
| 2-103 | B4 | 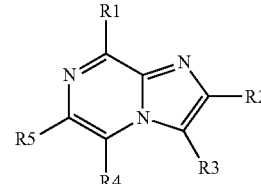 morpholine | —CONH2 | —H | —H | 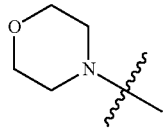 [SMILES: *N1CCOCC1] 3-chloroindol-4-yl |
| 2-104 | B4 | 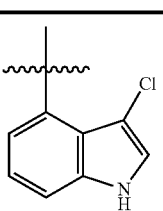 morpholine | —CONH2 | —H | —Cl | 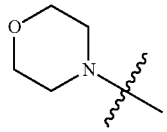 3-chloroindol-4-yl |
| 2-105 | B4 | 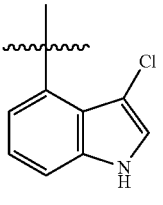 [SMILES: *c1cccc2[nH]cc(Cl)c12] morpholine | —CONH2 | —H | —H | 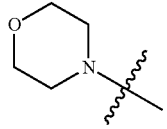 [SMILES: *N1CCOCC1] 3-chloro-5-fluoroindol-4-yl |
| 2-106 | B4 | 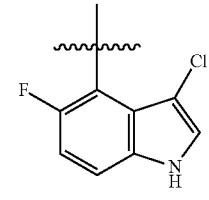 [SMILES: *c1c(F)ccc2[nH]cc(Cl)c12] morpholine | —CONH2 | —H | —Cl | 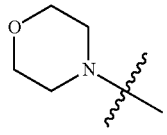 3-chloro-5-fluoroindol-4-yl |
| 2-107 | B13 | 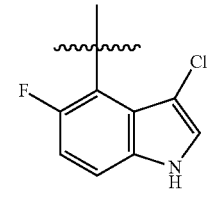 [SMILES: *c1c(F)ccc2[nH]cc(Cl)c12] morpholine | 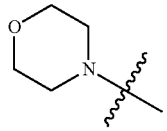 [SMILES: *N1CCOCC1] methyl propanoate | —H | —H | 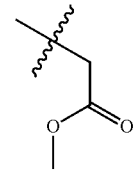 [SMILES: *CC(=O)OC] 1H-indazol-4-yl |
| 2-108 | B4 | 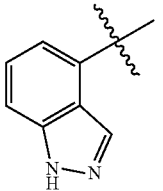 [SMILES: *c1cccc2[nH]ncc12] morpholine | 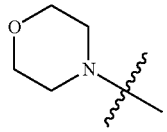 (4-methanesulfonyl-piperazin-1-yl)ethyl | —H | —Cl | 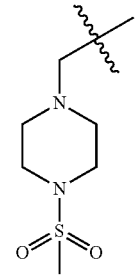 [SMILES: *CN1CCN(S(C)(=O)=O)CC1] 2-aminopyrimidin-5-yl |

TABLE 3-continued
Final Products prepared in accordance with the procedures described herein
| No. | Exp. | —R1 | —R2 | —R3 | —R4 | —R5 |
|---|---|---|---|---|---|---|
| 2-109 | B4 | 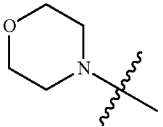 [SMILES: *N1CCOCC1] | 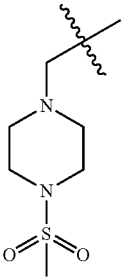 [SMILES: *CN1CCN(S(C)(=O)=O)CC1] | —H | —Cl | 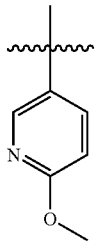 [SMILES: *c1ccc(OC)nc1] |
| 2-110 | B4 | 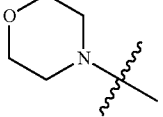 | 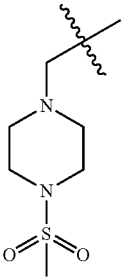 [SMILES: *CN1CCN(S(C)(=O)=O)CC1] | —H | —Cl | 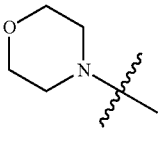 |
| 2-111 | B7 | 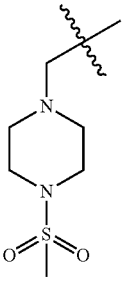 [SMILES: *CN1CCN(S(C)(=O)=O)CC1] | 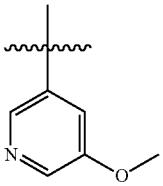 [SMILES: *c1cncc(OC)c1] | —H | —H | 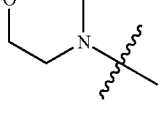 |
| 2-112 | B4 | 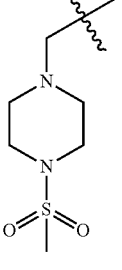 | 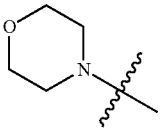 | —H | —Cl | 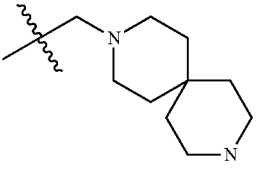 [SMILES: *CN1CCC2(CCNCC2)CC1] |

TABLE 3-continued

Final Products prepared in accordance with the procedures described herein

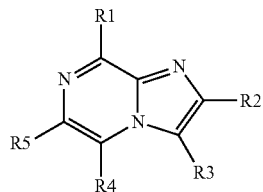

| No. | Exp. | —R1 | —R2 | —R3 | —R4 | —R5 |
|---|---|---|---|---|---|---|
| 2-113 | B4 | morpholine-N-CH< | piperazine-N-CH2-, N'-SO2CH3 | —H | —Cl | 2-oxoindolin-5-yl |
| 2-114 | B4 | morpholine-N-CH< | piperazine-N-CH2-, N'-SO2CH3 | —H | —Cl | 1H-pyrrolo[2,3-b]pyridin-5-yl |
| 2-115 | B4 | morpholine-N-CH< | piperazine-N-CH2-, N'-SO2CH3 | —H | —Cl | 4-chloro-1H-pyrrolo[2,3-b]pyridin-5-yl |
| 2-116 | B4 | morpholine-N-CH< | piperazine-N-CH2-, N'-SO2CH3 | —H | —Cl | 6-aminopyridin-3-yl |

TABLE 3-continued

Final Products prepared in accordance with the procedures described herein

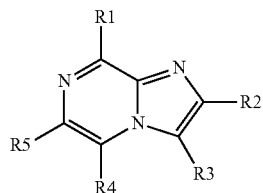

| No. | Exp. | —R1 | —R2 | —R3 | —R4 | —R5 |
|---|---|---|---|---|---|---|
| 2-117 | B7 | morpholinyl | octahydropyrrolo[3,4-c]pyrrol-2-ylmethyl | —H | —H | 1H-indazol-4-yl |
| 2-118 | B7 | morpholinyl | 2,8-diazaspiro[4.5]decan-2-ylmethyl | —H | —H | 1H-indazol-4-yl |
| 2-119 | B2 | piperidinyl | —CONH2 | —H | —H | pyridin-3-yl |
| 2-120 | B2 | piperidinyl | —CONH2 | —H | —H | 2-aminopyrimidin-5-yl |
| 2-121 | B4 | morpholinyl | (4-methylsulfonylpiperazin-1-yl)methyl | —H | —Cl | 4-carbamoylphenyl |

TABLE 3-continued
Final Products prepared in accordance with the procedures described herein
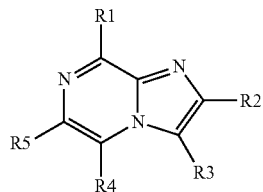
| No. | Exp. | —R1 | —R2 | —R3 | —R4 | —R5 |
|---|---|---|---|---|---|---|
| 2-122 | B4 | morpholine | piperazine-N-SO₂Me | —H | —H | 5-fluoro-3-chloro-1H-indol-4-yl |
| 2-123 | B4 | morpholine | piperazine-N-SO₂Me | —H | —Cl | 5-fluoro-1H-indol-4-yl |
| 2-124 | B4 | morpholine | piperazine-N-SO₂Me | —H | —Cl | 5-fluoro-3-chloro-1H-indol-4-yl |
| 2-125 | B1 | morpholine | piperazine-N-SO₂Me | —H | —H | pyrimidin-5-yl |

TABLE 3-continued
Final Products prepared in accordance with the procedures described herein
| No. | Exp. | —R1 | —R2 | —R3 | —R4 | —R5 |
|---|---|---|---|---|---|---|
| 2-126 | B1 | 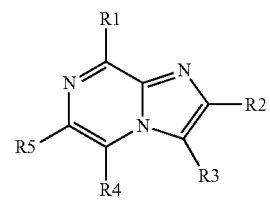 | 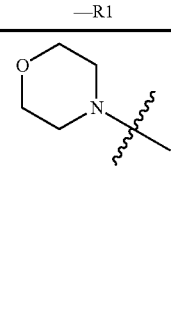 | —H | —H | 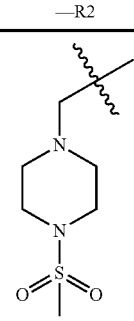 |
| 2-127 | B1 | 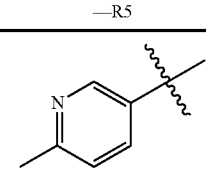 | 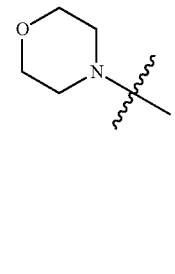 | —H | —H | 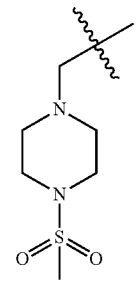 [SMILES: *CN1CCN(S(C)(=O)=O)CC1] |
| 2-128 | B17 | 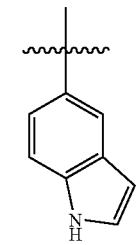 [SMILES: *c1ccc2[nH]ccc2c1] | 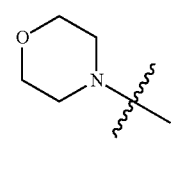 [SMILES: *N1CCOCC1] | —H | —H | 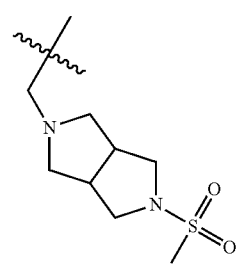 [SMILES: *CN1CC2CN(S(C)(=O)=O)CC2C1] |
| 2-129 | B17 | 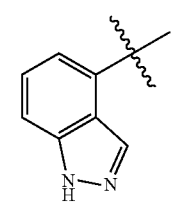 [SMILES: *c1cccc2[nH]ncc12] | 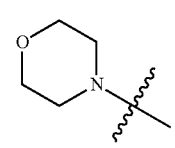 [SMILES: *N1CCOCC1] | —H | —H | 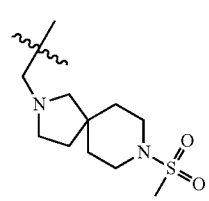 [SMILES: *CN1CCC2(CCN(S(C)(=O)=O)CC2)C1] |
| 2-130 | B17 | 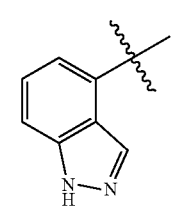 [SMILES: *c1cccc2[nH]ncc12] | 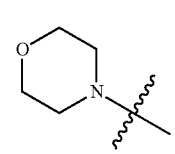 [SMILES: *N1CCOCC1] | —H | —H | 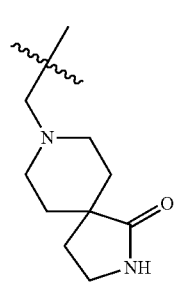 [SMILES: *CN1CCC2(CCNC2=O)CC1] |

TABLE 3-continued

Final Products prepared in accordance with the procedures described herein

| No. | Exp. | —R1 | —R2 | —R3 | —R4 | —R5 |
|---|---|---|---|---|---|---|
| 2-131 | B17 | morpholine | 2,8-diazaspiro[4.5]decan-1-one-8-yl-methyl | —H | —H | 1H-indazol-4-yl |
| 2-132 | B1 | 2-aminopyrimidin-5-yl | —Me | —H | —H | 2-aminopyrimidin-5-yl |
| 2-133 | B5 | morpholine | —H | 3-aminopiperidin-1-yl | —H | 1H-indazol-4-yl |
| 2-134 | B17 | morpholine | 2-(methylsulfonyl)-2,8-diazaspiro[4.5]decan-8-yl-methyl | —H | —H | 1H-indazol-4-yl |
| 2-135 | B4 | morpholine | 4-(methylsulfonyl)piperazin-1-yl-methyl | —H | —Cl | 6-methylpyridin-3-yl |

TABLE 3-continued
Final Products prepared in accordance with the procedures described herein
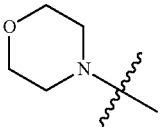 [SMILES: *N1CCOCC1]
| No. | Exp. | —R1 | —R2 | —R3 | —R4 | —R5 |
|---|---|---|---|---|---|---|
| 2-136 | B4 | 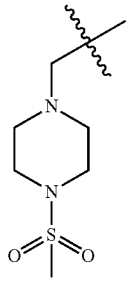 [SMILES: *CN1CCN(S(C)(=O)=O)CC1] | 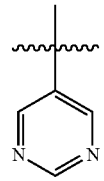 | —H | —Cl | 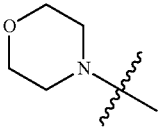 [SMILES: *N1CCOCC1] |
| 2-137 | B1 | 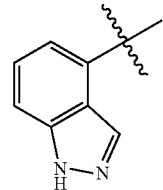 [SMILES: *c1cccc2[nH]ncc12] | —CO$_2$Et | —H | —H | 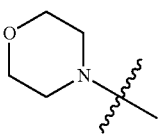 [SMILES: *N1CCOCC1] |
| 2-138 | B1 | 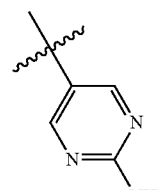 | —CO$_2$Et | —H | —H | 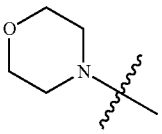 [SMILES: *N1CCOCC1] |
| 2-139 | B16 | 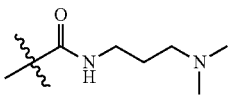 [SMILES: *C(=O)NCCCN(C)C] | 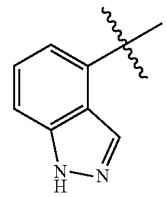 [SMILES: *c1cccc2[nH]ncc12] | —H | —H | 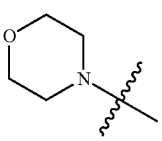 [SMILES: *N1CCOCC1] |
| 2-140 | B16 | 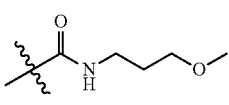 [SMILES: *C(=O)NCCCOC] | 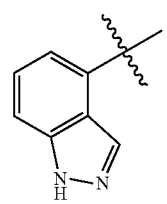 [SMILES: *c1cccc2[nH]ncc12] | —H | —H | 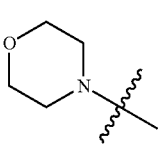 [SMILES: *N1CCOCC1] |
| 2-141 | B16 | 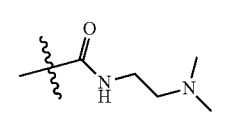 [SMILES: *C(=O)NCCN(C)C] | 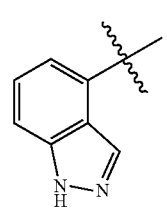 [SMILES: *c1cccc2[nH]ncc12] | —H | —H |  |

TABLE 3-continued
Final Products prepared in accordance with the procedures described herein
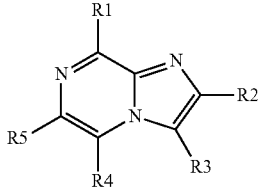
| No. | Exp. | —R1 | —R2 | —R3 | —R4 | —R5 |
|---|---|---|---|---|---|---|
| 2-142 | B16 | 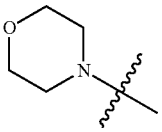 [SMILES: *N1CCOCC1] | 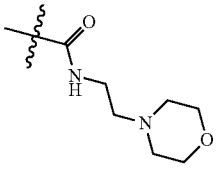 [SMILES: *C(=O)NCCN1CCOCC1] | —H | —H | 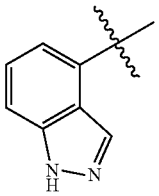 [SMILES: *c1cccc2[nH]ncc12] |
| 2-143 | B7 | 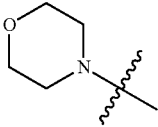 [SMILES: *N1CCOCC1] | —Me | 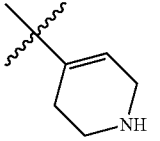 [SMILES: *C1=CCNCC1] | —H | 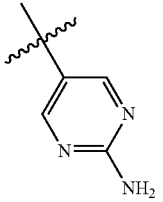 |
| 2-144 | B16 | 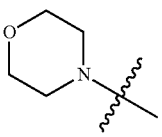 [SMILES: *N1CCOCC1] | 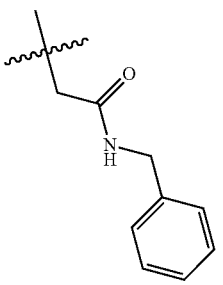 [SMILES: *CC(=O)NCc1ccccc1] | —H | —CH$_2$OH | 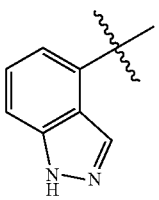 [SMILES: *c1cccc2[nH]ncc12] |
| 2-145 | B17 | 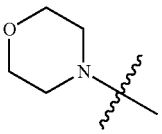 | 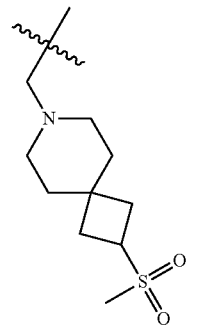 [SMILES: *CN1CCC2(CC1)CC(S(C)(=O)=O)C2] | —H | —H | 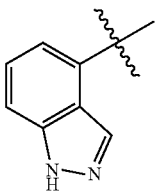 [SMILES: *c1cccc2[nH]ncc12] |
| 2-146 | B16 | 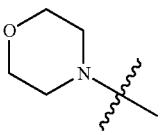 [SMILES: *N1CCOCC1] | 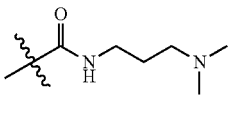 [SMILES: *C(=O)NCCCN(C)C] | —H | —H | 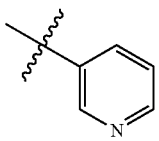 [SMILES: *c1cccnc1] |

TABLE 3-continued
Final Products prepared in accordance with the procedures described herein
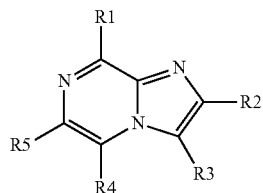
| No. | Exp. | —R1 | —R2 | —R3 | —R4 | —R5 |
|---|---|---|---|---|---|---|
| 2-147 | B16 | morpholine | C(=O)NHCH2CH2N(CH3)2 | —H | —H | 3-pyridyl |
| 2-148 | B16 | morpholine | C(=O)NHCH2CH2CH2OCH3 | —H | —H | 3-pyridyl |
| 2-149 | B17 | morpholine | CH2-(2,8-diazaspiro[5.5]undecane)-N-SO2CH3 | —H | —H | 1H-indazol-4-yl |
| 2-150 | B17 | morpholine | CH2-(2,7-diazaspiro[3.5]nonane)-N-SO2CH3 | —H | —H | 1H-indazol-4-yl |
| 2-151 | B4 | morpholine | CH2-(4-methylsulfonylpiperazin-1-yl) | —H | —Cl | 1H-indol-5-yl |

US 8,778,935 B2
TABLE 3-continued
Final Products prepared in accordance with the procedures described herein
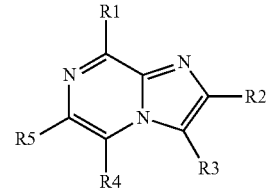
| No. | Exp. | —R1 | —R2 | —R3 | —R4 | —R5 |
|---|---|---|---|---|---|---|
| 2-152 | B1 | 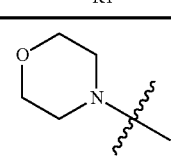 | 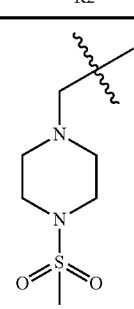 | —H | —H | 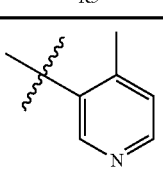 |
| 2-153 | B1 | 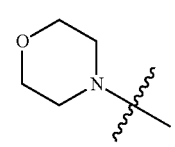 [SMILES: *N1CCOCC1] | 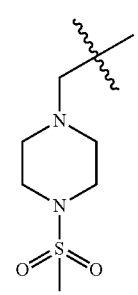 [SMILES: *CN1CCN(S(C)(=O)=O)CC1] | —H | —H | 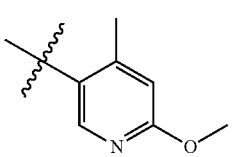 [SMILES: *c1cnc(OC)cc1C] |
| 2-154 | B16 | 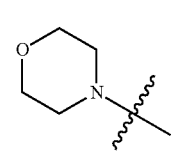 [SMILES: *N1CCOCC1] | 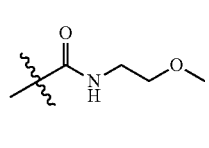 [SMILES: *C(=O)NCCOC] | —H | —H | 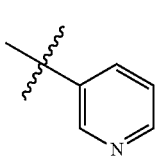 [SMILES: *c1cccnc1] |
| 2-155 | B18 | 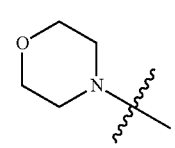 [SMILES: *N1CCOCC1] | 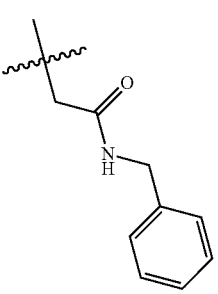 [SMILES: *CC(=O)NCc1ccccc1] | —H | 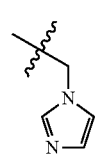 [SMILES: *Cn1ccnc1] | 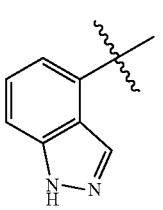 [SMILES: *c1cccc2[nH]ncc12] |
| 2-156 | B10 | 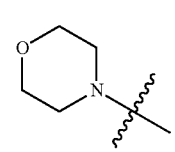 [SMILES: *N1CCOCC1] | —Me | 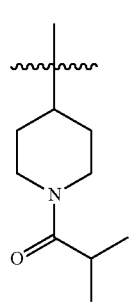 [SMILES: *C1CCN(C(=O)C(C)C)CC1] | —H | 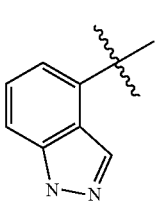 [SMILES: *c1cccc2[nH]ncc12] |

TABLE 3-continued
Final Products prepared in accordance with the procedures described herein
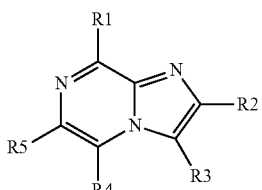
| No. | Exp. | —R1 | —R2 | —R3 | —R4 | —R5 |
|---|---|---|---|---|---|---|
| 2-157 | B16 | 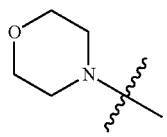 [SMILES: *N1CCOCC1] | 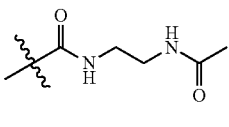 | —H | —H | 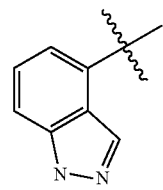 [SMILES: *c1cccc2[nH]ncc12] |
| 2-158 | B16 | 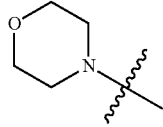 [SMILES: *N1CCOCC1] | 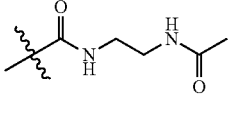 [SMILES: *C(=O)NCCNC(C)=O] | —H | —H | 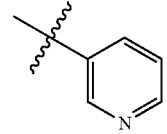 [SMILES: *c1cccnc1] |
| 2-159 | B16 | 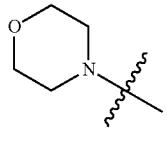 [SMILES: *N1CCOCC1] | 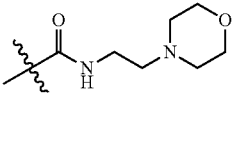 [SMILES: *C(=O)NCCN1CCOCC1] | —H | —H | 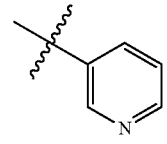 [SMILES: *c1cccnc1] |
| 2-160 | B16 | 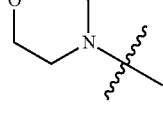 | 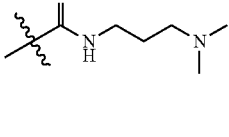 | —H | —H | 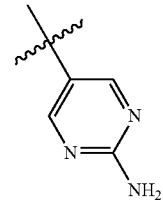 [SMILES: *c1cnc(N)nc1] |
| 2-161 | B16 | 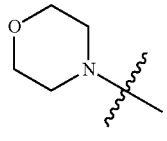 [SMILES: *N1CCOCC1] | 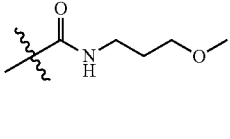 [SMILES: *C(=O)NCCCOC] | —H | —H | 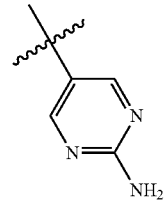 [SMILES: *c1cnc(N)nc1] |
| 2-162 | B16 | 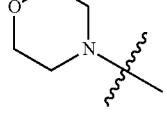 | 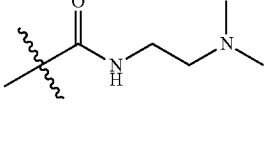 | —H | —H | 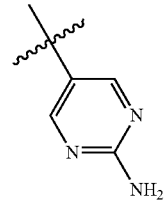 [SMILES: *c1cnc(N)nc1] |

TABLE 3-continued
Final Products prepared in accordance with the procedures described herein
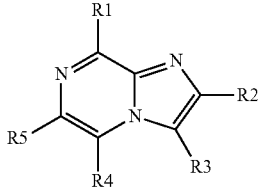
| No. | Exp. | —R1 | —R2 | —R3 | —R4 | —R5 |
|---|---|---|---|---|---|---|
| 2-163 | B16 | 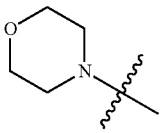 [SMILES: *N1CCOCC1] | 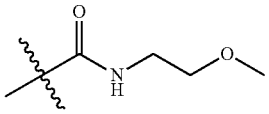 [SMILES: *C(=O)NCCOC] | —H | —H | 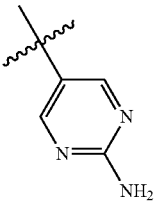 |
| 2-164 | B16 | 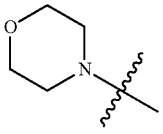 [SMILES: *N1CCOCC1] | 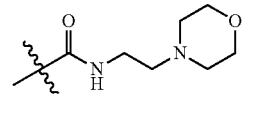 [SMILES: *C(=O)NCCN1CCOCC1] | —H | —H | 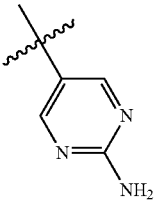 |
| 2-165 | B13 | 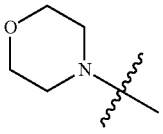 [SMILES: *N1CCOCC1] | 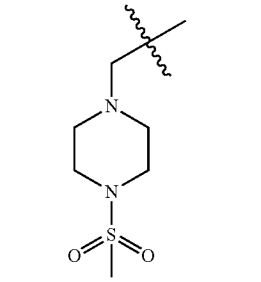 [SMILES: *CN1CCN(S(C)(=O)=O)CC1] | —Me | —H | 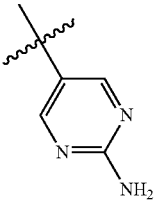 |
| 2-166 | B13 | 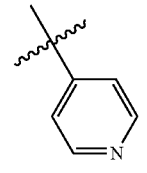 [SMILES: *c1ccncc1] | —Me | —H | —H | 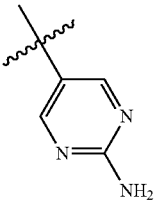 |
| 2-167 | B4 | 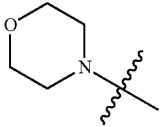 [SMILES: *N1CCOCC1] | 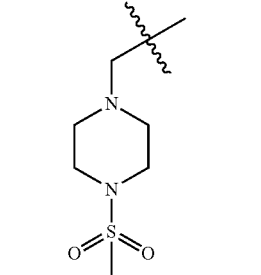 [SMILES: *CN1CCN(S(C)(=O)=O)CC1] | —H | —Cl | 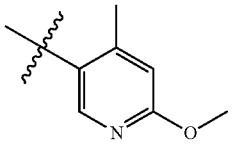 [SMILES: *c1cnc(OC)cc1C] |

TABLE 3-continued

Final Products prepared in accordance with the procedures described herein

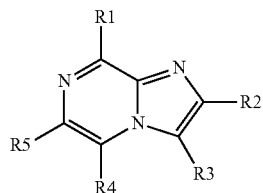

| No. | Exp. | —R1 | —R2 | —R3 | —R4 | —R5 |
|---|---|---|---|---|---|---|
| 2-168 | B13 | 4-pyridyl | —Me | —H | —H | indazol-4-yl |
| 2-169 | B17 | morpholinyl | 2-(7-methylsulfonyl-2,7-diazaspiro[3.5]nonan-2-yl)methyl | —H | —H | 2-amino-pyrimidin-5-yl |
| 2-170 | B17 | morpholinyl | (5-methylsulfonyl-hexahydropyrrolo[3,4-c]pyrrol-2-yl)methyl | —H | —H | 2-amino-pyrimidin-5-yl |
| 2-171 | B1 | morpholinyl | cyclopropyl | —H | —H | 2-amino-pyrimidin-5-yl |
| 2-172 | B1 | morpholinyl | —CF$_3$ | —H | —H | 2-amino-pyrimidin-5-yl |

TABLE 3-continued
Final Products prepared in accordance with the procedures described herein
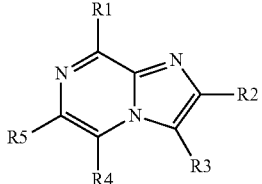
| No. | Exp. | —R1 | —R2 | —R3 | —R4 | —R5 |
|---|---|---|---|---|---|---|
| 2-173 | B4 | 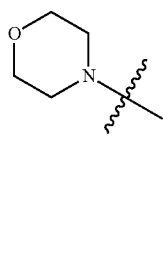 [SMILES: *N1CCOCC1] | 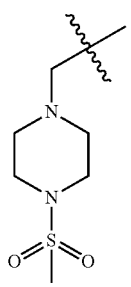 [SMILES: *CN1CCN(S(C)(=O)=O)CC1] | —H | —Cl | 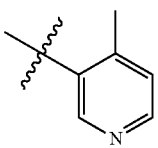 |
| 2-174 | B1 | 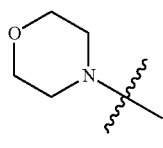 | —H | —H | —H | 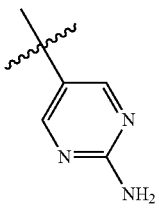 |
| 2-175 | B1 | 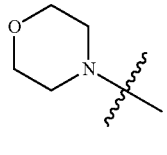 [SMILES: *N1CCOCC1] | 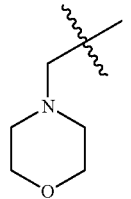 [SMILES: *CN1CCOCC1] | —H | —H | 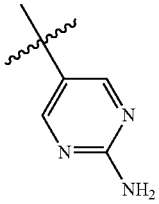 |
| 2-176 | B1 | 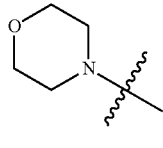 [SMILES: *N1CCOCC1] | 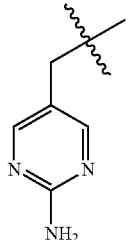 | —H | —H | 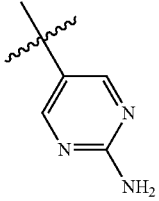 [SMILES: *c1cnc(N)nc1] |
| 2-177 | B19 | 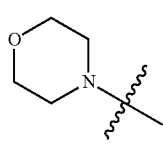 [SMILES: *N1CCOCC1] | 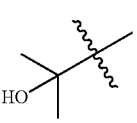 | —H | —H | 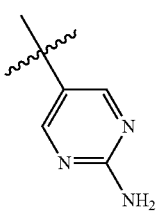 |

TABLE 3-continued
Final Products prepared in accordance with the procedures described herein
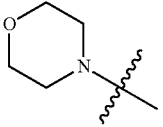 [SMILES: *N1CCOCC1]
| No. | Exp. | —R1 | —R2 | —R3 | —R4 | —R5 |
|---|---|---|---|---|---|---|
| 2-178 | B1 | 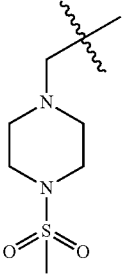 [SMILES: *CN1CCN(S(C)(=O)=O)CC1] | 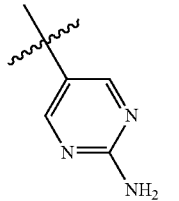 [SMILES: *c1cnc(N)nc1] | —Br | —H | 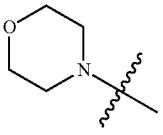 |
| 2-179 | B5 | 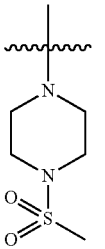 | —H | 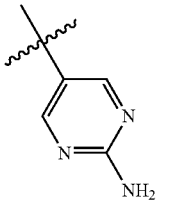 | —H | 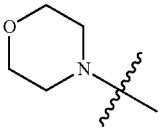 [SMILES: *N1CCOCC1] |
| 2-180 | B14 | 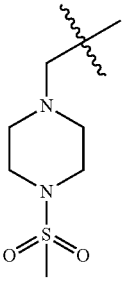 [SMILES: *CN1CCN(S(C)(=O)=O)CC1] | 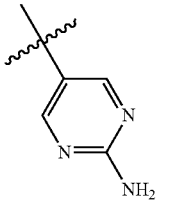 | —H | —CN | 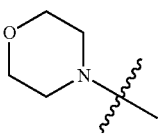 [SMILES: *N1CCOCC1] |
| 2-181 | B1 | 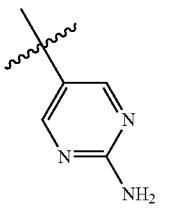 [SMILES: *c1cnc(N)nc1] | —Me | —H | —H | 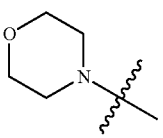 [SMILES: *N1CCOCC1] |
| 2-182 | B16 | 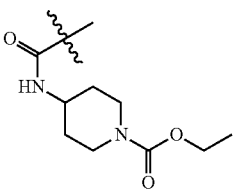 [SMILES: *C(=O)NC1CCN(C(=O)OCC)CC1] | 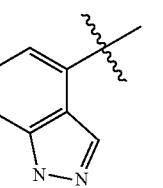 | —H | —H | 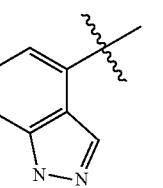 |

TABLE 3-continued

Final Products prepared in accordance with the procedures described herein

| No. | Exp. | —R1 | —R2 | —R3 | —R4 | —R5 |
|---|---|---|---|---|---|---|
| 2-183 | B1 | morpholine | piperazine-N-SO2Me (N-CH2 linker) | —Br | —H | indazol-4-yl |
| 2-184 | B16 | morpholine | —CONHMe | —H | —H | 2-aminopyrimidin-5-yl |
| 2-185 | B4 | morpholine | —Me | —H | —Cl | 2-aminopyrimidin-5-yl |
| 2-186 | B16 | morpholine | —C(=O)NH-CH2CH2-OMe | —H | —H | indazol-4-yl |
| 2-187 | B14 | morpholine | —Me | —H | —CN | 2-aminopyrimidin-5-yl |
| 2-188 | B16 | morpholine | —C(=O)NH-(piperidin-4-yl)-N-CO2Et | —H | —H | 2-aminopyrimidin-5-yl |

TABLE 3-continued
Final Products prepared in accordance with the procedures described herein
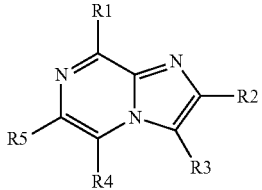
| No. | Exp. | —R1 | —R2 | —R3 | —R4 | —R5 |
|-----|------|-----|-----|-----|-----|-----|
| 2-189 | B4 | 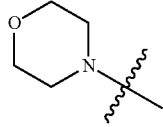 [SMILES: *N1CCOCC1] | —CONHMe | —H | —Cl | 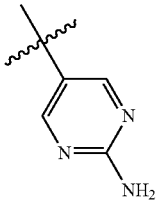 |
| 2-190 | B13 | 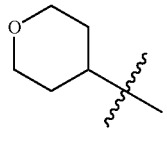 [SMILES: *C1CCOCC1] | —Me | —H | —H | 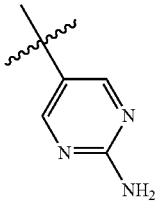 |
| 2-191 | B20 | 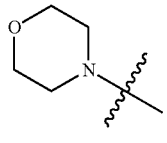 [SMILES: *N1CCOCC1] | 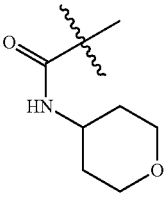 | —H | —H | 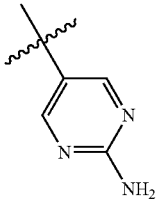 [SMILES: *c1cnc(N)nc1] |
| 2-192 | B20 | 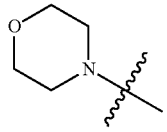 [SMILES: *N1CCOCC1] | 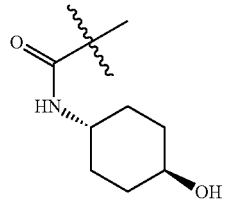 [SMILES: *C(=O)N[C@H]1CC[C@H](O)CC1] | —H | —H | 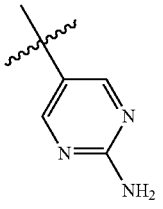 |
| 2-193 | B20 | 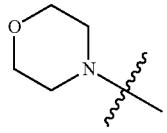 [SMILES: *N1CCOCC1] | 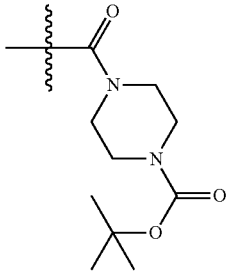 [SMILES: *C(=O)N1CCN(C(=O)OC(C)(C)C)CC1] | —H | —H | 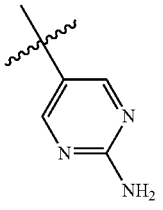 [SMILES: *c1cnc(N)nc1] |

TABLE 3-continued

Final Products prepared in accordance with the procedures described herein

| No. | Exp. | —R1 | —R2 | —R3 | —R4 | —R5 |
|---|---|---|---|---|---|---|
| 2-194 | B4 | morpholinyl-CH | C(O)NH-CH₂CH₂-OMe | —H | —Cl | 2-aminopyrimidin-5-yl |
| 2-195 | B1 | morpholinyl-CH | tetrahydropyran-4-yl | —H | —H | 2-aminopyrimidin-5-yl |
| 2-196 | B1 | morpholinyl-CH | CH₂-(4-methanesulfonyl-piperazin-1-yl) | —H | —H | 2-methylpyrimidin-5-yl |
| 2-197 | B1 | morpholinyl-CH | CH₂-(4-methanesulfonyl-piperazin-1-yl) | —H | —H | 1H-indazol-6-yl |
| 2-198 | B1 | morpholinyl-CH | CH₂-(4-methanesulfonyl-piperazin-1-yl) | —H | —H | 2-amino-3-methylpyridin-5-yl |

TABLE 3-continued
Final Products prepared in accordance with the procedures described herein
| No. | Exp. | —R1 | —R2 | —R3 | —R4 | —R5 |
|---|---|---|---|---|---|---|
| 2-199 | B1 | 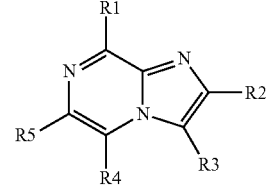 | 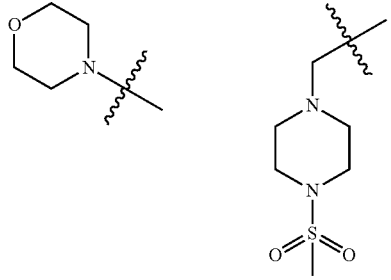 | —H | —H | 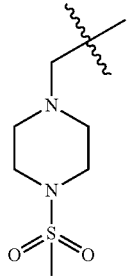 [SMILES: *CN1CCN(S(C)(=O)=O)CC1] |
| 2-200 | B1 | 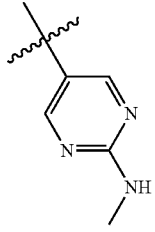 [SMILES: *c1cnc(NC)nc1] | 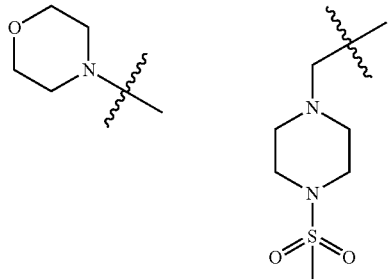 | —H | —H | 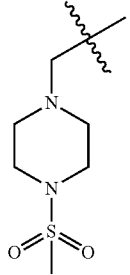 [SMILES: *CN1CCN(S(C)(=O)=O)CC1] |
| 2-201 | B1 | 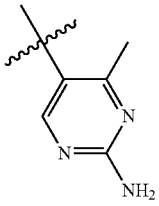 [SMILES: *c1cnc(N)nc1C] | 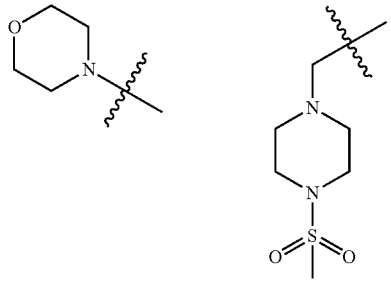 | —H | —H | 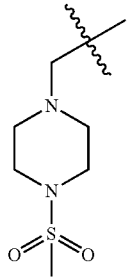 [SMILES: *CN1CCN(S(C)(=O)=O)CC1] |
| 2-202 | B1 | 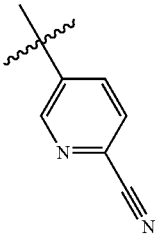 [SMILES: *c1ccc(C#N)nc1] | 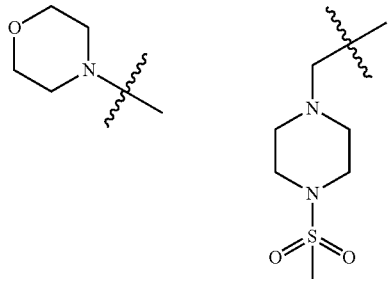 | —H | —H | 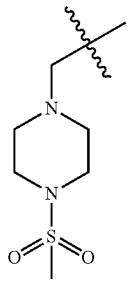 [SMILES: *CN1CCN(S(C)(=O)=O)CC1] |

TABLE 3-continued

Final Products prepared in accordance with the procedures described herein

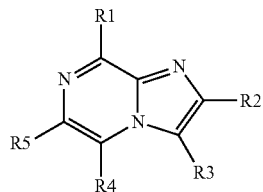

| No. | Exp. | —R1 | —R2 | —R3 | —R4 | —R5 |
|---|---|---|---|---|---|---|
| 2-203 | B1 | morpholinyl | 4-methylsulfonylpiperazin-1-ylmethyl | —H | —H | 2-aminopyridin-4-yl |
| 2-204 | B1 | morpholinyl | 4-methylsulfonylpiperazin-1-ylmethyl | —H | —H | 4-methoxypyridin-3-yl |
| 2-205 | B1 | morpholinyl | 4-methylsulfonylpiperazin-1-ylmethyl | —H | —H | 2-amino-3-fluoropyridin-5-yl |
| 2-206 | B4 | morpholinyl | 4-methylsulfonylpiperazin-1-ylmethyl | —H | —Cl | 6-cyanopyridin-3-yl |

TABLE 3-continued

Final Products prepared in accordance with the procedures described herein

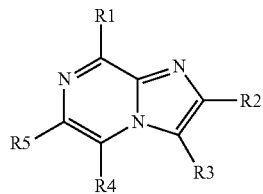

| No. | Exp. | —R1 | —R2 | —R3 | —R4 | —R5 |
|---|---|---|---|---|---|---|
| 2-207 | B4 | morpholinyl | 4-(methylsulfonyl)piperazin-1-ylmethyl | —H | —Cl | 2-(methylamino)pyrimidin-5-yl |
| 2-208 | B4 | morpholinyl | 4-(methylsulfonyl)piperazin-1-ylmethyl | —H | —Cl | 2-amino-4-methylpyrimidin-5-yl |
| 2-209 | B4 | morpholinyl | 4-(methylsulfonyl)piperazin-1-ylmethyl | —H | —Cl | 2-amino-4-(trifluoromethyl)pyrimidin-5-yl |
| 2-210 | B4 | morpholinyl | 4-(methylsulfonyl)piperazin-1-ylmethyl | —H | —Cl | 2-aminopyridin-4-yl |

TABLE 3-continued

Final Products prepared in accordance with the procedures described herein

| No. | Exp. | —R1 | —R2 | —R3 | —R4 | —R5 |
| --- | --- | --- | --- | --- | --- | --- |
| 2-211 | B4 | morpholinyl | 4-(methylsulfonyl)piperazin-1-ylmethyl | —H | —Cl | 4-methoxypyridin-3-yl |
| 2-212 | B4 | morpholinyl | 4-(methylsulfonyl)piperazin-1-ylmethyl | —H | —Cl | 2-methylpyrimidin-5-yl |
| 2-213 | B4 | morpholinyl | 4-(methylsulfonyl)piperazin-1-ylmethyl | —H | —Cl | 1H-indazol-6-yl |
| 2-214 | B1 | morpholinyl | —CO$_2$Et | —Me | —H | 2-aminopyrimidin-5-yl |
| 2-215 | B16 | morpholinyl | —C(O)NH-CH$_2$CH$_2$-OMe | —Me | —H | 2-aminopyrimidin-5-yl |

TABLE 3-continued

Final Products prepared in accordance with the procedures described herein

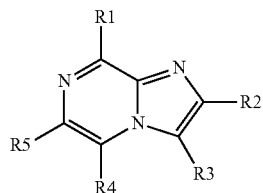

| No. | Exp. | —R1 | —R2 | —R3 | —R4 | —R5 |
|---|---|---|---|---|---|---|
| 2-216 | B20 | morpholinomethyl | —C(CH3)2C(O)NHCH2CH2OCH3 | —Cl | —H | 2-aminopyrimidin-5-yl |
| 2-217 | B15 | morpholinomethyl | —C(CH3)2C(O)NH2 | —Me | —H | 2-aminopyrimidin-5-yl |
| 2-218 | B13 | morpholinomethyl | (2,6-dimethyl-4-Boc-piperazin-1-yl)methyl | —H | —H | 2-aminopyrimidin-5-yl |
| 2-219 | B9 | morpholinomethyl | (2,6-dimethyl-4-methylsulfonyl-piperazin-1-yl)methyl | —H | —H | 2-aminopyrimidin-5-yl |

TABLE 3-continued
Final Products prepared in accordance with the procedures described herein
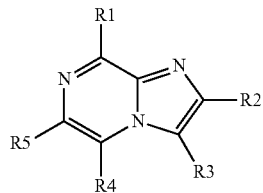
| No. | Exp. | —R1 | —R2 | —R3 | —R4 | —R5 |
|---|---|---|---|---|---|---|
| 2-220 | B13 | morpholinyl-CH< | piperazinyl-CH2- (N-SO2Et) | —H | —H | 2-aminopyrimidin-5-yl |
| 2-221 | B13 | morpholinyl-CH< | piperazinyl-CH2- (N-SO2-iBu) | —H | —H | 2-aminopyrimidin-5-yl |
| 2-222 | B13 | morpholinyl-CH< | thiomorpholine-1,1-dioxide-CH2- | —H | —H | 2-aminopyrimidin-5-yl |
| 2-223 | B13 | 3-(hydroxymethyl)morpholinyl-CH< | —Me | —H | —H | 2-aminopyrimidin-5-yl |

TABLE 3-continued
Final Products prepared in accordance with the procedures described herein
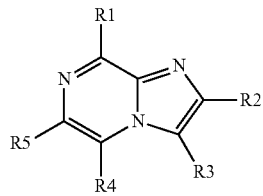
| No. | Exp. | —R1 | —R2 | —R3 | —R4 | —R5 |
|---|---|---|---|---|---|---|
| 2-224 | B13 | ![morpholine with CH2CO2Me] | —Me | —H | —H | ![2-aminopyrimidin-5-yl] |
| 2-225 | B13 | ![morpholine] | ![CH2-piperazine-SO2Ph] | —H | —H | ![2-aminopyrimidin-5-yl] |
| 2-226 | B13 | ![morpholine] | ![CH2-piperazine-NH] | —H | —H | ![2-aminopyrimidin-5-yl] |
| 2-227 | B13 | ![morpholine with CO2Me] | —Me | —H | —H | ![2-aminopyrimidin-5-yl] |

TABLE 3-continued

Final Products prepared in accordance with the procedures described herein

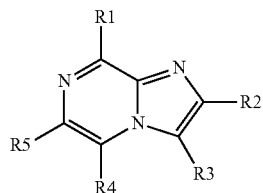

| No. | Exp. | —R1 | —R2 | —R3 | —R4 | —R5 |
|---|---|---|---|---|---|---|
| 2-228 | B13 | morpholine | 3-methylsulfonyl-3,8-diazabicyclo[3.2.1]octane-CH< | —H | —H | 2-aminopyrimidin-5-yl |
| 2-229 | B13 | morpholine | 4-hydroxypiperidine-CH< | —H | —H | 2-aminopyrimidin-5-yl |
| 2-230 | B13 | morpholine | 4-(dimethylaminoacetyl)piperazine-CH< | —H | —H | 2-aminopyrimidin-5-yl |
| 2-231 | B13 | morpholine | 4-((S)-2-acetoxypropanoyl)piperazine-CH< | —H | —H | 2-aminopyrimidin-5-yl |

TABLE 3-continued

Final Products prepared in accordance with the procedures described herein

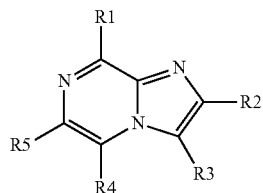

| No. | Exp. | —R1 | —R2 | —R3 | —R4 | —R5 |
|---|---|---|---|---|---|---|
| 2-232 | B13 | morpholinyl-C(CH3)2– | 4-Boc-piperazinyl-C(CH3)2– | —H | —H | 2-aminopyrimidin-5-yl-C(CH3)– |
| 2-233 | B13 | morpholinyl-C(CH3)2– | N-methyl-N-(1-methanesulfonylpiperidin-4-yl)aminoethyl | —H | —H | 2-aminopyrimidin-5-yl-C(CH3)– |
| 2-234 | B21 | morpholinyl-C(CH3)2– | 4-((S)-2-hydroxypropanoyl)piperazinyl-CH2-C(CH3)2– | —H | —H | 2-aminopyrimidin-5-yl-C(CH3)– |
| 2-235 | B13 | morpholinyl-C(CH3)2– | 4-methanesulfonyl-1,4-diazepan-1-yl-CH2-C(CH3)2– | —H | —H | 2-aminopyrimidin-5-yl-C(CH3)– |

TABLE 3-continued
Final Products prepared in accordance with the procedures described herein
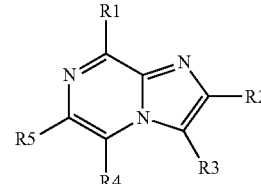
| No. | Exp. | —R1 | —R2 | —R3 | —R4 | —R5 |
|---|---|---|---|---|---|---|
| 2-236 | B12 | 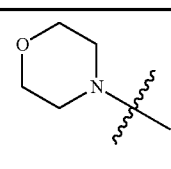 | 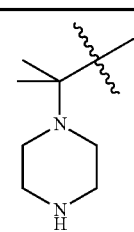 | —H | —H | 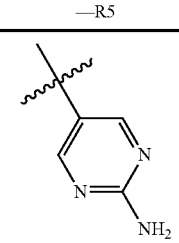 |
| 2-237 | B22 | 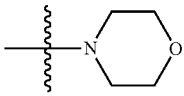 [SMILES: *N1CCOCC1] | —Me | —CO$_2$Et | —H | 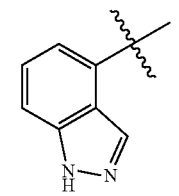 [SMILES: *c1cccc2[nH]ncc12] |
| 2-238 | B23 | 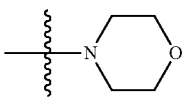 | —Me | —CO$_2$H | —H | 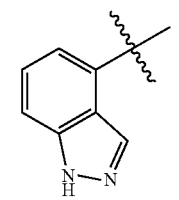 [SMILES: *c1cccc2[nH]ncc12] |
| 2-239 | B1 | 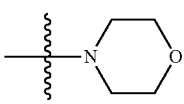 | —CHO | —H | —H | 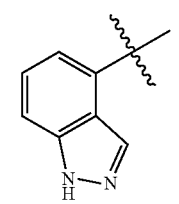 [SMILES: *c1cccc2[nH]ncc12] |
| 2-240 | B1 | 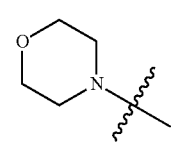 [SMILES: *N1CCOCC1] | 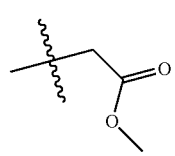 [SMILES: *CC(=O)OC] | —H | —CH$_2$OH | 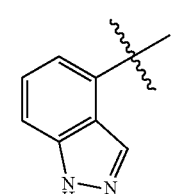 |
| 2-241 | B24 | 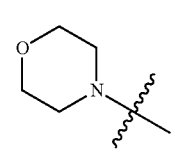 [SMILES: *N1CCOCC1] | —Me | 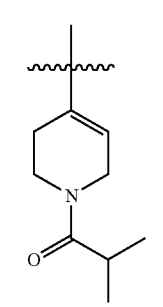 [SMILES: *C1=CCN(C(=O)C(C)C)CC1] | —H | 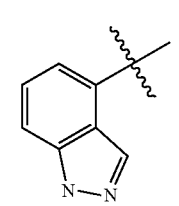 [SMILES: *c1cccc2[nH]ncc12] |

TABLE 3-continued

Final Products prepared in accordance with the procedures described herein

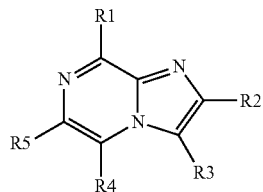

| No. | Exp. | —R1 | —R2 | —R3 | —R4 | —R5 |
|---|---|---|---|---|---|---|
| 2-242 | B1 | morpholinomethyl | 1-(methylsulfonyl)piperazinyl-t-butyl | —H | —H | 2-aminopyrimidin-5-yl |
| 2-243 | B25 | morpholinomethyl | —H | —Me | —H | 4-[3-(4-methylpiperazine-1-carbonyl)phenylureido]phenyl |
| 2-244 | B23 | morpholinomethyl | —H | —Me | —H | 4-[3-carboxyphenylureido]phenyl |
| 2-245 | B26 | morpholinomethyl | —H | —Me | —H | 4-[3-(methoxycarbonyl)phenylureido]phenyl |

TABLE 3-continued

Final Products prepared in accordance with the procedures described herein

| No. | Exp. | —R1 | —R2 | —R3 | —R4 | —R5 |
|---|---|---|---|---|---|---|
| 2-246 | A13 | 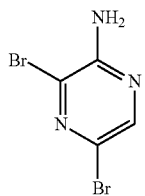 | —CO$_2$H | —H | —H | 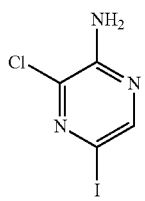 |

Experimental Part

Preparation of the Intermediates

Method A1
Preparation of Intermediate I-01.

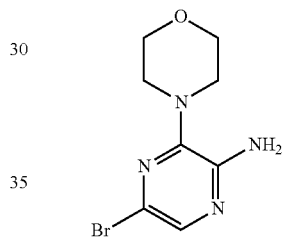

To a mixture of 2-amino pyrazine (50 g, 0.5 mol) in chloroform (1000 ml) cooled to 0° C. was added pyridine (100 ml, 1.21 mol) and bromine (54 ml, 1.05 mmol) dropwise. The mixture was stirred at rt for 16 h, then water was added. The organic phase was extracted, dried (MgSO$_4$), filtered and evaporated to obtain I-01, 48 g (Y: 36%) of a yellow solid which was dried in vacuo.

Preparation of Intermediate I-53

To a mixture of 2-amino-3-chloropyrazine (3.627 g, 28.00 mmol) in acetonitrile (20 mL), N-iodosuccinimide (6.929 g, 30.800 mmol) and trifluoroacetic acid (2.2 mL) were added. The reaction mixture was stirred at it for 18 h. EtOAc was added and the mixture was washed with Na$_2$S$_2$O$_3$, dried, filtered and evaporated. The residue was purified in by column chromatography (EtOAc:Cyclohexane, 0:100 to 40:60) to render 5.1 g of Intermediate I-53 (71%).

Method A2
Preparation of Intermediate I-02.

A solution of intermediate I-01 (15 g, 59.3 mmol) in morpholine (15 ml, 178 mmol) was heated at 120° C. in a Parr reactor for 48 h. A brown solid appears. The solid was suspended in DCM and washed with NaHCO$_3$ aq. sat (twice). The organic phase was dried (NaSO$_4$), filtered and evaporated to dryness to obtain 1-02, 14.8 g of a brown solid (Y: 96%)

Method A3
Preparation of Intermediate I-03.

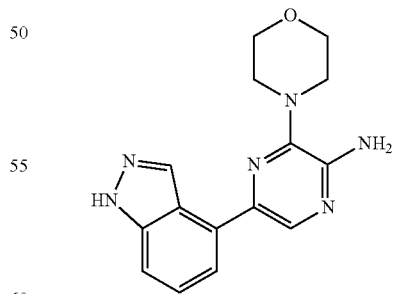

A mixture of intermediate I-02 (360 mg, 1.35 mmol), indazole-4-boronic acid hydrochloride (600 mg, 2.97 mmol), K$_2$CO$_3$ (2 mL of saturated solution), PdCl$_2$(dppf).DCM (112 mg, 0.135 mmol) in DME (5 mL) was heated under microwave irradiation for 10 min at 130° C. The reaction mixture was filtered through a celite pad, washing with DCM. The filtrate was dried over Na₂SO₄ and concentrated. The crude was purified by flash column chromatography (Isolute Si II 10 g cartridge) eluting with a gradient of DCM/MeOH (from 100% to 90:10) to yield 250 mg of the intermediate I-03 pure (Y: 62%).

Preparation of Intermediate I-69.

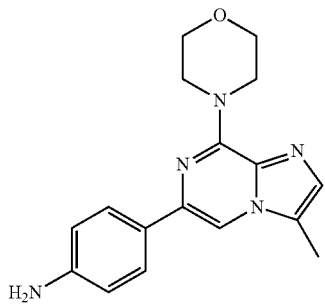 [SMILES: Cc1cnc2c(N3CCOCC3)nc(-c3ccc(N)cc3)cn12]

A mixture of Intermediate I-70 (45 mg, 0.15 mmol), 4-(4,4,5,5-tetramethyl-1,3,2-dioxaborolan-2-yl)aniline (40 mg, 0.18 mmol), PdCl₂(dppf) (12 mg, 0.02 mmol) and Na₂CO₃ (sat aq sol; 0.75 mL) in 1,2-DME (0.75 mL) was heated under microwave irradiation at 130° C. for 1 h. The mixture was diluted with DCM:MeOH, adsorbed on celite and purified by chromatography (Isolute 5 g; MeOH:DCM, 0:100 to 20:80) to give Intermediate I-69 (50 mg, 100%) as a yellow solid.

Method A4

Preparation of Intermediate I-05.

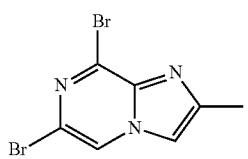

Intermediate I-01 (2 g, 7.9 mmol) was solved in 2-chloroacetone (3 ml,). The reaction was heated in a sealed tube at 90° C. for 16 h. A precipitate appears. Then Et₂O was added. The precipitate was filtered off as a salt. The resulting solid was suspended in DCM and treated with an aqueous saturated solution of Na₂CO₃. The organic phase was extracted, dried (MgSO₄), filtered and evaporated to obtain the intermediate I-05 (1.2 g of a brown solid, Y: 35%)

Preparation of Intermediate I-28.

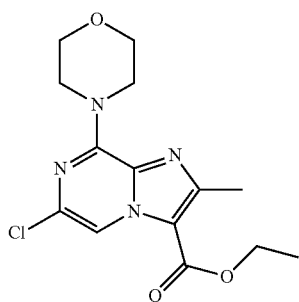 [SMILES: CCOC(=O)c1c(C)nc2c(N3CCOCC3)nc(Cl)cn12]

Intermediate I-02 (1.2 g, 4.7 mmol) and ethyl 2-chloroacetoacetate (2.3 g, 14.2 mmol) were suspended in EtOH (12 mL). The mixture was heated under microwave irradiation for 1 h at 150° C. After cooling down to room temperature, petroleum ether was added and the solid formed was filtered off. The filtrate was evaporated under reduced pressure and the residue was purified by flash chromatography on silica gel (c-Hex/EtAOAc 8:2) to obtain a solid that was washed with petroleum ether to give the desired product I-28 (231 mg, Y: 33%).

Preparation of Intermediate I-35.

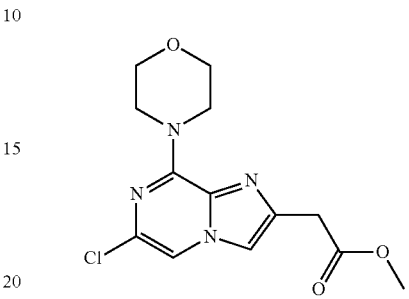

Intermediate I-02 (2 g, 7.72 mmol) and methyl 4-chloroacetoacetate (3.56 mL, 30.88 mmol) were heated in two sealed tubes (half of material in each tube) at 90° C. for 2 h. Volatiles were removed under reduced pressure and the residue was purified by flash chromatography on silica gel (c-Hex/EtAOAc 10:0 to 6:4) to obtain a solid that was washed with diethyl ether to render the desired product I-35 (1.17 g, Y: 49%).

Preparation of Intermediate I-57.

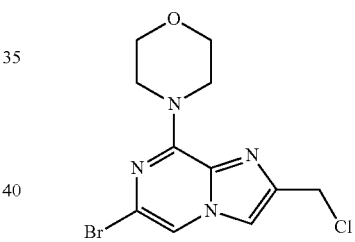

A mixture of Intermediate I-02 (8.17 g, 31.52 mmol) and 1,3-dichloroacetone (6.0 g, 47.29 mmol) in 2-propanol (15 mL) was heated in a sealed tube at 55° C. for 2 days. On cooling, the mixture was filtered and rinsed with Et₂O and MeOH. The solid was purified by flash chromatography on silica gel (MeOH:DCM, 5:95) and the product obtained was washed with MeOH and dried to give Intermediate I-57 (3.97 g, 38%).

Method A5

Preparation of Intermediate I-06.

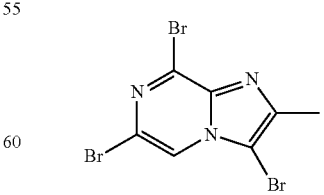

Intermediate I-05 (0.62 g, 2.13 mmol) was dissolved in CHCl₃ (4 mL) and N-bromosuccinimide (455 mg, 2.56 mmol) was added. The reaction mixture was heated under microwave irradiation at 120° C. for 1 h. On cooling, the mixture was adsorbed in silica and purified by Biotage column chromatography (DCM/MeOH from 100% to 95:5) to give intermediate I-06 (720 mg, Y: 91%) as a yellow solid.
Method A6
Preparation of Intermediate I-09.

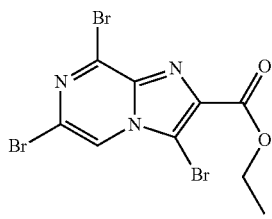 [SMILES: CCOC(=O)c1nc2c(Br)nc(Br)cn2c1Br]

Intermediate I-07 (1.00 g, 2.87 mmol) was dissolved in DCM (28 mL) and N-bromosuccinimide (0.61 g, 3.44 mmol) and trifluoroacetic acid (0.25 mL) were added. The reaction mixture was stirring at rt for 16 h and then heated at 60° C. for 2 h more. The reaction mixture was cooled, and washed with water. The organic phase was dried ($Na_2SO_4$), filtered and the solvent removed in vacuum. The residue was purified by biotage with a gradient cyclohexane/EtOAc: from 100% to 50:50 The desired fractions were collected to obtained 1.15 g of a white solid as intermediate I-09 (Y: 94%).
Method A7
Preparation of Intermediate I-10.

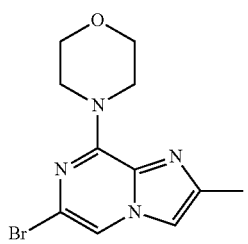 [SMILES: Cc1cn2cc(Br)nc(N3CCOCC3)c2n1]

A mixture of Intermediate I-05 (1.75 g, 6.015 mmol), morpholine (0.526 mL, 6.015 mmol) and DCM (20 mL) was stirred at it for 16 h. Additional morpholine (0.526 mL, 6.015 mmol) was added and the mixture was stirred at it for 18 h more. $Na_2CO_3$ sat. aq. was added. The organic phase was separated, dried ($Na_2SO_4$), filtered and evaporated till dryness to obtain 1.8 g of intermediate I-10 (Y: quantitative). The resulting product was used in the next step without further purification.
Preparation of Intermediate I-11.

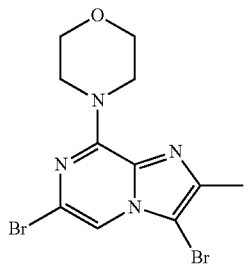 [SMILES: Cc1nc2c(N3CCOCC3)nc(Br)cn2c1Br]

Intermediate I-06 (0.72 g, 1.95 mmol) was dissolved in DCM (6 mL) and morpholine (0.68 mL, 7.79 mmol) was added in one portion. The reaction mixture was stirred at rt for 3 h. The mixture was purified, together with a second batch of the same reaction, by column chromatography (DCM/MeOH from 100% to 50:50) to give the expected product intermediate I-11 (980 mg, Y: 76%) as a clear yellow solid.
Preparation of Intermediate I-48

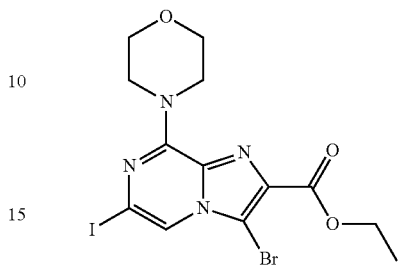

To a mixture of Intermediate I-47 (2.25 g, 5.22 mmol) in acetonitrile (20 mL) morpholine (0.59 mL, 6.79 mmol) and N,N-diisopropylethylamine (1.36 mL, 7.84 mmol) were added. The reaction mixture was heated under microwave irradiation at 160° C. for 30 min. On cooling, $NH_4Cl$ was added and the mixture was extracted with DCM. The organic layer was dried ($Na_2SO_4$), filtered and evaporated. The residue was precipitated with $Et_2O$ and MeOH to render Intermediate I-48 (1.875 g, 75%) as a white solid. The filtrate was evaporated and purified by column chromatography (Cyclohexane:EtOAc, 100:0 to 60:40) to render 620 mg of Intermediate I-48 (24%).
Preparation of Intermediate I-36.

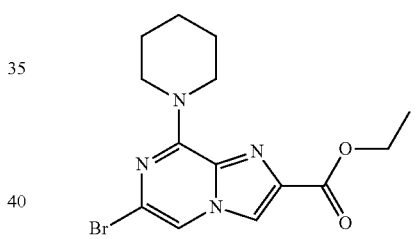

Intermediate I-07 (0.50 g, 1.40 mmol) was suspended in DCE (8 mL) and piperidine (0.18 mL, 1.7 mmol) was added dropwise. The reaction mixture was heated at 60° C. for 16 h. Additional piperidine (0.05 mL) was added and heating continued for 2 h. The suspension at RT was filtered affording a solid (impurities) and the filtrate that was concentrated. The resulting residue was triturated with Et2O to render another solid (impurities) and the filtrate that was concentrated to afford the required intermediate I-36 as light orange solid (400 mg, Y: 80%).
Method A8
Preparation of Intermediate I-13.

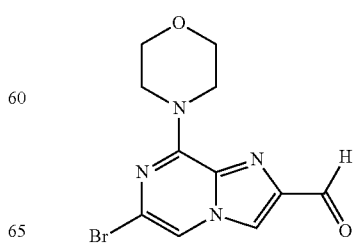

To a solution of intermediate I-12 (2 g, 5.6 mmol) in DCM (50 mL) was added dropwise DIBAL (3.8 mL, 1 M in toluene, 22.75 mmol) at −78° C. stirring at that temperature for 40 min. The reaction was quenched with cold methanol and stirred for 10 min. more. The mixture was poured into a biphasic mixture of saturated NaHCO₃ and DCM and allowed to warm to room temperature with occasional stirring. It was then passed though a Celite bed to remove a gelatinous mass, and the bed was throughly washed with DCM. After the organic layer was separated, the aqueous layer was extrated with DCM. The combined organic phase was dried (Na₂SO₄), filtered and concentrated under reduced pressure to obtain a light yellow solid, 1.674 g, Y: 96% as intermediate I-13 which was used in next reaction step without further purification.
Method A9
Preparation of Intermediate I-14.

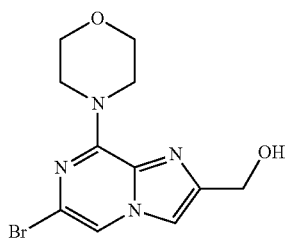

To a stirred slurry of LiAlH₄ (556 mg, 14.64 mmol) in dry THF was slowly added intermediate I-12 (5.63 mmol) in THF (28 mL) at 0° C. After the addition, the reaction mixture was stirred at room temperature for 2 h and quenched with saturated NH₄Cl/NH₄OH. The mixture was poured into CHCl₃/MeOH (3:1) and it was then passed though a Celite bed to remove a gelatinous mass, and the bed was thoroughly washed with CHCl₃. The organic layer was washed with saturated NaCl. The organic phase was dried (Na₂SO₄), filtered and evaporated under reduced pressure to obtain the expected product I-14 as a light yellow solid (1.02 g, Y: 57% yield) which was used in next reaction step without further purification.
Preparation of Intermediate I-40

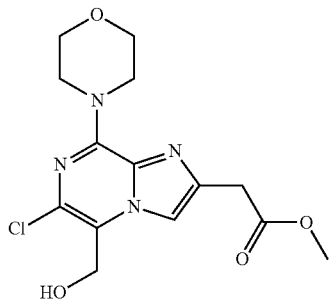 [SMILES: COC(=O)Cc1cn2c(CO)c(Cl)nc(N3CCOCC3)c2n1]

A solution of Intermediate I-39 (1 g, 2.952 mmol) in THF (10 mL) was slowly added to a stirred slurry of NaBH₄ (123 mg, 3.247 mmol) in dry THF (11 mL) at 0° C. The mixture was stirred 2 h at rt. The solvent was removed and the residue was suspended in H₂O and extracted with EtOAc. The organic layer was dried (Na₂SO₄), filtered and evaporated concentrated. The residue was used in the next experiment without further purification.

Preparation of Intermediate I-49

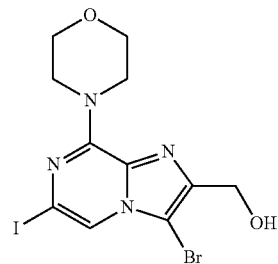 [SMILES: OCc1nc2c(N3CCOCC3)nc(I)cn2c1Br]

To a solution of Intermediate I-48 (1.3 g, 2.7 mmol) in DCM (25 mL) was added diisobutylaluminum hydride (1M in toluene) (2.7 mL, 2.7 mmol) dropwise at 0° C. The reaction mixture was stirred at rt for 16 h and more DIBAL (2.7 mL) was added. Stirring was continued at rt for 2 days and another eq. of DIBAL was added (2.7 mL). After 2 days the reaction was quenched with cold MeOH, stirred for 10 min and poured into a biphasic mixture of H₂O/DCM. The suspension was filtered off to render Intermediate I-49 (0.86 g). The organic layer was extracted with DCM, dried, filtered and evaporated to render Intermediate I-49 (320 mg) as a white solid.
Method A10
Preparation of Intermediate I-16

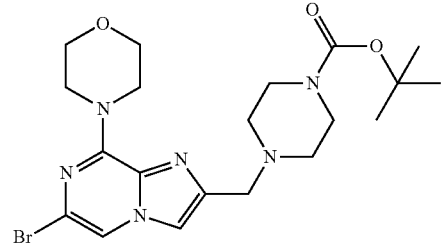 [SMILES: CC(C)(C)OC(=O)N1CCN(Cc2cn3cc(Br)nc(N4CCOCC4)c3n2)CC1]

A mixture of intermediate I-13 (520 mg, 1.67 mmol), 1-boc-piperazine (405 mg, 2.17 mmol) and trimethyl orthoformate (1.83 mL, 16.71 mmol) was stirred in 1,2-dichloroethane (14 mL) for 6 h at room temperature. Then sodium triacetoxyborohydride (425 mg, 2.0 mmol) was added and the reaction mixture was stirred for 48 h at room temperature. The mixture was then quenched with brine and extracted with DCM. The organic phase was dried (Na₂SO₄), filtered and evaporated in vacuo. The residue was purified by silica gel column chromatography in Biotage by eluting it with cyclohexane/ethyl acetate and then with DCM/MeOH to obtain intermediate I-16, 475 mg, Y: 60% as a light yellow solid.
Method A11
Preparation of Intermediate I-17.

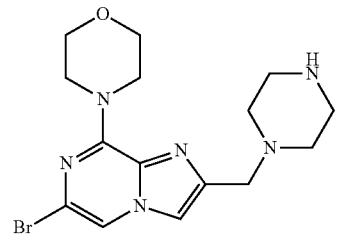 [SMILES: Brc1cn2cc(CN3CCNCC3)nc2c(N2CCOCC2)n1]

Intermediate I-16 (0.380 mg, 0.789 mmol) was dissolved in DCM (10 mL) and 2N HCl (2 mL) was added and the reaction was stirred at rt for 16 h. Because only starting material was observed, the solvent was evaporated and THF 3 mL and 3 mL HCl (2N) were added and the reaction mixture was stirred for 2 h. The solvent was removed in vacuo to obtain intermediate I-17 as a chlorohydrate salt (307 mg, Y: 93%) which was used in the next reaction without further purification.

Method A12

Preparation of Intermediate I-23.

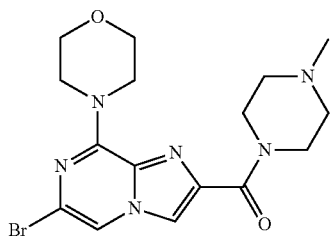 [SMILES: CN1CCN(C(=O)c2cn3cc(Br)nc(N4CCOCC4)c3n2)CC1]

Methylpiperazine (0.282 mmol, 32 μL) and AlMe₃ 2M in hexanes (0.282 mmol, 0.14 mL) in dry DCM (4 mL) was stirred at rt for 15 min. Then intermediate I-12 (100 mg, 0.282 mmol) was added and the mixture was stirred at rt for 3 h and then at 40° C. overnight. The reaction was quenched with sat sol of ammonium chloride and diluted with DCM. The organic phase was dried (Na₂SO₄), filtered and evaporated to afford a residue which was triturated with Et₂O-DCM precipitating an off white solid as an impurity. The filtrate was purified by flash chromatography (Biotage Hex-EtOAc from 100% to 70:30 and then DCM-MeOH/NH₃ 7N 80:20 to obtain 67 mg (Y: 48%) of required product as intermediate I-23.

Method A13

Preparation of Intermediate I-29

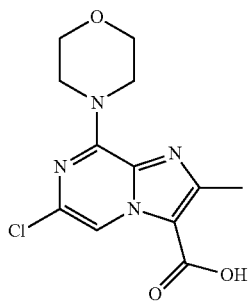 [SMILES: Cc1nc2c(N3CCOCC3)nc(Cl)cn2c1C(=O)O]

2N NaOH (0.85 mL) was added to a stirred mixture of intermediate I-28 in MeOH. The reaction was stirred at 50° C. for 1.5 h and at reflux for 20 min. The solvent was evaporated and water was added and the pH was adjusted to 4 by addition of AcOH. The mixture was diluted with EtOAc (until a clear solution was obtained (ca 250 mL). The layers were separated and the aqueous layer was extracted twice with EtOAc. The organic layer was dried and evaporated. The residue was azeotropically dried with toluene to give 261 mg (Y: 100%) of desired product I-29 which was used in next reaction step without further purification.

Method A14

Preparation of Intermediate I-27

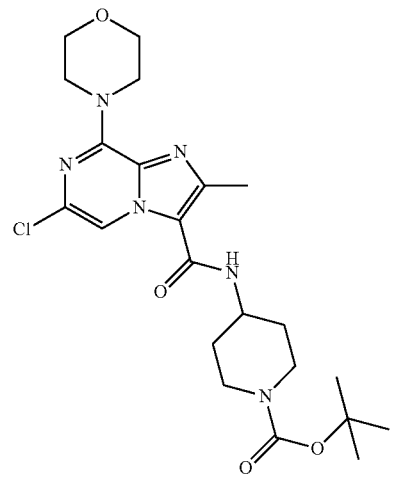 [SMILES: Cc1nc2c(N3CCOCC3)nc(Cl)cn2c1C(=O)NC1CCN(C(=O)OC(C)(C)C)CC1]

4-Amine-1-BOC piperidine was added to a stirred mixture of intermediate I-29, DIPEA and HATU in DMF. The reaction was stirred at rt for 4 h. The reaction mixture was directly chromatographed on silica gel (biotage c-Hex/EtOAc 10 to 100% EtOAc) to obtain the desired product (233 mg, Y: for two steps: 69%).

Method A15

Preparation of Intermediate I-30

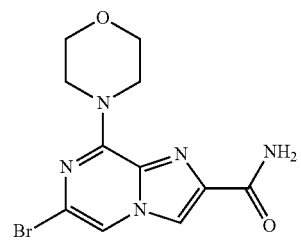 [SMILES: NC(=O)c1cn2cc(Br)nc(N3CCOCC3)c2n1]

Intermediate I-12 (240 mg) in a seal tube, was suspended in a solution of MeOH/NH₃ 7N. The reaction mixture was heated at 100° C. for 16 h. The solvent was evaporated to dryness and the residue was washed with MeOH and Et₂O. the resulting yellow solid was dried in vacuo to obtain 200 mg of desired product I-30. Alternatively, a precipitate may appear, which may be filtered off to obtain the desired product I-30.

Method A16

Preparation of Intermediate I-44

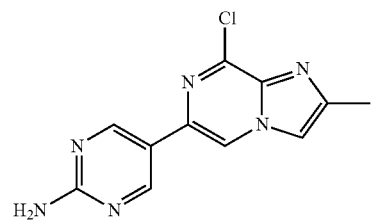 [SMILES: Cc1cn2cc(-c3cnc(N)nc3)nc(Cl)c2n1]

A mixture of Intermediate I-43 (0.15 g, 0.51 mmol), 2-aminopyrimidine-5-boronic acid, pinacol ester (136 mg, 0.613 mmol) and PdCl₂(dppf) (42 mg, 0.051 mmol) and sat. sol. Na₂CO₃ (1.96 mL) in 1,2-DME (1.96 mL) was stirred at r.t. for 1 h 30 min. DCM was added and the mixture was washed with H₂O and sat. NaCl. The organics were dried (Na₂SO₄), filtered and evaporated. The residue was purified by column chromatography (DCM:MeOH, 99:1 to 90:10) to render Intermediate I-44 (10 mg, 8%) as a beige solid.
Method A18
Preparation of Intermediate I-39

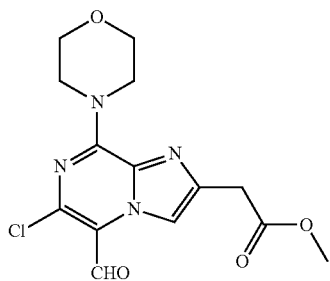 [SMILES: COC(=O)Cc1cn2c(C=O)c(Cl)nc(N3CCOCC3)c2n1]

To a solution of Intermediate I-35 (3/6 g, 12.11 mmol) in DMF (120 mL) was added POCl₃ (3.38 mL, 36.34 mmol) at −20° C. The mixture was stirred at rt overnight under N₂ and diluted with H₂O/ice. The white solid was filtered off and dried to render 2.95 g (63%) of Intermediate I-39. It was used in the next experiment without further purification.
Method A20
Preparation of Intermediate I-50

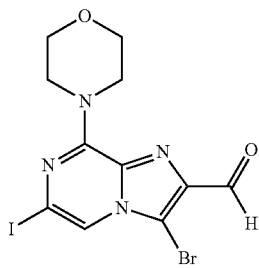 [SMILES: O=Cc1nc2c(N3CCOCC3)nc(I)cn2c1Br]

To a solution of Intermediate I-49 (1.18 g, 2.7 mmol) in CHCl₃ (54 mL) activated MnO₂ (4.0 g, 45.93 mmol) was added. The reaction mixture was refluxed for 8 h. On cooling, the mixture was filtered through celite. The filtrate was evaporated to render Intermediate I-50 (0.67 g). It was used in the next reaction without further purification.
Method A21
Preparation of Intermediate I-58

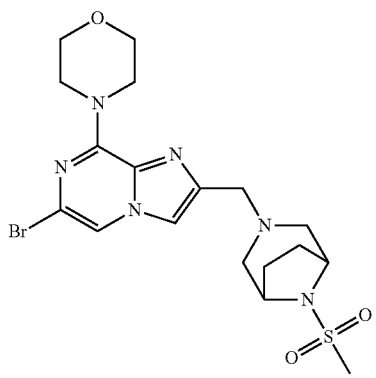 [SMILES: CS(=O)(=O)N1C2CCC1CN(Cc1cn3cc(Br)nc(N4CCOCC4)c3n1)C2]

To a suspension of Intermediate I-57 (0.232 g, 0.7 mmol) and K₂CO₃ (0.193 g, 1.4 mmol) in Acetonitrile (20 mL) was added 8-methanesulfonyl-3,8-diaza-bicyclo[3.2.1]octane ((0.133 g, 0.7 mmol). The reaction mixture was refluxed for 24 h and concentrated. The residue was suspended in DCM and washed with brine. The organic layer was dried, filtered and evaporated. The residue was triturated from MeOH to give Intermediate I-58 (0.189 g, 56%) as a white solid.
Method A22
Preparation of Intermediate I-60

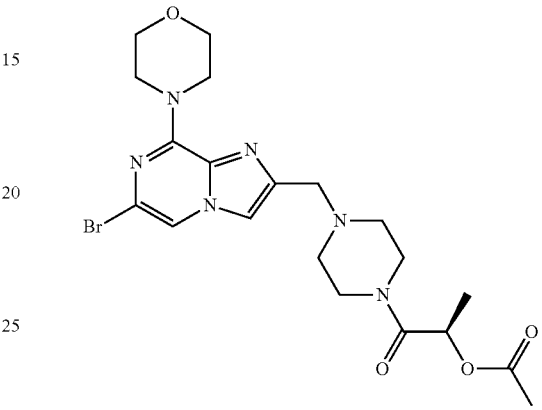

To a solution of Intermediate I-17 (100 mg, 0.297 mmol), BOP (158 mg, 0.356 mmol) and (s)-(−)-2-acetoxypropionic acid (41 mg, 0.356 mmol) in CH₂Cl₂ (3 mL), Et₃N (0.083 mL, 0.594 mmol) was added. The mixture was stirred at RT for 2 days. CH₂Cl₂ was added and the mixture was washed with water. The organic layer was dried over Na₂SO₄, filtered and evaporated. The residue was purified by column chromatography (Biotage, CH₂Cl₂:MeOH, 100:0 to 60:40) to give Intermediate I-60 (130 mg, 88%) as a colourless oil.
Method A23
Preparation of Intermediate I-61

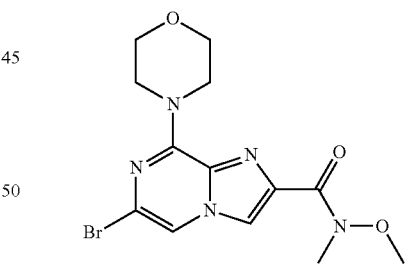

A 2M solution of trimethylaluminum in hexanes (5.5 mL, 11.02 mmol) was added to a mixture of N,O-dimethylhydroxylamine hydrochloride (1.075 g, 11.02 mmol) in DCM (10 mL) and the reaction was stirred at it for 40 min. A solution of Intermediate I-12 (0.783 g, 2.20 mmol) in DCM (16 mL) was added and the reaction mixture was stirred at 40° C. for 2 h. On cooling, the mixture was carefully quenched with 1N HCl and diluted with DCM. After 30 min stirring layers were separated and the aqueous layer was extracted with DCM (×2). The combined organic layers were washed with brine, dried, filtered and evaporated. The residue was purified by column chromatography (Biotage, cHex/EtOAc 50:50 to 0:100) to give Intermediate I-61 (545 mg, 67%).

Method A24
Preparation of Intermediate I-62

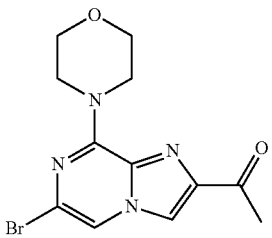

To a mixture of Intermediate I-61 (545 mg, 1.47 mmol) in THF (15 mL) was added MeMgBr (2.2 mL, 2.2 mmol) at 0° C. The reaction was stirred at 0° C. for 1 h. Additional MeMgBr (1.1 mL, 1.1 mmol) was added and the reaction was stirred at 0° C. for 1 h. The mixture was quenched with sat NH₄Cl, and extracted with EtOAc (×3). The combined organic layers were dried, filtered and evaporated to give Intermediate I-62 (458 mg, 96%).

Method A25
Preparation of Intermediate I-63

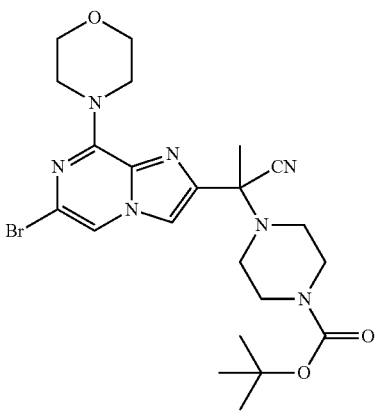 [SMILES: CC(C)(C)OC(=O)N1CCN(C(C)(C#N)c2cn3cc(Br)nc(N4CCOCC4)c3n2)CC1]

To a mixture of Intermediate I-62 (0.1 g, 0.308 mmol) and 1-Boc-piperazine (0.115 g, 0.615 mmol) in DCM (4 mL) was added Ti(iPrO)₄ (0.182 mL, 0.615 mmol). The reaction was stirred at reflux for 2 h. Et₂AlCN (0.62 mL, 0.615 mmol) was added and the reaction mixture was stirred at reflux for 5 h. On cooling, the mixture was quenched with sat NaHCO₃ and extracted with EtOAc (×3). The combined organic layers were washed with brine, dried, filtered and evaporated. The residue was purified by column chromatography (biotage, cHex/EtOAc 10:90 to 0:100) to give Intermediate I-63 (100 mg, 63%).

Method A26
Preparation of Intermediate I-64

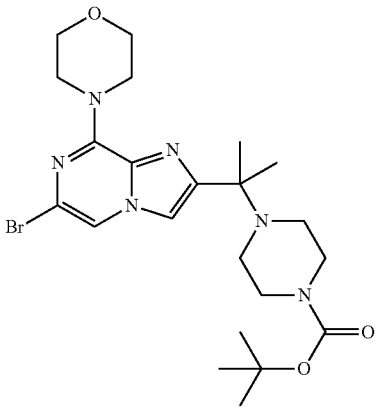 [SMILES: CC(C)(C)OC(=O)N1CCN(C(C)(C)c2cn3cc(Br)nc(N4CCOCC4)c3n2)CC1]

To a stirred solution of MeMgBr (1 mL, 0.96 mmol) was added a solution of Intermediate I-63 (50 mg, 0.096 mmol) in THF (1.5 mL) at 0° C. The reaction was stirred at 0° C. for 4 h and the mixture was poured onto ice cold sat NH₄Cl. The mixture was extracted with EtOAc and the combined organic layers were dried, filtered and evaporated. The residue was purified by column chromatography (biotage, cHex/EtOAc 10:90 to 0:100) to give Intermediate I-64 (22 mg, 45%).

Method A27
Preparation of Intermediate I-68

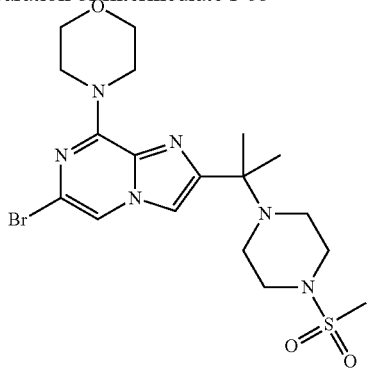 [SMILES: CC(C)(c1cn2cc(Br)nc(N3CCOCC3)c2n1)N1CCN(S(C)(=O)=O)CC1]

MsCl (0.046 mL, 0.589 mmol) was added to solution of Intermediate I-67 (0.175 g, 0.393 mmol) and TEA (0.274 mL, 1.96 mmol) in DCM (4 mL) at 0° C. The reaction mixture was stirred at rt for 3 h and poured onto sat NaHCO₃. The mixture was extracted with DCM and the combined organic layers were dried, filtered and evaporated. The residue was purified on silica gel (DCM:MeOH, 90:10) to afford Intermediate I-68 (133 mg, 70%).

Method A28
Preparation of Intermediate I-70

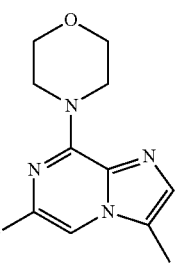

To a solution of Intermediate I-02 (150 mg, 0.58 mmol) in Toluene (6.8 mL), 2-chloro-1,1-dimethoxypropane (0.758 mL, 5.8 mmol) and p-toluensulfonic acid (18 mg, 0.09 mmol) were added. The reaction mixture was refluxed for 24 h and additional amounts of 2-chloro-1,1-dimethoxypropane (10 eq) and p-toluensulfonic acid (0.16 eq) were added. The reaction mixture was refluxed for 15 h and the solvent was removed. The residue was purified by column chromatography (Isolute 10 g; AcOEt-cyclohexane 0:100 to 50:50) to give the Intermediate I-70 (55 mg, 32%) as a beige solid.

Example B1

Preparation of Final Product 2-01

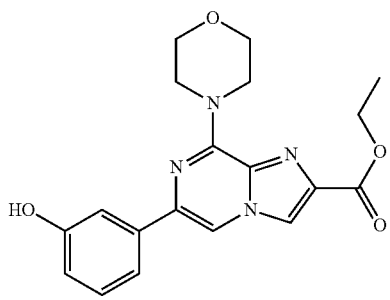 [SMILES: CCOC(=O)c1cn2cc(-c3cccc(O)c3)nc(N3CCOCC3)c2n1]

A mixture of intermediate I-12 (100 mg, 0.282 mmol), 3-hydroxyphenylboronic acid (85 mg, 0.685 mmol), and PdCl$_2$(dppf).DCM (23 mg. 0.028 mmol) in DME (1.2 mL) was added a saturated aqueous solution of sodium carbonate (1 mL). The mixture was heated to 130° C. under microwave irradiation for 3 min. The reaction mixture was cooled, diluted with chloroform, washed with brine. The organic phase was dried (Na$_2$SO$_4$), filtered and the solvent removed in vacuo. The residue was purifired by biotage chromatography with a gradient cyclohexane/EtOAc: from 100% to 50:50. The desired fractions were collected and the solvent evaporated. The resulting solid was crystallised with MeOH to obtain a white solid as final product 2-01 (44 mg, Y: 68% yield).

Preparation of Final Product 2-10

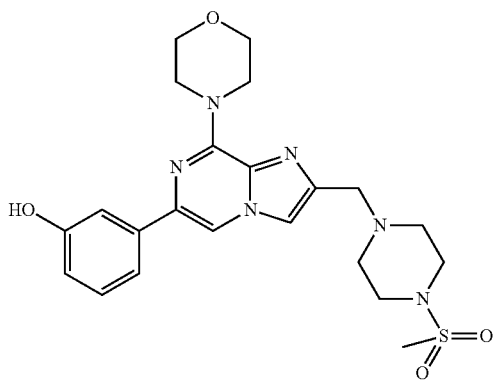 [SMILES: CS(=O)(=O)N1CCN(Cc2cn3cc(-c4cccc(O)c4)nc(N4CCOCC4)c3n2)CC1]

A mixture of intermediate I-18 (200 mg, 0.435 mmol), 3-hydroxyphenylboronic acid (132 mg, 0.985 mmol), and PdCl$_2$(dppf).DCM (36 mg. 0.044 mmol) in DME (1.8 mL) was added an aqueous saturated solution of potassium carbonate (1 mL). The mixture was heated to 130° C. under microwave irradiation for 3 min. The reaction mixture was cooled, diluted with chloroform, washed with brine. The organic phase was dried (Na$_2$SO$_4$), filtered and evaporated. The residue was purified by biotage chromatography and eluted with a gradient DCM/MeOH: from 100% to 50:50. The desired fractions were collected and the resulting residue was purified again with EtOAc and then EtOAc/MeOH 20:1. The desired fractions were collected to obtain a white solid, 27 mg, Y: 13%, as final product 2-10.

Preparation of Final Product 2-11

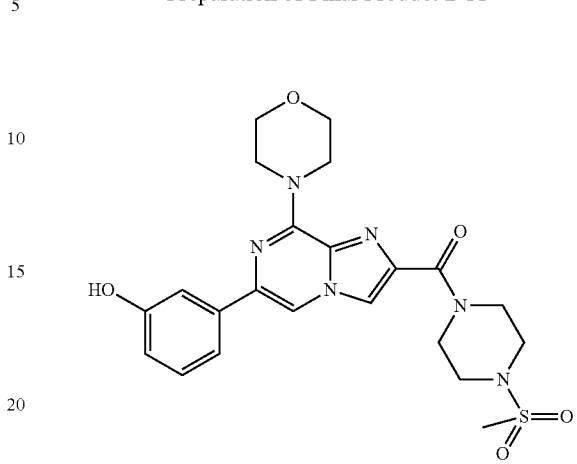

Intermediate I-24 (165 mg, 0.349 mmol), 3-hydroxyphenylboronic acid (0.523 mmol, 72 mg) and PdCl$_2$(dppf).DCM (0.035 mmol, 29 mg) were suspended in a saturated solution of sodium carbonate (1.8 mL) and 1,2-DME (1.8 mL). The mixture was heated under microwave irradiation at 130° C. for 10 min. The mixture was diluted with DCM and washed with water. The organic layer was dried (Na$_2$SO$_4$), filtered and evaporated. The resulting residue was purified by Biotage chromatography (DCM-EtOAc from 50:50 to 100% of EtOAc) to afford a product still impure which was repurified using DCM-MeOH 95:5. The resulting oil was precipitated with DCM-MeOH-Et$_2$O (approx. 10:1:5) to give the desired product 2-11 (63 mg, Y: 36%).

Preparation of Final Product 2-13

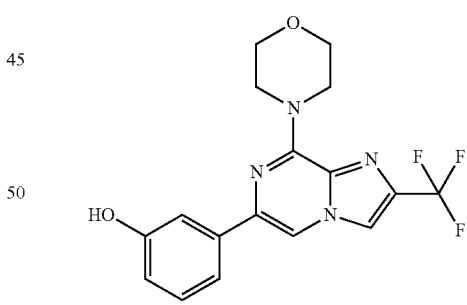

A mixture of intermediate I-26 (225 mg, 0.641 mmol), 3-hydroxyphenylboronic acid (194 mg, 1.410 mmol), and PdCl$_2$(dppf).DCM (53 mg, 0.064 mmol) in DME (2.8 mL) was added a saturated aqueous solution of potassium carbonate (0.5 mL). The mixture was heated to 130° C. under microwave irradiation for 3 min. The reaction mixture was cooled, diluted with DCM, washed with brine. The organic phase was dried (Na$_2$SO$_4$), filtered and the solvent removed in vacuum. The resulting residue was purified by biotage chromatography and eluted with a gradient EtOAc/MeOH: from 100% to 50:50. The desired fractions were collected to yield a yellow solid which was crystallised in MeOH to obtain the desired product 2-13 (150 mg, Y: 64%).

Preparation of Final Product 2-14

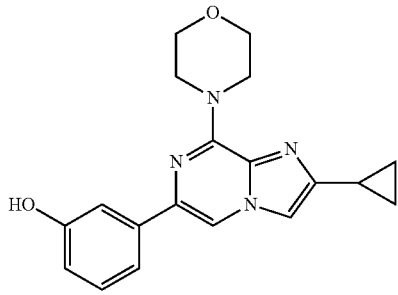 [SMILES: Oc1cccc(-c2cn3cc(C4CC4)nc3c(N3CCOCC3)n2)c1]

Intermediate I-15 (210 mg, 0.650 mmol), 3-hydroxyphenylboronic acid (0.975 mmol, 134 mg) and PdCl$_2$(dppf).DCM (0.065 mmol, 54 mg) were suspended in saturated solution of sodium carbonate (2.6 mL) and 1,2-DME (2.6 mL). The mixture was heated under microwave irradiation at 130° C. for 10 min. The mixture was diluted with DCM and washed with water. The organic layer was dried (Na$_2$SO$_4$), filtered and the solvent was evaporated in vacuo. The resulting residue was purified by flash chromatography (DCM-EtOAc from 100% to 40:60) to afford the desired product 2-14 (69 mg, Y: 31%) as a white solid.

Preparation of Final Product 2-15

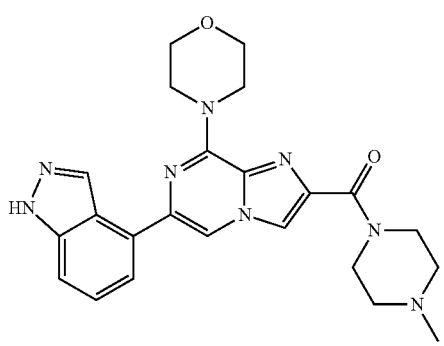 [SMILES: CN1CCN(C(=O)c2cn3cc(-c4cccc5[nH]ncc45)nc(N4CCOCC4)c3n2)CC1]

Intermediate I-23 (50 mg, 0.122 mmol), indazole-4-boronic acid hydrochloride (0.183 mol, 36 mg) and PdCl$_2$(dppf).DCM (0.012 mmol, 10 mg) were suspended in a saturated solution of sodium carbonate (0.6 mL) and 1,2-DME (0.6 mL). The mixture was heated under microwave irradiation at 130° C. for 10 min. The mixture was diluted with DCM and washed with brine. The organic layer was dried (Na$_2$SO$_4$), filtered and the solvent was evaporated. The resulting residue was purified by flash chromatography (DCM-MeOH/NH$_3$ 7N from 100% to 90:10). The desired fractions were collected to obtain final product 2-15 (48 mg, Y: 88%) as a white solid.

Preparation of Final Product 2-16

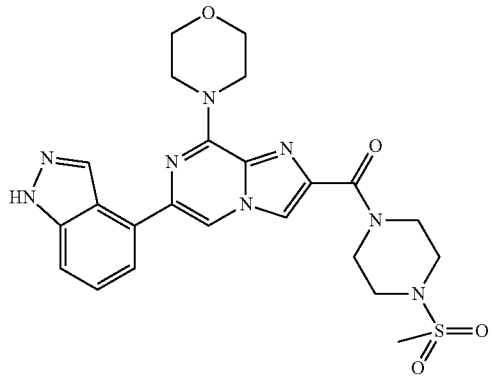 [SMILES: CS(=O)(=O)N1CCN(C(=O)c2cn3cc(-c4cccc5[nH]ncc45)nc(N4CCOCC4)c3n2)CC1]

Intermediate I-24 (55 mg, 0.116 mmol), indazole-4-boronic acid hydrochloride (0.174 mmol, 35 mg) and PdCl$_2$(dppt).DCM (0.012 mmol, 10 mg) were suspended in a saturated solution of sodium carbonate (0.6 mL) and 1,2-DME (0.6 mL). The mixture was heated under microwave irradiation at 130° C. for 10 min. The mixture was diluted with DCM and washed with water. The organic layer was dried (Na$_2$SO$_4$), filtered and the solvent evaporated in vacuo. The resulting residue was purified by flash chromatography (EtOAc-MeOH from 100% to 98:2) to obtain the desired final product 2-16 as a white solid (32 mg, Y: 54%).

Preparation of Final Product 2-17

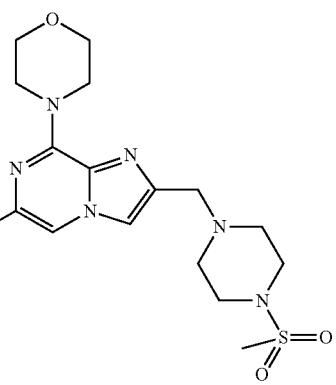

A mixture of intermediate I-18 (160 mg, 0.348 mmol), PdCl$_2$(dppf).DCM (cat. amount), a saturated solution of K$_2$CO$_3$ (0.5 mL), indazole-4-boronic acid hydrochloride (150 mg, 0.766 mmol), in DME (3.5 mL) was heated under microwave irradiation at 130° C. for 10 min. The mixture was diluted with DCM (30 mL), washed with brine (40 mL). The organic phase was dried (Na$_2$SO$_4$), filtered and concentrated. The crude was purified by Biotage flash column chromatography eluting with a gradient of EtOAc/MeOH (from 100% to 60:40), the resulting solid was triturated with MeOH and filtered to obtain the desired product 2-17 (43 mg) as a white solid.

Preparation of Final Product 2-18

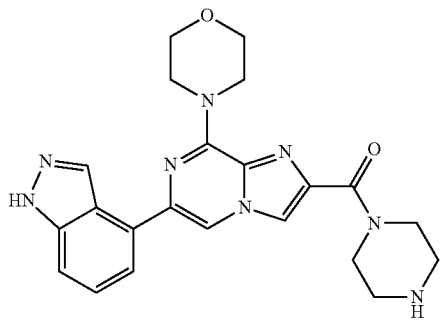 [SMILES: O=C(c1cn2cc(-c3cccc4[nH]ncc34)nc(N3CCOCC3)c2n1)N1CCNCC1]

Intermediate I-25 (150 mg, 0.303 mmol), indazole-4-boronic acid hydrochloride (1.5 equiv, 0.454 mmol, 90 mg) and PdCl$_2$(dppf)$_2$.DCM (0.1 equiv, 0.03 mmol, 25 mg) were suspended in sat sol of sodium carbonate (1.5 mL) and 1,2-DME (1.5 mL). The mixture was heated under microwave irradiation at 130° C. for 10 min. The mixture was diluted with DCM and washed with water. The organic layer was dried over sodium sulfate to yield the crude product which was purified by flash chromatography (EtOAc-MeOH 0-5%) to afford the required (120 mg as yellow solid, 75%). This product (120 mg, 0.225 mmol) was suspended in dry methanol (2.25 mL) and AmberlystR(5) (400 mg) was added. The mixture was slowly stirred at rt for 48 h. The resin was washed with MeOH, and then with MeOH—NH$_3$ 7N. This phase was collected and evaporated to obtain final product 2-18 as a syrup (83 mg, Y: 85%).

Preparation of Final Product 2-19

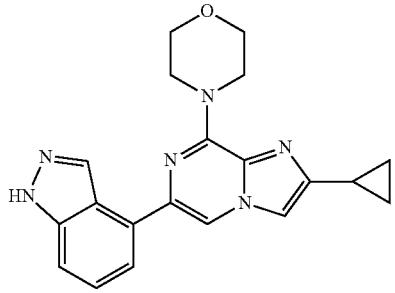 [SMILES: c1cc(-c2cn3cc(C4CC4)nc3c(N3CCOCC3)n2)c2cn[nH]c2c1]

Intermediate I-15 (140 mg, 0.433 mmol), 4-indazoleboronic acid (1.5 equiv, 0.650 mmol, 129 mg) and PdCl$_2$(dppf).DCM (0.043 mmol, 36 mg) were suspended in a saturated solution of sodium carbonate (2 mL) and 1,2-DME (2 mL). The mixture was heated under microwave irradiation at 130° C. for 10 min. The mixture was diluted with DCM and washed with water. The organic layer was dried (Na$_2$SO$_4$), filtered and evaporated. The residue was purified by flash chromatography (DCM-EtOAc from 80:20 to 100% on EtOAc) and then by HPLC to afford final product 2-19 (40 mg, Y: 26%).

Preparation of Final Product 2-20

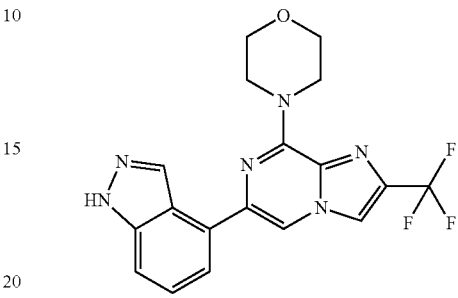

A reaction mixture of intermediate I-26 (140 mg, 0.4 mmol), indazole-4-boronic acid hydrochloride (175 mg, 0.87 mmol), K$_2$CO$_3$ (300 mg), PdCl$_2$(dppf).DCM (cat amount) in DME (3 mL) and water (1 mL), was heated under microwave irradiation at 130° C. for 10 min. The dark reaction mixture was diluted with DCM (25 mL), washed with saturated solution of NaHCO$_3$ (2×30 mL) and brine (30 mL). The organic phase was dried (Na$_2$SO$_4$), filtered and concentrated. The resulting residue was purified by flash column chromatography eluting with a gradient system of DCM/MeOH (from 100% to 97:3). The desired fractions were collected and precipitated with DCM/cyclohexane, to obtain the final product 2-20 (40 mg, Y: 26%).

Preparation of Final Product 2-23

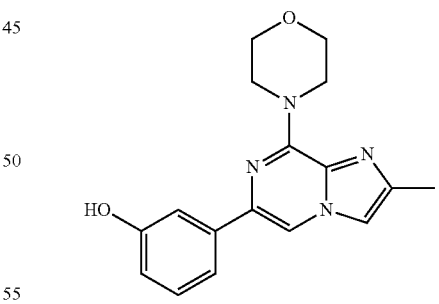

A mixture of intermediate I-10 (100 mg, 0.337 mmol), 3-hydroxyphenylboronic acid (0.102 g, 0.740 mmol), and PdCl$_2$(dppf).DCM (28 mg, 0.034 mmol) in DME (1.463 mL) was added an aqueous saturated solution of potassium carbonate (0.5 mL). The mixture was heated to 130° C. under microwave irradiation for 10 min. The reaction mixture was cooled, diluted with DCM, washed with brine. The organic phase was dried (Na$_2$SO$_4$), filtered and the solvent removed in vacuum. The residue was purified by biotage chromatography and eluted with a gradient EtOAc/MeOH from 100% to 50:50. The desired fractions were collected and the residue was crystallised in DCM to obtain the desired product 2-23 (44 mg, Y: 42%).

Preparation of Final Product 2-24

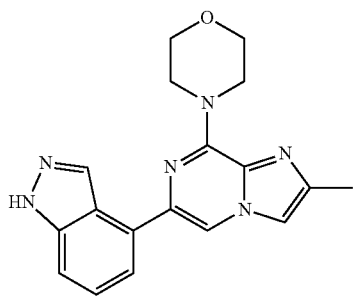 [SMILES: Cc1cn2cc(-c3cccc4[nH]ncc34)nc(N3CCOCC3)c2n1]

A mixture of intermediate I-10 (700 mg, 2.356 mmol), indazole-4-boronic acid hydrochloride (701 mg, 3.534 mmol) and PdCl$_2$(dppf).DCM (190 mg. 0.235 mmol) in DME (11 mL) was added a saturated aqueous solution of potassium carbonate (11 mL). The mixture was heated to 130° C. in the microwave for 0.5 h. The reaction mixture was diluted with EtOAc and washed with water. The organic phase was separated, dried (Na$_2$SO$_4$), filtered and evaporated to give a brown oil. This residue was purified column chromatography (hexane/EtOAc mixtures) to give the desired product 2-24 as green foam (456 mg, 58% yield).

Preparation of Final Product 2-27

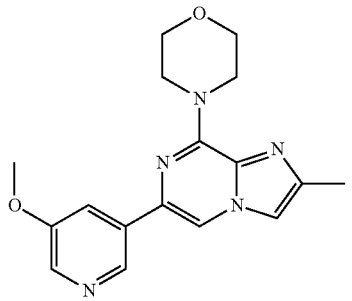 [SMILES: COc1cncc(-c2cn3cc(C)nc3c(N3CCOCC3)n2)c1]

A mixture of intermediate I-10 (200 mg, 0.673 mmol), 3-methoxypyridine-5-boronic acid pinacol ester (348 mg, 1.481 mmol), and PdCl$_2$(dppf).DCM (56 mg. 0.067 mmol) in DME (2.9 mL) was added a saturated solution of sodium carbonate (1 mL). The mixture was heated to 130° C. under microwave irradiation for 10 min. The reaction mixture was cooled, diluted with DCM, washed with brine. The organic phase was dried (Na$_2$SO$_4$), filtered and the solvent removed in vacuum. The residue was purified by biotage chromatography twice and eluted with a gradient EtOAc/MeOH from 100% to 50:50. The desired fractions were collected to obtain 120 mg of the desired product 2-27 as a yellow solid (Y: 55%).

Preparation of Final Product 2-42

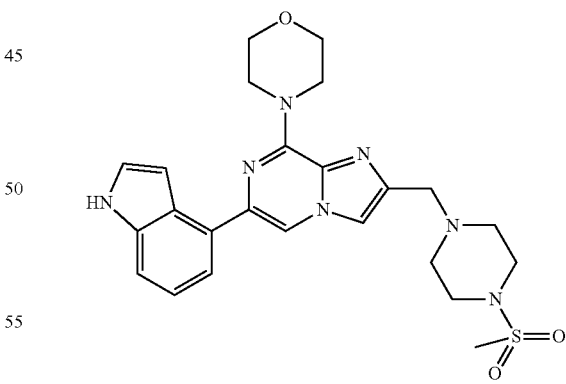

Intermediate I-11 (1.36 g, 3.62 mmol) was suspended in DME (5 mL) and indazole-4-boronic acid.HCl (0.86 g, 4.34 mmol), PdCl$_2$(dppf).DCM (300 mg, 0.36 mmol), K$_2$CO$_3$ (1.5 g, 10.85 mmol) and H$_2$O (2.5 mL) were added. The reaction mixture was heated under microwave irradiation at 130° C. for 30 min. On cooling, the mixture was evaporated and the residue was purified by column chromatography (DCM/MeOH from 100% to 98:2) to give the expected product 2-42 (230 mg, Y: 15%) as a yellow solid.

Preparation of Final Product 2-71

A mixture of intermediate I-18 (100 mg, 0.218 mmol), PdCl$_2$(dppf).DCM (cat. amount), a saturated solution of K$_2$CO$_3$ (1 mL), indol-4-boronic acid hydrochloride (53 mg, 0.327 mmol), in DME (1 mL) was heated under microwave irradiation at 130° C. for 10 min. The mixture was diluted with DCM (30 mL), washed with brine (40 mL). The organic phase was dried (Na$_2$SO$_4$), filtered and concentrated. The crude was purified by Biotage flash column chromatography eluting with a gradient of DCM/MeOH (from 100% to 50:50) to obtain the desired product 2-71 (39 mg) as a white solid.

Preparation of Final Product 2-70

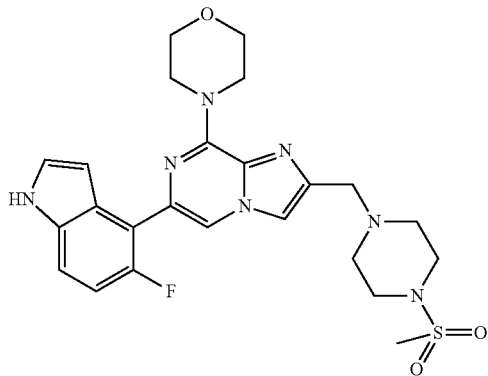 [SMILES: CS(=O)(=O)N1CCN(Cc2cn3cc(-c4c(F)ccc5[nH]ccc45)nc(N4CCOCC4)c3n2)CC1]

A mixture of intermediate I-18 (100 mg, 0.218 mmol), PdCl₂(dppf).DCM (cat. amount), a saturated solution of K₂CO₃ (0.5 mL), 5-fluoro-4-(4,4,5,5-tetramethyl-1,3,2-dioxaborolan-2-yl)-1-tert-butyldimethylsilyl-indole (98 mg, 0.26 mmol, CAS: 1072009-08-5), in DME (1 mL) was heated under microwave irradiation at 130° C. for 1 h. The organic phase was concentrated. The crude was purified by Biotage flash column chromatography eluting with a gradient of DCM/MeOH (from 100% to 90:10) to obtain the desired product 2-70 (39 mg) as a white solid.

Preparation of Final Product 2-35

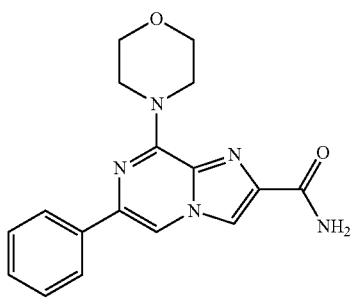 [SMILES: NC(=O)c1cn2cc(-c3ccccc3)nc(N3CCOCC3)c2n1]

Intermediate I-30 (50 mg, 0.15 mmol) was dissolved in DME (1 mL) and phenylboronic acid (22 mg, 0.18 mmol), K₂CO₃ (64 mg, 0.46 mmol), PdCl₂(dppf)-DCM (13 mg, 15 umol) and H₂O (0.5 mL) were added. The mixture was heated under microwave irradiation at 130° C. for 1 h. On cooling, the mixture was purified by column chromatography (Biotage, 25-S, 5% to 10% MeOH in DCM), and the product obtained was precipitated with Et₂O and filtered to give the expected product 2-35 (45 mg, Y: 91%) as a white solid.

Preparation of Final Product 2-63

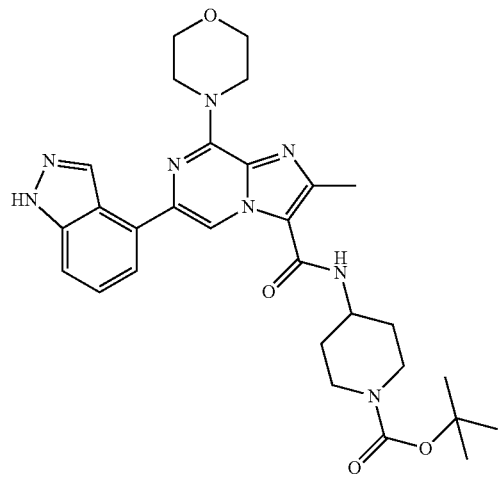 [SMILES: Cc1nc2c(N3CCOCC3)nc(-c3cccc4[nH]ncc34)cn2c1C(=O)NC1CCN(C(=O)OC(C)(C)C)CC1]

PdCl₂(dppf) was added to a degassed mixture of intermediate I-27 (100 mg, 0.21 mmol), indazol 4-boronic acid hydrochloride (0.091 g, 0.43 mmol) and an aqueous saturated solution of Na₂CO₃ (0.25 mL) in DME (1 mL). The vial was sealed and heated at 130° C. under microwaves for 10 min. The mixture was diluted with EtOAc, washed with water, brine, dried and evaporated. The residue was purified by Biotage chromatography in DCM/MeOH 2 to 10% MeOH) to obtain 52 mg of desired compound 2-63.

Example B2

Preparation of Final Product 2-21

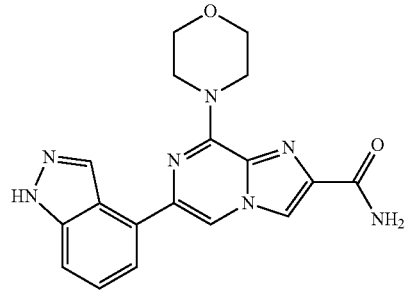 [SMILES: NC(=O)c1cn2cc(-c3cccc4[nH]ncc34)nc(N3CCOCC3)c2n1]

A suspension of final compound 2-52 (160 mg, 0.5 mmol) in MeOH/NH₃ 7N was heated in a sealed tube at 90° C. for 16 h. A precipitate appears which was filtered off to obtain 75 mg of the desired product 2-21 as a brown solid (Y: 41%)

Preparation of Final Product 2-77

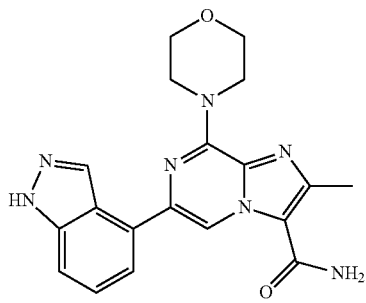 [SMILES: Cc1nc2c(N3CCOCC3)nc(-c3cccc4[nH]ncc34)cn2c1C(N)=O]

To a mixture of intermediate I-32 (70 mg, 0.185 mmol) with dry DMF (3 drops) in benzene (2 mL) was added oxalyl chloride (2 equiv, 0.370 mmol, 31 uL). The mixture was stirred at rt for 3 h, then same amount of reagents was added and stirring continued for 1 h. No reaction observed so volatiles were removed under reduced pressure and the residue was dissolved in dioxane (2 mL) and NH$_3$ in dioxane 0.5N (2 mL) was added. The mixture was stirred at it overnight and solvent was evaporated under vacuum. The residue was purified by preparative HPLC affording 3 mg of final product 2-77 (Y: 4%).

Example B3

Preparation of Final Product 2-22

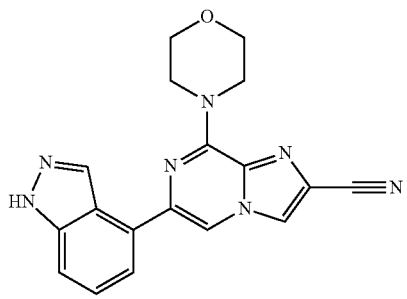 [SMILES: N#Cc1cn2cc(-c3cccc4[nH]ncc34)nc(N3CCOCC3)c2n1]

Final product 2-21 (50 mg, 0.138 mmol) in POCl$_3$ (2 ml) was heated to reflux for 2 h. The solvent was evaporated in vacuo and the residue was suspended in DCM and Na$_2$SO$_4$ aq. solution. The organic phase was extracted, dried (MgSO$_4$), filtered and evaporated to obtain a light brown solid which was washed with Et$_2$O. The precipitate was filtered and dried to obtain the desired product 2-22 (25 mg, Y: 53%) as a pure solid.

Example B4

Preparation of Final Product 2-33

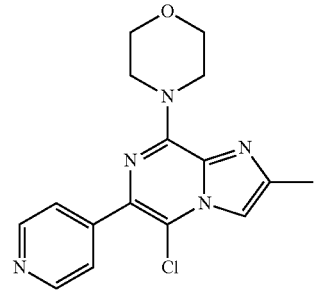 [SMILES: Cc1cn2c(Cl)c(-c3ccncc3)nc(N3CCOCC3)c2n1]

A mixture of final product 2-31 (50 mg, 0.169 mmol) and NCS (18 mg, 0.135 mmol, 0.8 eq) in THF (2 mL) was heated at 60° C. for 18 h. A saturated solution of NaHCO$_3$ was added and the mixture was extracted with EtOAc. The organic phase was separated, dried (Na$_2$SO$_4$), filtered and evaporated till dryness. The residue was purified by using a sep-pack in a manifold, eluent: cyclohexane/EtOAc, 2/1. The desired fractions were collected and the solvent was evaporated till dryness to obtain 15 mg, Y: 27% of desired product 2-33.

Preparation of Final Product 2-54

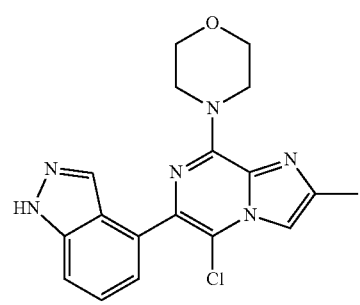 [SMILES: Cc1cn2c(Cl)c(-c3cccc4[nH]ncc34)nc(N3CCOCC3)c2n1]

A mixture of final product 2-24 (60 mg, 0.179 mmol) and NCS (31 mg, 0.233 mmol) in dioxane (2 mL) was heated at 50° C. for 18 h. The organic phase was evaporated till dryness. The residue was purified by using column chromatography (hexane/EtOAc mixtures) and then by HPLC. The desired fractions were collected and the solvent was evaporated till dryness to obtain 9 mg, Y: 14% of desired product 2-54.

Preparation of Final Product 2-56

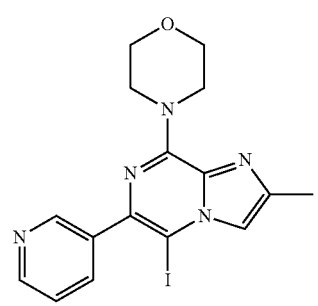 [SMILES: Cc1cn2c(I)c(-c3cccnc3)nc(N3CCOCC3)c2n1]

A mixture of final product 2-31 (0.2 g, 0.677 mmol) and NIS (233 mg, 1.016 mmol) in THF (4 mL) was heated at 65° C. for 18 h. A saturated solution of NaHCO₃ was added and the mixture was extracted with EtOAc. The organic phase was separated, dried (Na₂SO₄), filtered and evaporated till dryness. The residue was purified by using a sep-pack in a manifold and then by HPLC. The desired fractions were collected and the solvent was evaporated till dryness to obtain 2 mg of desired product 2-56.

Preparation of Final Product 2-60

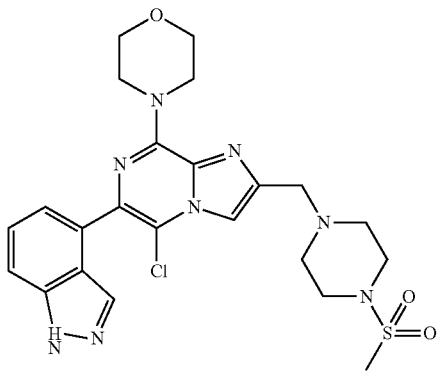 [SMILES: CS(=O)(=O)N1CCN(Cc2cn3c(Cl)c(-c4cccc5[nH]ncc45)nc(N4CCOCC4)c3n2)CC1]

A mixture of final product 2-17 (45 mg, 0.1 mmol) and NCS (20 mg, 0.15 mmol) in acetonitrile (2 mL) was stirred at room temperature for 4 h. A saturated solution of NaHCO₃ was added and the mixture was extracted with EtOAc. The organic phase was separated, dried (Na₂SO₄), filtered and evaporated till dryness. The residue was purified by column chromatography (DCM/MeOH 100% to 95:5) and then by HPLC. The desired fractions were collected and the solvent was evaporated till dryness to obtain 10 mg, of desired product 2-60.

Preparation of Final Product 2-12

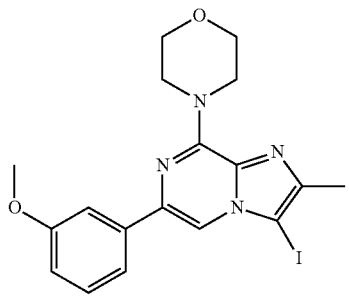 [SMILES: COc1cccc(-c2cn3c(I)c(C)nc3c(N3CCOCC3)n2)c1]

To a solution of final product 2-32 (1.249 mmol) in THF (4.5 mL) was added NIS (1.249 mmol) and the reaction mixture was stirred at it for 24 h. Excess of NIS (0.31 mmol, 70 mg) was added stirring the reaction for 16 h more. A saturated aqueous solution of NaHCO₃ and DCM was added.

The organic phase was extracted, dried (Na₂SO₄), filtered and evaporated. The residue was purified by flash chromatography in Biotage, eluent: CH₂Cl₂—AcOEt/CH₂Cl₂ to obtain 38.6 mg of final product 2-12 and 41 mg of the corresponding regioisomer, final product 2.53.

Preparation of Final Product 2-96

Final product 2-93 (30 mg, 88 umol) was suspended in acetonitrile (2 mL) and NCS (12 mg, 88 umol) was added. The mixture was stirred at rt for 15 h and filtered to render a solid that was reprecipitated (DMSO/MeOH/formic acid) affording the final product 2-96 (15 mg, 42%) as a yellow solid with purity of 90% (contaminated with 10% starting material).

Preparation of Final Product 2-108

Final product 2-50 (50 mg, 0.11 mmol) was suspended in DCM (1 mL) and NCS (14 mg, 0.11 mmol) was added. The mixture was stirred at rt for 20 h. The suspension was filtered and rinsed with DCM to render the final product 2-108 (41 mg, 76%) as white solid.

Preparation of Final Product 2-112

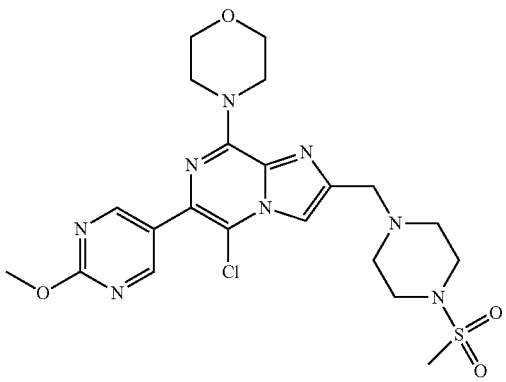 [SMILES: COc1ncc(-c2nc(N3CCOCC3)c3nc(CN4CCN(S(C)(=O)=O)CC4)cn3c2Cl)cn1]

Final product 2-67 (35 mg, 72 μmol) was suspended in DCM (1 mL) and NCS (10 mg, 72 umol) was added. The mixture was stirred at rt for 20 h. NaHCO$_3$ sat sol was added to the mixture and it was extracted with DCM (×2). The combined organic layer was dried, filtered and concentrated. The residue was precipitated with diethyl ether to afford the final product 2-112 (35 mg, 93%) as white solid

Example B5

Preparation of Final Product 2-38

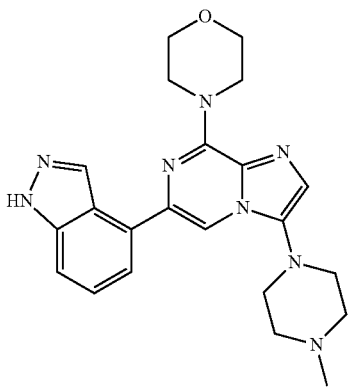 [SMILES: CN1CCN(c2cnc3c(N4CCOCC4)nc(-c4cccc5[nH]ncc45)cn23)CC1]

Benzotriazole (0.7 g, 5.9 mmol) and 1-methylpiperazine (0.660 mL, 5.9 mmol) were stirred in ethanol (20 mL) at rt for 10 min. Glyoxal (0.360 mL of 40% aqueous solution, 2.9 mmol) was added to the reaction mixture, and the stirring was continued for 16 h. The light yellow solution was concentrated under vacuum and precipitated. A light yellow-crystal solid appeared when the resulted oil was washed with diethyl ether to yield a 1.6 g of a solid which was used in next reaction step without further purification. 210 mg (0.44 mmol) of this solid and intermediate I-03 (130 mg, 0.44 mmol) were dissolved in DCE and refluxed for 5 h. The reaction mixture was cooled to rt and then KOH (powder, 250 mg) was added. The mixture was stirred for 20 min at rt, filtered off and washed (DCM). The solvent was concentrated under reduced pressure. The resulting residue was purified by flash column chromatography eluting with a gradient of DCM/MeOH (from 100% to 96:4), yielding final product 2-38, 30 mg, Y: 16%.

Preparation of Final Product 2-41

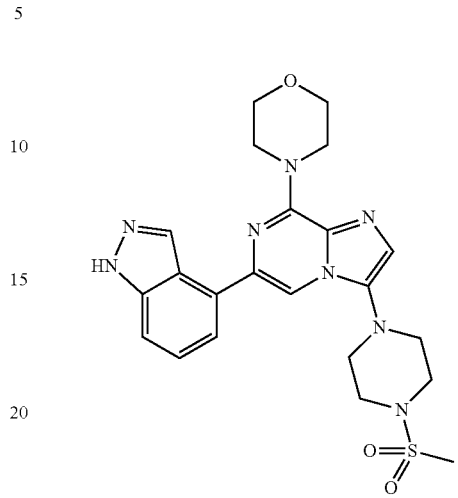

A mixture of benzotriazole (300 mg, 2.43 mmol) 4-methylsulfonylpiperazine (400 mg, 2.43 mmol) in EtOH (20 mL) was stirred for 20 min. Glyoxal (0.160 mL of a 40% w solution in water, 1.2 mmol) was added, and the resultant mixture was stirred for 16 h. The white solid formed was filtered off, washing with EtOH and diethylether to yield 280 mg that was used in next reaction step without further purification. Another batch of this reaction was progressed. 497 mg (0.844 mmol) of this solid and intermediate I-03 were heated in DCE under reflux for 6 h. The reaction mixture was cooled to rt, KOH (156 mg powder) was added and the resulted mixture was stirred at rt for 1 h. The reaction mixture was filtered off and the filtrate was concentrated under vacuum to yield a residue which was purified by flash column chromatography (eluting with a gradient of DCM/MeOH/NH$_3$ 7N (from 100% to 95:5), to yield desired final product 2-41 (50 mg, Y: 12.3%).

Example B6

Preparation of Final Product 2-43

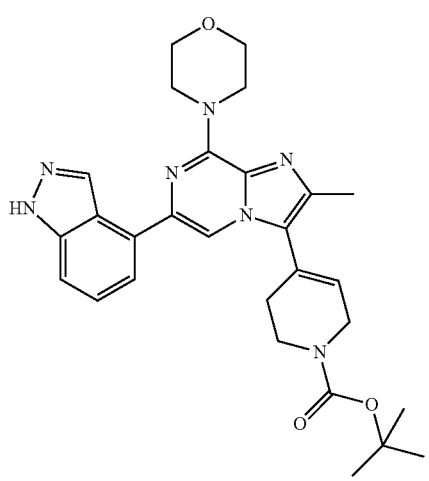 [SMILES: Cc1nc2c(N3CCOCC3)nc(-c3cccc4[nH]ncc34)cn2c1C1=CCN(C(=O)OC(C)(C)C)CC1]

Final product 2-42 (230 mg, 0.56 mmol) was dissolved in 1,4-dioxane (3 mL) and Pd(PPh₃)₄ (64 mg, 56 umol), Cs₂CO₃ (363 mg, 1.11 mmol), 1-N-boc-4-(4,4,5,5-tetramethyl-[1,3,2]dioxaborolan-2-yl)-3,6-dihydro-2H-pyridine (198 mg, 0.64 mmol) and H₂O (2 mL) were added. The mixture was heated under microwave irradiation at 140° C. for 1 h. On cooling, the solvents were removed and the residue was purified by column chromatography (DCM/MeOH from 98:2 to 94:6) to give the final product 2-43 (260 mg, Y: 91%) as a yellow solid.

Example B7

Preparation of Final Product 2-44

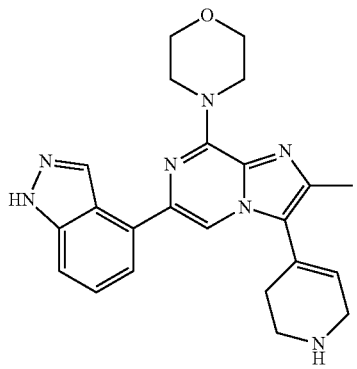 [SMILES: Cc1nc2c(N3CCOCC3)nc(-c3cccc4[nH]ncc34)cn2c1C1=CCNCC1]

Final product 2-43 (200 mg, 0.39 mmol) was dissolved in MeOH (7 mL) and Amberlyst(r) 15 (1 g, 4.7 mmol) was added. The reaction mixture was stirred at rt for 24 h and filtered. The resin was suspended in MeOH/NH₃₇N (10 mL), stirred for 10 min and filtered. This treatment was repeated 3 times. The filtrates were together evaporated and the residue was precipitated from DCM (5 mL) and filtered to give the expected product 2-44 (43 mg, Y: 27%), as a white solid.

Example B8

Preparation of Final Product 2-45

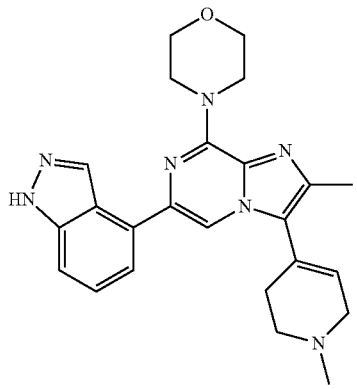 [SMILES: Cc1nc2c(N3CCOCC3)nc(-c3cccc4[nH]ncc34)cn2c1C1=CCN(C)CC1]

Final product 2-44 (35 mg, 84 umol) was suspended in DCM (1.5 mL) and formaldehyde (0.1 mL, 1.26 mmol) and sodium cyanoborohydride (32 mg, 0.5 mmol) were added. The reaction mixture was stirred at it for 20 h. The reaction was adsorbed in silica and purified by column chromatography (DCM/MeOH from 96:4 to 70:30) and then by HPLC to give the expected product 2-45 (3.2 mg) as a white solid.

Preparation of Final Product 2-58

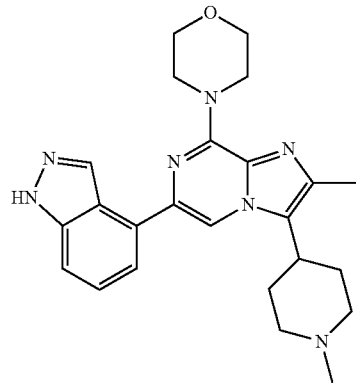 [SMILES: Cc1nc2c(N3CCOCC3)nc(-c3cccc4[nH]ncc34)cn2c1C1CCN(C)CC1]

Final product 2-57 (20 mg, 48 umol) was suspended in DCM (1.5 mL) and formaldehyde (52 µl, 0.72 mmol) and sodium cyanoborohydride (18 mg, 0.29 mmol) were added. The reaction mixture was stirred at it for 1 h. The reaction was adsorbed in silica and purified by column chromatography (DCM/MeOH from 96:4 to 70:30) and then by HPLC to give the expected product 2-58 (9 mg) as a white solid.

Example B9

Preparation of Final Product 2-46

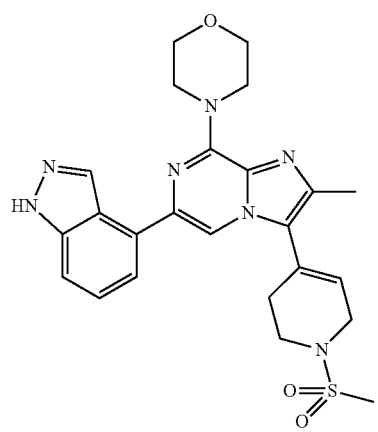 [SMILES: Cc1nc2c(N3CCOCC3)nc(-c3cccc4[nH]ncc34)cn2c1C1=CCN(S(C)(=O)=O)CC1]

Final product 2-44 (30 mg, 72 umol) was suspended in acetonitrile (1 mL) and DIPEA (19 µL, 0.11 mmol) and MeSO₂Cl (6 µL, 79 umol) were added. The solution was stirred at rt for 2.5 h. Excess of MeSO₂Cl (3 µl, 0.5 eq) was added. The reaction mixture was stirred for 3 days and evaporated. The residue was dissolved in HCl 1M (10 mL) and extracted with DCM (3×7 mL). The organic phase was dried (Na₂SO₄), filtered and the solvent evaporated in vacuo. The resulting residue was purified by HPLC to give the expected product 2-46 (10 mg, Y: 28%) as a white solid.

Example B10

Preparation of Final Product 2-47

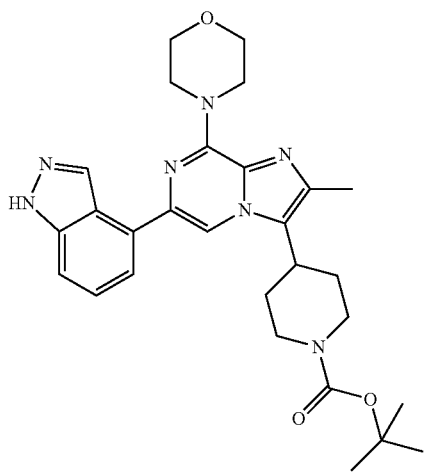 [SMILES: Cc1nc2c(N3CCOCC3)nc(-c3cccc4[nH]ncc34)cn2c1C1CCN(C(=O)OC(C)(C)C)CC1]

Final product 2-43 (50 mg, 97 umol) was dissolved in MeOH (100 mL) and hydrogenated in the H-Cube (Pd/C 10%, 60° C., Full H$_2$, 1 mL/min). The resulting solution was evaporated and the residue was purified by HPLC to give the expected product 2-47 (14 mg, Y: 28%) as a white solid.

Example B11

Preparation of Final Product 2-30

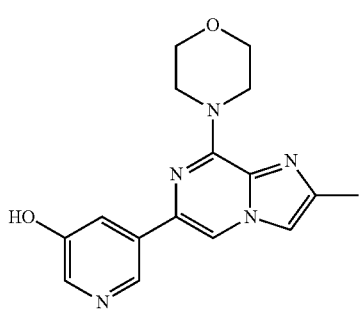 [SMILES: Cc1cn2cc(-c3cncc(O)c3)nc(N3CCOCC3)c2n1]

Boron fluoride-dimethyl sulfide complex (0.226 mL, 2.151 mmol) was added to a stirred solution of final product 2-27 (70 mg, 0.2165 mmol) in DCM (1.3 mL) at rt The mixture was stirred at rt for 24 h. Additional amount of boron fluoride-dimethyl sulfide complex (2.1 mL) was added, and the mixture was stirred at rt for 48 h more. A saturated solution of NaHCO$_3$ was added and the mixture was extracted with DCM/MeOH 90:1. The organic phase was separated, dried (Na$_2$SO$_4$), filtered and evaporated to dryness. The residue was purified by biotage chromatography and eluted with a gradient DCM/MeOH from 100% to 50:50. The desired fractions were collected to obtain 20 mg of desired product 2-30 as a solid (Y: 30%).

Preparation of Final Product 2-88

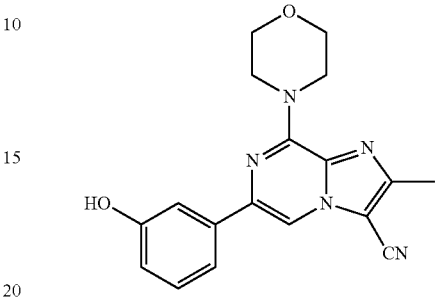

Boron trifluoride-dimethyl sulfide complex (0.084 mL, 0.8 mmol) was added to a stirred solution of final product 2-62 (28 mg, 0.08 mmol) in DCM (1.5 mL) at rt. The mixture was stirred at rt for 24 h. Additional amount of boron fluoride-dimethyl sulfide complex (total of 0.3 mL) was added, and the mixture was stirred at rt for 48 h more. Then, THF (1 mL) was added and the mixture was heated at 50° C. for 53 h. A saturated solution of NaHCO$_3$ was added and the mixture was extracted with DCM/MeOH 90:1. The organic phase was separated, dried (Na$_2$SO$_4$), filtered and evaporated to dryness. The residue was purified by biotage chromatography and eluted with a gradient DCM/MeOH from 100% to 95:5. The desired fractions were collected to obtain 7 mg of desired product 2-88 as a solid (Y: 26%).

Example B12

Preparation of Final Product 2-57

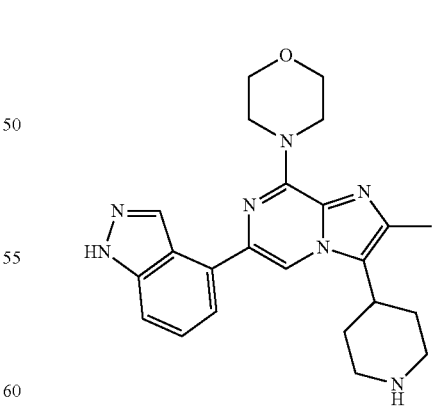

Final Product 2-47 (174 mg, 0.34 mmol) was dissolved in MeOH (7 ml) and Amberlyst 15 (1 g) was added. The reaction mixture was stirred at room temperature for 24 h and filtered. The resin was suspended in MeOH/NH$_3$ 7N stirred for 10 min. and the organic phase was collected. The solvent was evaporated and the residue was precipitated with MeOH, and then purified by HPLC to obtain 9 mg as a formiate salt of Final product 2-57.

Preparation of Final Product 2-236

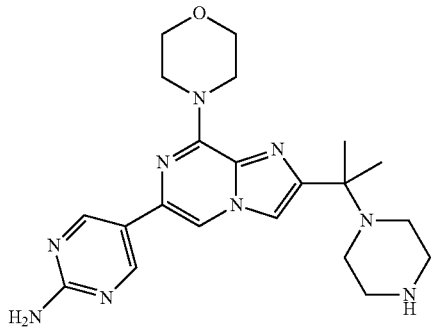 [SMILES: CC(C)(c1cn2cc(-c3cnc(N)nc3)nc(N3CCOCC3)c2n1)N1CCNCC1]

A 4M solution of HCl in dioxane (1 mL) was added at 0° C. to Final product 2-232 (12 mg, 0.023 mmol). The reaction mixture was stirred at it for 3 h. Solvents were removed and the residue was purified by column chromatography (Isolute SCX-2 cartridge, MeOH to NH₃ 7N in MeOH) to give Final product 2-236 (9 mg, 92%).

Example B13

Preparation of Final Product 2-52

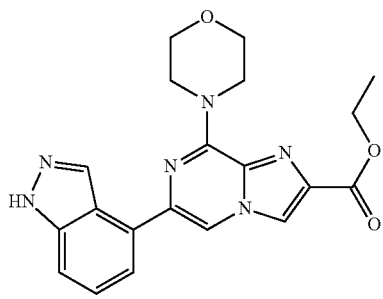 [SMILES: CCOC(=O)c1cn2cc(-c3cccc4[nH]ncc34)nc(N3CCOCC3)c2n1]

To a reaction mixture of intermediate I-12 (150 mg, 0.42 mmol), indazole-4-boronic acid hydrochloride (0.93 mmol, 0.150 mg), and PdCl₂(dppf).DCM (35 mg, 0.042 mmol) in DME (2 ml), was added a saturated solution of potassium carbonate (0.5 ml). The mixture was heated at 130° C. under microwave irradiation for 10 min. A precipitate appears which was filtered, washed with DCM and dried. The resulting solid (0.160 mg, Y: 96%) is the expected final compound 2-52 and was used in next reaction step without further purification.

Preparation of Final Product 2-92

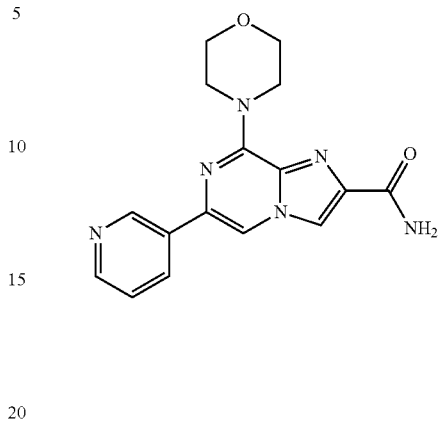

Intermediate I-30 (100 mg, 0.31 mmol) was dissolved in DME (2 mL) and pyridine-3-boronic acid (45 mg, 0.37 mmol), K₂CO₃ (127 mg, 0.92 mmol), PdCl₂(dppf).DCM and water (1 mL) were added. The reaction mixture was heated under microwave irradiation at 130° C. for 1 h. The volatiles were removed under vacuum and the residue was purified by flash chromatography (DCM-MeOH 95:5 to 90:10). The product obtained was precipitated in MeOH affording the final product 2-92 as off-white solid (96 mg, 97%).

Preparation of Final Product 2-93

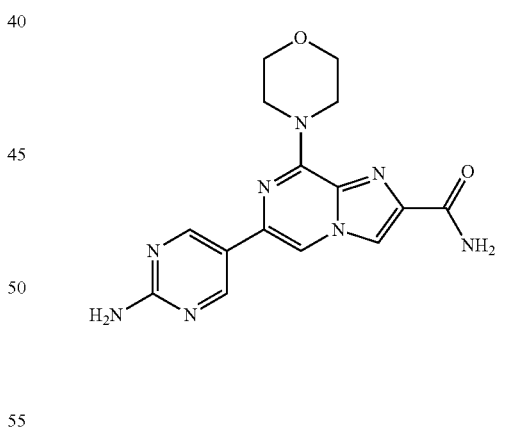

Intermediate I-30 (100 mg, 0.31 mmol) was dissolved in DME (2 mL) and 2-aminopyrimidine-5-boronic acid pinacol ester (81 mg, 0.37 mmol), K₂CO₃ (127 mg, 0.92 mmol), PdCl₂(dppf).DCM and water (1 mL) were added. The reaction mixture was heated under microwave irradiation at 130° C. for 1 h. The volatiles were removed under vacuum and the residue was purified by flash chromatography (DCM-MeOH 95:5 to 90:10). The product obtained was precipitated in MeOH affording the final product 2-93 as off-white solid (96 mg, 97%).

Preparation of Final Product 2-165

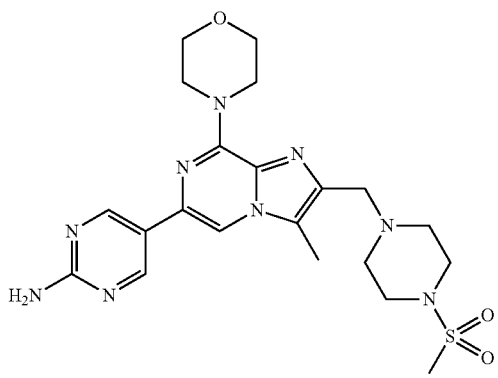 [SMILES: Cc1c(CN2CCN(S(C)(=O)=O)CC2)nc2c(N3CCOCC3)nc(-c3cnc(N)nc3)cn12]

Final product 2-178 (50 mg, 0.087 mmol) was dissolved in 1,4-dioxane (0.3 mL) and Pd(PPh$_3$)$_4$ (10 mg, 0.009 mmol), Cs$_2$CO$_3$ (57 mg, 0.174 mmol), methylboronic acid (6 mg, 0.1 mmol) and water (0.2 mL) were added. The mixture was heated under microwave irradiation at 140° C. for 1 h. Water was added and the mixture was extracted with DCM. The organics were dried (Na$_2$SO$_4$), filtered and evaporated. The residue was purified by column chromatography-TLC in the Chromatotron (DCM:MeOH, 15:1) twice. The desired fractions were collected and evaporated to obtain Final compound 2-165 (22 mg, 52%).

Example B14

Preparation of Final Product 2-62

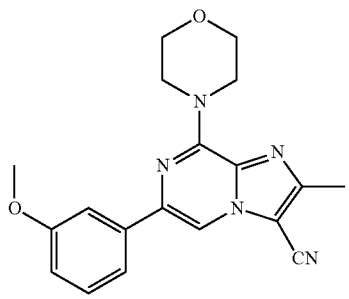 [SMILES: COc1cccc(-c2cn3c(C#N)c(C)nc3c(N3CCOCC3)n2)c1]

To a solution of final Product 2-12 (0.087 mmol) in DMF dry (1 ml) was added zinc cyanide (0.091 mmol), tris(dibenzylidenaceton)dipalladium (Pd$_2$ dba$_3$) (0.004 mmol), 1,1'-bis(diphenylphosphino)ferrocene (DPPF) (0.011 mmol). The mixture was heated at 140° C. for 1 h under microwave irradiation. The solution was diluted with ethyl acetate, washed with water and a saturated solution of NaCl. The organic phase was dried (Na$_2$SO$_4$), filtered and the solvent evaporated. The residue was purified by flash column chromatography, eluent: CH$_2$Cl$_2$—AcOEt/CH$_2$Cl$_2$ 1:100-1:50 to obtain 22.9 mg as a white solid of compound 2-62.

Preparation of Final Product 2-36

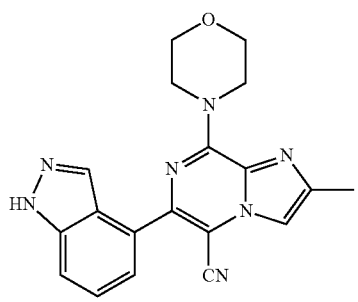 [SMILES: Cc1cn2c(C#N)c(-c3cccc4[nH]ncc34)nc(N3CCOCC3)c2n1]

A mixture of final product 2-73 (38 mg, 0.163 mmol), Zn(CN)$_2$ (10 mg, 0.087 mmol), diphenylphosphineferrocene (6 mg, 0.01 mmol) and Pd$_2$(dba)$_3$ (4 mg, 0.004 mmo) in DMF (0.5 mL) was heated for 1 h at 120° C. under microwave irradiation. Then, more Zn(CN)2 (10 mg, 0.087 mmol), dppf (6 mg, 0.01 mmol, 0.125 eq) and Pd$_2$(dba)$_3$ (4 mg, 0.004 mmol, 0.05 eq) were added and the mixture was heated 1.5 h at 120° C. under microwave irradiation. This excess was added twice. The solvent was removed in vacuo and the residue was purified by column chromatography (EtOAc and EtOAc/MeOH mixtures) and then by HPLC to obtain 1.2 mg of desired product 2-36.

Example B15

Preparation of Final Product 2-79

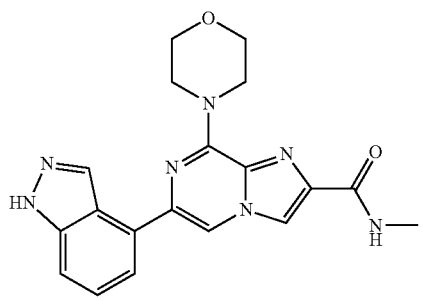 [SMILES: CNC(=O)c1cn2cc(-c3cccc4[nH]ncc34)nc(N3CCOCC3)c2n1]

Final product 2-52 (25 mg, 0.064 mmol) was suspended in EtOH (1.5 mL) and methyl amine (2M in THF, 1.27 mmol, 0.7 mL) was added. The reaction mixture was heated in a sealed tube at 100° C. for 18 h. The reaction mixture was then directly adsorbed in silica to be purified by column chromatography (5% to 10% of MeOH in DCM) rendering 5 mg of the final product 2-79 as a white solid (Y. 21%).

Preparation of Final Product 2-217

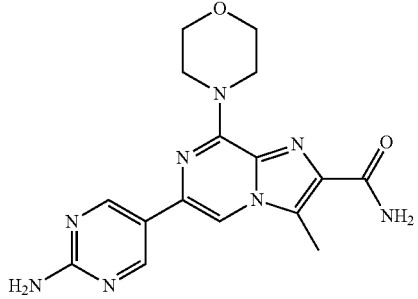 [SMILES: Cc1c(C(N)=O)nc2c(N3CCOCC3)nc(-c3cnc(N)nc3)cn12]

Final product 2-214 (300 mg, 0.78 mmol) was suspended in MeOH/NH$_3$ 7N (10 mL) and heated under microwave irradiation at 130° C. for 24 h. The mixture was evaporated and purified by column chromatography (MeOH in DCM, 100:0 to 40:60) rendering 80 mg of final product 2-217 as a white solid (Y. 29%).

Example B16

Preparation of Final Product 2-87

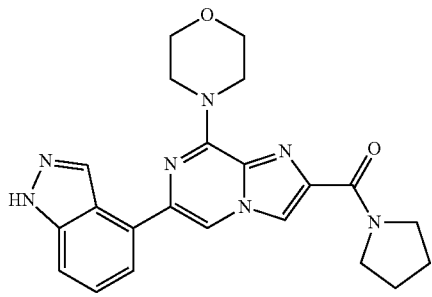 [SMILES: O=C(c1cn2cc(-c3cccc4[nH]ncc34)nc(N3CCOCC3)c2n1)N1CCCC1]

Pyrrolidine (0.54 mmol, 45 uL) was dissolved in EtOH (5 mL) in a sealed tube and AlMe$_3$ (0.54 mmol, 0.26 mL) was added. The mixture was stirred at rt for 15 min and then, the final product 2-52 (0.27 mmol, 105 mg) was added. The reaction mixture was stirred at rt for 1 h and 4 h at 40° C. On cooling, the reaction was carefully quenched with NH$_4$Cl sat sol and extracted with CHCl$_3$-iPrOH 1:1 (×3). The combined organic layer was dried, filtered and concentrated. The crude product was purified by flash chromatography (DCM-MeOH 96:4 to 90:10) rendering the final product 2-87 (15 mg, 13%) as white solid.

Preparation of Final Product 2-139

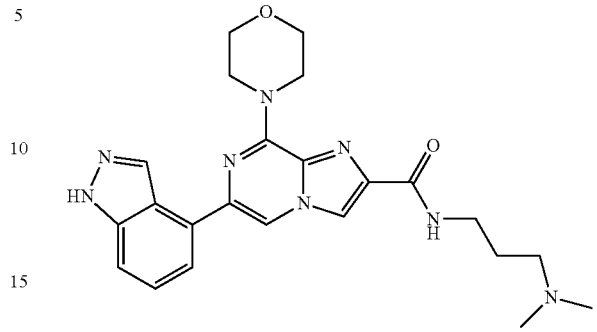

Final product 2-52 (0.127 mmol, 50 mg) was dissolved in EtOH (3 mL) and N,N-dimethyl-1,3-propanediamine (1.27 mmol, 0.16 mL) and AlMe$_3$ (1.27 mmol, 0.64 mL) were added. The mixture was heated at 150° C. for 3 days and under microwave irradiation at 180° C. for 1 h. On cooling, the reaction was carefully quenched with NH$_4$Cl sat. sol. and extracted with DCM (×2). The combined organic layers were dried, filtered and concentrated. The crude product was purified by flash chromatography (DCM-MeOH:NH$_3$(7N); 100:0 to 80:20) rendering the final product 2-139 (18 mg, 31%) as white solid.

Example B17

Preparation of Final Product 2-97

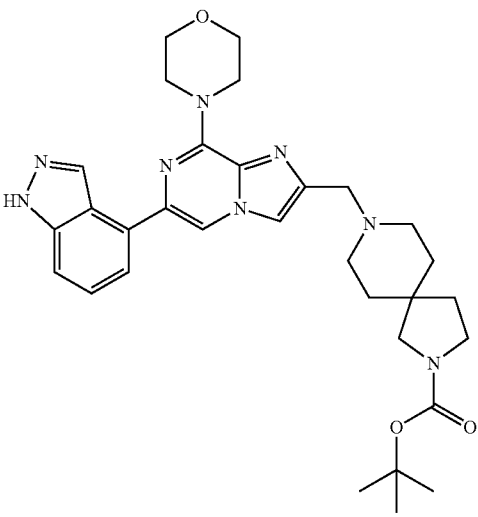 [SMILES: CC(C)(C)OC(=O)N1CCC2(CCN(Cc3cn4cc(-c5cccc6[nH]ncc56)nc(N5CCOCC5)c4n3)CC2)C1]

A mixture of intermediate I-34 (100 mg, 0.28 mmol), AcOH (40 uL, 0.52 mmol), 2,8-diaza-spiro[4.5]decane-2-carboxylic acid tert-butyl ester hydrochloride (90 mg, 0.29 mmol) in DCE (5 mL) was stirred at rt for 40 min. Then, NaBH(OAc)$_3$ (90 mg, 0.40 mmol) was added and stirring continued for 5 h. The reaction mixture was quenched by adding 4N aq sol of KOH and it was extracted with EtOAc (×2). The combined organic layer was washed with brine, dried (Na₂SO₄), filtered and concentrated the crude product (150 mg, 93%) that was used in next reaction step without further purification. Part of this crude product (50 mg) was further purified by preparative HPLC rendering the final product 2-97 (13 mg).
Method B18

Preparation of Final Product 2-155

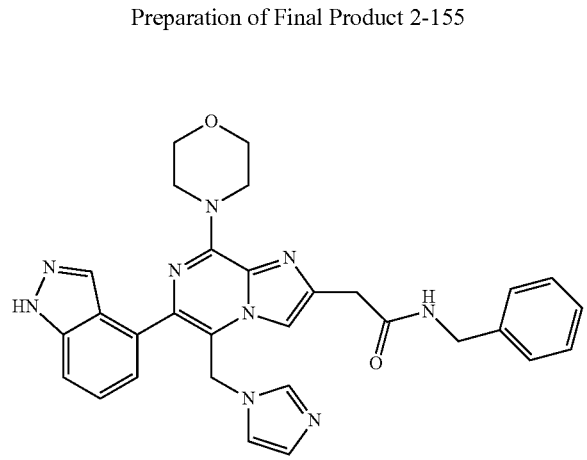

A mixture of iodine (34 mg, 0.133 mmol), triphenylphosphine (29 mg, 0.111 mmol) and imidazole (9 mg, 0.133 mmol) in DMF (2 mL) was stirred at RT for 1 h. Then, Final product 2-144 (55 mg, 0.111 mmol) was added and the mixture was stirred at 70° C. overnight. The mixture was evaporated and the residue was purified by using a sep-pack in a manifold (DCM:MeOH, 92:8) to render 10 mg of Final product 2-155 (16%).
Method B19

Preparation of Final Product 2-177

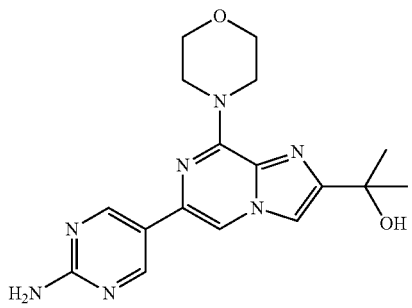 [SMILES: CC(C)(O)c1cn2cc(-c3cnc(N)nc3)nc(N3CCOCC3)c2n1]

Final product 2-138 (0.3 g, 0.81 mmol) was suspended in THF (6 mL) and MeMgCl (3M, 2.7 mL, 8.1 mmol) was slowly added at 0° C. The reaction mixture was stirred for 4 h and then carefully quenched with H₂O. The resulting mixture was purified by column chromatography (DCM:MeOH, 95:5 to 85:15). The product obtained was precipitated with DCM and drops of MeOH and filtered to render Final product 2-177 (20 mg, 7%) as a yellow solid. The filtrate was evaporated and purified by column chromatography (DCM:MeOH, 95:5 to 85:15) and by prep-HPLC to give Final product 2-177 (38 mg, 13%) as a yellow solid.
Method B20

Preparation of Final Product 2-191

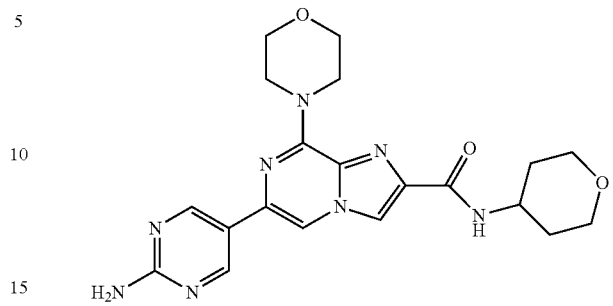

To a solution of Intermediate I-52 (50 mg, 0.146 mmol), BOP (78 mg, 0.176 mmol) and 4-aminotetrahydropyran.HCl (0.024 mL, 0.176 mmol) in DCM (1.5 mL) was added Et₃N (0.041 mL, 0.293 mmol). The mixture was stirred at rt for 2 h. DCM was added and the mixture was washed with water. The organic phase was dried, filtered and evaporated. The residue was purified by column chromatography (DCM:MeOH, 100:0 to 60-40) and by prep-HPLC to render 4 mg (6%) of Final product 2-191 as a white solid.
Method B21

Preparation of Final Product 2-234

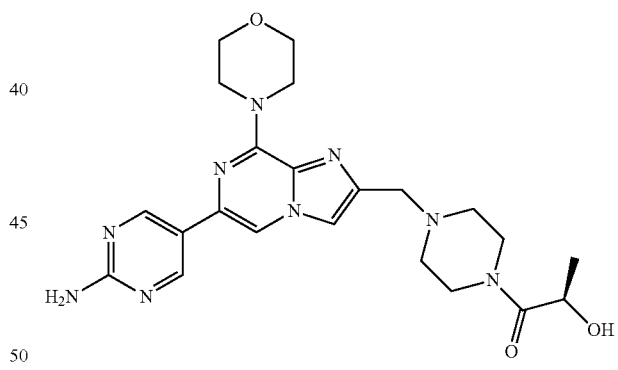

Final product 2-231 (40 mg, 0.078 mmol) was suspended in sodium methoxide 0.5 M in MeOH, 3 mL) and the reaction mixture was stirred at RT for 45 min. H₂O (3 mL) was added, the solution was slightly acidified with HCl and extracted with n-BuOH. The organics were dried over Na₂SO₄, filtered and evaporated. The residue was purified by chromatotron (DCM:MeOH, 10:1). The residue was dissolved in MeOH (4 mL), amberlyst (0.3 g) was added and the mixture was stirred at rt for 2 h, filtered and washed with MeOH. The resine was suspended in NH₃/MeOH (7 N, 35 mL) and stirred for 1 h. The mixture was filtered and the filtrate was evaporated. The residue was purified by chromatotron (DCM/MeOH, 10:1) to give Final product 2-234 (12 mg, 33%) as a white solid.
Method B22

Preparation of Final Product 2-237

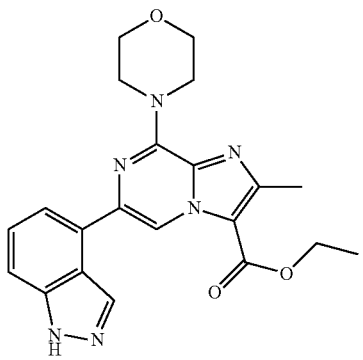 [SMILES: CCOC(=O)c1c(C)nc2c(N3CCOCC3)nc(-c3cccc4[nH]ncc34)cn12]

Intermediate I-28 (500 mg, 1.540 mmol), indazole-4-boronic acid hydrochloride (3.387 mmol, 672 mg) and PdCl$_2$(dppf).DCM (0.154 mmol, 127 mg) were suspended in a saturated solution of sodium carbonate (1.5 mL) and 1,2-DME (7 mL). The mixture was heated under microwave irradiation at 130° C. for 10 min. The mixture was diluted with EtOAc and washed with water. The organic layer was dried (Na$_2$SO$_4$), filtered and the solvent evaporated in vacuo. The resulting residue was purified by flash chromatography (DCM-MeOH from 100:0 to 96:4) to obtain the Final Product 2-237 as a white solid (88 mg, Y: 14%).
Method B23

Preparation of Final Product 2-238

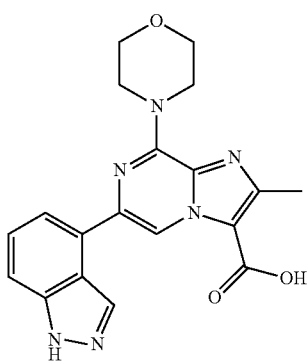 [SMILES: Cc1nc2c(N3CCOCC3)nc(-c3cccc4[nH]ncc34)cn2c1C(=O)O]

Final Product 2-237 (88 mg, 0.217 mmol) was suspended in MeOH (2 mL) and treated with 2N NaOH (0.24 mL, 0.48 mmol). The reaction mixture was refluxed for 4 h. Solvents were evaporated and the residue was dissolved in EtOAc, treated with AcOH and washed with water. The organic layer was dried, filtered and evaporated to give the Final Product 2-238 (82 mg, 100%).
Method B24

Preparation of Final Product 2-241

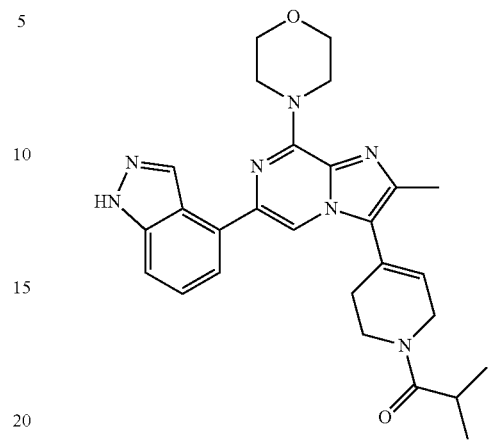

To a solution of Final product 2-44 (50 mg, 0.12 mmol) and N,N-diisopropylethylamine (0.031 mL, 0.181 mmol) in acetonitrile (2 mL) was added isobutyryl chloride (0.014 mL, 0.132 mmol). The mixture was stirred at rt for 4 h and evaporated. H$_2$O was added and the mixture was extracted with DCM. The organic layer was dried (Na$_2$SO$_4$), filtered and evaporated to render Final Product 2-241 (51 mg, 87%).
Method B25

Preparation of Final Product 2-243

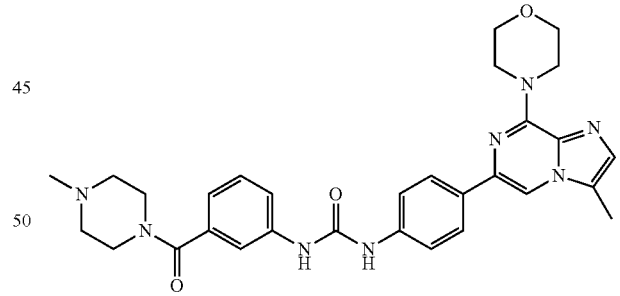

A mixture of Final Compound 2-245/Intermediate I-69 (62 mg, 0.13 mmol), 1-methylpiperazine (0.019 mL, 0.17 mmol), TEA (0.024 mL, 0.17 mmol), HOBT (26 mg, 0.17 mmol) and EDCI (33 mg, 0.17 mmol) in THF (1 mL) was stirred at rt overnight and evaporated. The residue was purified by column chromatography (Isolute 5 g; MeOH:DCM, 1:99 to 20:80 and Flash-NH2 5 g; MeOH:DCM, 0:100 to 2:98) to give the Final Product 2-243 (49 mg, 67%) as a white solid.
Method B26

Preparation of Final Product 2-245

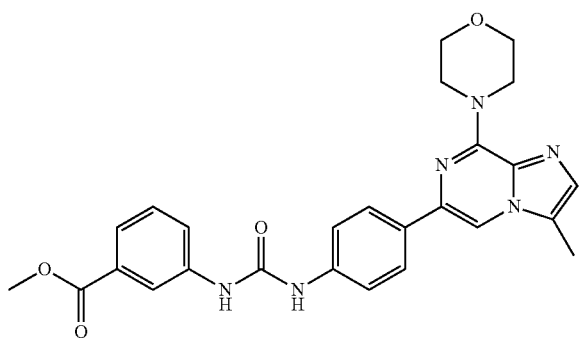 [SMILES: COC(=O)c1cccc(NC(=O)Nc2ccc(-c3cn4c(C)cnc4c(N4CCOCC4)n3)cc2)c1]

To a solution of Intermediate I-69 (50 mg, 0.16 mmol) in DCM (1.3 mL) was added methyl 4-isocyanatobenzoate (31 mg, 0.18 mmol). The reaction mixture was stirred at rt for 5 h. Cyclohexane was added and the mixture was filtered to give Final Product 2-245 (46 mg) as a beige solid. The filtrate was evaporated and the residue was purified by column chromatography (Isolute 5 g; MeOH:DCM, 0:100 to 5:95) to give Final product 2-245 (25 mg) as a light yellow solid. Total yield: 91%.

General Procedure

The HPLC measurement was performed using a HP 1100 from Agilent Technologies comprising a pump (binary) with degasser, an autosampler, a column oven, a diode-array detector (DAD) and a column as specified in the respective methods below. Flow from the column was split to a MS spectrometer. The MS detector was configured with an electrospray ionization source or API/APCI. Nitrogen was used as the nebulizer gas. The source temperature was maintained at 150° C. Data acquisition was performed with ChemStation LC/MSD quad, software.

Method 1

Reversed phase HPLC was carried out on a RP—C18 Gemini column (150×4.6 mm, 5 um); 10 min. linear gradient of 50-100% acetonitrile in water+100% acetonitrile in water 2 min): 210 nm and 254 or DAD.

Method 2

Reversed phase HPLC was carried out on a Gemini-NX C18 (100×2.0 mm; 5 um), Solvent A: water with 0.1% formic acid; Solvent B: acetonitrile with 0.1% formic acid. Gradient: 5% of B to 100% of B within 8 min at 50° C., DAD.

Method 3

Reversed phase HPLC was carried out on a Gemini-NX C18 (100×2.0 mm; 5 um), Solvent A: water with 0.1% formic acid; Solvent B: acetonitrile with 0.1% formic acid. Gradient: 5% of B to 40% of B within 8 min at 50° C., DAD.

Method 4

Reversed phase HPLC was carried out on a Gemini-NX C18 (100×2.0 mm; 5 um), Solvent A: water with 0.1% formic acid; Solvent B: acetonitrile with 0.1% formic acid. Gradient: 0% of B to 30% of B within 8 min at 50° C., DAD.

Method 5

Reversed phase HPLC was carried out on a Gemini C18 (50×2.0 mm; 3 um),

Solvent A: water with 0.1% formic acid; Solvent B: acetonitrile with 0.1% formic acid. Gradient: 10% of B to 95% of B within 4 min at 50° C., DAD.

TABLE 4

Analytical data and PI3Kα activity - $R_t$ means retention time (in minutes), $[M + H]^+$ means the protonated mass of the compound, method refers to the method used for (LC)MS.

| Cpd. Nr. | $R_t$ | $[M + 1]^+$ | Meth. | PI3Kα IC50 (μM) | $^1$H NMR (300 MHz; δ in ppm, J in Hz) |
|---|---|---|---|---|---|
| 2-01 | 4.882 | 369.1 | 1 | 0.158 (++) | DMSO δ 9.52 (s, 1H), 8.49 (d, J = 16.6, 2H), 7.32 (m, 3H), 6.78 (dd, J = 7.9, 1.5, 1H), 4.32 (dt, J = 13.0, 6.4, 6H), 3.80 (m, 4H), 1.32 (t, J = 7.1, 3H). |
| 2-02 | 9.199 | 341.1 | 1 | 19 | DMSO δ 9.58 (s, 1H), 8.38 (s, 1H), 7.99 (s, 1H), 7.31 (m, 2H), 7.15 (t, J = 7.8, 1H), 6.69 (d, J = 7.8, 1H), 4.22 (m, 4H), 3.72 (m, 4H). |
| 2-03 | 10.433 | 325.1 | 1 | 10 | DMSO) δ 10.01 (s, 1H), 9.53 (s, 1H), 8.60 (s, 1H), 8.51 (s, 1H), 7.38 (m, 2H), 7.25 (t, J = 7.8, 1H), 6.78 (d, J = 7.6, 1H), 4.32 (s, 4H), 3.81 (s, 4H). |
| 2-04 | 8.396 | 327.1 | 1 | 0.639 (++) | $^1$H NMR (300 MHz, DMSO) δ 9.46 (s, 1H), 8.50 (s, 1H), 7.81 (s, 1H), 7.38 (m, 2H), 7.23 (t, J = 7.9, 1H), 6.75 (d, J = 7.8, 1H), 4.59 (s, 2H), 4.23 (m, 4H), 3.78 (m, 4H). |
| 2-05 | 7.277 | 495.3 | 1 | 0.476 | DMSO δ 9.48 (s, 1H), 8.45 (s, 1H), 7.82 (s, 1H), 7.36 (m, 2H), 7.24 (d, J = 7.7, 1H), 6.74 (d, J = 7.5, 1H), 4.23 (m, 4H), 3.78 (m, 4H), 3.62 (s, 2H), 3.35 (m, 4H), 2.40 (m, 4H), 1.38 (s, 9H). |
| 2-06 | 4.707 | 437.2 | 1 | 0.451 (++) | DMSO δ 9.48 (s, 1H), 8.45 (s, 1H), 7.83 (s, 1H), 7.36 (dd, J = 11.7, 5.0, 2H), 7.22 (t, J = 7.9, 1H), 6.74 (dd, J = 7.9, 1.6, 1H), 4.23 (m, 4H), 3.77 (m, 4H), 3.62 (s, 2H), 3.40 (m, 4H), 2.41-2.39 (m, 4H), 1.96 (s, 3H). |
| 2-07 | 4.577 | 409.2 | 1 | 27 | DMSO δ 9.48 (s, 1H), 8.45 (s, 1H), 7.80 (s, 1H), 7.37 (dd, J = 12.2, 5.0, 2H), 7.22 (t, J = 7.9, 1H), 6.74 (d, J = 9.5, 1H), 4.24 (m, 4H), 3.78 (m, 4H), 3.58 (s, 2H), 2.42-2.31 (m, 4H), 2.14 (s, 4H), 1.39 (s, 3H). |

TABLE 4-continued

Analytical data and PI3Kα activity - $R_t$ means retention time (in minutes), [M + H]⁺ means the protonated mass of the compound, method refers to the method used for (LC)MS.

| Cpd. Nr. | $R_t$ | [M + 1]⁺ | Meth. | PI3Kα IC50 (μM) | ¹H NMR (300 MHz; δ in ppm, J in Hz) |
|---|---|---|---|---|---|
| 2-08 | 4.714 | 409.2 | 1 | 0.54 (++) | DMSO δ 9.48 (s, 1H), 8.46 (s, 1H), 7.86 (s, 1H), 7.74 (s, 1H), 7.38 (dd, J = 11.8, 5.0, 2H), 7.23 (t, J = 7.9, 1H), 6.75 (dd, J = 8.0, 1.7, 1H), 4.24 (m, 4H), 3.78 (m, 4H), 3.69 (s, 2H), 3.16 (m, 2H), 2.64 (t, J = 5.3, 2H). |
| 2-09 | 4.601 | 396.2 | 1 | 0.444 (++) | DMSO δ 9.48 (s, 1H), 8.45 (s, 1H), 7.83 (s, 1H), 7.38 (m, 2H), 7.22 (t, J = 7.9, 1H), 6.74 (dd, J = 7.5, 2.0, 1H), 4.24 (m, 4H), 3.78 (m, 4H), 3.58 (m, 6H), 2.45 (m, 4H). |
| 2-10 | 4.409 | 473.2 | 1 | 0.037 (+++) | DMSO δ 9.48 (s, 1H), 8.46 (s, 1H), 7.83 (s, 1H), 7.37 (dd, J = 11.9, 4.9, 2H), 7.23 (t, J = 7.8, 1H), 6.75 (dd, J = 7.9, 1.7, 1H), 4.24 (m, 4H), 3.78 (m, 4H), 3.67 (s, 2H), 3.12 (m, 4H), 2.87 (s, 3H), 2.56 (m, 4H). |
| 2-11 | 6.401 | 487 | 1 | 0.044 | DMSO δ 9.51 (s, 1H), 8.49 (s, 1H), 8.34 (s, 1H), 7.37 (m, 2H), 7.25 (t, J = 7.8, 1H), 6.77 (d, J = 8.1, 1H), 4.25 (s, 6H), 3.80 (s, 6H), 3.22 (s, 4H), 2.92 (s, 3H). |
| 2-12 | 5.599 | 397.1 | 1 | ++ | CDCl₃ δ 7.67 (d, J = 0.7, 1H), 7.35 (t, J = 7.9 Hz, 1H), 7.22 (m, 1H), 7.18 (m, 1H), 6.95 (ddd, J = 8.2, 2.6, 0.9 Hz, 1H), 4.28 (m, 4H), 3.85 (s, 3H), 3.84 (m, 4H), 2.46 (s, 3H). |
| 2-13 | 7.691 | 365.1 | 1 | 0.108 (++) | DMSO δ 9.53 (s, 1H), 8.50 (d, J = 13.9, 2H), 7.38 (dd, J = 9.6, 4.9, 2H), 7.26 (t, J = 7.8, 1H), 6.79 (dd, J = 7.9, 1.6, 1H), 4.25 (m, 4H), 3.80 (m, 4H). |
| 2-14 | 7.025 | 337 | 1 | 0.34 (++) | DMSO δ 9.46 (s, 1H), 8.38 (s, 1H), 7.69 (s, 1H), 7.37 (dd, J = 12.3, 5.0, 2H), 7.21 (t, J = 7.9, 1H), 6.73 (dd, J = 7.9, 1.6, 1H), 4.21 (m, 4H), 3.77 (m, 4H), 2.03 (ddd, J = 13.2, 8.3, 4.9, 1H), 0.92 (m, 2H), 0.79 (m, 2H). |
| 2-15 | 3.131 | 447.2 | 1 | 0.741 (++) | DMSO δ 13.25 (s, 1H), 8.65 (s, 1H), 8.55 (s, 1H), 8.40 (s, 1H), 7.67 (d, J = 6.8, 1H), 7.58 (m, 1H), 7.45 (m, 1H), 4.29 (s, 4H), 4.08 (s, 2H), 3.82 (s, 4H), 3.70 (s, 2H), 2.48 (s, 4H), 2.28 (s, 3H). |
| 2-16 | 4.152 | 511.2 | 1 | 0.254 (++) | DMSO δ 13.24 (s, 1H), 8.65 (s, 1H), 8.55 (s, 1H), 8.44 (s, 1H), 7.67 (d, J = 7.0, 1H), 7.58 (d, J = 8.3, 1H), 7.45 (t, J = 7.7, 1H), 4.29 (s, 6H), 3.82 (s, 6H), 3.23 (s, 4H), 2.92 (s, 3H). |
| 2-17 | 3.171 | 497.20 | 1 | 0.095 | DMSO δ 13.20 (s, 1H), 8.58 (d, J = 15.8, 2H), 7.99 (d, J = 37.6, 1H), 7.52 (m, 3H), 4.27 (d, J = 4.4, 4H), 3.81 (m, 4H), 3.70 (s, 2H), 3.14 (t, J = 9.4, 4H), 2.87 (s, 3H), 2.58 (s, 4H). |
| 2-18 | 3.745 | 432.5 | 1 | 0.182 (++) | DMSO δ 8.64 (s, 1H), 8.55 (s, 1H), 8.40 (s, 1H), 8.30 (s, 1H), 7.66 (d, J = 7.1, 1H), 7.58 (d, J = 8.3, 1H), 7.44 (m, 1H), 4.89 (br s, 1H), 4.28 (br s, 4H), 4.07 (br s, 1H), 3.81 (br s, 4H), 3.70 (br s, 1H), 2.92 (brs, 4H) (rotamers observed) |
| 2-19 | 4.151 | 361.2 | 1 | 0.438 | DMSO) δ 13.26 (s, 1H), 8.53 (s, 3H), 7.79 (s, 1H), 7.62 (d, J = 7.1, 1H), 7.55 (d, J = 8.2, 1H), 7.42 (d, J = 7.5, 1H), 4.24 (s, 4H), 3.79 (s, 4H), 2.06 (m, 1H), 0.94 (m, 2H), 0.81 (m, 2H). |
| 2-20 | 4.63 | 389.10 | 1 | 1.8 | DMSO δ 13.26 (s, 1H), 8.59 (m, 3H), 7.67 (d, J = 7.1, 1H), 7.60 (d, J = 8.3, 1H), 7.45 (m, 1H), 4.28 (s, 4H), 3.82 (m, 4H). |
| 2-21 | 5.25 | 364.1 | 1 | — | DMSO δ 13.20 (s, 1H), 8.58 (s, 1H), 8.50 (s, 1H), 8.34 (s, 1H), 7.83 (s, 1H), 7.61 (d, J = 7.1, 1H), 7.52 (d, J = 8.2, 1H), 7.39 (m, 2H), 4.27 (s, 4H), 3.75 (s, 4H). |
| 2-22 | 6.72 | 346 | 1 | 0.618 (++) | DMSO δ 13.19 (s, 1H), 8.73 (s, 1H), 8.58 (s, 1H), 8.47 (s, 1H), 7.61 (d, J = 7.1, 1H), 7.53 (d, J = 8.2, 1H), 7.38 (t, J = 7.7, 1H), 4.21 (s, 4H), 3.75 (m, 4H). |
| 2-23 | 5.438 | 311.1 | 1 | 0.096 (+++) | DMSO δ 9.45 (s, 1H), 8.43 (s, 1H), 7.69 (d, J = 0.7, 1H), 7.38 (m, 2H), 7.22 (t, J = 7.9, 1H), 6.74 (dd, J = 8.0, 1.6, 1H), 4.23 (m, 4H), 3.78 (m, 4H). |

TABLE 4-continued

Analytical data and PI3Kα activity - R$_t$ means retention time (in minutes), [M + H]$^+$ means the protonated mass of the compound, method refers to the method used for (LC)MS.

| Cpd. Nr. | R$_t$ | [M + 1]$^+$ | Meth. | PI3Kα IC50 (μM) | $^1$H NMR (300 MHz; δ in ppm, J in Hz) |
|---|---|---|---|---|---|
| 2-24 | 5.576 | 335.1 | 1 | 2.6 (+) | DMSO δ 13.19 (s, 1H), 8.58 (s, 1H), 8.55 (s, 1H), 7.79 (s, 1H), 7.64 (d, J = 7.1, 1H), 7.54 (d, J = 8.2, 1H), 7.42 (m, 1H), 4.26 (m, 4H), 3.80 (m, 4H), 2.37 (s, 3H). |
| 2-25 | 6.033 | 334.1 | 1 | 10 | DMSO δ 11.18 (s, 1H), 8.48 (s, 1H), 8.05 (d, J = 0.7, 1H), 7.70 (d, J = 0.7, 1H), 7.58 (d, J = 1.4, 2H), 7.37 (m, 1H), 6.43 (m, 1H), 4.26 (m, 4H), 3.80 (m, 4H), 2.35 (m, 3H). |
| 2-26 | 3.350 | 296.1 | 1 | 10 | DMSO δ 9.09 (m, 1H), 8.56 (s, 1H), 8.48 (dd, J = 4.8, 1.6, 1H), 8.24 (m, 1H), 7.64 (d, J = 0.8, 1H), 7.40 (ddd, J = 8.0, 4.7, 0.7, 1H), 4.19 (m, 4H), 3.71 (m, 4H), 2.29 (s, 3H). |
| 2-27 | 4.651 | 326.1 | 1 | 3.9 (+) | DMSO δ 8.78 (s, 1H), 8.65 (s, 1H), 8.26 (s, 1H), 7.85 (s, 1H), 7.69 (s, 1H), 4.24 (d, J = 4.4, 4H), 3.90 (s, 3H), 3.77 (m, 4H), 2.36 (s, 3H). |
| 2-28 | 5.758 | 388.1 | 1 | 50 | DMSO δ 9.89 (s, 1H), 8.53 (s, 1H), 7.96 (s, 1H), 7.79 (s, 1H), 7.72 (d, J = 7.7, 1H), 7.45 (t, J = 7.9, 1H), 7.26 (d, J = 7.9, 1H), 4.32 (s, 4H), 3.85 (d, J = 4.4, 4H), 3.08 (s, 3H), 2.41 (s, 3H). |
| 2-29 | 4.843 | 367.2 | 1 | 3 | DMSO δ 8.62 (s, 1H), 8.39 (s, 1H), 7.82 (d, J = 8.3, 2H), 7.66 (s, 1H), 7.46 (d, J = 8.2, 3H), 6.03 (s, 1H), 4.22 (s, 4H), 3.77 (s, 4H), 2.65 (d, J = 3.5, 3H), 2.34 (s, 3H). |
| 2-30 | 3.726 | 312.1 | 1 | 0.235 (++) | DMSO δ 9.97 (s, 1H), 8.61 (s, 1H), 8.57 (s, 1H), 8.09 (d, J = 2.4, 1H), 7.70 (d, J = 3.5, 2H), 4.24 (d, J = 4.5, 4H), 3.78 (m, 4H), 2.35 (s, 3H). |
| 2-31 | 3.512 | 296.1 | 1 | 10 | DMSO δ 8.69 (s, 1H), 8.56 (d, J = 5.9, 2H), 7.87 (d, J = 6.0, 2H), 7.66 (s, 1H), 4.20 (m, 4H), 3.71 (m, 4H), 2.30 (s, 3H). |
| 2-32 | NMR | | | — | CDCl$_3$ δ 7.84 (s, 1H), 7.48 (m, 1H), 7.42 (d, J = 7.9, 1H), 7.31 (t, J = 7.9, 1H), 7.26 (s, 1H), 6.87 (dd, J = 8.1, 1.8, 1H), 4.32 (m, 4H), 3.88 (m, 4H), 3.85 (s, 3H), 2.41 (s, 3H). |
| 2-33 | 4.509 | 330.1 | 1 | — | CDCl$_3$ δ 8.62 (dd, J = 4.6, 1.6, 2H), 7.68 (dd, J = 4.5, 1.6, 2H), 7.55 (m, 1H), 4.20 (m, 4H), 3.79 (dd, J = 10.4, 5.7, 4H), 2.38 (t, J = 0.5, 3H). |
| 2-34 | 5.260 | 330.1 | 1 | — | CDCl$_3$ δ 8.99 (d, J = 1.8, 1H), 8.55 (dd, J = 4.8, 1.6, 1H), 8.04 (m, 1H), 7.50 (d, J = 0.6, 1H), 7.31 (m, 1H), 4.22 (m, 4H), 3.80 (m, 4H), 2.40 (d, J = 0.5, 3H). |
| 2-35 | 4.78 | 324.1 | 2 | — | DMSO δ 8.57 (s, 1H), 8.29 (s, 1H), 7.97 (d, J = 7.4, 2H), 7.87 (s, 1H), 7.47 (t, J = 7.3, 3H), 7.37 (t, J = 7.2, 1H), 4.31 (s, 4H), 3.80 (d, J = 4.4, 4H). |
| 2-36 | 4.31 | 360.1 | 2 | — | MeOD δ 8.26 (s, 1H), 7.77 (s, 1H), 7.70 (d, J = 8.9, 1H), 7.62 (d, J = 7.1, 2H), 7.52 (d, J = 8.2, 1H), 4.54 (m, 4H), 3.86 (m, 4H), 2.47 (s, 3H). |
| 2-37 | 3.37 | 395.20 | 1 | ++ | DMSO δ 9.45 (s, 1H), 7.79 (s, 1H), 7.42 (d, J = 6.9, 2H), 7.23 (m, 2H), 6.75 (d, J = 7.4, 1H), 4.26 (m, 4H), 3.77 (m, 4H), 3.02 (m, 4H), 2.56 (m, 4H), 2.27 (s, 3H). |
| 2-38 | 3.06 | 419.2 | 1 | ++ | CDCl$_3$ δ 10.16 (s, 1H), 8.51 (s, 1H), 7.80 (s, 1H), 7.55 (d, J = 6.6, 1H), 7.42 (m, 2H), 7.17 (s, 1H), 4.32 (m, 4H), 3.84 (m, 4H), 3.07 (m, 4H), 2.59 (s, 4H), 2.34 (s, 3H). |
| 2-39 | 4.12 | 459.20 | 1 | ++ | DMSO δ 9.46 (s, 1H), 7.88 (s, 1H), 7.40 (m, 3H), 7.23 (t, J = 7.8, 1H), 6.76 (d, J = 7.3, 1H), 4.27 (s, 4H), 3.77 (s, 4H), 3.38 (s, 4H), 3.13 (s, 4H), 2.98 (s, 3H). |
| 2-40 | 2.90 | 381.20 | 1 | ++ | DMSO δ 9.45 (s, 1H), 7.81 (s, 1H), 7.42 (m, 2H), 7.23 (m, 2H), 6.75 (d, J = 8.8, 1H), 4.26 (s, 4H), 3.77 (m, 4H), 2.93 (s, 8H). |
| 2-41 | 6.065 | 483.2 | 1 | ++ | DMSO δ 13.20 (s, 1H), 8.45 (s, 1H), 7.97 (s, 1H), 7.61 (dd, J = 7.1, 0.6, 1H), 7.57 (d, J = 8.3, 1H), 7.44 (m, 1H), 7.40 (d, J = 3.8, |

TABLE 4-continued

Analytical data and PI3Kα activity - $R_t$ means retention time (in minutes), $[M + H]^+$ means the protonated mass of the compound, method refers to the method used for (LC)MS.

| Cpd. Nr. | $R_t$ | $[M + 1]^+$ | Meth. | PI3Kα IC50 (μM) | $^1$H NMR (300 MHz; δ in ppm, J in Hz) |
|---|---|---|---|---|---|
| | | | | | 1H), 4.30 (s, 4H), 3.80 (m, 4H), 3.37 (m, 4H), 3.17 (m, 4H), 2.98 (s, 3H). |
| 2-42 | 7.644 | 413.1 | 1 | — | DMSO δ 13.22 (s, 1H), 8.46 (s, 1H), 8.05 (s, 1H), 7.61 (dd, J = 16.1, 7.7, 2H), 7.43 (t, J = 7.7, 1H), 4.27 (s, 4H), 3.80 (s, 4H), 2.38 (s, 3H). |
| 2-43 | 8.144 | 516.3 | 1 | — | DMSO δ 13.12 (s, 1H), 8.35 (s, 1H), 7.96 (s, 1H), 7.51 (dd, J = 11.0, 7.7, 2H), 7.34 (m, 1H), 6.02 (s, 1H), 4.21 (s, 4H), 4.03 (s, 2H), 3.74 (s, 4H), 3.57 (s, 2H), 2.38 (s, 2H), 2.28 (s, 3H), 1.38 (s, 9H). |
| 2-44 | 3.836 | 416.2 | 1 | 0.731 (++) | DMSO δ 13.13 (s, 1H), 8.34 (s, 1H), 7.95 (s, 1H), 7.50 (m, 2H), 7.35 (t, J = 7.8, 1H), 6.01 (s, 1H), 4.21 (s, 4H), 3.74 (m, 4H), 3.39 (s, 2H), 2.93 (s, 2H), 2.28 (s, 3H), 2.23 (s, 2H). |
| 2-45 | 7.145 | 430.2 | 1 | — | DMSO δ 8.33 (s, 1H), 8.12 (s, 1H), 7.91 (s, 1H), 7.51 (d, J = 5.0, 1H), 7.49 (d, J = 6.2, 1H), 7.35 (dd, J = 8.3, 7.1, 1H), 5.98 (s, 1H), 4.21 (m, 4H), 3.73 (m, 4H), 3.11 (s, 2H), 2.64 (m, 2H), 2.38 (m, 2H), 2.31 (s, 3H), 2.27 (s, 3H). |
| 2-46 | 6.306 | 494.2 | 1 | — | DMSO δ 13.25 (bs, 1H), 8.43 (s, 1H), 8.22 (s, 1H), 7.56 (t, J = 7.0, 2H), 7.41 (dd, J = 8.3, 7.2, 1H), 6.12 (s, 1H), 4.25 (m, 4H), 3.98 (d, J = 2.6, 2H), 3.81 (m, 4H), 3.49 (m, 2H), 3.00 (s, 3H), 2.55 (m, 2H), 2.36 (s, 3H). |
| 2-47 | 7.661 | 518.3 | 1 | — | DMSO δ 13.17 (s, 1H), 8.49 (s, 1H), 8.26 (s, 1H), 7.62 (d, J = 7.1, 1H), 7.56 (d, J = 8.2, 1H), 7.42 (m, 1H), 4.26 (s, 4H), 4.09 (d, J = 12.2, 2H), 3.79 (s, 4H), 3.47 (s, 1H), 2.95 (s, 2H), 2.41 (s, 3H), 1.80 (s, 4H), 1.42 (s, 9H). |
| 2-48 | 3.697 | 359.1 | 1 | — | CDCl$_3$ δ 7.57 (d, J = 0.7, 1H), 7.36 (m, 3H), 6.95 (dt, J = 6.5, 2.6, 1H), 4.28 (m, 4H), 3.87 (m, 7H), 2.47 (d, J = 0.5, 3H). |
| 2-49 | 1.596 | 345.1 | 1 | ++ | DMSO δ 9.54 (s, 1H), 7.87 (s, 1H), 7.25 (t, J = 8.1, 1H), 7.15 (dd, J = 5.1, 3.0, 2H), 6.80 (m, 1H), 4.17 (m, 4H), 3.74 (m, 4H), 2.39 (s, 3H). |
| 2-50 | 2.33 | 474.2 | 2 | 0.001 | DMSO δ 8.77 (s, 2H), 8.41 (s, 1H), 7.76 (s, 1H), 6.83 (s, 2H), 4.22 (d, J = 4.5, 4H), 3.77 (m, 4H), 3.66 (s, 2H), 3.11 (d, J = 4.8, 4H), 2.87 (s, 3H), 2.55 (s, 4H). |
| 2-51 | 4.95 | 405.2 | 1 | — | DMSO δ 13.21 (s, 1H), 8.42 (s, 1H), 7.92 (s, 1H), 7.59 (dd, J = 16.1, 7.7, 2H), 7.43 (m, 1H), 7.29 (s, 1H), 4.30 (s, 4H), 3.79 (m, 4H), 2.94 (m, 8H). |
| 2-52 | NMR | | | 0.676 | DMSO δ 8.66-8.32 (m, 2H), 7.74-7.15 (m, 3H), 4.29 (d, J = 7.3, 5H), 3.76 (s, 4H), 1.25 (t, J = 15.7, 3H). |
| 2-53 | NMR | | | — | CDCl$_3$ δ 7.67 (d, J = 0.7 Hz, 1H), 7.35 (t, J = 7.9 Hz, 1H), 7.22 (m, 1H), 7.18 (m, 1H), 6.95 (ddd, J = 8.2, 2.6, 0.9 Hz, 1H), 4.28 (m, 4H), 3.87 (s, 3H), 3.85 (m, 4H), 2.46 (s, 3H). |
| 2-54 | 1.42 | 369.1 | 2 | 0.266 (++) | CDCl$_3$ δ 10.06 (s, 1H), 8.19 (d, J = 0.6, 1H), 7.61 (s, 1H), 7.50 (m, 3H), 4.30 (m, 4H), 3.83 (m, 4H), 2.49 (m, 3H). |
| 2-55 | 1.43 | 413.0 | 2 | 12 | CDCl$_3$ δ 8.13 (s, 1H), 7.66 (s, 1H), 7.54 (dt, J = 7.2, 3.6, 1H), 7.47 (m, 2H), 4.29 (m, 4H), 3.86 (m, 4H), 2.49 (s, 3H). |
| 2-56 | 4.192 | 422.0 | 2 | 0.253 | CDCl$_3$ δ 9.10 (d, J = 1.8, 1H), 8.54 (dd, J = 4.8, 1.6, 1H), 8.16 (m, 1H), 7.87 (m, 1H), 7.31 (dd, J = 7.9, 4.4, 1H), 4.25 (m, 4H), 3.80 (m, 4H), 2.40 (s, 3H). |
| 2-57 | 3.89 | 418.2 | 1 | 0.144 (++) | DMSO δ 8.50 (d, J = 0.7, 1H), 8.44 (s, 1H), 8.32 (s, 1H), 7.63 (d, J = 7.0, 1H), 7.56 (d, J = 8.3, 1H), 7.42 (dd, J = 8.2, 7.2, 1H), 4.27 (m, 4H), 3.79 (m, 4H), 3.51 (t, J = 12.2, 1H), 3.25 (dd, J = 15.8, 8.2, 2H), |

TABLE 4-continued

Analytical data and PI3Kα activity - $R_t$ means retention time (in minutes), [M + H]⁺ means the protonated mass of the compound, method refers to the method used for (LC)MS.

| Cpd. Nr. | $R_t$ | [M + 1]⁺ | Meth. | PI3Kα IC50 (µM) | ¹H NMR (300 MHz; δ in ppm, J in Hz) |
|---|---|---|---|---|---|
| 2-58 | 2.80 | 432.2 | 2 | ++ | 2.95 (t, J = 11.7, 2H), 2.43 (s, 3H), 2.15 (t, J = 11.6, 2H), 1.82 (m, 2H). DMSO δ 8.50 (s, 1H), 8.26 (s, 1H), 8.20 (d, J = 7.4, 2H), 7.63 (d, J = 7.1, 1H), 7.55 (t, J = 9.4, 1H), 7.43 (dd, J = 8.2, 7.3, 1H), 4.26 (m, 4H), 3.79 (m, 4H), 3.33 (t, J = 12.3, 1H), 3.17 (d, J = 11.2, 2H), 2.57 (t, J = 11.1, 2H), 2.49 (s, 4H), 2.44 (s, 3H), 2.12 (m, 2H), 1.86 (d, J = 12.1, 2H). |
| 2-59 | 6.37 | 496.2 | 1 | — | DMSO δ 13.17 (s, 1H), 8.50 (s, 1H), 8.27 (s, 1H), 7.63 (d, J = 7.1, 1H), 7.56 (d, J = 8.3, 1H), 7.43 (dd, J = 8.2, 7.2, 1H), 4.27 (s, 4H), 3.80 (m, 4H), 3.72 (d, J = 11.5, 2H), 2.98 (d, J = 13.4, 2H), 2.94 (s, 3H), 2.45 (s, 3H), 1.96 (s, 4H). |
| 2-60 | 4.70 | 4.97 | 2 | ++ | DMSO δ 13.19 (s, 1H), 8.08 (s, 1H), 8.00 (s, 1H), 7.61 (d, J = 8.1, 1H), 7.45 (m, 1H), 7.38 (dd, J = 7.1, 1.0, 1H), 4.19 (m, 4H), 3.76 (m, 4H), 3.14 (m, 4H), 2.88 (s, 3H), 2.59 (m, 4H). |
| 2-61 | 3.14 | 488.2 | 2 | 4.5 | CDCl₃ δ 8.71 (d, J = 2.4, 1H), 8.08 (dd, J = 8.6, 2.5, 1H), 7.82 (s, 1H), 7.49 (s, 1H), 6.83 (d, J = 8.7, 1H), 4.37 (m, 4H), 4.00 (s, 3H), 3.90 (m, 4H), 3.77 (s, 2H), 3.30 (m, 4H), 2.80 (s, 3H), 2.71 (m, 4H). |
| 2-62 | 2.28 | 350.1 | 2 | — | CDCl₃ δ 7.99 (s, 1H), 7.48 (m, 2H), 7.37 (t, J = 8.1, 1H), 6.95 (m, 1H), 4.35 (m, 4H), 3.89 (m, 7H), 2.57 (s, 3H). |
| 2-63 | 7.53 | 561.3 | 1 | — | DMSO δ 13.25 (s, 1H), 8.83 (s, 1H), 8.43 (s, 1H), 8.09 (d, J = 7.7, 1H), 7.62 (d, J = 7.1, 1H), 7.58 (d, J = 8.3, 1H), 7.44 (dd, J = 8.1, 7.4, 1H), 4.33-4.21 (m, 4H), 4.13-4.00 (m, 1H), 3.93 (d, J = 13.1, 2H), 3.86-3.76 (m, 4H), 2.98-2.85 (m, 2H), 2.55 (s, 3H), 1.89 (d, J = 10.2, 2H), 1.55-1.42 (m, 2H), 1.41 (s, 9H). |
| 2-64 | 2.94 | 461.2 | 2 | + | DMSO δ 13.27 (s, 1H), 8.81 (s, 1H), 8.58-8.48 (m, 1H), 8.43 (s, 1H), 8.32 (d, J = 7.5, 1H), 8.28-8.20 (m, 1H), 7.63 (d, J = 7.1, 1H), 7.59 (d, J = 8.3, 1H), 7.45 (dd, J = 8.2, 7.2, 1H), 4.32-4.24 (m, 4H), 4.20-4.10 (m, 1H), 3.86-3.78 (m, 4H), 3.15-3.00 (m, 2H), 2.58 (s, 3H), 2.16-2.03 (m, 2H), 1.85-1.68 (m, 2H). Two protons are missing, most likely under the water signal |
| 2-65 | 0.37 | 488.2 | 2 | + | CDCl₃ δ 8.71 (d, J = 1.7, 1H), 8.31 (d, J = 2.8, 1H), 7.95 (s, 1H), 7.77 (dd, J = 2.7, 1.8, 1H), 7.51 (s, 1H), 4.38 (m, 4H), 3.96 (s, 3H), 3.91 (m, 4H), 3.77 (s, 2H), 3.30 (m, 4H), 2.80 (s, 3H), 2.72 (m, 4H). |
| 2-66 | 0.367 | 473.2 | 2 | 0.169 | DMSO δ 8.51 (d, J = 2.1, 1H), 8.33 (s, 1H), 7.90 (dd, J = 8.7, 2.4, 1H), 7.76 (s, 1H), 6.50 (d, J = 8.6, 1H), 6.10 (s, 2H), 4.22 (s, 4H), 3.78 (d, J = 4.6, 4H), 3.65 (s, 2H), 3.11 (s, 4H), 2.87 (s, 3H), 2.54 (d, J = 8.2, 4H). |
| 2-67 | 3.44 & 3.99 | 489.2 | 2 | ++ | DMSO δ 9.12 (s, 2H), 8.57 (s, 1H), 7.81 (s, 1H), 4.25 (d, J = 4.4, 4H), 3.97 (s, 3H), 3.77 (m, 4H), 3.68 (s, 2H), 3.11 (d, J = 4.8, 4H), 2.87 (s, 3H), 2.56 (s, 4H). |
| 2-68 | 2.54 & 2.64 | 500.2 | 2 | 11 | DMSO) δ 8.65 (s, 1H), 8.04 (d, J = 8.5, 2H), 8.00 (s, 1H), 7.94 (d, J = 8.5, 2H), 7.83 (s, 1H), 7.38 (s, 1H), 4.27 (s, 4H), 3.79 (m, 4H), 3.68 (s, 2H), 3.12 (s, 4H), 2.87 (s, 3H), 2.56 (s, 4H). |
| 2-69 | 2.75 | 512.2 | 2 | — | DMSO δ 10.47 (s, 1H), 8.43 (s, 1H), 7.81 (s, 1H), 7.80 (d, J = 5.5, 1H), 7.78 (m, 1H), 6.88 (d, J = 8.0, 1H), 4.23 (d, J = 4.5, 4H), 3.78 (m, 4H), 3.66 (s, 2H), 3.55 (s, 2H), 3.11 (d, J = 4.7, 4H), 2.87 (s, 3H), 2.56 (s, 4H). |

TABLE 4-continued

Analytical data and PI3Kα activity - $R_t$ means retention time (in minutes), [M + H]$^+$ means the protonated mass of the compound, method refers to the method used for (LC)MS.

| Cpd. Nr. | $R_t$ | [M + 1]$^+$ | Meth. | PI3Kα IC50 (μM) | $^1$H NMR (300 MHz; δ in ppm, J in Hz) |
|---|---|---|---|---|---|
| 2-70 | 3.18 | 514 | 2 | — | DMSO δ 11.25 (s, 1H), 8.24 (d, J = 2.1, 1H), 7.93 (s, 1H), 7.41 (m, 2H), 7.02 (dd, J = 11.2, 8.8, 1H), 6.70 (s, 1H), 4.21 (s, 4H), 3.78 (m, 4H), 3.69 (s, 2H), 3.12 (s, 4H), 2.87 (s, 3H), 2.57 (s, 4H). |
| 2-71 | 4.15 & 4.73 | 496.2 | 2 | — | CDCl$_3$ δ 8.51 (s, 1H), 7.97 (s, 1H), 7.53 (dd, J = 7.3, 0.6, 1H), 7.50 (s, 1H), 7.43 (d, J = 8.1, 1H), 7.28 (m, 2H), 6.98 (s, 1H), 4.37 (m, 4H), 3.89 (m, 4H), 3.77 (s, 2H), 3.27 (m, 4H), 2.77 (s, 3H), 2.71 (m, 4H). |
| 2-72 | 3.53 & 3.89 | 500.2 | 2 | — | CDCl$_3$ δ 8.37 (s, 1H), 8.12 (d, J = 7.8, 1H), 8.00 (s, 1H), 7.75 (d, J = 7.6, 1H), 7.51 (dd, J = 13.2, 5.3, 2H), 4.37 (m, 4H), 3.90 (m, 4H), 3.76 (m, 2H), 3.29 (m, 4H), 2.79 (s, 3H), 2.71 (m, 4H). |
| 2-73 | 5.37 | 461.0 | 2 | — | CDCl$_3$ δ 10.14 (m, 1H), 8.06 (d, J = 0.9, 1H), 7.70 (d, J = 0.7, 1H), 7.54 (dt, J = 8.1, 1.0, 1H), 7.46 (t, J = 7.6, 1H), 7.40 (dd, J = 7.0, 1.2, 1H), 4.29 (m, 4H), 3.84 (m, 4H), 2.48 (d, J = 0.4, 3H). |
| 2-74 | 4.55 | 392.1 | 2 | 0.092 | DMSO δ 13.23 (s, 1H), 8.65 (s, 1H), 8.56 (s, 1H), 8.44 (t, J = 6.1, 1H), 8.40 (s, 1H), 7.67 (d, J = 7.1, 1H), 7.58 (d, J = 8.3, 1H), 7.44 (m, 1H), 4.34 (s, 4H), 3.83 (m, 4H), 3.40 (s, 2H), 1.15 (t, J = 7.1, 3H). |
| 2-75 | 2.81 | 497.2 | 2 | 0.113 | DMSO δ 11.65 (s, 1H), 8.75 (d, J = 1.9, 1H), 8.49 (s, 1H), 8.41 (d, J = 1.7, 1H), 7.75 (s, 1H), 7.43 (m, 1H), 6.45 (dd, J = 3.3, 1.8, 1H), 4.21 (s, 4H), 3.73 (s, 4H), 3.61 (s, 2H), 3.06 (s, 4H), 2.80 (s, 3H), 2.50 (s, 4H). |
| 2-76 | 4.67 | 539.1 | 2 | — | DMSO δ 13.27 (s, 1H), 8.82 (s, 1H), 8.44 (s, 1H), 8.18 (d, J = 7.7, 1H), 7.60 (dd, J = 11.7, 7.9, 2H), 7.45 (m, 4H), 4.29 (d, J = 7.8, 4H), 4.03 (s, 1H), 3.82 (s, 4H), 3.58 (d, J = 12.1, 2H), 2.95 (m, 2H), 2.92 (s, 3H), 2.58 (s, 3H), 2.02 (d, J = 10.9, 2H), 1.66 (dd, J = 20.4, 11.1, 2H). |
| 2-77 | 4.12 | 378.1 | 2 | — | DMSO δ 13.25 (s, 1H), 9.06 (s, 1H), 8.44 (s, 1H), 7.60 (dd, J = 11.9, 7.7, 3H), 7.45 (dd, J = 8.3, 7.2, 1H), 4.27 (m, 4H), 3.81 (m, 4H), 2.61 (s, 3H). |
| 2-78 | 2.78 | 419.2 | 2 | — | DMSO δ 13.23 (s, 1H), 8.42 (d, J = 0.8, 1H), 7.87 (s, 1H), 7.63 (d, J = 7.0, 1H), 7.57 (d, J = 8.3, 1H), 7.43 (dd, J = 8.3, 7.2, 1H), 7.28 (s, 1H), 4.30 (m, 4H), 3.79 (m, 4H), 3.32 (s, 2H), 3.25 (dd, J = 28.1, 16.1, 2H), 2.80 (dd, J = 20.2, 9.4, 2H), 1.86 (d, J = 10.1, 2H), 1.53 (m, 2H). |
| 2-79 | 4.23 | 378.1 | 2 | 0.11 | DMSO δ 13.23 (s, 1H), 8.64 (s, 1H), 8.56 (s, 1H), 8.40 (s, 1H), 8.38 (d, J = 5.0, 1H), 7.67 (d, J = 7.1, 1H), 7.58 (d, J = 8.3, 1H), 7.44 (dd, J = 8.2, 7.3, 1H), 4.34 (d, J = 4.4, 4H), 3.83 (m, 4H), 2.84 (d, J = 4.8, 3H). |
| 2-81 | 3.54 and 3.88 | 515.2 | 3 | 0.21 | DMSO δ 10.58 (s, 1H), 8.87 (s, 1H), 8.56 (s, 1H), 8.28 (d, J = 9.1, 1H), 8.14 (d, J = 8.9, 1H), 7.81 (s, 1H), 4.25 (s, 4H), 3.78 (s, 4H), 3.67 (s, 2H), 3.12 (s, 4H), 2.87 (s, 3H), 2.55 (s, 4H), 2.11 (s, 3H). |
| 2-82 | 3.99 and 4.26 | 529.2 | 3 | 0.158 | DMSO δ 8.61 (s, 1H), 8.41 (s, 1H), 7.80 (m, 3H), 7.46 (d, J = 8.7, 2H), 6.02 (d, J = 4.7, 1H), 4.23 (s, 4H), 3.77 (m, 4H), 3.65 (s, 2H), 3.11 (s, 4H), 2.86 (s, 3H), 2.64 (d, J = 4.6, 3H), 2.54 (d, J = 4.6, 4H). |
| 2-83 | 4.79 and 4.96 | 541.2 | 3 | 0.21 | CDCl$_3$ δ 8.74 (d, J = 1.7, 1H), 8.22 (d, J = 1.9, 1H), 7.81 (s, 1H), 7.47 (s, 1H), 5.08 (s, 2H), 4.36 (m, 4H), 3.90 (m, 4H), 3.76 (s, 2H), 3.29 (m, 4H), 2.79 (s, 3H), 2.70 (m, 4H). |
| 2-84 | 4.43 and 4.75 | 522.2 | 3 | — | DMSO δ 13.33 (s, 1H), 8.23 (s, 1H), 7.95 (s, 1H), 7.72 (d, J = 8.0, 1H), 7.52 (dd, J = 13.2, 7.0, 2H), 4.46 (s, 4H), 3.80 (m, 4H), |

TABLE 4-continued

Analytical data and PI3Kα activity - $R_t$ means retention time (in minutes), $[M + H]^+$ means the protonated mass of the compound, method refers to the method used for (LC)MS.

| Cpd. Nr. | $R_t$ | $[M + 1]^+$ | Meth. | PI3Kα IC50 (μM) | $^1$H NMR (300 MHz; δ in ppm, J in Hz) |
|---|---|---|---|---|---|
| | | | | | 3.74 (s, 2H), 3.13 (s, 4H), 2.88 (s, 3H), 2.59 (s, 4H). |
| 2-86 | 4.40 | 392.1 | 1 | 0.891 | CDCl$_3$ δ 8.49 (s, 1H), 8.04 (s, 1H), 7.93 (s, 1H), 7.47 (m, 2H), 7.39 (m, 2H), 4.36 (m, 4H), 3.84 (m, 4H), 3.47 (s, 3H), 3.10 (s, 3H). |
| 2-87 | 4.87 | 418.2 | 1 | 0.355 | DMSO δ 13.24 (s, 1H), 8.63 (s, 1H), 8.56 (s, 1H), 8.43 (s, 1H), 7.66 (d, J = 7.1, 1H), 7.58 (d, J = 8.3, 1H), 7.44 (dd, J = 8.2, 7.3, 1H), 4.30 (d, J = 4.3, 4H), 3.95 (t, J = 6.6, 2H), 3.81 (m, 4H), 3.53 (t, J = 6.7, 2H), 1.87 (m, 4H). |
| 2-88 | 0.98 | 336.1 | 1 | — | DMSO δ 9.60 (s, 1H), 8.26 (s, 1H), 7.48 (d, J = 6.8, 2H), 7.25 (t, J = 8.1, 1H), 6.80 (d, J = 8.6, 1H), 4.23 (s, 4H), 3.79 (d, J = 4.3, 4H). |
| 2-89 | 0.39 | 472.2 | 3 | 33 | CDCl$_3$ δ 7.78 (s, 1H), 7.71 (d, J = 8.5, 2H), 7.43 (s, 1H), 6.74 (d, J = 8.5, 2H), 4.33 (m, 4H), 3.89 (m, 4H), 3.74 (s, 2H), 3.28 (m, 4H), 2.78 (s, 3H), 2.70 (m, 4H). |
| 2-90 | 2.21 and 3.02 | 447.2 | 3 | 6 | DMSO δ 12.93 (s, 1H), 8.22 (s, 1H), 8.11 (s, 1H), 7.89 (s, 1H), 7.74 (s, 1H), 4.22 (m, 4H), 3.76 (m, 4H), 3.65 (s, 2H), 3.11 (m, 4H), 2.87 (s, 3H), 2.55 (m, 4H). |
| 2-91 | 2.69 | 325.1 | 3 | 3.9 | DMSO δ 8.79 (s, 1H), 8.65 (dd, J = 4.6, 1.6, 2H), 8.31 (s, 1H), 7.93 (dd, J = 4.6, 1.6, 3H), 7.51 (s, 1H), 4.33 (s, 4H), 3.79 (m, 4H). |
| 2-92 | 3.29 | 325.1 | 3 | — | DMSO δ 9.16 (d, J = 1.7, 1H), 8.67 (s, 1H), 8.57 (dd, J = 4.7, 1.6, 1H), 8.31 (m, 2H), 7.90 (s, 1H), 7.49 (dd, J = 7.4, 4.8, 2H), 4.33 (s, 4H), 3.79 (m, 4H). |
| 2-93 | 3.01 | 341.1 | 1 | — | DMSO δ 8.78 (s, 2H), 8.44 (s, 1H), 8.21 (s, 1H), 7.86 (s, 1H), 7.46 (s, 1H), 6.88 (s, 2H), 4.29 (s, 4H), 3.77 (m, 4H). |
| 2-94 | 4.37 | 363.1 | 1 | 0.944 | DMSO δ 11.27 (s, 1H), 8.49 (s, 1H), 8.42 (s, 1H), 7.86 (s, 1H), 7.56 (d, J = 6.8, 1H), 7.45 (t, J = 6.0, 3H), 7.18 (t, J = 7.7, 1H), 6.94 (s, 1H), 4.32 (s, 4H), 3.80 (m, 4H). |
| 2-95 | 4.28 | 381.1 | 1 | 0.891 | DMSO δ 11.27 (s, 1H), 8.41 (s, 1H), 8.29 (t, J = 3.7, 1H), 7.87 (s, 1H), 7.43 (m, 3H), 7.03 (dd, J = 11.3, 8.8, 1H), 6.72 (s, 1H), 4.27 (s, 4H), 3.78 (m, 4H). |
| 2-96 | 3.32 | 375.1 | 1 | — | DMSO δ 8.66 (s, 2H), 8.35 (s, 1H), 7.98 (s, 1H), 7.56 (s, 1H), 6.99 (s, 2H), 4.25 (s, 4H), 3.76 (m, 4H). |
| 2-97 | 0.29 | 573.3 | 4 | 4.5 | DMSO δ 13.21 (s, 1H), 8.60 (s, 1H), 8.55 (s, 1H), 7.90 (s, 1H), 7.64 (d, J = 7.0, 1H), 7.55 (d, J = 8.3, 1H), 7.42 (dd, J = 8.2, 7.3, 1H), 4.27 (m, 4H), 3.80 (m, 4H), 3.62 (s, 2H), 3.26 (t, J = 6.8, 4H), 3.05 (s, 2H), 2.40 (s, 2H), 1.66 (dd, J = 12.0, 6.1, 2H), 1.49 (s, 4H), 1.38 (s, 9H). |
| 2-98 | 3.73 | 587.4 | 1 | 7.2 | DMSO δ 13.19 (s, 1H), 8.61 (s, 1H), 8.55 (s, 1H), 7.93 (s, 1H), 7.64 (d, J = 7.0, 1H), 7.56 (d, J = 8.3, 1H), 7.43 (m, 1H), 4.27 (m, 4H), 3.80 (m, 4H), 3.73 (s, 2H), 3.28 (s, 4H), 2.54 (s, 4H), 1.48 (s, 4H), 1.38 (s, 10H), 1.35 (s, 4H). |
| 2-99 | 3.45 | 545.3 | 1 | 7.9 | DMSO δ 13.21 (s, 1H), 8.60 (s, 1H), 8.55 (s, 1H), 7.91 (s, 1H), 7.64 (d, J = 7.0, 1H), 7.55 (d, J = 8.3, 1H), 7.42 (m, 1H), 4.27 (s, 4H), 3.81 (m, 4H), 3.71 (s, 2H), 3.48 (m, 4H), 3.10 (d, J = 10.9, 2H), 2.76 (s, 2H), 2.58 (dd, J = 14.6, 8.4, 2H), 1.38 (s, 9H). |
| 2-100 | 3.68 | 573.3 | 1 | 5.3 | DMSO δ 13.21 (s, 1H), 8.60 (s, 1H), 8.55 (s, 1H), 7.90 (s, 1H), 7.65 (d, J = 7.1, 1H), 7.55 (d, J = 8.3, 1H), 7.42 (m, 1H), 4.26 (m, 4H), 3.80 (m, 4H), 3.71 (s, 2H), 3.28 (m, 4H), 2.64 (t, J = 6.8, 2H), 2.47 (s, 2H), 1.59 (t, J = 6.8, 2H), 1.44 (s, 4H), 1.38 (s, 9H). |

TABLE 4-continued

Analytical data and PI3Kα activity - $R_t$ means retention time (in minutes), $[M + H]^+$ means the protonated mass of the compound, method refers to the method used for (LC)MS.

| Cpd. Nr. | $R_t$ | $[M + 1]^+$ | Meth. | PI3Kα IC50 (μM) | $^1$H NMR (300 MHz; δ in ppm, J in Hz) |
|---|---|---|---|---|---|
| 2-101 | 2.60 | 359.1 | 1 | — | DMSO δ 8.70 (dd, J = 4.5, 1.6, 2H), 8.42 (s, 1H), 8.02 (s, 1H), 7.81 (m, 2H), 7.59 (s, 1H), 4.27 (s, 4H), 3.77 (m, 4H). |
| 2-102 | 3.01 | 359.1 | 1 | — | DMSO δ 8.96 (d, J = 1.7, 1H), 8.63 (dd, J = 4.8, 1.5, 1H), 8.40 (s, 1H), 8.17 (m, 1H), 8.01 (s, 1H), 7.58 (s, 1H), 7.53 (dd, J = 7.9, 4.8, 1H), 4.26 (s, 4H), 3.76 (m, 4H). |
| 2-103 | 4.27 | 397.1 | 1 | 34 | DMSO δ 11.57 (s, 1H), 8.36 (s, 1H), 8.06 (s, 1H), 7.86 (s, 1H), 7.54 (d, J = 2.6, 1H), 7.48 (m, 1H), 7.44 (m, 1H), 7.22 (m, 1H), 7.16 (d, J = 6.1, 1H), 4.23 (s, 4H), 3.76 (m, 4H). |
| 2-104 | 4.74 | 431.1 | 1 | 93 | DMSO δ 11.58 (s, 1H), 8.36 (m, 1H), 8.01 (s, 1H), 7.58 (s, 1H), 7.53 (s, 1H), 7.52 (s, 1H), 7.25 (m, 1H), 7.11 (dd, J = 7.2, 0.8, 1H), 4.17 (m, 4H), 3.73 (t, J = 4.7, 4H). |
| 2-105 | 4.34 | 415.1 | 1 | 123 | DMSO δ 11.62 (s, 1H), 8.35 (m, 1H), 8.09 (s, 1H), 7.88 (s, 1H), 7.58 (d, J = 2.7, 1H), 7.49 (dd, J = 8.9, 4.3, 2H), 7.11 (m, 1H), 4.20 (s, 4H), 3.73 (t, J = 4.6, 4H). |
| 2-106 | 4.76 | 449.1 | 1 | 28 | DMSO δ 11.68 (s, 1H), 8.38 (s, 1H), 8.03 (s, 1H), 7.59 (s, 2H), 7.54 (dd, J = 8.9, 4.3, 1H), 7.14 (m, 1H), 4.17 (m, 4H), 3.73 (t, J = 4.7, 4H). |
| 2-107 | 4.61 | 393.1 | 1 | 2.6 | DMSO δ 13.13 (s, 1H), 8.57 (s, 1H), 8.49 (s, 1H), 7.90 (s, 1H), 7.59 (d, J = 7.1, 1H), 7.49 (d, J = 8.3, 1H), 7.36 (m, 1H), 4.18 (m, 4H), 3.81 (s, 2H), 3.74 (m, 4H), 3.59 (s, 3H). |
| 2-108 | 2.43 and 2.58 | 508.2 | 1 | — | DMSO δ 8.57 (s, 2H), 7.87 (s, 1H), 6.89 (s, 2H), 4.11 (m, 4H), 3.69 (m, 4H), 3.62 (d, J = 14.9, 2H), 3.05 (m, 4H), 2.80 (s, 3H), 2.48 (m, 4H). |
| 2-109 | 3.49 | 522.2 | 1 | 1 | DMSO δ 8.57 (s, 1H), 8.06 (m, 2H), 6.93 (d, J = 7.2, 1H), 4.19 (s, 4H), 3.91 (s, 3H), 3.75 (s, 6H), 3.16 (s, 2H), 2.89 (s, 3H), 2.54 (s, 2H). |
| 2-110 | 2.96 | 522.2 | 1 | — | CDCl$_3$ δ 8.68 (d, J = 1.6, 1H), 8.35 (d, J = 2.8, 1H), 7.79 (s, 1H), 7.63 (dd, J = 2.6, 1.8, 1H), 4.31 (m, 4H), 3.94 (s, 3H), 3.88 (m, 4H), 3.83 (s, 2H), 3.33 (s, 4H), 2.80 (s, 3H), 2.75 (s, 4H). |
| 2-111 | 2.39 | 487.3 | 3 | 0.813 | DMSO δ 8.60 (s, 1H), 8.55 (d, J = 0.5, 1H), 8.38 (s, 1H), 7.89 (s, 1H), 7.64 (d, J = 7.0, 1H), 7.56 (d, J = 8.3, 1H), 7.42 (dd, J = 8.2, 7.3, 1H), 4.26 (m, 4H), 3.80 (m, 4H), 3.63 (s, 2H), 2.96 (s, 4H), 2.45 (s, 4H), 1.54 (s, 4H), 1.48 (s, 4H). |
| 2-112 | 3.10 | 523.2 | 1 | — | DMSO δ 8.94 (s, 2H), 7.95 (s, 1H), 4.15 (s, 4H), 3.93 (s, 3H), 3.69 (m, 6H), 3.06 (s, 3H), 2.82 (s, 4H), 2.51 (m, 4H). |
| 2-113 | 2.95 | 546.2 | 1 | — | DMSO δ 10.52 (s, 1H), 7.97 (s, 1H), 7.58 (m, 2H), 6.91 (d, J = 8.6, 1H), 4.20 (s, 4H), 3.76 (m, 6H), 3.55 (s, 2H), 3.16 (s, 4H), 2.87 (s, 3H), 2.65 (s, 4H). |
| 2-114 | 3.15 | 531.2 | 2 | — | DMSO δ 11.81 (s, 1H), 8.57 (d, J = 2.1, 1H), 8.29 (d, J = 2.0, 1H), 7.97 (s, 1H), 7.54 (m, 1H), 6.54 (dd, J = 3.4, 1.8, 1H), 4.20 (m, 4H), 3.76 (m, 4H), 3.73 (s, 2H), 3.14 (t, J = 7.7, 4H), 2.87 (s, 3H), 2.56 (m, 4H). |
| 2-115 | 3.66 | 565.2 | 2 | — | DMSO δ 12.18 (s, 1H), 8.66 (d, J = 2.0, 1H), 8.22 (d, J = 2.1, 1H), 7.99 (s, 1H), 7.77, (s, 1H), 4.21 (s, 4H), 3.77 (m, 4H), 3.74 (s, 2H), 3.12 (m, 4H), 2.87 (s, 3H), 2.58 (s, 4H). |
| 2-116 | 1.67 | 507.0 | 2 | — | DMSO δ 8.34 (d, J = 2.2, 1H), 7.92 (s, 1H), 7.77 (dd, J = 8.6, 2.4, 1H), 6.52 (d, J = 8.7, 1H), 6.22 (s, 2H), 4.17 (m, 4H), 3.75 (m, 4H), 3.71 (s, 2H), 3.11 (m, 4H), 2.87 (s, 3H), 2.54 (m, 4H). |

TABLE 4-continued

Analytical data and PI3Kα activity - $R_t$ means retention time (in minutes), [M + H]⁺ means the protonated mass of the compound, method refers to the method used for (LC)MS.

| Cpd. Nr. | $R_t$ | [M + 1]⁺ | Meth. | PI3Kα IC50 (μM) | ¹H NMR (300 MHz; δ in ppm, J in Hz) |
|---|---|---|---|---|---|
| 2-117 | 0.32 | 445.2 | 3 | 0.851 | DMSO δ 8.60 (s, 1H), 8.55 (d, J = 0.6, 1H), 7.90 (s, 1H), 7.64 (d, J = 7.0, 1H), 7.56 (d, J = 8.3, 1H), 7.42 (dd, J = 8.2, 7.3, 1H), 4.27 (m, 4H), 3.80 (m, 4H), 3.72 (s, 2H), 2.96 (m, 4H), 2.65 (t, J = 6.7, 2H), 1.62 (m, 4H). |
| 2-118 | 0.32 and 2.30 | 473.2 | 3 | 1.5 | DMSO δ 8.60 (s, 1H), 8.56 (d, J = 0.6, 1H), 8.35 (s, 1H), 7.91 (s, 1H), 7.64 (d, J = 7.1, 1H), 7.56 (d, J = 8.3, 1H), 7.42 (dd, J = 8.1, 7.3, 1H), 4.27 (m, 4H), 3.80 (m, 4H), 3.72 (s, 2H), 2.96 (m, 4H), 2.65 (t, J = 6.8, 2H), 1.62 (m, 6H). |
| 2-119 | 3.40 | 323.2 | 2 | 0.093 | DMSO δ 9.15 (m, 1H), 8.60 (m, 1H), 8.57 (m, 1H), 8.30 (m, 1H), 8.27 (m, 1H), 7.77 (m, 1H), 7.50 (m, 2H), 4.32 (m, 4H), 1.69 (m, 6H). |
| 2-120 | 3.82 | 339.2 | 2 | 1.3 | DMSO δ 8.76 (s, 2H), 8.37 (s, 1H), 8.19 (s, 1H), 7.73 (s, 1H), 7.45 (s, 1H), 6.86 (s, 2H), 4.28 (s, 4H), 1.67 (s, 6H). |
| 2-121 | 2.91 | 534.2 | 2 | — | DMSO δ 8.04 (s, 1H), 7.98 (s, 1H), 7.96 (d, J = 8.4, 2H), 7.83 (d, J = 8.3, 2H), 7.44 (s, 1H), 4.20 (s, 4H), 3.76 (s, 4H), 3.72 (s, 2H), 3.13 (s, 4H), 2.87 (s, 3H), 2.57 (s, 4H). |
| 2-122 | 3.18 | 548.2 | 2 | 50 | DMSO δ 11.60 (s, 1H), 8.07 (s, 1H), 7.86 (s, 1H), 7.57 (d, J = 2.6, 1H), 7.48 (dd, J = 8.9, 4.3, 1H), 7.10 (m, 1H), 4.13 (s, 4H), 3.72 (t, J = 4.6, 4H), 3.69 (s, 2H), 3.13 (s, 4H), 2.87 (s, 3H), 2.58 (s, 4H). |
| 2-123 | 3.46 | 548.2 | 2 | — | DMSO δ 11.31 (s, 1H), 7.96 (s, 1H), 7.48 (dd, J = 9.0, 4.0, 1H), 7.42 (t, J = 2.7, 1H), 7.03 (dd, J = 10.3, 8.9, 1H), 6.29 (s, 1H), 4.11 (m, 4H), 3.73 (m, 4H), 3.72 (s, 2H), 3.13 (m, 4H), 2.87 (s, 3H), 2.59 (s, 4H). |
| 2-124 | 3.58 | 582.2 | 2 | — | DMSO δ 11.66 (s, 1H), 7.96 (s, 1H), 7.59 (d, J = 2.6, 1H), 7.53 (dd, J = 8.9, 4.3, 1H), 7.13 (m, 1H), 4.12 (ddd, J = 18.3, 13.5, 8.9, 4H), 3.72 (m, 4H), 3.70 (s, 2H), 3.13 (d, J = 4.7, 4H), 2.87 (s, 3H), 2.60 (s, 4H). |
| 2-125 | 3.31 | 459.2 | 3 | — | CDCl₃ δ 9.23 (s, 2H), 9.20 (s, 1H), 7.95 (s, 1H), 7.52 (s, 1H), 4.40 (m, 4H), 3.90 (m, 4H), 3.77 (s, 2H), 3.29 (m, 4H), 2.79 (s, 3H), 2.71 (m, 4H). |
| 2-126 | 2.21 | 472.2 | 3 | 0.776 | CDCl₃ δ 8.97 (s, 1H), 8.09 (d, J = 5.6, 1H), 7.90 (s, 1H), 7.49 (s, 1H), 7.24 (m, 1H), 4.36 (s, 4H), 3.89 (s, 4H), 3.76 (s, 2H), 3.28 (s, 4H), 2.78 (s, 3H), 2.70 (s, 4H), 2.60 (s, 3H). |
| 2-127 | 4.27 | 497.2 | 3 | 37 | CDCl₃ δ 10.38 (s, 1H), 8.31 (s, 1H), 8.13 (s, 1H), 7.90 (m, 2H), 7.52 (d, J = 8.8, 1H), 7.46 (s, 1H), 4.35 (m, 4H), 3.88 (m, 4H), 3.74 (s, 2H), 3.26 (m, 4H), 2.76 (s, 3H), 2.69 (m, 4H). |
| 2-128 | 2.71 and 2.86 | 523.3 | 2 | — | CDCl₃ δ 8.54 (d, J = 0.7, 1H), 7.94 (s, 1H), 7.48 (m, 3H), 7.39 (dd, J = 8.2, 6.9, 1H), 4.34 (m, 4H), 3.84 (m, 4H), 3.79 (s, 2H), 3.38 (dd, J = 9.6, 6.6, 2H), 3.16 (dd, J = 9.5, 2.4, 2H), 2.87 (m, 4H), 2.82 (s, 3H), 2.53 (d, J = 6.0, 2H). |
| 2-129 | 2.73 and 3.03 | 551.3 | 2 | 2.5 | CDCl₃ δ 8.54 (d, J = 0.7, 1H), 7.96 (s, 1H), 7.49 (m, 3H), 7.41 (dd, J = 8.3, 6.9, 1H), 4.35 (m, 4H), 3.86 (m, 4H), 3.81 (s, 2H), 3.16 (dd, J = 12.8, 6.3, 4H), 2.78 (m, 2H), 2.74 (s, 3H), 2.55 (s, 2H), 1.69 (m, 6H). |
| 2-130 | 2.57 and 2.80 | 487.3 | 2 | 1.4 | CDCl₃ δ 8.53 (m, 1H), 7.90 (t, J = 10.1, 1H), 7.49 (m, 3H), 7.38 (m, 1H), 6.23 (m, 1H), 4.33 (m, 4H), 3.85 (m, 4H), 3.73 (s, 2H), 3.31 (m, 2H), 3.00 (m, 2H), 2.27 (m, 2H), 2.03 (m, 4H), 1.48 (m, 2H). |
| 2-131 | 2.57 and 2.71 | 487.3 | 2 | 14 | CDCl₃ δ 10.84 (s, 1H), 8.53 (d, J = 0.8, 1H), 7.96 (s, 1H), 7.49 (m, 3H), 7.41 (dd, J = 8.3, 6.9, 1H), 5.89 (s, 1H), 4.35 (m, 4H), 3.86 (m, 4H), 3.71 (s, 2H), 3.18 (s, 2H), |

TABLE 4-continued

Analytical data and PI3Kα activity - $R_t$ means retention time (in minutes), $[M + H]^+$ means the protonated mass of the compound, method refers to the method used for (LC)MS.

| Cpd. Nr. | $R_t$ | $[M + 1]^+$ | Meth. | PI3Kα IC50 (μM) | ¹H NMR (300 MHz; δ in ppm, J in Hz) |
|---|---|---|---|---|---|
| | | | | | 2.55 (d, J = 20.1, 4H), 2.21 (s, 2H), 1.71 (t, J = 5.4, 4H). |
| 2-132 | 2.74 | 320.2 | 2 | — | DMSO δ 9.66 (s, 2H), 8.93 (s, 1H), 8.92 (s, 2H), 7.87 (s, 1H), 7.23 (s, 2H), 6.90 (s, 2H), 2.46 (s, 3H). |
| 2-133 | 4.47 | 419.3 | 3 | — | DMSO δ 13.24 (s, 1H), 8.47 (s, 1H), 8.05 (s, 1H), 7.66 (d, J = 7.0, 1H), 7.57 (d, J = 8.2, 1H), 7.44 (d, J = 7.4, 1H), 7.31 (s, 1H), 4.29 (s, 4H), 3.80 (m, 4H), 3.27 (d, J = 9.8, 2H), 2.96 (dt, J = 17.2, 9.6, 2H), 2.82 (t, J = 8.7, 1H), 1.92 (m, 2H), 1.63 (dd, J = 56.7, 6.4, 2H). |
| 2-134 | 3.04 | 551.3 | 2 | 5.2 | DMSO δ 13.20 (s, 1H), 8.59 (s, 1H), 8.56 (s, 1H), 7.89 (s, 1H), 7.64 (d, J = 7.1, 1H), 7.55 (d, J = 8.3, 1H), 7.42 (dd, J = 8.2, 7.3, 1H), 4.27 (m, 4H), 3.80 (m, 4H), 3.58 (s, 6H), 2.99 (s, 3H), 2.40 (s, 4H), 1.71 (s, 4H), 1.39 (s, 2H). |
| 2-135 | 0.56 | 506.2 | 3 | — | CDCl₃ δ 8.91 (d, J = 2.0 Hz, 1H), 7.97 (dd, J = 8.1, 2.3 Hz, 1H), 7.71 (s, 1H), 7.22 (d, J = 8.1 Hz, 1H), 4.27 (m, 4H), 3.83 (m, 4H), 3.76 (s, 2H), 3.26 (m, 4H), 2.76 (s, 3H), 2.68 (m, 4H), 2.60 (s, 3H). |
| 2-136 | 3.43 and 3.85 | 493.2 | 3 | — | CDCl₃ δ 9.23 (s, 1H), 9.20 (s, 2H), 7.76 (s, 1H), 4.32 (m, 4H), 3.87 (m, 4H), 3.80 (s, 2H), 3.30 (m, 4H), 2.79 (s, 3H), 2.71 (m, 4H). |
| 2-137 | 5.00 | 393.2 | 2 | 0.676 | DMSO δ 13.15 (s, 1H), 8.60 (s, 2H), 8.53 (s, 1H), 7.62 (dd, J = 26.6, 4.9 Hz, 2H), 7.44 (m, 1H), 4.34 (s, 6H), 3.83 (s, 4H), 1.35 (t, J = 6.1 Hz, 3H). |
| 2-138 | 3.99 | 370.2 | 2 | 0.012 | CDCl₃ δ 8.78 (s, 2H), 8.06 (s, 1H), 7.75 (s, 1H), 5.14 (s, 2H), 4.40 (s, 6H), 3.87 (s, 4H), 1.40 (t, J = 7.0 Hz, 3H). |
| 2-139 | 2.75 and 2.86 | 449.3 | 2 | — | DMSO δ 8.65 (s, 1H), 8.56 (s, 1H), 8.41 (m, 1H), 7.67 (d, J = 7.1 Hz, 1H), 7.59 (d, J = 8.7 Hz, 1H), 7.44 (dd, J = 8.2, 7.3 Hz, 1H), 4.34 (m, 4H), 3.84 (m, 4H), 3.33 (m, 2H), 2.30 (m, 2H), 2.16 (s, 6H), 1.70 (d, J = 7.0 Hz, 2H). |
| 2-140 | 4.60 | 436.2 | 2 | — | DMSO δ 13.24 (s, 1H), 8.65 (s, 1H), 8.56 (s, 1H), 8.41 (s, 1H), 7.68 (d, J = 6.5 Hz, 1H), 7.58 (d, J = 8.4 Hz, 1H), 7.44 (dd, J = 8.3, 7.3 Hz, 1H), 4.34 (m, 4H), 3.83 (m, 4H), 3.38 (m, 4H), 326 (s, 3H), 1.80 (m, 2H). |
| 2-141 | 3.94 and 4.24 | 435.3 | 3 | 0.065 | DMSO δ 13.24 (s, 1H), 8.65 (s, 1H), 8.56 (s, 1H), 8.42 (s, 1H), 7.68 (d, J = 7.1 Hz, 1H), 7.58 (d, J = 8.2 Hz, 1H), 7.44 (dd, J = 8.2, 7.2 Hz, 1H), 4.34 (m, 4H), 3.84 (m, 4H), 3.41 (dd, J = 12.7, 6.1 Hz, 2H), 2.27 (m, 2H), 2.24 (s, 6H). |
| 2-142 | 2.90 | 477.3 | 2 | 0.038 | DMSO δ 13.24 (s, 1H), 8.65 (s, 1H), 8.56 (s, 1H), 8.42 (s, 1H), 7.68 (d, J = 6.8 Hz, 1H), 7.58 (d, J = 8.5 Hz, 1H), 7.44 (m, 1H), 4.34 (s, 4H), 3.84 (m, 4H), 3.59 (m, 4H), 3.43 (dd, J = 12.1, 6.7 Hz, 2H), 2.45 (m, 6H). |
| 2-143 | 3.05 | 393.2 | 3 | — | DMSO δ 8.83 (s, 2H), 7.99 (s, 1H), 6.81 (s, 2H), 6.00 (m, 1H), 4.22 (m, 4H), 3.75 (m, 4H), 3.35 (m, 2H), 3.15 (m, 2H), 2.34 (m, 2H), 2.30 (s, 3H). |
| 2-144 | 4.33 | 498.3 | 2 | — | DMSO δ 13.15 (s, 1H), 8.54 (t, J = 5.9 Hz, 1H), 8.08 (s, 1H), 7.96 (s, 1H), 7.59 (d, J = 8.3 Hz, 1H), 7.42 (dd, J = 8.2, 7.2 Hz, 1H), 7.29 (m, 5H), 5.45 (s, 1H), 4.67 (s, 2H), 4.32 (d, J = 5.9 Hz, 2H), 4.19 (m, 4H), 3.74 (m, 6H). |
| 2-145 | 2.91 | 537.3 | 2 | 3 | DMSO δ 13.20 (s, 1H), 8.60 (s, 1H), 8.55 (d, J = 0.7 Hz, 1H), 7.90 (s, 1H), 7.64 (d, J = 7.1 Hz, 1H), 7.55 (d, J = 8.3 Hz, 1H), 7.42 (dd, J = 8.2, 7.2 Hz, 1H), 4.27 (m, 4H), |

TABLE 4-continued

Analytical data and PI3Kα activity - R$_t$ means retention time (in minutes), [M + H]$^+$ means the protonated mass of the compound, method refers to the method used for (LC)MS.

| Cpd. Nr. | R$_t$ | [M + 1]$^+$ | Meth. | PI3Kα IC50 (μM) | $^1$H NMR (300 MHz; δ in ppm, J in Hz) |
|---|---|---|---|---|---|
| 2-146 | 3.24 | 397.2 | 2 | 0.295 | 3.81 (m, 4H), 3.59 (m, 6H), 2.98 (s, 3H), 2.40 (s, 4H), 1.72 (t, J = 4.8 Hz, 4H). DMSO δ 9.16 (s, 1H), 8.67 (s, 1H), 8.58 (d, J = 4.1 Hz, 1H), 8.43 (t, J = 5.3 Hz, 1H), 8.33 (s, 1H), 8.31 (s, 1H), 7.50 (dd, J = 7.6, 5.0 Hz, 1H), 4.33 (s, 4H), 3.81 (s, 4H), 3.39 (m, 4H), 3.25 (s, 3H), 1.78 (m, 2H). |
| 2-147 | 0.38 and 1.62 | 396.2 | 3 | 0.832 | DMSO δ 9.16 (dd, J = 2.2, 0.6 Hz, 1H), 8.68 (s, 1H), 8.58 (dd, J = 4.8, 1.6 Hz, 1H), 8.33 (q, J = 1.9 Hz, 1H), 8.30 (s, 2H), 7.50 (ddd, J = 8.0, 4.8, 0.6 Hz, 1H), 4.33 (m, 4H), 3.81 (m, 4H), 3.39 (dd, J = 13.2, 6.7 Hz, 2H), 2.42 (t, J = 6.9 Hz, 2H), 2.19 (s, 6H). |
| 2-148 | 3.04 | 383.2 | 2 | 0.617 | DMSO δ 9.16 (d, J = 1.7 Hz, 1H), 8.67 (s, 1H), 8.58 (dd, J = 4.7, 1.6 Hz, 1H), 8.41 (t, J = 5.0 Hz, 1H), 8.31 (m, 2H), 7.50 (dd, J = 8.0, 4.8 Hz, 1H), 4.33 (m, 4H), 3.81 (m, 4H), 3.48 (m, 4H), 3.28 (s, 3H). |
| 2-149 | 3.08 | 565.3 | 2 | 1.3 | DMSO δ 13.20 (s, 1H), 8.61 (s, 1H), 8.55 (d, J = 0.8 Hz, 1H), 7.91 (s, 1H), 7.64 (dd, J = 7.1, 0.6 Hz, 1H), 7.55 (d, J = 8.3 Hz, 1H), 7.43 (dd, J = 8.3, 7.2 Hz, 1H), 4.28 (m, 4H), 3.81 (m, 4H), 3.66 (s, 2H), 3.08 (m, 4H), 2.84 (s, 3H), 2.50 (s, 4H), 1.49 (s, 8H). |
| 2-150 | 2.97 | 537.3 | 2 | 2.8 | DMSO δ 13.21 (s, 1H), 8.61 (s, 1H), 8.55 (d, J = 0.8 Hz, 1H), 7.90 (s, 1H), 7.65 (dd, J = 7.1, 0.5 Hz, 1H), 7.56 (d, J = 8.3 Hz, 1H), 7.43 (dd, J = 8.3, 7.2 Hz, 1H), 4.27 (m, 4H), 3.80 (m, 6H), 3.13 (s, 4H), 3.05 (m, 4H), 2.82 (s, 3H), 1.77 (m, 4H). |
| 2-151 | 5.73 | 530.2 | 3 | — | DMSO δ 11.22 (s, 1H), 8.19 (s, 1H), 7.93 (s, 1H), 7.47 (s, 2H), 7.41 (m, 1H), 6.51 (m, 1H), 4.20 (m, 4H), 3.77 (m, 4H), 3.72 (s, 2H), 3.13 (m, 4H), 2.87 (s, 3H), 2.57 (m, 4H). |
| 2-152 | 0.32 | 472.2 | 3 | 0.468 | CDCl$_3$ δ 8.55 (s, 1H), 8.43 (d, J = 5.0 Hz, 1H), 7.55 (s, 1H), 7.46 (s, 1H), 7.16 (d, J = 5.0 Hz, 1H), 4.26 (m, 4H), 3.82 (m, 4H), 3.73 (s, 2H), 3.24 (m, 4H), 2.75 (s, 3H), 2.67 (m, 4H), 2.42 (s, 3H). |
| 2-153 | 3.07 | 502.2 | 2 | 2.4 | CDCl$_3$ δ 8.12 (s, 1H), 7.50 (s, 1H), 7.44 (s, 1H), 6.63 (s, 1H), 4.26 (m, 4H), 3.93 (s, 3H), 3.83 (m, 4H), 3.74 (s, 2H), 3.26 (m, 4H), 2.76 (s, 3H), 2.68 (m, 4H), 2.37 (s, 3H). |
| 2-154 | 3.04 | 383.2 | 2 | 0.166 | DMSO δ 9.16 (d, J = 1.7 Hz, 1H), 8.67 (s, 1H), 8.58 (dd, J = 4.7, 1.6 Hz, 1H), 8.41 (t, J = 5.0, 1H), 8.31 (m, 2H), 7.50 (dd, J = 8.0, 4.8, 1H), 4.33 (m, 4H), 3.81 (m, 4H), 3.48 (s, 4H), 3.28 (s, 3H). |
| 2-155 | 3.08 | 548.2 | 2 | — | DMSO δ 13.23 (s, 1H), 8.49 (t, J = 5.9, 1H), 8.07 (s, 1H), 7.84 (s, 1H), 7.78 (s, 1H), 7.62 (d, J = 8.4, 1H), 7.46-7.37 (m, 1H), 7.37-7.20 (m, 5H), 7.16 (d, J = 6.8, 1H), 6.96 (d, J = 3.9, 2H), 5.48 (s, 2H), 4.29 (d, J = 5.9, 2H), 4.22 (s, 4H), 3.81-3.69 (m, 4H), 3.65 (s, 2H). |
| 2-156 | 4.98 | 488.3 | 2 | — | CDCl$_3$ δ 8.53 (s, 1H), 7.80 (s, 1H), 7.62-7.34 (m, 3H), 4.89 (s, 1H), 4.36 (m, 4H), 4.12 (m, 1H), 3.89 (m, 4H), 3.25 (m, 2H), 2.86 (m, 1H), 2.62 (m, 1H), 2.46 (s, 3H), 1.90 (m, 4H), 1.16 (m, 6H). |
| 2-157 | 3.93 | 449.2 | 2 | 0.776 | DMSO δ 13.23 (s, 1H), 8.64 (s, 1H), 8.80 (m, 2H), 8.42 (s, 1H), 8.05 (m, 1H), 7.67 (d, J = 6.8, 1H), 7.57 (d, J = 8.3, 1H), 7.45 (m, 1H), 4.34 (m, 4H), 3.85 (m, 4H), 3.35 (m, 2H), 3.26 (m, 2H), 1.82 (s, 3H). |
| 2-158 | 2.75 | 410.2 | 2 | 2.3 | DMSO δ 9.17 (d, J = 1.6 Hz, 1H), 8.67 (s, 1H), 8.57 (m, 2H), 8.32 (m, 2H), 8.05 (m, 1H), 7.50 (dd, J = 7.7, 5.1, 1H), 4.34 (m, 4H), |

TABLE 4-continued

Analytical data and PI3Kα activity - $R_t$ means retention time (in minutes), [M + H]$^+$ means the protonated mass of the compound, method refers to the method used for (LC)MS.

| Cpd. Nr. | $R_t$ | [M + 1]$^+$ | Meth. | PI3Kα IC50 (μM) | $^1$H NMR (300 MHz; δ in ppm, J in Hz) |
|---|---|---|---|---|---|
| 2-159 | 0.37 | 438.2 | 3 | 0.398 | 3.81 (m, 4H), 3.33 (m, 2H), 3.24 (m, 2H), 1.80 (s, 3H). DMSO δ 9.16 (d, J = 1.6, 1H), 8.68 (s, 1H), 8.58 (dd, J = 4.7, 1.6, 1H), 8.28 (m, 3H), 7.50 (dd, J = 8.0, 4.2, 1H), 4.33 (s, 4H), 3.78 (m, 4H), 3.55 (m, 4H), 3.42 (m, 2H), 2.49 (m, 2H), 2.45 (m, 4H). |
| 2-160 | 0.37 | 426.2 | 3 | — | DMSO δ 8.79 (s, 2H), 8.57 (s, 1H), 8.46 (s, 1H), 8.23 (s, 1H), 6.89 (s, 2H), 4.31 (s, 4H), 3.81 (s, 4H), 2.35 (s, 2H), 2.25 (s, 6H), 1.69 (m, 2H), 1.23 (s, 2H). |
| 2-161 | 3.73 | 413.1 | 2 | — | DMSO δ 8.77 (s, 2H), 8.44 (s, 1H), 8.39 (m, 1H), 8.21 (s, 1H), 6.88 (s, 2H), 4.29 (s, 4H), 3.79 (s, 4H), 3.38 (m, 4H), 3.25 (s, 3H), 1.75 (m, 2H). |
| 2-162 | 0.39 and 2.74 | 412.3 | 3 | — | DMSO δ 8.79 (s, 2H), 8.46 (s, 1H), 8.30 (s, 1H), 8.23 (s, 1H), 6.89 (s, 2H), 4.30 (s, 4H), 3.80 (s, 4H), 3.39 (s, 2H), 2.42 (s, 2H), 2.20 (s, 6H). |
| 2-163 | 5.57 | 399.2 | 3 | — | DMSO δ 8.78 (s, 2H), 8.45 (s, 1H), 8.36 (s, 1H), 8.23 (s, 1H), 6.88 (s, 2H), 4.29 (m, 4H), 4.80 (m, 4H), 3.46 (m, 4H), 3.27 (s, 3H). |
| 2-164 | 0.37 and 2.85 | 454.3 | 3 | 0.011 | DMSO δ 8.77 (s, 2H), 8.45 (s, 1H), 8.28 (m, 1H), 8.20 (s, 1H), 6.88 (s, 2H), 4.29 (s, 4H), 3.79 (s, 4H), 3.59 (s, 4H), 3.49 (m, 2H), 2.43 (m, 6H). |
| 2-165 | 0.38 | 488.3 | 3 | — | DMSO δ 8.81 (s, 2H), 8.09 (s, 1H), 6.75 (s, 2H), 4.16 (s, 4H), 3.69 (m, 4H), 3.58 (s, 2H), 3.02 (s, 4H), 2.78 (s, 3H), 2.44 (m, 7H). |
| 2-166 | 2.48 | 304.1 | 2 | 1.8 | DMSO δ 9.14 (s, 1H), 8.96 (s, 2H), 8.80 (s, 4H), 7.98 (s, 1H), 6.96 (s, 2H), 2.50 (s, 3H). |
| 2-167 | 3.49 | 536.2 | 2 | — | CDCl$_3$ δ 8.10 (s, 1H), 7.70 (s, 1H), 6.68 (s, 1H), 4.24 (m, 4H), 3.96 (s, 3H), 3.82 (m, 4H), 3.75 (s, 2H), 3.28 (m, 4H), 2.80 (s, 3H), 2.71 (m, 4H), 2.23 (s, 2H). |
| 2-168 | 3.21 | 327.2 | 2 | 26 | DMSO δ 13.31 (s, 1H), 9.33 (s, 1H), 8.81 (m, 4H), 8.67 (s, 1H), 8.11 (s, 1H), 7.81 (d, J = 7.1, 1H), 7.64 (d, J = 8.3, 1H), 7.52 (m, 1H), 2.53 (s, 3H). |
| 2-169 | 0.33 and 3.07 | 514.3 | 3 | 0.11 | DMSO δ 8.76 (s, 2H), 8.40 (s, 1H), 7.70 (s, 1H), 6.82 (s, 2H), 4.22 (m, 4H), 3.76 (m, 4H), 3.69 (s, 2H), 3.32 (s, 4H), 3.04 (s, 4H), 2.81 (s, 3H), 1.74 (m, 4H). |
| 2-170 | 2.14 | 500.3 | 2 | — | DMSO δ 8.76 (s, 2H), 8.40 (s, 1H), 7.75 (s, 1H), 6.82 (s, 2H), 4.22 (m, 4H), 3.76 (m, 4H), 3.68 (s, 2H), 3.38 (m, 2H), 2.96 (dd, J = 9.9, 3.8, 2H), 2.90 (s, 3H), 2.81 (m, 2H), 2.59 (m, 2H). |
| 2-171 | 4.13 | 338.2 | 2 | 0.05 | DMSO δ 8.76 (s, 2H), 8.34 (s, 1H), 7.63 (s, 1H), 6.81 (s, 2H), 4.19 (m, 4H), 3.75 (m, 4H), 2.03 (m, 1H), 0.91 (m, 2H), 0.79 (m, 2H). |
| 2-172 | 4.72 | 366.2 | 2 | 0.032 | DMSO δ 8.79 (s, 2H), 8.47 (d, J = 0.8, 1H), 8.44 (s, 1H), 6.92 (s, 2H), 4.23 (m, 4H), 3.78 (m, 4H). |
| 2-173 | 0.33 and 2.59 | 506.2 | 3 | — | CDCl$_3$ δ 8.54 (s, 2H), 7.74 (s, 1H), 7.30 (d, J = 4.2, 1H), 4.25 (m, 4H), 3.86 (s, 2H), 3.83 (m, 4H), 3.32 (m, 4H), 2.79 (s, 7H), 2.32 (s, 3H). |
| 2-174 | 3.11 | 298.2 | 2 | 0.191 | DMSO δ 8.78 (s, 2H), 8.46 (s, 1H), 7.89 (d, J = 1.0, 1H), 7.56 (d, J = 1.0, 1H), 6.84 (s, 2H), 4.26 (m, 4H), 3.76 (m, 4H). |
| 2-175 | 0.32 and 2.40 | 397.2 | 3 | 0.083 | DMSO δ 8.76 (s, 2H), 8.40 (s, 1H), 7.75 (s, 1H), 6.83 (s, 2H), 4.22 (m, 4H), 3.76 (m, 4H), 3.57 (m, 6H), 2.44 (m, 4H). |
| 2-176 | 4.29 | 405.2 | 3 | — | DMSO δ 8.75 (s, 2H), 8.37 (s, 1H), 8.19 (d, J = 6.4, 2H), 7.58 (s, 1H), 6.82 (s, 2H), 6.46 (s, 2H), 4.21 (d, J = 4.4, 4H), 3.85 (s, 2H), 3.76 (m, 4H). |

TABLE 4-continued

Analytical data and PI3Kα activity - R$_t$ means retention time (in minutes), [M + H]$^+$ means the protonated mass of the compound, method refers to the method used for (LC)MS.

| Cpd. Nr. | R$_t$ | [M + 1]$^+$ | Meth. | PI3Kα IC50 (μM) | $^1$H NMR (300 MHz; δ in ppm, J in Hz) |
|---|---|---|---|---|---|
| 2-177 | 3.45 | 356.2 | 2 | — | DMSO δ 8.77 (s, 2H), 8.42 (s, 1H), 7.67 (s, 1H), 6.82 (s, 2H), 5.09 (s, 1H), 4.23 (s, 4H), 3.76 (s, 4H), 1.48 (s, 6H). |
| 2-178 | 2.72 | 553.2 | 2 | — | DMSO δ 8.81 (s, 2H), 8.04 (s, 1H), 6.82 (s, 2H), 4.18 (s, 4H), 3.71 (m, 4H), 3.60 (s, 2H), 3.03 (s, 4H), 2.79 (s, 3H), 2.48 (d, J = 4.7, 4H). |
| 2-179 | 3.76 | 460.2 | 2 | — | DMSO δ 8.88 (s, 2H), 7.91 (s, 1H), 7.30 (s, 1H), 6.89 (s, 2H), 4.25 (s, 4H), 3.75 (m, 4H), 3.39 (m, 4H), 3.12 (m, 4H), 2.99 (s, 3H). |
| 2-180 | 0.32 and 3.18 | 499.2 | 3 | — | DMSO δ 8.74 (s, 2H), 7.88 (s, 1H), 7.23 (s, 2H), 4.44 (s, 4H), 3.77 (s, 4H), 3.70 (s, 2H), 3.12 (s, 4H), 2.87 (s, 3H), 2.56 (s, 4H). |
| 2-181 | 3.17 | 312.2 | 2 | 0.11 | DMSO δ 8.76 (s, 2H), 8.37 (s, 1H), 7.61 (s, 1H), 6.80 (s, 2H), 4.21 (s, 4H), 3.75 (s, 4H), 2.33 (s, 3H). |
| 2-182 | 5.08 | 519.2 | 2 | 0.245 | DMSO δ 13.24 (s, 1H), 8.64 (s, 1H), 8.55 (s, 1H), 8.43 (s, 1H), 8.12 (d, J = 8.6, 1H), 7.67 (d, J = 7.1, 1H), 7.58 (d, J = 8.1, 1H), 7.43 (d, J = 8.2, 1H), 4.33 (s, 4H), 4.05 (m, 6H), 3.83 (m, 4H), 2.91 (m, 1H), 1.77 (m, 2H), 1.56 (m, 2H), 1.20 (t, J = 7.1, 3H). |
| 2-183 | 3.45 | 576.2 | 2 | 0.17 | DMSO δ 13.22 (s, 1H), 8.46 (s, 1H), 8.11 (s, 1H), 7.65 (d, J = 7.1, 1H), 7.60 (d, J = 8.3, 1H), 7.46 (d, J = 7.3, 1H), 4.30 (m, 4H), 3.82 (m, 4H), 3.71 (s, 2H), 3.11 (m, 4H), 2.86 (s, 3H), 2.58 (m, 4H). |
| 2-184 | 3.05 | 355.2 | 2 | — | DMSO δ 8.64 (s, 2H), 8.30 (s, 1H), 8.22 (s, 1H), 8.07 (s, 1H), 6.74 (s, 2H), 4.16 (m, 4H), 3.65 (m, 4H), 2.68 (d, J = 3.9, 3H). |
| 2-185 | 4.10 | 346.2 | 2 | — | DMSO δ 8.62 (s, 2H), 7.85 (d, J = 0.8, 1H), 6.94 (s, 2H), 4.17 (m, 4H), 3.74 (m, 4H), 2.38 (d, J = 0.5, 3H). |
| 2-186 | 4.15 | 422.2 | 2 | 0.066 | DMSO δ 13.17 (s, 1H), 8.58 (s, 1H), 8.49 (s, 1H), 8.35 (s, 1H), 8.31 (m, 1H), 7.61 (d, J = 7.2, 1H), 7.51 (d, J = 8.2, 1H), 7.39 (d, J = 7.2, 1H), 4.27 (m, 4H), 3.77 (m, 4H), 3.42 (m, 4H), 3.21 (s, 4H). |
| 2-187 | 4.02 | 337.2 | 2 | — | DMSO δ 8.74 (s, 2H), 7.83 (s, 1H), 7.20 (s, 2H), 4.43 (s, 4H), 3.76 (m, 4H), 2.37 (s, 3H). |
| 2-188 | 4.03 | 496.2 | 2 | 0.003 | DMSO δ 8.77 (s, 2H), 8.44 (s, 1H), 8.25 (s, 1H), 8.09 (d, J = 8.5, 1H), 6.88 (s, 2H), 4.28 (s, 4H), 4.04 (m, 5H), 3.79 (m, 4H), 2.87 (s, 2H), 1.78 (d, J = 9.9, 2H), 1.57 (dt, J = 12.2, 8.4, 2H), 1.19 (t, J = 7.1, 3H). |
| 2-189 | 3.39 | 389.2 | 2 | — | DMSO δ 8.65 (s, 2H), 8.46 (s, 1H), 8.33 (s, 1H), 6.99 (s, 2H), 4.26 (s, 4H), 3.78 (m, 4H), 2.83 (d, J = 4.8, 3H). |
| 2-190 | 3.11 | 311.2 | 2 | — | CDCl$_3$ δ 8.83 (d, J = 1.8, 2H), 8.14 (s, 1H), 7.44 (s, 1H), 5.43 (s, 2H), 4.10 (dd, J = 11.4, 3.4, 2H), 3.84 (m, 1H), 3.67 (t, J = 11.5, 2H), 2.49 (s, 3H), 2.15 (m, 2H), 1.90 (m, 2H). |
| 2-191 | 3.53 | 425.2 | 2 | 0.013 | DMSO δ 8.71 (s, 2H), 8.38 (s, 1H), 8.18 (s, 1H), 8.03 (d, J = 8.4, 1H), 6.81 (s, 2H), 4.22 (m, 4H), 3.96 (s, 1H), 3.83 (d, J = 11.1, 2H), 3.73 (m, 4H), 3.33 (m, 2H), 1.66 (m, 4H). |
| 2-192 | 3.40 | 439.2 | 2 | 0.01 | DMSO δ 8.70 (s, 2H), 8.37 (s, 1H), 8.15 (s, 1H), 7.83 (d, J = 8.5, 1H), 6.80 (s, 2H), 4.50 (d, J = 4.4, 1H), 4.20 (s, 4H), 3.72 (m, 4H), 3.33 (m, 1H), 1.75 (m, 4H), 1.42 (m, 2H), 1.18 (m, 2H). |
| 2-193 | 4.64 | 510.3 | 2 | — | DMSO δ 8.77 (s, 2H), 8.44 (s, 1H), 8.22 (s, 1H), 6.89 (s, 2H), 4.24 (m, 4H), 4.02 (m, 2H), 3.78 (m, 4H), 3.63 (m, 2H), 3.41 (m, 4H), 1.42 (s, 9H). |
| 2-194 | 3.77 | 433.3 | 2 | — | DMSO δ 8.66 (s, 2H), 8.50 (s, 1H), 8.36 (s, 1H), 7.00 (s, 2H), 4.25 (m, 4H), 3.78 (m, 4H), 3.48 (m, 4H), 3.28 (s, 3H). |

TABLE 4-continued

Analytical data and PI3Kα activity - $R_t$ means retention time (in minutes), $[M + H]^+$ means the protonated mass of the compound, method refers to the method used for (LC)MS.

| Cpd. Nr. | $R_t$ | $[M + 1]^+$ | Meth. | PI3Kα IC50 (μM) | $^1$H NMR (300 MHz; δ in ppm, J in Hz) |
|---|---|---|---|---|---|
| 2-195 | 4.52 | 382.2 | 2 | — | DMSO δ 8.76 (s, 2H), 8.37 (s, 1H), 7.65 (s, 1H), 6.81 (s, 2H), 4.23 (m, 4H), 3.92 (d, J = 9.5, 2H), 3.77 (m, 4H), 3.46 (t, J = 10.8, 2H), 2.93 (m, 1H), 1.91 (d, J = 12.5, 2H), 1.69 (m, 2H). |
| 2-196 | 2.58 | 473.2 | 2 | 0.021 | DMSO δ 9.20 (s, 2H), 8.67 (s, 1H), 7.83 (s, 1H), 4.26 (m, 4H), 3.78 (m, 4H), 3.68 (s, 2H), 3.12 (m, 4H), 2.87 (s, 3H), 2.66 (s, 3H), 2.56 (m, 4H). |
| 2-197 | 2.96 | 497.2 | 2 | — | DMSO δ 13.13 (s, 1H), 8.64 (s, 1H), 8.16 (s, 1H), 8.08 (s, 1H), 7.85 (s, 1H), 7.81 (d, J = 8.6, 1H), 7.69 (d, J = 8.5, 1H), 4.28 (m, 4H), 3.81 (m, 4H), 3.68 (s, 2H), 3.12 (s, 4H), 2.87 (s, 3H), 2.57 (s, 4H). |
| 2-198 | 0.37 | 487.2 | 2 | — | DMSO δ 8.39 (s, 1H), 8.35 (s, 1H), 7.76 (s, 2H), 5.96 (s, 2H), 4.22 (m, 4H), 3.77 (m, 4H), 3.66 (s, 2H), 3.11 (m, 4H), 2.87 (s, 3H), 2.56 (m, 4H), 2.11 (s, 3H). |
| 2-199 | 0.37 and 2.47 | 488.2 | 2 | — | DMSO δ 8.82 (s, 2H), 8.40 (s, 1H), 7.77 (s, 1H), 7.31 (q, J = 4.9, 1H), 4.23 (m, 4H), 3.76 (m, 4H), 3.66 (s, 2H), 3.10 (m, 4H), 2.87 (s, 3H), 2.84 (d, J = 4.8, 3H), 2.53 (m, 4H). |
| 2-200 | 0.36 and 1.99 | 488.2 | 2 | 0.032 | DMSO δ 8.24 (s, 1H), 8.05 (s, 1H), 7.81 (s, 1H), 6.67 (s, 2H), 4.17 (m, 4H), 3.75 (m, 4H), 3.67 (s, 2H), 3.11 (m, 4H), 2.87 (s, 3H), 2.55 (m, 4H), 2.39 (s, 3H). |
| 2-201 | 0.35 and 2.88 | 483.2 | 2 | 3.3 | DMSO δ 9.33 (d, J = 2.3, 1H), 8.84 (s, 1H), 8.56 (dd, J = 8.2, 2.2, 1H), 8.13 (d, J = 8.2, 1H), 7.86 (s, 1H), 4.28 (s, 4H), 3.78 (m, 4H), 3.69 (s, 2H), 3.12 (m, 4H), 2.87 (s, 3H), 2.56 (m, 4H). |
| 2-202 | 0.36 and 2.75 | 542.2 | 2 | — | DMSO δ 8.56 (s, 1H), 8.08 (s, 1H), 7.86 (s, 1H), 7.45 (s, 2H), 4.16 (m, 4H), 3.72 (m, 4H), 3.67 (s, 2H), 3.11 (m, 4H), 2.87 (s, 3H), 2.52 (m, 4H). |
| 2-203 | 0.36 | 473.2 | 2 | — | DMSO δ 8.55 (s, 1H), 7.94 (d, J = 5.4, 1H), 7.86 (s, 1H), 7.07 (s, 1H), 6.97 (d, J = 6.9, 1H), 5.97 (s, 2H), 4.26 (m, 4H), 3.78 (m, 4H), 3.67 (s, 2H), 3.12 (m, 4H), 2.87 (s, 3H), 2.56 (m, 4H). |
| 2-204 | 0.35 | 488.2 | 2 | 10 | DMSO δ 9.11 (s, 1H), 8.60 (s, 1H), 8.43 (d, J = 5.7, 1H), 7.95 (s, 1H), 7.18 (d, J = 5.8, 1H), 4.21 (m, 4H), 3.99 (s, 3H), 3.79 (m, 4H), 3.67 (s, 2H), 3.12 (m, 4H), 2.87 (s, 3H), 2.56 (m, 4H). |
| 2-205 | 0.36 and 2.23 | 491.2 | 2 | — | DMSO δ 8.43 (s, 1H), 8.38 (s, 1H), 7.85 (d, J = 12.7, 1H), 7.75 (s, 1H), 6.39 (s, 2H), 4.23 (m, 4H), 3.77 (m, 4H), 3.66 (s, 2H), 3.11 (m, 4H), 2.87 (s, 3H), 2.52 (m, 4H). |
| 2-206 | 3.20 | 517.2 | 2 | 3.7 | DMSO δ 9.16 (d, J = 1.4, 1H), 8.44 (dd, J = 8.1, 2.2, 1H), 8.18 (d, J = 8.2, 1H), 8.05 (s, 1H), 4.22 (m, 4H), 3.76 (m, 4H), 3.73 (s, 2H), 3.12 (m, 4H), 2.87 (s, 3H), 2.56 (m, 4H). |
| 2-207 | 2.72 and 2.85 | 522.2 | 2 | 0.011 | DMSO δ 8.70 (s, 2H), 7.95 (s, 1H), 7.45 (m, 1H), 4.19 (m, 4H), 3.75 (m, 4H), 3.71 (s, 2H), 3.12 (m, 4H), 2.86 (s, 3H), 2.83 (d, J = 6.3, 3H), 2.56 (m, 4H). |
| 2-208 | 0.36 and 2.32 | 522.2 | 2 | — | DMSO δ 8.15 (s, 1H), 7.93 (s, 1H), 6.76 (s, 2H), 4.15 (m, 4H), 3.74 (m, 4H), 3.72 (s, 2H), 3.12 (m, 4H), 2.87 (s, 3H), 2.57 (m, 4H), 2.19 (s, 3H). |
| 2-209 | 2.96 and 3.09 | 576.2 | 2 | — | DMSO δ 8.56 (s, 1H), 7.96 (s, 1H), 7.59 (s, 2H), 4.14 (m, 4H), 3.72 (m, 6H), 3.12 (m, 4H), 2.87 (s, 3H), 2.54 (m, 4H). |
| 2-210 | 0.37 and 1.70 | 507.2 | 2 | — | DMSO δ 7.98 (m, 2H), 6.84 (m, 2H), 6.04 (s, 2H), 4.20 (m, 4H), 3.76 (m, 4H), 3.72 (s, 2H), 3.12 (m, 4H), 2.87 (s, 3H), 2.53 (m, 4H). |
| 2-211 | 0.36 | 522.2 | 2 | — | DMSO δ 8.53 (d, J = 5.8, 1H), 8.40 (s, 1H), 7.94 (s, 1H), 7.20 (d, J = 5.9, 1H), 4.14 (m, |

TABLE 4-continued

Analytical data and PI3Kα activity - $R_t$ means retention time (in minutes), [M + H]⁺ means the protonated mass of the compound, method refers to the method used for (LC)MS.

| Cpd. Nr. | $R_t$ | [M + 1]⁺ | Meth. | PI3Kα IC50 (μM) | ¹H NMR (300 MHz; δ in ppm, J in Hz) |
|---|---|---|---|---|---|
| | | | | | 4H), 3.86 (s, 3H), 3.73 (m, 6H), 3.12 (m, 4H), 2.87 (s, 3H), 2.57 (m, 4H). |
| 2-212 | 2.85 | 507.2 | 2 | — | MeOD δ 9.13 (s, 2H), 8.02 (s, 1H), 4.30 (m, 4H), 3.85 (dd, J = 9.2, 4.5, 4H), 3.82 (s, 2H), 3.27 (m, 4H), 2.86 (s, 3H), 2.77 (s, 3H), 2.71 (m, 4H). |
| 2-213 | 3.24 | 531.2 | 2 | — | MeOD δ 8.10 (s, 1H), 7.99 (s, 1H), 7.92 (s, 1H), 7.84 (d, J = 8.4, 1H), 7.56 (d, J = 8.2, 1H), 4.27 (m, 4H), 3.83 (m, 6H), 3.27 (m, 4H), 2.84 (s, 3H), 2.68 (m, 4H). |
| 2-214 | 4.16 | 384.2 | 2 | — | DMSO δ 8.91 (s, 2H), 8.23 (s, 1H), 6.89 (s, 2H), 4.32 (m, 6H), 3.78 (m, 4H), 2.74 (s, 3H), 1.33 (t, J = 7.1, 3H). |
| 2-215 | 0.35 | 413.2 | 2 | — | DMSO δ 8.90 (s, 2H), 8.27 (s, 1H), 8.20 (s, 1H), 6.86 (s, 2H), 4.28 (m, 4H), 3.78 (m, 4H), 3.45 (m, 4H), 3.28 (s, 3H), 2.75 (s, 3H). |
| 2-216 | 3.76 | 433.2 | 2 | — | DMSO δ 8.91 (s, 2H), 8.44 (s, 1H), 8.20 (s, 1H), 6.92 (s, 2H), 4.29 (s, 4H), 3.79 (s, 4H), 3.45 (m, 4H), 3.25 (s, 3H). |
| 2-217 | 4.79 | 355.2 | 3 | — | DMSO δ 8.90 (s, 2H), 8.18 (s, 1H), 7.77 (s, 1H), 7.35 (s, 1H), 6.85 (s, 2H), 4.28 (s, 4H), 3.77 (m, 4H), 2.74 (s, 3H). |
| 2-218 | 3.53 and 3.76 | 524.3 | 2 | 0.028 | DMSO δ 8.75 (s, 2H), 8.38 (s, 1H), 7.78 (s, 1H), 6.82 (s, 2H), 4.25 (s, 4H), 4.00 (s, 2H), 3.76 (s, 6H), 2.36 (s, 2H), 1.34 (s, 9H), 1.15 (d, J = 5.8, 6H). |
| 2-219 | 0.39 | 502.2 | 3 | 0.003 | DMSO δ 8.76 (s, 2H), 8.39 (s, 1H), 7.80 (s, 1H), 6.82 (s, 2H), 4.25 (s, 4H), 4.02 (s, 2H), 3.76 (m, 4H), 3.34 (m, 2H), 2.84 (s, 3H), 2.53 (m, 2H), 1.20 (d, J = 5.8, 6H). |
| 2-220 | 0.43 | 488.2 | 3 | 0.013 | DMSO δ 8.77 (s, 2H), 8.41 (s, 1H), 7.76 (s, 1H), 6.83 (s, 2H), 4.23 (m, 4H), 3.77 (m, 4H), 3.65 (s, 2H), 3.18 (m, 4H), 3.04 (q, J = 7.4, 2H), 2.51 (m, 4H), 1.20 (t, J = 7.4, 3H). |
| 2-221 | 3.73 and 4.03 | 516.3 | 3 | 0.011 | DMSO δ 8.76 (s, 2H), 8.41 (s, 1H), 7.76 (s, 1H), 6.83 (s, 2H), 4.22 (m, 4H), 3.76 (m, 4H), 3.66 (s, 2H), 3.14 (m, 4H), 2.88 (s, 2H), 2.51 (m, 4H), 2.11 (m, 1H), 1.01 (d, J = 6.5, 6H). |
| 2-222 | 4.07 | 445.1 | 3 | 0.082 | DMSO δ 8.57 (s, 2H), 8.21 (s, 1H), 7.60 (s, 1H), 6.63 (s, 2H), 4.03 (s, 4H), 3.61 (s, 2H), 3.56 (m, 4H), 2.89 (m, 4H), 2.76 (m, 4H). |
| 2-223 | 2.74 | 342.2 | 2 | — | DMSO δ 8.80 (s, 2H), 8.35 (s, 1H), 7.60 (s, 1H), 6.79 (s, 2H), 5.43 (s, 1H), 4.83 (t, J = 5.2, 1H), 4.07 (d, J = 11.5, 1H), 3.95 (d, J = 8.9, 1H), 3.80 (m, 1H), 3.59 (m, 1H), 3.36 (m, 2H), 2.33 (s, 3H). |
| 2-224 | 3.60 | 384.2 | 2 | 25.4 | DMSO δ 8.77 (s, 2H), 8.39 (s, 1H), 7.62 (s, 1H), 6.80 (s, 2H), 5.51 (s, 2H), 3.93 (m, 1H), 3.80 (m, 1H), 3.70 (m, 1H), 3.59 (m, 1H), 3.46 (s, 3H), 3.34 (m, 1H), 2.86 (m, 1H), 2.72 (m, 1H), 2.32 (s, 3H). |
| 2-225 | 4.23 | 536.3 | 3 | — | DMSO δ 8.74 (s, 2H), 8.35 (s, 1H), 7.70 (m, 6H), 6.82 (s, 2H), 4.20 (s, 4H), 3.74 (m, 4H), 3.60 (s, 2H), 2.90 (s, 4H), 2.50 (m, 4H). |
| 2-226 | 0.36 | 396.3 | 4 | 0.077 | DMSO δ 8.76 (s, 2H), 8.40 (s, 1H), 7.72 (s, 1H), 6.82 (s, 2H), 4.22 (s, 4H), 3.76 (m, 4H), 3.55 (s, 2H), 3.35 (s, 1H), 2.69 (m, 4H), 2.37 (m, 4H). |
| 2-227 | 3.58 | 370.2 | 2 | 6.09 | CDCl₃ δ 8.74 (s, 2H), 7.77 (s, 1H), 7.27 (s, 1H), 5.59 (s, 2H), 4.53 (d, J = 11.7, 1H), 4.05 (t, J = 12.2, 1H), 3.95 (dd, J = 11.8, 3.7, 1H), 3.81 (m, 1H), 3.76 (s, 3H), 3.63 (m, 1H), 2.42 (s, 3H). |
| 2-228 | 0.35 and 2.84 | 500.4 | 3 | 0.108 | DMSO δ 8.77 (s, 2H), 8.40 (s, 1H), 7.80 (s, 1H), 6.83 (s, 2H), 4.21 (m, 4H), 3.76 (m, 4H), 3.63 (s, 2H), 3.38 (s, 2H), 3.19 (dd, J = 10.7, 2.3, 2H), 2.96 (d, J = 10.0, 2H), 2.85 (s, 3H), 1.99 (m, 2H), 1.66 (q, J = 6.1, 2H). |

TABLE 4-continued

Analytical data and PI3Kα activity - R$_t$ means retention time (in minutes), [M + H]$^+$ means the protonated mass of the compound, method refers to the method used for (LC)MS.

| Cpd. Nr. | R$_t$ | [M + 1]$^+$ | Meth. | PI3Kα IC50 (μM) | $^1$H NMR (300 MHz; δ in ppm, J in Hz) |
|---|---|---|---|---|---|
| 2-229 | 0.35 and 0.87 | 411.3 | 3 | 0.114 | DMSO δ 8.76 (s, 2H), 8.40 (s, 1H), 7.72 (s, 1H), 6.82 (s, 2H), 4.52 (d, J = 4.1, 1H), 4.22 (s, 4H), 3.76 (m, 4H), 3.56 (s, 2H), 3.42 (m, 1H), 2.75 (m, 2H), 2.10 (t, J = 9.7, 2H), 1.69 (m, 2H), 1.40 (m, 2H). |
| 2-230 | 0.34 | 481.4 | 3 | 0.034 | DMSO δ 8.77 (s, 2H), 8.41 (s, 1H), 7.76 (s, 1H), 6.83 (s, 2H), 4.23 (s, 4H), 3.76 (m, 4H), 3.62 (s, 2H), 3.52 (m, 2H), 3.44 (m, 2H), 3.05 (s, 2H), 2.43 (m, 4H), 2.16 (s, 6H). |
| 2-231 | 0.34 | 510.4 | 3 | 0.085 | DMSO δ 8.77 (s, 2H), 8.41 (s, 1H), 7.77 (s, 1H), 6.83 (s, 2H), 5.34 (q, J = 6.8, 1H), 4.23 (s, 4H), 3.77 (m, 4H), 3.64 (s, 2H), 3.45 (m, 4H), 2.49 (m, 2H), 2.41 (m, 2H), 2.02 (s, 3H), 1.28 (d, J = 6.7, 3H). |
| 2-232 | 0.42 and 3.03 | 524.2 and 424.2 | 2 | — | MeOD δ 8.80 (s, 2H), 8.18 (s, 1H), 7.70 (s, 1H), 7.54 (m, 2H), 4.31 (s, 4H), 3.85 (s, 4H), 3.40 (s, 4H), 2.52 (s, 4H), 1.54 (s, 6H), 1.42 (s, 9H). |
| 2-233 | 2.40 and 2.87 | 502.2 | 3 | — | DMSO δ 8.80 (s, 2H), 8.44 (s, 1H), 7.77 (s, 1H), 6.86 (s, 2H), 4.25 (m, 4H), 3.79 (m, 6H), 3.59 (s, 3H), 2.87 (m, 3H), 2.72 (m, 2H), 2.28 (s, 3H), 1.91 (m, 2H), 1.54 (m, 2H). |
| 2-234 | 0.39 | 468.2 | 3 | — | DMSO δ 8.77 (s, 2H), 8.42 (s, 1H), 7.77 (s, 1H), 6.85 (s, 2H), 4.85 (d, J = 7.0, 1H), 4.40 (m, 1H), 4.23 (m, 4H), 3.78 (m, 4H), 3.64 (s, 2H), 3.44 (m, 4H), 2.40 (m, 4H), 1.16 (d, J = 6.5, 3H). |
| 2-235 | 0.41 and 2.71 | 488.2 | 3 | — | DMSO δ 8.76 (s, 2H), 8.42 (s, 1H), 7.76 (s, 1H), 6.84 (s, 2H), 4.23 (m, 4H), 3.78 (m, 6H), 3.34 (m, 4H), 2.89 (s, 3H), 2.73 (m, 4H), 1.79 (m, 2H). |
| 2-236 | 0.41 | 424.2 | 3 | — | MeOD δ 8.71 (s, 2H), 8.07 (s, 1H), 7.58 (s, 1H), 4.20 (m, 4H), 3.75 (m, 4H), 3.21 (s, 2H), 2.73 (m, 4H), 2.50 (m, 4H), 1.39 (s, 6H). |
| 2-237 | 4.70 | 407.1 | 5 | — | DMSO δ 13.29 (s, 1H), 9.17 (s, 1H), 8.45 (s, 1H), 7.63 (m, 2H), 7.47 (m, 1H), 4.42 (q, J = 7.1, 2H), 4.28 (m, 4H), 3.82 (m, 4H), 2.64 (s, 3H), 1.40 (t, J = 7.1, 3H). |
| 2-238 | 4.07 | 379.1 | 5 | — | |
| 2-239 | 3.92 | 349.1 | 5 | — | |
| 2-240 | 3.65 | 423.2 | 5 | — | |
| 2-241 | 4.34 | 486.3 | 5 | — | |
| 2-242 | 0.40 and 3.01 | 502.3 | 3 | 0.016 | DMSO δ 8.77 (s, 2H), 8.37 (s, 1H), 7.72 (s, 1H), 6.82 (s, 2H), 4.25 (s, 4H), 3.77 (m, 4H), 3.07 (s, 4H), 2.84 (s, 3H), 2.54 (m, 4H), 1.47 (s, 6H). |
| 2-243 | 2.97 | 555.1 | 2 | — | DMSO δ 8.89 (d, J = 10.8, 2H), 8.18 (s, 1H), 8.02 (d, J = 8.7, 2H), 7.54 (dd, J = 8.5, 6.5, 4H), 7.34 (d, J = 8.9, 2H), 4.27 (m, 4H), 3.78 (m, 4H), 3.49 (m, 4H), 2.50 (s, 3H), 2.31 (m, 4H), 2.19 (s, 3H). |
| 2-244 | 4.58 | 473.4 | 2 | 0.144 | DMSO δ 9.22 (s, 1H), 9.07 (s, 1H), 8.22 (s, 1H), 8.03 (d, J = 8.6, 2H), 7.88 (d, J = 8.7, 2H), 7.57 (m, 5H), 7.41 (s, 1H), 4.24 (m, 4H), 3.78 (m, 4H), 2.50 (s, 3H). |
| 2-245 | 5.33 | 487.3 | 2 | — | DMSO δ 9.14 (s, 1H), 8.96 (s, 1H), 8.19 (s, 1H), 8.02 (d, J = 8.7, 2H), 7.90 (d, J = 8.7, 2H), 7.58 (m, 5H), 7.36 (s, 1H), 4.27 (m, 4H), 3.81 (s, 3H), 3.78 (m, 4H), 2.50 (s, 3H). |

Biological activity in PI3Kα for certain examples is represented in Table 4 by semi-quantative results: IC50 > 1 μM (+), IC50 < 100 nM (+++), 100 nM < IC50 < 1 μM (++). Biological activity in PI3Kα for certain examples is also represented in Table 4 by quantative results.

TABLE 5

IC50 of AKT Phosphorylation Inhibition of some representative compounds of the examples (μM), as tested in the cell assay procedure described above.

| Cpd. Nr. | p-AKT cell |
| --- | --- |
| 2-01 | 0.132 |
| 2-10 | 0.048 |
| 2-13 | 0.714 |
| 2-16 | 0.503 |
| 2-17 | 0.391 |
| 2-50 | 0.008 |
| 2-66 | 0.014 |
| 2-67 | 0.198 |
| 2-74 | 0.037 |
| 2-75 | 0.077 |
| 2-79 | 0.042 |
| 2-119 | 0.087 |
| 2-142 | 0.116 |
| 2-154 | 1.05 |
| 2-164 | 0.034 |
| 2-171 | 0.379 |
| 2-172 | 0.149 |
| 2-175 | 0.469 |
| 2-186 | 0.281 |
| 2-188 | 0.060 |
| 2-191 | 0.034 |
| 2-192 | 0.070 |
| 2-196 | 0.134 |
| 2-219 | 0.244 |
| 2-220 | 0.098 |
| 2-221 | 0.135 |
| 2-222 | 0.095 |

The invention claimed is:

1. A compound of formula I,

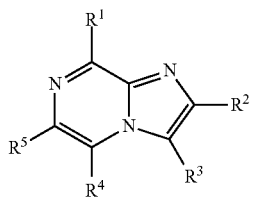

wherein:
R$^1$ represents: N-morpholinyl which is unsubstituted or substituted by one or more B$^1$ and/or =O substituents;
R$^2$ independently represents:
(i) Q$^1$;
(ii) C$_{1-12}$ alkyl optionally substituted by one or more substituents selected from =O, =S, =N(R$^{10a}$) and Q$^2$; or
(iii) a fragment of formula IA,

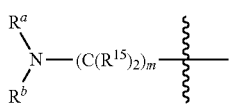

m represents 0, 1, 2, 3, 4, 5 or 6;
R$^3$ represents:
(i) hydrogen;
(ii) Q$^1$;
(iii) C$_{1-12}$ alkyl optionally substituted by one or more substituents selected from =O, =S, =N(R$^{10a}$) and Q$^2$; or (iv) a fragment of formula IA,

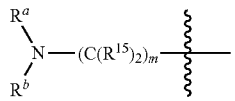

m represents 0, 1, 2, 3, 4, 5 or 6;
each R$^{15}$ represents
hydrogen, halogen or C$_{1-6}$ alkyl optionally substituted by one or more substituents selected from E$^1$; or
the two R$^{15}$ groups may be linked together to form, along with the requisite carbon atom to which those R$^{15}$ groups are necessarily attached a 3- to 6-membered spiro-cyclic ring, which ring optionally contains one or more double bonds, and optionally contains a further heteroatom selected from nitrogen, sulfur and oxygen, and which ring is optionally substituted by one or more substituents selected from E$^2$;
R$^a$ and R$^b$ are linked together, along with the requisite nitrogen atom to which they are necessarily attached, to form a first 3- to 7-membered cyclic group, optionally containing one further heteroatom selected from nitrogen, sulfur and oxygen, and which ring:
(a) is fused to a second ring that is either a 3- to 7-membered saturated heterocycloalkyl group containing one to four heteroatoms selected from oxygen, sulfur and nitrogen, a 3- to 12-membered saturated carbocyclic ring, or an unsaturated 5- to 12-membered carbocyclic or heterocyclic ring;
(b) comprises a linker group —(C(R$^x$)$_2$)$_p$— and/or —(C(R$^x$)$_2$)$_r$—O—(C(R$^x$)$_2$)$_s$— wherein p is 1 or 2; r is 0 or 1; s is 0 or 1; and each R$^x$ independently represents hydrogen or C$_{1-6}$ alkyl, linking together any two non-adjacent atoms of the first 3- to 7-membered ring to form a bridged structure; or
(c) comprises a second ring that is either a 3- to 12-membered saturated carbocyclic ring or a 3- to 7-membered saturated heterocycloalkyl group containing one to four heteroatoms selected from oxygen and nitrogen, and which second ring is linked together with the first ring via a single carbon atom common to both rings to form a spiro-cycle,
all of which cyclic groups, defined by the linkage of R$^a$ and R$^b$, are optionally substituted by one or more substituents selected from =O and E$^3$;
R$^4$ represents hydrogen, chlorine, bromine, iodine, —CN, —C(O)R$^{10b}$, or methyl, optionally substituted by one or more substituents selected from E$^4$; wherein E$^4$ represents heteroaryl or —OR$^{20}$;
R$^5$ represents heteroaryl, optionally substituted by one or more substituents selected from E$^5$;
each Q$^1$ and Q$^2$ independently represents, on each occasion when used herein:
halogen, —CN, —NO$_2$, —N(R$^{10a}$)R$^{11a}$, —OR$^{10a}$, —C(=Y)—R$^{10a}$, —C(=Y)—OR$^{10a}$, —C(=Y)N(R$^{10a}$)R$^{11a}$, —OC(=Y)—R$^{10a}$, —OC(=Y)—OR$^{10a}$, —OC(=Y)N(R$^{10a}$)R$^{11a}$, —OS(O)$_2$OR$^{10a}$, —OP(=Y)(OR$^{10a}$)(OR$^{11a}$), —OP(OR$^{10a}$)(OR$^{11a}$), —N(R$^{12a}$)C(=Y)R$^{11a}$, —N(R$^{12a}$)C(=Y)OR$^{11a}$, —N(R$^{12a}$)C(=Y)N(R$^{10a}$)R$^{11a}$, —NR$^{12a}$S(O)$_2$R$^{10a}$, —NR$^{12a}$S(O)$_2$N(R$^{10a}$)R$^{11a}$, —S(O)$_2$N(R$^{10a}$)R$^{11a}$, —SC(=Y)R$^{10a}$, —S(O)$_2$R$^{10a}$, —SR$^{10a}$, —S(O)R$^{10a}$, C$_{1-12}$ alkyl, heterocycloalkyl, which latter two groups are optionally substituted by one or more substituents selected from =O, =S, =N($R^{10a}$) and $E^6$, aryl or heteroaryl, which latter two groups are optionally substituted by one or more substituents selected from $E^7$;

each $B^1$ independently represents halogen, —$NO_2$, —CN, —N($R^{10a}$)$R^{11a}$, —$OR^{10a}$, —C(=Y)—$R^{10a}$, —C(=Y)—$OR^{10a}$, —C(=Y)N($R^{10a}$)$R^{11a}$, —N($R^{12a}$)C(=Y)$R^{11a}$, —N($R^{12a}$)C(=Y)$OR^{11a}$, —N($R^{12a}$)C(=Y)N($R^{10a}$)$R^{11a}$, —$NR^{12a}S(O)_2R^{10a}$, —$NR^{12a}S(O)_2$N($R^{10a}$)$R^{11a}$, —$S(O)_2$N($R^{10a}$)$R^{11a}$, —SC(=Y)$R^{10a}$, —SC(=Y)$OR^{10a}$, —$S(O)_2R^{10a}$, $C_{1-12}$ alkyl, heterocycloalkylc which latter two groups are optionally substituted by one or more substituents selected from =O and $E^8$, aryl or heteroaryl, which latter two groups are optionally substituted by one or more substituents selected from $E^9$;

or, any two $B^1$ substituents, when attached to the same carbon atom may be linked together to form, a 3- to 12-membered spirocyclic ring, optionally containing one or more heteroatoms, which ring optionally contains one or more double bonds, and which ring is itself optionally substituted by one or more substituents selected from halogen, =O and $C_{1-3}$ alkyl optionally substituted by one or more fluorine atoms;

each $R^{10a}$, $R^{11a}$, $R^{12a}$, and $R^{10b}$ independently represent, on each occasion when used herein, hydrogen, $C_{1-12}$ alkyl, heterocycloalkyl, which latter two groups are optionally substituted by one or more substituents selected from =O, =S, =N($R^{20}$) and $E^{10}$, aryl or heteroaryl, which latter two groups are optionally substituted by one or more sub stituents selected from $E^{11}$; or any relevant pair of $R^{10a}$, $R^{11a}$ and $R^{12a}$ may be linked together to form a 3- to 20-membered ring, optionally containing one or more heteroatoms, optionally containing one or more unsaturations, and which ring is optionally substituted by one or more substituents selected from =O, =S, =N($R^{20}$) and $E^{12}$;

each $E^1$, $E^2$, $E^3$, $E^5$, $E^6$, $E^7$, $E^8$, $E^9$, $E^{10}$, $E^{11}$ and $E^{12}$ independently represents, on each occasion when used herein:
(i) $Q^4$;
(ii) $C_{1-12}$ alkyl optionally substituted by one or more substituents selected from =O and $Q^5$; or any two $E^1$, $E^2$, $E^3$, $E^5$, $E^6$, $E^7$, $E^8$, $E^9$, $E^{10}$, $E^{11}$ or $E^{12}$ groups may be linked together to form a 3- to 12-membered ring, optionally containing one or more unsaturations, and which ring is optionally substituted by one or more substituents selected from =O and $J^1$;

each $Q^4$ and $Q^5$ independently represent, on each occasion when used herein:
halogen, —CN, —$NO_2$, —N($R^{20}$)$R^{21}$, —$OR^{20}$, —C(=Y)—$R^{20}$, —C(=Y)—$OR^{20}$, —C(=Y)N($R^{20}$)$R^{21}$, —OC(=Y)—$R^{20}$, —OC(=Y)—$OR^{20}$, —OC(=Y)N($R^{20}$)$R^{21}$, —$OS(O)_2OR^{20}$, —OP(=Y)($OR^{20}$)($OR^{21}$), —OP($OR^{20}$)($OR^{21}$), —N($R^{22}$)C(=Y)$R^{21}$, —N($R^{22}$)C(=Y)$OR^{21}$, —N($R^{22}$)C(=Y)N($R^{20}$)$R^{21}$, —$NR^{22}S(O)_2R^{20}$, —$NR^{22}S(O)_2$N($R^{20}$)$R^{21}$, —$S(O)_2$N($R^{20}$)$R^{21}$, —SC(=Y)$R^{20}$, —$S(O)_2R^{20}$, —$SR^{20}$, —S(O)$R^{20}$, $C_{1-6}$ alkyl, heterocycloalkyl, which latter two groups are optionally substituted by one or more substituents selected from =O and $J^2$, aryl or heteroaryl, which latter two groups are optionally substituted by one or more substituents selected from $J^3$;

each Y independently represents, on each occasion when used herein, =O, =S, =$NR^{23}$ or =N—CN;

each $R^{20}$, $R^{21}$, $R^{22}$ and $R^{23}$ independently represent, on each occasion when used herein, hydrogen, $C_{1-6}$ alkyl, heterocycloalkyl, which latter two groups are optionally substituted by one or more substituents selected from $J^4$ and =O, aryl or heteroaryl which latter two groups are optionally substituted by one or more substituents selected from $J^5$; or any relevant pair of $R^{20}$, $R^{21}$ and $R^{22}$ may be linked together to form a 3- to 20-membered ring, optionally containing one or more heteroatoms, optionally containing one or more unsaturations, and which ring is optionally substituted by one or more substituents selected from $J^6$ and =O;

each $J^1$, $J^2$, $J^3$, $J^4$, $J^5$ and $J^6$ independently represents, on each occasion when used herein:
(i) $Q^7$;
(ii) $C_{1-6}$ alkyl or heterocycloalkyl, both of which are optionally substituted by one or more substituents selected from =O and $Q^8$;

each $Q^7$ and $Q^8$ independently represents, on each occasion when used herein:
—CN, halogen, —N($R^{50}$)$R^{51}$, —$OR^{50}$, —C(=$Y^a$)—$R^{50}$, —C(=$Y^a$)—$OR^{50}$, —C(=$Y^a$)N($R^{50}$)$R^{51}$, —N($R^{52}$)C(=$Y^a$)$R^{51}$, —$NR^{52}S(O)_2R^{50}$, —$S(O)_2R^{50}$, —$SR^{50}$, —S(O)$R^{50}$ or $C_{1-6}$ alkyl optionally substituted by one or more fluorine atoms;

each $Y^a$ independently represents, on each occasion when used herein, =O, =S, =$NR^{53}$ or =N—CN;

each $R^{50}$, $R^{51}$, $R^{52}$ and $R^{53}$ independently represents, on each occasion when used herein, hydrogen or $C_{1-6}$ alkyl optionally substituted by one or more substituents selected from fluorine, —$OR^{60}$ and —N($R^{61}$)$R^{62}$; or any relevant pair of $R^{50}$, $R^{51}$ and $R^{52}$ may be linked together to form, a 3- to 8-membered ring, optionally containing one or more heteroatoms, optionally containing one or more unsaturations, and which ring is optionally substituted by one or more substituents selected from =O and $C_{1-3}$ alkyl;

$R^{60}$, $R^{61}$ and $R^{62}$ independently represent hydrogen or $C_{1-6}$ alkyl optionally substituted by one or more fluorine atoms;

or a pharmaceutically acceptable ester, amide, solvate or salt thereof.

2. A compound as claimed in claim 1 wherein:
each $Q^7$ and $Q^8$ independently represents, on each occasion when used herein halogen, —N($R^{50}$)$R^{51}$, —$OR^{50}$, —C(=$Y^a$)—$R^{50}$, —C(=$Y^a$)—$OR^{50}$, —C(=$Y^a$)N($R^{50}$)$R^{51}$, —N($R^{52}$)C(=$Y^a$)$R^{51}$, —$NR^{52}S(O)_2R^{50}$, —$S(O)_2R^{50}$, —$SR^{50}$, —S(O)$R^{50}$ or $C_{1-6}$ alkyl optionally substituted by one or more fluorine atoms.

3. A compound as claimed in claim 1, wherein:
$R^2$ independently represent
a substituent selected from halogen, —CN, —N($R^{10a}$)$R^{11a}$, —C(=Y)$OR^{10a}$, —C(=Y)—$R^{10a}$, —C(=Y)—N($R^{10a}$)$R^{11a}$, $C_{1-6}$ alkyl, optionally substituted by one or more substituents selected from $E^6$ and heterocycloalkyl, which heterocycloalkyl group is optionally substituted by one or more substituents selected from =O and $E^6$;

$R^4$ represents hydrogen, chlorine, bromine, iodine or —CN;

$R^5$ represents heteroaryl, optionally substituted by one or more substituents selected from $E^5$;

each $R^{10a}$, $R^{11a}$, $R^{12a}$, and $R^{10b}$ independently represents hydrogen or $C_{1-6}$ alkyl optionally substituted by one or more substituents selected from =O and $E^{10}$;

or any relevant pair of $R^{10a}$, $R^{11a}$ and $R^{12a}$ is linked together to form a 4- to 8-membered ring, optionally containing a further heteroatom, and optionally substituted by one or more substituents selected from =O and $E^{12}$;

and/or each $E^1, E^2, E^3, E^5, E^6, E^7, E^8, E^9, E^{10}, E^{11}$ and $E^{12}$ independently represents $C_{1-12}$ alkyl optionally substituted by one or more substituents selected from =O and $Q^5$.

4. A compound as claimed in claim 1, wherein each $Q^4$ and $Q^5$ independently represent halogen, —N($R^{20}$)$R^{21}$, —O$R^{20}$, —C(=Y)—O$R^{20}$, —C(=Y)N($R^{20}$)$R^{21}$, —N($R^{22}$)C(=Y)$R^{21}$, —N($R^{22}$)C(=Y)N($R^{20}$)$R^{21}$, —N$R^{22}$S(O)$_2R^{20}$, —S(O)$_2$ $R^{20}$ and/or $C_{1-6}$ alkyl, optionally substituted by one or more substituents selected from =O and $J^2$; and/or each $R^{20}$, $R^{21}$, $R^{22}$ and $R^{23}$ independently represents hydrogen or $C_{1-6}$ alkyl optionally substituted by one or more substituents selected from =O and $J^4$;

or any relevant pair of $R^{20}$, $R^{21}$ and $R^{22}$ is linked together to form a 4- to 8-membered ring, optionally containing a further heteroatom, and optionally substituted by one or more substituents selected from =O and $J^6$.

5. A compound as claimed in claim 1, wherein:

each $J^1, J^2, J^3, J^4, J^5$ and $J^6$ independently represent $C_{1-6}$ alkyl optionally substituted by one or more substituents selected from $Q^8$;

each $Q^7$ and $Q^8$ independently represent halogen, —N($R^{50}$)$R^{51}$, —O$R^{50}$, —C(=$Y^a$)—O$R^{50}$, —C(=$Y^a$)—$R^{50}$, —S(O)$_2R^{50}$ or $C_{1-3}$ alkyl optionally substituted by one or more fluorine atoms;

each $R^{50}$, $R^{51}$, $R^{52}$ and $R^{53}$ independently represents hydrogen or $C_{1-6}$ alkyl optionally substituted by one or more fluorine atoms; and/or each $R^{60}$, $R^{61}$ and $R^{62}$ independently represents hydrogen or $C_{1-2}$ alkyl.

6. A pharmaceutical formulation comprising a compound of claim 1, or a pharmaceutically acceptable ester, amide, solvate or salt thereof, in admixture with a pharmaceutically acceptable adjuvant, diluent or carrier.

7. A combination product comprising:

(A) a compound according to claim 1, or a pharmaceutically-acceptable ester, amide, solvate or salt thereof; and (B) another therapeutic agent that is useful in the treatment of cancer and/or a proliferative disease, wherein each of components (A) and (B) is formulated in admixture with a pharmaceutically-acceptable adjuvant, diluent or carrier.

8. A compound as defined in claim 1, wherein $R^2$ represents —CN, —C(=Y)—$R^{10a}$, C(=Y)—O$R^{10a}$, —C(=Y)N($R^{10a}$)$R^{11a}$, a $C_{1-12}$ alkyl group optionally substituted by one or more substituents selected from =O, =S, =N($R^{10a}$) and $E^6$, an aryl group, or a 6-membered heteroaryl group, where the aryl and 6-membered heteroaryl groups are optionally substituted by one or more substituents selected from $E^7$.

9. A compound as defined in claim 1, wherein $R^2$ represents —CN, —C(=Y)—$R^{10a}$, —C(=Y)—O$R^{10a}$, —C(=Y)N($R^{10a}$)$R^{11a}$, a $C_{1-12}$ alkyl group optionally substituted by one or more substituents selected from =O, =S, =N($R^{10a}$) and $E^6$, or an aryl group optionally substituted by one or more substituents selected from $E^7$.

* * * * *

UNITED STATES PATENT AND TRADEMARK OFFICE
CERTIFICATE OF CORRECTION

| | | |
|---|---|---|
| PATENT NO. | : 8,778,935 B2 | Page 1 of 1 |
| APPLICATION NO. | : 13/264544 | |
| DATED | : July 15, 2014 | |
| INVENTOR(S) | : Joaquin Pastor Fernández et al. | |

It is certified that error appears in the above-identified patent and that said Letters Patent is hereby corrected as shown below:

In the Claims:

At column 246, claim number 1, line number 21, delete "sub stituents" and replace it with --substituents--.

At column 247, claim number 1, line number 30, delete "sub stituents" and replace it with --substituents--.

Signed and Sealed this
Twenty-fourth Day of March, 2015

Michelle K. Lee
*Director of the United States Patent and Trademark Office*

UNITED STATES PATENT AND TRADEMARK OFFICE
CERTIFICATE OF CORRECTION

PATENT NO. : 8,778,935 B2
APPLICATION NO. : 13/264544
DATED : July 15, 2014
INVENTOR(S) : Joaquín Pastor Fernández et al.

Page 1 of 1

It is certified that error appears in the above-identified patent and that said Letters Patent is hereby corrected as shown below:

Title page, item (73) Delete "(73) Assignee: Centro Nacional de Investigaciones Oncologicas (CNIO)" and replace it with --(73) Assignee: Fundacion Centro Nacional de Investigaciones Oncologicas Carlos III--

Signed and Sealed this
Twenty-eighth Day of June, 2016

Michelle K. Lee
*Director of the United States Patent and Trademark Office*